(12) United States Patent
Sarafraz-Yazdi et al.

(10) Patent No.: US 11,407,840 B2
(45) Date of Patent: Aug. 9, 2022

(54) ANTIBODIES TO M(H)DM2/4 AND THEIR USE IN DIAGNOSING AND TREATING CANCER

(71) Applicant: NomoCan Pharmaceuticals LLC, New York, NY (US)

(72) Inventors: Ehsun Sarafraz-Yazdi, New York, NY (US); Brad R. Evans, New York, NY (US)

(73) Assignee: NomoCan Pharmaceuticals LLC, New York, NY (US)

( * ) Notice: Subject to any disclaimer, the term of this patent is extended or adjusted under 35 U.S.C. 154(b) by 0 days.

(21) Appl. No.: 17/328,597

(22) Filed: May 24, 2021

(65) Prior Publication Data
US 2022/0144968 A1    May 12, 2022

Related U.S. Application Data

(63) Continuation of application No. 16/634,022, filed as application No. PCT/US2018/043908 on Jul. 26, 2018.

(60) Provisional application No. 62/537,914, filed on Jul. 27, 2017.

(51) Int. Cl.
| | |
|---|---|
| *A61K 39/00* | (2006.01) |
| *C07K 16/32* | (2006.01) |
| *A61K 47/64* | (2017.01) |
| *A61P 35/00* | (2006.01) |
| *A61K 33/243* | (2019.01) |
| *A61K 31/337* | (2006.01) |
| *A61K 31/513* | (2006.01) |
| *A61K 31/7068* | (2006.01) |
| *A61K 45/06* | (2006.01) |
| *G01N 33/574* | (2006.01) |

(52) U.S. Cl.
CPC ............ *C07K 16/32* (2013.01); *A61K 31/337* (2013.01); *A61K 31/513* (2013.01); *A61K 31/7068* (2013.01); *A61K 33/243* (2019.01); *A61K 45/06* (2013.01); *A61K 47/643* (2017.08); *A61P 35/00* (2018.01); *G01N 33/5748* (2013.01); *A61K 2039/505* (2013.01); *C07K 2317/21* (2013.01); *C07K 2317/24* (2013.01); *C07K 2317/34* (2013.01); *C07K 2317/56* (2013.01); *C07K 2317/565* (2013.01); *C07K 2317/73* (2013.01); *C07K 2317/734* (2013.01)

(58) Field of Classification Search
CPC ............. C07K 16/32; C07K 2317/21; C07K 2317/24; C07K 2317/34; C07K 2317/56; C07K 2317/565; C07K 2317/734; A61P 35/00; G01N 33/5748; A61K 2039/505
See application file for complete search history.

(56) References Cited

U.S. PATENT DOCUMENTS

| | | | |
|---|---|---|---|
| 9,765,117 | B2 | 9/2017 | Pincus |
| 2011/0183915 | A1 | 7/2011 | Pincus et al. |
| 2012/0177566 | A1 | 7/2012 | Pincus et al. |
| 2014/0030319 | A1 | 1/2014 | Tocque et al. |

FOREIGN PATENT DOCUMENTS

| | | |
|---|---|---|
| JP | 11-511980 A | 10/1999 |
| WO | WO 93/20238 A2 | 10/1993 |
| WO | WO 95/14233 A2 | 5/1995 |
| WO | WO 2013/143026 A1 | 10/2013 |
| WO | WO 2016/054555 A2 | 4/2016 |
| WO | WO 2019/023460 A1 | 1/2019 |
| WO | WO 2020/159504 A1 | 8/2020 |

OTHER PUBLICATIONS

Alagkiozidis, I. et al. (2017) "Synergy between Paclitaxel and Anti-Cancer Peptide PNC-27 in the Treatment of Ovarian Cancer" Annals of Clinical & Laboratory Science, 47(3):271-281.
Alley, S.C. et al. (Aug. 2010) "Antibody-drug conjugates: targeted drug delivery for cancer" Curr Opin Chem Biol, 14(4):529-537.
Banda, N.K. et al. (Oct. 2008) "Initiation of the alternative pathway of murine complement by immune complexes is dependent on N-glycans in IgG antibodies" Arthritis Rheum, 58:2081-3089.
Bartel, F. et al. (Jul. 2002) "Alternative and aberrant splicing of MDM2 mRNA in human cancer" Cancer Cell, 2(1):9-15.

(Continued)

*Primary Examiner* — Lei Yao
(74) *Attorney, Agent, or Firm* — Cooley LLP; Amy Mandragouras; Maya Elbert

(57) ABSTRACT

The present invention relates to certain anti-M(H)DM2/4 antibodies or antigen-binding fragments thereof, pharmaceutical compositions comprising anti-M(H)DM2/4 antibodies or antigen-binding fragments thereof, antibody-drug conjugates comprising anti-M(H)DM2/4 antibodies or antigen-binding fragments thereof bound to a cytotoxic drug, and the use of such antibodies, fragments, compositions and conjugates for treating cancer and/or for preventing metastases. In particular, described herein are certain antibodies or antigen-binding fragments thereof that specifically bind to extracellularly accessible epitopes of M(H)DM2/4 and inhibit tumor growth in vivo, pharmaceutical compositions comprising such antibodies or fragments, antibody-drug conjugates comprising such antibodies or fragments, and the use of such antibodies, fragments, compositions and conjugates for treating cancer or for preventing metastasis.

20 Claims, 40 Drawing Sheets
Specification includes a Sequence Listing.

(56) References Cited

OTHER PUBLICATIONS

Bartel, F. et al. (Jan. 2004) "MDM2 and Its Splice Variant Messenger RNAs: Expression in Tumors and Down-Regulation Using Antisense Oligonucleotides" Mol Cancer Res, 2:29-35.

Bechara, C. and S. Sagan (2013) "Cell-penetrating peptides: 20 years later, where do we stand?" FEBS Lett, 587(12):1693-1702.

Bellmunt, J. et al. (Mar. 2017) "Pembrolizumab as second-line therapy for advanced urothelial carcinoma" N Engl J Med, 376:1015-1026.

Benosman, S. et al. (Sep. 2007) "Multiple neurotoxic stresses converge on MDMX proteolysis to cause neuronal apoptosis" Cell Death and Differentiation, 14(12):2047-2057.

Besingi, R.N. et al. (2015) "Extracellular protease digestion to evaluate membrane protein cell surface localization" Nat Protoc, 10(12):2074-2080.

Bolhassani, A. (2011) "Potential efficacy of cell-penetrating peptides for nucleic acid and drug delivery in cancer" Biochim Biophys Acta. 1816(2):232-246.

Borghaei, H. et al. (Oct. 2015) "Nivolumab versus docetaxel in advanced nonsquamous non-small-cell lung cancer" N Engl J Med, 373:1627-1639.

Bowne, W.B. et al. (2008) "The penetratin sequence in the anticancer PNC-28 peptide causes tumor cell necrosis rather than apoptosis of human pancreatic cancer cells" Ann Surg Oncol, 15(12):3588-3600.

Brown, M. et al. (Jan. 1996) "Tolerance to single, but not multiple, amino acid replacements in antibody $V_H$ CDR2. A means of minimizing B cell wastage from somatic hypermutation" J Immunol, 156(9):3285-3291.

Chames, P. et al. (2009) "Bispecific antibodies for cancer therapy: the light at the end of the tunnel?" MAbs, 1(6):539-547.

Champiat, S. et al. (2017) "Hyperprogressive disease is a new pattern of progression in cancer patients treated by anti-PD-1/PD-L1" Clin Cancer Res, 23:1920-1928.

Chen, J. et al. (Jul. 1993) "Mapping of the p53 and mdm-2 interaction domains" Mol Cell Biol, 13(7):4107-4114.

Davitt, K. et al. (2014) "The Anti-Cancer Peptide, PNC-27, Induces Tumor Cell Necrosis of a Poorly Differentiated Non-Solid Tissue Human Leukemia Cell Line that Depends on Expression of HDM-2 in the Plasma Membrane of these Cells" Annals of Clinical & Laboratory Science, 44(3):241-248.

Do, T.N. et al. (2003) "Preferential induction of necrosis in human breast cancer cells by a p53 peptide derived from the MDM2 binding site" Oncogene, 22(10):1431-1444.

Du, S. et al. (2018) "Blockade of Tumor-Expressed PD-1 promotes lung cancer growth" Oncoimmunology, 7(4):e1408747; 9 pages.

Dupont, E. et al. (2015) "Penetratin Story: An Overview" Methods Mol Biol, 1324:29-37.

Evans, S.C. et al. (2001) "An alternatively spliced HDM2 product increases p53 activity by inhibiting HDM2" Oncogene, 20:4041-4049.

Fang, J. et al. (Mar. 2005) "Apigenin inhibits VEGF and HIF-1 expression via PI3K/AKT/p70S6K1 and HDM2/p53 pathways" FASEB J, 19(3):342-353.

Ferrara, R. et al. (Sep. 2018) "Hyperprogressive disease in patients with advanced non-small cell lung cancer treated with PD-1/PD-L1 inhibitors or with single agent chemotherapy" JAMA Oncol, 4(11):1543-1552.

Ferris, R.L. et al. (Oct. 2016) "Nivolumab for recurrent squamous cell carcinoma of the head and neck" N Engl J Med, 375:1856-1867.

Fridman, J.S. et al. (Sep. 2003) "Tumor promotion by Mdm2 splice variants unable to bind p53" Cancer Res, 63(18):5703-5706.

Gleeson et al. (2016) "Targeting HDM-2 Over-Expression in Multi-Drug Resistant Ovarian Cancer" Academic Surgical Congress Abstracts Archive. Abstract 04.21; asc-abstracts.org/abs2016/4-21-targeting-hdm-2-over-expression-in-multi-drug-resistant-Ovarian-cancer; 2 pages.

Gramer, M.J. et al. (2013) "Production of stable bispecific IgG1 by controlled Fab-arm exchange. Scalability from bench to large-scale manufacturing by application of standard approaches" MAbs, 5:962-973.

Idusogie, E.E. et al. (2001) "Engineered antibodies with increased activity to recruit complement" J Immunol, 166(4):2571-2575.

International Patent Application No. PCT/US2018/043908: International Search Report and Written Opinion; dated Jan. 21, 2019, 23 pages.

International Patent Application No. PCT/US2018/043908: Invitation to Pay Additional Fees with Partial International Search and Provisional Opinion; dated Nov. 14, 2018, 21 pages.

International Patent Application No. PCT/US2019/015900: International Search Report and Written Opinion; dated Sep. 3, 2019, 27 pages.

International Patent Application No. PCT/US2019/015900: Invitation to Pay Additional Fees with Partial International Search and Provisional Opinion; dated Jul. 10, 2019, 25 pages.

Iwakuma, T. and Lozano, G. (Dec. 2003) "MDM2, An Introduction" Molecular Cancer Research, 1:993-1000.

Jain, M. et al. (Sep. 2005) "Penetratin improves tumor retention of single-chain antibodies: a novel step toward optimization of radioimmunotherapy of solid tumors" Cancer Res, 65(17):7840-7846.

Kanovsky, M. et al. (Oct. 2001) "Peptides from the amino terminal mdm-2-binding domain of p53, designed from conformational analysis, are selectively cytotoxic to transformed cells" Proc Natl Acad Sci USA, 98(22):12438-12443.

Kasim, V. et al. (May 2014) "Synergistic cooperation of MDM2 and E2F1 contributes to TAp73 transcriptional activity" Biochem Biophys Res Commun, 449(3):319-326.

Kato, S. et al. (Aug. 2017) "Hyperprogressors after immunotherapy: analysis of genomic alterations associated with accelerated growth rate" Clin Cancer Res, 23:4242-4250.

Kleemann, E. et al. (2005) "Nano-carriers for DNA delivery to the lung based upon a TAT-derived peptide covalently coupled to PEG-PEI" J Control Release, 109(1-3):299-316.

Konterman, R.E. (Mar./Apr. 2012) "Dual targeting strategies with bispecific antibodies" MAbs, 4(2):182-197.

Lazar, G.A. et al. (Mar. 2006) "Engineered antibody Fc variants with enhanced effector function" PNAS, 103(11): 4005-4010.

Li, B. et al. (Apr. 2008) "Development of novel tetravalent anti-CD20 antibodies with potent tumor activity" Cancer Res, 68:2400-2408.

Li, G. et al. (Jan. 2015) "Enriched environment inhibits mouse pancreatic cancer growth and down-regulates the expression of mitochondria-related genes in cancer cells" Sci Rep, 5:7856, DOI: 10.1038/srep07856; 9 pages.

Liang, H. et al. (2004) "Genomic organization of the human MDM2 oncogene and relationship to its alternatively spliced mRNAs" Gene, 338:217-223.

Liu. S.D. et al. (2014) "Afucosylated antibodies increase activation of FCγRIIIa-dependent signaling components to intensify processes promoting ADCC" Cancer Immunol Res, 3(2):173-183.

Lukas, J. et al. (Apr. 2001) "Alternative and Aberrant Messenger RNA Splicing of the mdm2 Oncogene in Invasive Breast Cancer" Cancer Res, 61:3212-3219.

Macor, P. et al. (Apr. 2006) "Complement activated by chimeric anti-folate receptor antibodies is an efficient effector system to control ovarian carcinoma" Cancer Res, 66(7):3876-3883.

Matsumoto, R. (Feb. 1998) "Short alternative splice transcripts of the mdm2 oncogene correlate to malignancy in human astrocytic neoplasms" Cancer Res, 58:609-613.

McIntyre, R.M. (2015) "Mouse models of colorectal cancer as preclinical models" Bioassays, 37(8):909-920.

Muller, S. et al. (Feb. 2005) "TransMabs: cell-penetrating antibodies, the next generation" Expert Opin Biol Ther, 5(2):237-241.

Olson, D.C. et al. (1993) "Identification and characterization of multiple mdm-2 proteins and mdm-2-p53 protein complexes" Oncogene, 8:2353-2360.

Olson, E.S. et al. (2009) "In vivo characterization of activatable cell penetrating peptides for targeting protease activity in cancer" Integr Biol, 1(5-6): 382-393.

(56) References Cited

OTHER PUBLICATIONS

Page, D.B. et al. (2014) "Immune modulation in cancer with antibodies" Annu Rev Med, 65:185-202.

Paterson, A.M. et al. (Aug. 2011) "The Programmed Death-1 Ligand 1:B7-1 Pathway Restrains Diabetogenic Effector T Cells In Vivo" J Immunol, 187(3):1097-1105.

Polsky, D. et al. (Dec. 2002) "HDM2 Protein Overexpression and Prognosis in Primary Malignant Melanoma" J Natl Cancer Inst, 94(23):1803-1806.

Rayburn, E. et al. (2005) "MDM2 and Human Malignancies: Expression, Clinical Pathology, Prognostic Markers, and Implications for Chemotherapy" Current cancer Drug Targets, 5:27-41.

Richards, J.O. et al. (Aug. 2008) "Optimization of antibody binding to FcgammaRIIa enhances macrophage phagocytosis of tumor cells" Mol Cancer Ther, 7(8):2517-2527.

Rosal, R. et al. (2005) "The role of alpha-helical structure in p53 peptides as a determinant for their mechanism of cell death: necrosis versus apoptosis" Adv Drug Deliv Rev, 57:653-660.

Rosso, M. et al. (2014) "Splice variants of MDM2 in oncogenesis" Subcell Biochem, 85:247-261.

Rudikoff, S. et al. (Mar. 1982) "Single amino acid substitution altering antigen-binding specificity" Proc Natl Acad Sci, 79:1979-1983.

Ryan, M.C. et al. (Nov. 2007) "Antibody targeting of B-cell maturation antigen on malignant plasma cells" Mol Cancer Ther, 6(11):3009-3018.

Saada-Bouzid, E. et al. (2017) "Hyperprogression during anti-PD-1/PD-L1 therapy in patients with recurrent and/or metastatic head and neck squamous cell carcinoma" Ann Oncol, 28:1605-1611.

Sarafraz-Yazdi, E. et al. (Feb. 2010) "Anti-cancer peptide PNC-27 adopts an HDM2-binding conformation and kills cancer cells by binding to HDM2 in their membranes" PNAS, 107(5):1918-1923.

Sarafraz-Yazdi, E. et al. (Apr. 2010) "Abstract 5770: MDM2 protein variants expression in the plasma membrane of cancer cells: A target for anti-cancer peptide PNC-27" AACR 101st Annual Meeting 2010, Washington DC. Cancer Res, 70(8 Suppl):5770, https://doi.org/10.1158/1538-7445.AM10-5770; 2 pages.

Satoh, M.M. et al. (2006) "Non-fucosylated therapeutic antibodies as next-generation therapeutic antibodies" Expert Opin Biol Ther, 6(11):1161-1173.

Scholzen, T. et al. (2000) "The Ki-67 protein: from the known and the unknown" Journal of Cellular Physiology, 182(3): 311-322.

Schülein, R. et al. (1996) "Membrane Targeting and Determination of Transmembrane Topology of the Human Vasopressin V2 Receptor" J Biol Chem, 271(46):28844-28852.

Schuster, K. et al. (2007) "MDM2 splice variants predominantly localize to the nucleoplasm mediated by a COOH-terminal nuclear localization signal" Mol Cancer Res, 5(4):403-412.

Shaikh, M.F. et al. (2016) "Emerging Role of MDM2 as Target for Anti-Cancer Therapy: A Review" Annals of Clinical & Laboratory Science, 46(6):627-634.

Sharma, S. et al. (1999) "T Cell-Derived IL-10 Promotes Lung Cancer Growth by Suppressing Both T Cell and APC Function" J Immunol, 163(9):5020-5028.

Shields, R.L. et al. (Mar. 2001) "High resolution mapping of the binding site on human IgG1 for Fcgamma RI, Fcgamma RII, Fcgamma RIII, and FcRn and design of IgG1 variants with improved binding to the FcgammaR" J Biol Chem, 276(9):6591-604.

Shin, M.C. et al. (2013) "Cell-penetrating peptides: achievements and challenges in application for cancer treatment" J Biomed Mater Res Part A, 102(2):575-587.

Shultz, L.D. et al. (May 2005) "Human Lymphoid and Myeloid Cell Development in NOD/LtSz-scid IL2Rgamma$^{null}$ Mice Engrafted with Mobilized Human Hemopoietic Stem Cells" J Immunol, 174(10):6477-6489.

Sigalas, A.H. et al. (Aug. 1996) "Alternatively spliced mdm2 transcripts with loss of p53 binding domain sequences: transforming ability and frequent detection in human cancer" Nat Med, 2(8):912-917.

Singavi, A.K et al. (Sep. 2017) "Predictive Biomarkers for Hyper-Progression (HP) in Response to immune Checkpoint Inhibitors (ICI)—Analysis of Somatic Alterations (SAs)" Ann Oncol, 28(Suppl 5):405, Abstract 1140PD, doi:10.1093/annonc/mdx376; 1 page.

Sookraj, K.A. et al. (2010) "The anti-cancer peptide, PNC-27, induces tumor cell lysis as the intact peptide" Cancer Chemother Pharmacol, 66(2):325-331.

Steinman, H.A. et al. (2004) "An Alternative Splice Form of Mdm2 Induces p53-independent Cell Growth and Tumorigenesis" The Journal of Biological Chemistry, 279(6):4877-4886.

Steurer, W. et al. (1995) "Ex vivo coating of islet cell allografts with murine CTLA4/Fc promotes graft tolerance" J Immunol, 155(3):1165-1174.

Tamborini, E. et al. (2001) "Analysis of the molecular species generated by MDM2 gene amplification in liposarcomas" Int J Cancer, 92:790-796.

Taubert, H. et al. (2000) "A MboII polymorphism in exon 11 of the human MDM2 gene occurring in normal blood donors and in soft tissue sarcoma patients: an indication for an increased cancer susceptibility?" Mutat Res, 456:39-44.

Torchilin, V.P. et al. (Feb. 2003) "Cell transfection in vitro and in vivo with nontoxic TAT peptide-liposome-DNA complexes" Proc Natl Acad Sci USA, 100(4):1972-1977.

Volk, E.L. et al. (Jun. 2009) "The MDM2-A splice variant of MDM2 alters transformation in vitro and the tumor spectrum in both Arf-null and p53-null models of tumorigenesis" Mol Cancer Res, 7(6):863-869.

Wang, H. et al. (Dec. 2017) "PNC-27 Targeting Plasma Membrane HDM2: A Potentially Novel Therapeutic Approach for Acute Myeloid Leukemia (AML)" Blood, 130:2518; 3 pages.

William, C. (Aug. 2002) "Peptide blockade of HIFalpha degradation modulates cellular metabolism and angiogenesis" Proc Natl Acad Sci USA, 99(16):10423-10428.

Yang, J.-Y. et al. (Oct. 2006) "MDM2 promotes cell motility and invasiveness by regulating E-cadherin degradation" Mol Cell Biol, 26(19):7269-7282.

Zheng, T. et al. (Apr. 2010) "Disruption of p73-MDM2 binding synergizes with gemcitabine to induce apoptosis in HuCCT1 cholangiocarcinoma cell line with p53 mutation" Tumor Biol, 31(4):287-295.

Zuazo-Ibarra, M. et al. (May 2018) "Highly differentiated CD4 T cells unequivocally identify primary resistance and risk of hyperprogression to PD-L1/PD-1 immune checkpoint blockade in lung cancer" bioRxiv preprint, https://doi.org/10.1101/320176, 21 pages.

Eymin, B. et al. (Apr. 2002) "Mdm2 overexpression and p14(ARF) inactivation are two mutually exclusive events in primary human lung tumors" Oncogene, 21(17):2750-2761. doi: 10.1038/sj.onc.1205359.

mAb NMC-103 Sequences (CDRs as defined by IMGT)

Heavy Chain Variable Region DNA Sequence

Gaggtgcagctgcaggagtctggaggaggcttggtgcagcctggaggttctctgagactcctgtacaacttcactcattactacatgagctggtcc
gccagcctccaggcaaggcacttgagtggttgggcttattagaaataaagctaaggttacacagcagagtacagtgcatctgtgaaggtcgttcaccatcccagag
ataattcccaaagcatcctctatcttcaaatgaacacctgagacctgaggacagtgccacttattactgtgcaagagatattggggacaactggggtcaaggaacctagt
caccgtctcctcag (SEQ ID NO: 132)

Predicted Protein Sequence of Heavy Chain Variable Region

Complementarity determining regions (CDRs) are underlined.

EVQLQESGGGLVQPGGSLRLSCTTSGFTFTHYYMSWVRQPPGKALEWLGFIRNKAKGYTAEYSASVKGRFTISRDNSQSILYLQMNTL
RPEDSATYYCARDIGDNWGQGTLVTVSS (SEQ ID NO: 36)

Light Chain Variable Region DNA Sequence

Gatattgtgatgacgcaggtctcctttccaatccagtcactcttggaacatcagctcccatctcctgcaggtctagtaagaatctcctacatagtaatggcatcactattgt
attggtatctgcagaggccaggccaggccagtctcctcagctctcgatatctcggtgtcaatctcggagtccaaacaggttcagtgcagtgagtcaggaactgattc
acactgagaatcagcagagtggaggctgaggatgtggttattctgtgctcaactgctagaactccgtacacgttcggagggggaccaagttggaaataaaac
(SEQ ID NO: 134)

Predicted Protein Sequence of Light Chain Variable Region

Complementarity determining regions (CDRs) are underlined.

DIVMTQAAFSNPVTLGTSASISCRSSKNLLHSNGITYLVWYLQRPGQSPQLLISRVSNLASGVPNRFSGSESGTDFTLRISRVEAEDVGVY
FCAQLLELPYTFGGGTKLEIK (SEQ ID NO: 37)

FIG. 20 mAb NMC-204 Sequences (CDRs as defined by IMGT)

Heavy Chain Variable Region DNA Sequence

Gaggtgcagctgcaggagtctggagctgagcctggagcctgtcctgcaaggcttctggcgacacccttcagcggtctctgatgcactgggcg
atgcagaggctggacaaggcctggatggattggagagattcatcttaatagaggtactaacaatgagaagttcaaggccaagtgactgtggacac
atcctccagcacgctacgtggatctcagcagctgacctgagaactctgcggtctattactgtgcaagaagcccgggtttgcttactgggccaagggactctggtc
actgtctctgcag (SEQ ID NO: 136)

Predicted Protein Sequence of Heavy Chain Variable Region
Complementarity determining regions (CDRs) are underlined.

EVQLQESGSVLVRPGASVKLSCKASGDTLSGSWMHWAMQRPGQGLEWIGEIHLNRGTTNYNEKFKGKATVTVDTSSSTAYVDLSSLT
SEDSAVYYCARSPGFAYWGQGTLVTVSA (SEQ ID NO: 38)

Light Chain Variable Region DNA Sequence

Ggcattgtgatgaccaggctgcaccctgtacctgtcactcctggagagtcagtatcatcctgcagttctagtaagagtctctgcatagtaatgcaacagttactt
gtattggttcctgcagaggccaggccagtccctcagctcctgatatatcgcagtgtccaagacagttcagtggcagtgggactctcaggaactgctt
tcacactgagaatcactagagtggaggctgaggatgtgggtgttattactgtatgcaacatctagaatatccttcacgttcggctcggggacaaagttgaaataaaac
(SEQ ID NO: 138)

Predicted Protein Sequence of Light Chain Variable Region
Complementarity determining regions (CDRs) are underlined.

GIVMTQAAPSVPVTPGESVSISCRSSKSLLHSNGNSYLYWFLQRPGQSPQLLIYRMSNLASGVPDRFSGSGSGTAFTLRITRVEAEDVGV
YYCMQHLEYPFTFGSGTKLEIK (SEQ ID NO: 39)

FIG. 21 mAb NMC-303 Sequences (CDRs as defined by Kabat)

Heavy chain variable region DNA sequence (with leader sequence) (408 bp)
Leader sequence-FR1-CDR1-FR2-CDR2-FR3-CDR3-FR4. Leader sequence is bold but not underlined.
ATGGGATGGAACTATATCATCCTCTTTTTGGTAGCAACAGGTACAGGTGTCCACTCCCAGGTCCAACTGCAGCAGCCTGGGGCTGA
ACTGGTGAAGCCTGGGGCTTCAGTGAAGTTGTCCTGCAAGGCTTCTGGCTACACCTTCACCAGTTACTATATGTACTGGGTGAAGC
AGAGGCCTGGACAAGGCCTTGAGTGGATTGGGGGATTAATCCTAGAAATGGTGGTACTAACTTCAATGAGAAGTTCAAGAACAA
GGCCACACTGACTGCAGACAAATCCTCCACCAGCAACTCAGTAGCCTGACATCGAGGACTCGGGTCTATTACTG
TACAAGATCTGGTTACTATGCTATGGACTATTGGGGTCAAGGAACCTCAGTCACCGTCTCCTCA (SEQ ID NO: 133)

Heavy chain variable region protein sequence (with leader sequence) (136 aa)

Leader sequence-FR1-CDR1-FR2-CDR2-FR3-CDR3-FR4. (CDRs) are underlined. Leader sequence is bold but not underlined.
MGWNYIILFLVATATGVHSQVQLQQPGAELVKPGASVKLSCKASGYTFTSYYMYWVKQRPGQGLEWIGGINPRNGGTNFNEKFKNK
ATLTADKSSTTAYMQLSSLTSEDSAVYYCTRSGYYAMDYWGQGTSVTVSS (SEQ ID NO: 135)

Light chain variable region DNA sequence (with leader sequence) (381 bp)
Leader sequence-FR1-CDR1-FR2-CDR2-FR3-CDR3-FR4. Leader sequence is bold but not underlined.
ATGATGTCCTGCTCAGTTCCTGCTGCTCTGCTTGCTGGGAGACAGGTCACCATGACTCAGTCTCCAGCTTCCCTGTCTGCATCTCTGG
GAGACAGAGTCACCATCAGCTGCAGGGCAAGTCAGGACATTAGCAACATTAGCAATTTTTAAACTGGTATCAGCAG
AAACCAGGAAACTGTAAACTCCTGATCTACTACACATCAGAGATTACACTCAGGAGTCCCATCAAGGTTCAGTGGCAGTGGGTCT
GGAACAGATTATTCTCACCATTAGCAACCTGGAGCAAGAAGATATTGCCACTTACTTTTGCCAACAGGGTAATACGCTTCCTCGG
ACGTTCGGTGGAGGCACCAAGCTGGAAATCAAA (SEQ ID NO: 137)

Light chain variable region protein sequence (with leader sequence) (127 aa)
Leader sequence-FR1-CDR1-FR2-CDR2-FR3-CDR3-FR4. (CDRs) are underlined. Leader sequence is bold but not underlined.
MMSSAQFLGLLLLCFQGTRCDIQMTQTTSSLSASLGDRVTISCRASQDISNFLNWYQQKPDGTVKLLIYYTSRLHSGVPSRFSGSGSGT
DYSLTISNLEQEDIATYFCQQGNTLPRTFGGGTKLEIK (SEQ ID NO: 139)

FIG. 22

ANTIBODIES TO M(H)DM2/4 AND THEIR USE IN DIAGNOSING AND TREATING CANCER

1. CROSS-REFERENCE TO RELATED APPLICATIONS

This application is a continuation of U.S. application Ser. No. 16/634,022, national stage of International Patent Application No. PCT/US2018/043908, filed Jul. 26, 2018, which claims the benefit of U.S. Provisional Patent Application No. 62/537,914, filed Jul. 27, 2017, the disclosure of each of which is hereby incorporated herein by reference herein in its entirety.

2. REFERENCE TO SEQUENCE LISTING SUBMITTED ELECTRONICALLY

This application incorporates by reference a Sequence Listing submitted electronically in ASCII format via EFS-Web, and is hereby incorporated by reference in its entirety. Said ASCII copy, created on Mar. 23, 2022, is named NOMO_001_03US_Sequence_Listing and is 88434 bytes in size.

3. FIELD

The present invention relates to certain anti-M(H)DM2/4 antibodies or antigen-binding fragments thereof, pharmaceutical compositions comprising anti-M(H)DM2/4 antibodies or antigen-binding fragments thereof, antibody-drug conjugates comprising anti-M(H)DM2/4 antibodies or antigen-binding fragments thereof bound to a cytotoxic drug, and the use of such antibodies, fragments, compositions and conjugates for treating cancer and/or for preventing metastases.

4. BACKGROUND

The MDM2 (MDM2 is a mouse homologue of HDM2) protein is composed of 489 amino acids and contains a p53 binding domain, two nuclear localization signals (amino acids 176-182 and 464-471), and zinc-finger motifs (amino acids 297-326 and 436-477) (see UniProt website, at UniProt Accession No. P23804). Its human homologue, HDM2, is composed of 491 amino acids and contains a p53 binding domain, two nuclear localization signals (amino acids 179-185 and 466-473) and zinc-finger motifs (amino acids 299-328 and 438-479) (see UniProt website, at UniProt Accession No. Q00987). Mouse protein MDM4 (also identified as MDMX) is a homologue of the MDM2 protein (see UniProt website, at UniProt Accession No. 035618), and both MDM2 and MDM4 are major negative regulators of p53 (Wade et al., 2013, Nat Rev. Cancer 13:83-96; Marine et al., 2004, Cell Cycle 3:900-904; Momand et al., 2011, Gene 486:23-30). HDM4 (also identified as HDMX) is a human homologue of MDM4 (see UniProt website, at UniProt Accession No. 015151). The most conserved domain within all M(H)DM2 and M(H)DM4 proteins is the RING domain which is responsible for ubiquitination of its target proteins, including p53 protein, and heterodimerization between M(H)DM2 and M(H)DM4. M(H)DM4 is required for M(H)DM2-mediated polyubiquitination of p53. A distinctive feature of M(H)DM2 and M(H)DM4 are their very complex expression pattern. Multiple-sized transcripts and protein products of M(H)DM2 have been identified in cancer cells by a number of groups (Olson et al., 1993, Oncogene 8:2353-2360; Bartel et al., 2002, Cancer Cell 2:9-15 ("Bartel 2002"); Sigalas et al., 1996, Nat. Med. 2:912-917 ("Sigalas 1996"); Iwakuma & Lozano, 2003, Mol. Cancer Res. 1:993-1000 ("Iwakuma & Lozano 2003")). Many types of human cancers overexpress MDM2 protein and a common characteristic among these cancers is an associated increase in mdm2 splice variants. These M(H)DM2 variants have been shown to be expressed in a variety of tumors such as human ovarian, bladder, breast and astrocytic neoplasms, glioblastomas, leukemia and pediatric Rhabdomyosarcoma tumors (reviewed by Iwakuma & Lozano 2003; Rosso et al., 2014, Subcell Biochem. 85:247-61 ("Rosso 2014")). Most interestingly they have been found to be more frequent in tumors of advanced stage (Bartel 2002). The multiple-sized M(H)DM2 transcripts that have been shown to be splice variants forms of the M(H)DM2 mRNA have been reported to be expressed more frequently in tumor cells than in normal cells (Bartel et al., 2004, Mol. Cancer Res. 2:29 ("Bartel 2004")). It has been proposed that a mRNA surveillance system exists in untransformed cells, which degrades spliced transcripts and protects the cells from errors of transcription, mRNA processing, or mRNA transport whereas in transformed cells this system may not be functioning correctly (Bartel 2004). Moreover, some of these variants in cancer cells encode protein products, which have been shown to transform NIH3T3 cells in vitro, and some promoted tumor formation in mouse model (Sigalas 1996; Volk el. al., 2009, Mol Cancer Res. 7(6): 863-869).

To date more than 70 different M(H)DM2 splice variants have been identified (Bartel 2002; Bartel 2004; Rosso 2014). Some of the variants, for example MDM2-A and MDM2-B, are common to several tumor types (Sigalas 1996). Others have only been found in specific tumors, for example MDM2-FB25 and MDM2-FB26 in pediatric rhabdomyosarcoma. Several short forms of these alternatively spliced MDM2 transcripts correlate with high-grade malignancy in human ovarian tumors, bladder carcinomas and astrocytic tumors (Sigalas 1996; Matsumoto et al., 1998, Cancer Res. 58:609-613; Tamborini et al., 2001, Int. J. Cancer 92:790-796; Steinman et al., 2004, JBC 279:4877-4886). It has also been shown that aberrant mdm2 (281-, 254-, and 219-bp) and alternative mdm2 (653-bp) splice products strongly associated with shorter overall patient survival in breast cancer (Lukas et al., 2001, Cancer Res. 61:3212).

Several studies have evaluated the cellular localization of various human and murine M(H)DM2 protein variants to predict potential activities. In 25% of non-small cell lung carcinomas, M(H)DM2 variants were aberrantly localized to the cytoplasm (Evans et al., 2001, Oncogene 20:4041-4049). This result led to the discovery that the cytoplasmic compartmentalization of the full-length M(H)DM2 was due to binding and sequestration by an alternative-spliced M(H)DM2 product (HDM2ALT1). In another study, MDM2-D 150-230 localized to the cytoplasm of U20S cells (Schuster et al., 2007, Mol. Cancer Res. 5:403-412 ("Schuster 2007")). Both of these M(H)DM2 protein variants lacked part of the NH2-terminal region that contains a nuclear localization signal (NLS), suggesting that loss of this signal prevented the nuclear entry of these two proteins (Schuster 2007). Taken together, these data show that cellular localization of M(H)DM2 protein variants is highly complex.

Various M(H)DM4 protein variants have also been characterized, including splicing variant MDMX-S(Lenos and Jochemsen, 201, J. Biomed Biotechnol., doi: 10. 1155/201/876173).

HDM2 was found to be expressed in the plasma membrane of cancer cells (Sarafraz-Yazdi et al., 2010, PNAS 107:1918-1923 ("Sarafraz-Yazdi 2010"). Further, anti-cancer peptides, PNC-27 and PNC-28, which bind to HDM2 expressed in the cancer cell membranes and kill cancer cells by inducing necrosis, have been developed (Sarafraz-Yazdi 2010; Davitt et al., 2014, Annals Clin. Lab. Sci. 44:241248) (the amino acid sequences of PNC-27 and PNC-28 are provided in Table I of U.S. Patent Application Publication No. 2012/0177566). PNC-27 has been reported to bind within amino acids 25-109 of HDM2 (Do et al., 2003, Oncogene 22(10): 1431-1444 ("Do 2003"); Chene, 2003, Nat. Rev. Cancer 3(2): 102-109). Also, U.S. Patent Application Publication No. 2012/0177566 discloses methods of selectively necrosing cells by administering to the cells a compound (such as PNC-27 and PNC-28), including an HDM-2 targeting component and a cytotoxic component attached to the HDM-2 targeting component, wherein said compound comprises a membrane-active form. The membrane active function of PNC-27 and PNC-28 peptides (which comprise a membrane resident peptide ("MRP") and a p53 sequence) is only achieved if the cargo (i.e., the p53 sequence component) is attached to the MRP component so as to form a cytotoxic structure (Kanovsky et al, 2001, PNAS 98:12438-12443 ("Kanovsky 2001"); Bowne et al., 2008, Ann Surg Oncol. 15:3588-3600 "Bowne2008")). When either the MRP component or the HDM-2 targeting component (i.e. p53 component) were used separately, they were found to be non-cytotoxic to cancer cells (Kanovsky 2001; Do 2003), demonstrating lack of activity of the MRP component alone and the HDM-2 targeting component alone. When recombinantly expressed inside the cell, the HDM-2 targeting component was observed to cause apoptosis (Bowne 2008). U.S. Pat. No. 9,765,117 discloses HDM2 targeting peptides and fusion peptides comprising an HDM2 targeting peptide and a transmembrane penetrating sequence, such as MRP; it is disclosed that MRP is required for induction of cell necrosis (see col. 4, lines 27-28). U.S. Pat. No. 9,765,117 indicates that expression of the p53 HDM2 targeting sequence in the absence of the MRP in cancer cells causes p53-dependent apoptosis and not tumor necrosis (see col. 4, lines 29-32).

The cell-penetrating peptides ("CPPs") (such as MRPs, Membrane Transduction Domain of Antennapedia, trans-activating transcriptional activator ("TAT") and Penetratin peptides) enable cellular membrane delivery of the peptides, and molecules attached to the peptides, to plasma membrane lipid bilayers, including those of normal healthy cells. These peptides were shown to efficiently transport various biologically active molecules inside living cells (Bechara et al., 2013, FEBS Lett. 587:1693-1702, Dupont et al., 2015, Methods Mol. Biol. 1324:29-37). The use of these CPPs (such as MRPs, Membrane Transduction Domain of Antennapedia, TAT and Penetratin peptides) linked to various cargos (such as other peptides, DNA, RNA, small molecules, antibodies or fragments thereof) have been demonstrated to improve pharmacokinetics, bio-distribution, retention, uptake and delivery of these cargos to various tumors in vitro and in vivo (Torchilin et al., 2003, PNAS 100:1972-1977; Shin et al., 2014, J. Biomed. Mater Res. A. 102:575-587; Kleemann et al., 2005, J. Control Release 109:299-316; Olson et al., 2009, Integr. Biol (Camb) 1:382-393; Jain et al., 2005, Cancer Res. 65:7840-7846; William et al., 2002, PNAS 99:10423-10428; Bolhassani, 201, Biochim Biophys. Acta 1816:232-246). While most of these CPPs are used as cargo-delivery entities, Penetratin and MRP peptides have been reported to form a unique cytotoxic membrane-active structure upon linkage to their cargo (Rosal et al., 2005, Adv Drug Deliv Rev 57:653-60 ("Rosal 2005"); Bowne 2008; Kanovsky 2001). PNC-27 and PNC-28 peptides are examples of Penetratin-/MRP-cargo conjugates that exhibit a cytotoxic function that is dependent on the attachment and linkage of their cargo to the MRP, which is required for the formation of their membrane active structure, and hence, cytotoxic function (Kanovsky 2001; Rosal 2005; Bowne 2008).

There is long-standing unmet need in the art to effectively treat cancer, such as metastatic cancer, and to prevent metastasis in patients.

5. SUMMARY OF THE INVENTION

In one aspect, described herein is an antibody or a fragment thereof that specifically binds to an extracellularly accessible epitope of M(H)DM2/4. In particular, described herein are antibodies or fragments thereof that specifically bind to an extracellularly accessible epitope of M(H)DM2/4, wherein said antibodies or fragments inhibit tumor growth in vivo (or inhibit tumor cell proliferation in vivo). In certain embodiments, the antibodies or fragments described herein are not bound to a cell-penetrating peptide (e.g., a membrane resident peptide). In certain embodiments, the antibodies or fragments described herein are not bound to a cytotoxic component (i.e., not bound to a cytotoxic agent).

In one aspect, described herein are antibodies or fragments thereof that specifically bind to an extracellularly accessible epitope of M(H)DM2/4, wherein the antibody or fragment specifically binds to a peptide, wherein the sequence of the peptide consists of MCNTNMSVPTD-GAVT (SEQ ID NO:1), TTSQIPASEQE (SEQ ID NO:2), or CPVCRQPIQMIVLTYFP (SEQ ID NO:3). In particular, described herein are antibodies or fragments that specifically bind to M(H)DM2/4 (e.g., HDM2), wherein the antibody or fragment specifically binds to an extracellularly accessible epitope of M(H)DM2/4, wherein the antibody or fragment specifically binds to a peptide, wherein the sequence of the peptide consists of MCNTNMSVPTDGAVT (SEQ ID NO:1), TTSQIPASEQE (SEQ ID NO:2), or CPVCRQPIQMIVLTYFP (SEQ ID NO:3). In one embodiment, the antibody or fragment binds to an extracellularly accessible epitope of M(H)DM2/4, wherein the antibody or fragment specifically binds to a peptide, wherein the sequence of the peptide is MCNTNMSVPTDGAVT (SEQ ID NO: 1). In one embodiment, the antibody or fragment binds to an extracellularly accessible epitope of M(H)DM2/4, wherein the antibody or fragment specifically binds to a peptide, wherein the sequence of the peptide is TTSQI-PASEQE (SEQ ID NO:2). In one embodiment, the antibody or fragment binds to an extracellularly accessible epitope of M(H)DM2/4, wherein the antibody or fragment specifically binds to a peptide, wherein the sequence of the peptide is CPVCRQPIQMIVLTYFP (SEQ ID NO:3). In certain embodiments, described herein is an antibody or a fragment thereof that specifically binds to an extracellularly accessible epitope of M(H)DM2/4 contained within a peptide of SEQ ID NO: 1, SEQ ID NO:2, or SEQ ID NO:3. In one embodiment, described herein is an antibody or a fragment thereof that specifically binds to an extracellularly accessible epitope of M(H)DM2/4 contained within a peptide of SEQ ID NO: 1. In one embodiment, described herein is an antibody or a fragment thereof that specifically binds to an extracellularly accessible epitope of M(H)DM2/4 contained within a peptide of SEQ ID NO:2. In one embodiment, described herein is an antibody or a fragment thereof that specifically binds to an extracellularly accessible epitope of M(H)DM2/4 contained within a peptide of SEQ ID NO:3.

In one aspect, described herein is a humanized antibody or a fragment thereof that specifically binds to HDM2, said antibody or fragment comprising: (i) a heavy chain variable region (VH) comprising VH complementarity determining region ("CDR") 1, VH CDR 2, and VH CDR3; said VH CDR 1, VH CDR 2 and VH CDR 3 being the CDRs of a VH that has an amino acid sequence selected from the group consisting of SEQ ID NO:36, SEQ ID NO:38, and SED ID NO:40, or (ii) a light chain variable region (VL) comprising VL CDR 1, VL CDR 2 and VL CDR 3 being the CDRs of a VL that has an amino acid sequence selected from the group consisting of SEQ ID NO:37, SEQ ID NO:39, and SEQ ID NO:41. In one embodiment, the humanized antibody or a fragment that specifically binds to HDM2 comprises a VH wherein VH CDR 1, VH CDR 2 and VH CDR 3 are of a VH having the amino acid sequence of SEQ ID NO:36. In one embodiment, the humanized antibody or a fragment that specifically binds to HDM2 comprises a VH wherein VH CDR 1, VH CDR 2 and VH CDR 3 are of a VH having the amino acid sequence of SEQ ID NO:38. In one embodiment, the humanized antibody or a fragment that specifically binds to HDM2 comprises a VH wherein VH CDR 1, VH CDR 2 and VH CDR 3 are of a VH having the amino acid sequence of SEQ ID NO:40. In one embodiment, the humanized antibody or a fragment that specifically binds to HDM2 comprises a VL wherein VL CDR 1, VL CDR 2 and VL CDR 3 are of a VL having the amino acid sequence of SEQ ID NO:37 (and, optionally, a VH wherein VH CDR 1, VH CDR 2 and VH CDR 3 are of a VH having the amino acid sequence of SEQ ID NO: 36). In one embodiment, the humanized antibody or a fragment that specifically binds to HDM2 comprises a VL wherein VL CDR 1, VL CDR 2 and VL CDR 3 are of a VL having the amino acid sequence of SEQ ID NO:39 (and, optionally, a VH wherein VH CDR 1, VH CDR 2 and VH CDR 3 are of a VH having the amino acid sequence of SEQ ID NO: 38). In one embodiment, the humanized antibody or a fragment that specifically binds to HDM2 comprises a VL wherein VL CDR 1, VL CDR 2 and VL CDR 3 are of a VL having the amino acid sequence of SEQ ID NO:41 (and, optionally, the a VH wherein VH CDR 1, VH CDR 2 and VH CDR 3 are of a VH having the amino acid sequence of SEQ ID NO:40).

In one aspect, described herein is an antibody or a fragment thereof that specifically binds to M(H)DM2/4, said antibody or fragment comprising a heavy chain variable region (VH) comprising VH complementarity determining region ("CDR") 1, VH CDR 2, and VH CDR 3, wherein:
(i) the VH CDR 1 has the amino acid sequence GFTFTHY (SEQ ID NO: 18), the VH CDR 2 has the amino acid sequence RNKAKGYT (SEQ ID NO: 19), and the VH CDR 3 has the amino acid sequence DIGDN (SEQ ID NO:20);
(ii) the VH CDR 1 has the amino acid sequence GFTFTHYYMS (SEQ ID NO:42), the VH CDR 2 has the amino acid sequence FIRNKAKGYTAE (SEQ ID NO:45), and the VH CDR 3 has the amino acid sequence DIGDN (SEQ ID NO:20);
(iii) the VH CDR 1 has the amino acid sequence HYYMS (SEQ ID NO:43), the VH CDR 2 has the amino acid sequence FIRNKAKGYTAEYSASVKG (SEQ ID NO:46), and the VH CDR 3 has the amino acid sequence DIGDN (SEQ ID NO:20);
(iv) the VH CDR 1 has the amino acid sequence THYYMS (SEQ ID NO:44), the VH CDR 2 has the amino acid sequence WLGFIRNKAKGYTAE (SEQ ID NO:47), and the VH CDR 3 has the amino acid sequence ARDIGD (SEQ ID NO:48); or
(v) the VH CDR 1 has the amino acid sequence FTFTHYY (SEQ ID NO: 144), the VH CDR 2 has the amino acid sequence IRNKAKGYTA (SEQ ID NO: 145), and the VH CDR 3 has the amino acid sequence ARDIGDN (SEQ ID NO: 146).

In one aspect, described herein is an antibody or a fragment thereof that specifically binds to M(H)DM2/4 (e.g., HDM2), said antibody or fragment comprising a heavy chain variable region (VH) comprising VH complementarity determining region ("CDR") 1, VH CDR 2, and VH CDR 3, wherein:
(i) the VH CDR 1 has the amino acid sequence GDTLSGS (SEQ ID NO:24), the VH CDR 2 has the amino acid sequence HLNRGT (SEQ ID NO:25), and the VH CDR 3 has the amino acid sequence SPGFAY (SEQ ID NO:26);
(ii) the VH CDR 1 has the amino acid sequence GDTLSGSWMH (SEQ ID NO:52), the VH CDR 2 has the amino acid sequence EIHLNRGTTN (SEQ ID NO: 55), and the VH CDR 3 has the amino acid sequence SPGFAY (SEQ ID NO:26);
(iii) the VH CDR 1 has the amino acid sequence GSWMH (SEQ ID NO:53), the VH CDR 2 has the amino acid sequence EIHLNRGTTNYNEKFKG (SEQ ID NO:56), and the VH CDR 3 has the amino acid sequence SPGFAY (SEQ ID NO:26);
(iv) the VH CDR 1 has the amino acid sequence SGSWMH (SEQ ID NO: 54), the VH CDR 2 has the amino acid sequence WIGEIHLNRGTTN (SEQ ID NO:57), and the VH CDR 3 has the amino acid sequence ARSPGFA (SEQ ID NO: 58); or
(v) the VH CDR 1 has the amino acid sequence GDTLSGSW (SEQ ID NO: 148), the VH CDR 2 has the amino acid sequence IHLNRGTT (SEQ ID NO: 143), and the VH CDR 3 has the amino acid sequence ARSPGFA (SEQ ID NO:58).

In one aspect, provided herein is an antibody or a fragment thereof that specifically binds to M(H)DM2/4 (e.g., HDM2), said antibody or fragment comprising a heavy chain variable region (VH) comprising VH complementarity determining region ("CDR") 1, VH CDR 2, and VH CDR 3, wherein:
(i) the VH CDR 1 has the amino acid sequence GYTFTSY (SEQ ID NO: 30), the VH CDR 2 has the amino acid sequence NPRNGG (SEQ ID NO: 31), and the VH CDR 3 has the amino acid sequence SGYYAMDY (SEQ ID NO:32);
(ii) the VH CDR 1 has the amino acid sequence GYTFTSYYMY (SEQ ID NO:62), the VH CDR 2 has the amino acid sequence GINPRNGGTN (SEQ ID NO: 65), and the VH CDR 3 has the amino acid sequence SGYYAMDY (SEQ ID NO:32);
(iii) the VH CDR 1 has the amino acid sequence SYYMY (SEQ ID NO:63), the VH CDR 2 has the amino acid sequence GINPRNGGTNFNEKFKN (SEQ ID NO: 66), and the VH CDR 3 has the amino acid sequence SGYYAMDY (SEQ ID NO:32); or
(iv) the VH CDR 1 has the amino acid sequence TSYYMY (SEQ ID NO:64), the VH CDR 2 has the amino acid sequence WIGGINPRNGGTN (SEQ ID NO: 67), and the VH CDR 3 has the amino acid sequence TRSGYYAMD (SEQ ID NO:68)..

In one aspect, described herein is a humanized antibody or a fragment thereof that specifically binds to HDM2, said antibody or fragment comprising a heavy chain variable region (VH) comprising VH complementarity determining region ("CDR") 1, VH CDR 2, and VH CDR 3, wherein:
(i) the VH CDR 1 has the amino acid sequence GFTFTHY (SEQ ID NO: 18), the VH CDR 2 has the amino acid sequence RNKAKGYT (SEQ ID NO: 19), and the VH CDR 3 has the amino acid sequence DIGDN (SEQ ID NO:20);
(ii) the VH CDR 1 has the amino acid sequence GFTFTHYYMS (SEQ ID NO:42), the VH CDR 2 has the amino acid sequence FIRNKAKGYTAE (SEQ ID NO:45), and the VH CDR 3 has the amino acid sequence DIGDN (SEQ ID NO:20);
(iii) the VH CDR 1 has the amino acid sequence HYYMS (SEQ ID NO:43), the VH CDR 2 has the amino acid sequence FIRNKAKGYTAEYSASVKG (SEQ ID NO:46), and the VH CDR 3 has the amino acid sequence DIGDN (SEQ ID NO:20);
(iv) the VH CDR 1 has the amino acid sequence THYYMS (SEQ ID NO:44), the VH CDR 2 has the amino acid sequence WLGFIRNKAKGYTAE (SEQ ID NO:47), and the VH CDR 3 has the amino acid sequence ARDIGD (SEQ ID NO:48); or
(v) the VH CDR 1 has the amino acid sequence FTFTHYY (SEQ ID NO: 144), the VH CDR 2 has the amino acid sequence IRNKAKGYTA (SEQ ID NO: 145), and the VH CDR 3 has the amino acid sequence ARDIGDN (SEQ ID NO: 146).

In one aspect, described herein is a humanized antibody or a fragment thereof that specifically binds to HDM2, said antibody or fragment comprising a VH, wherein the VH comprises VH CDR1, VH CDR2, and VH CDR 3, wherein:
(i) the VH CDR 3 has the amino acid sequence DIGDN (SEQ ID NO:20);
(ii) the VH CDR 3 has the amino acid sequence ARDIGD (SEQ ID NO:48); or
(iii) the VH CDR 3 has the amino acid sequence ARDIGDN (SEQ ID NO: 146).

In one aspect, described herein is a humanized antibody or a fragment thereof that specifically binds to HDM2, said antibody or fragment comprising a light chain variable region (VL) comprising VL complementarity determining region ("CDR") 1, VL CDR 2, and VL CDR 3, wherein:
(i) the VL CDR 1 has the amino acid sequence RSSKNLLHSNGITYLY (SEQ ID NO:21), the VL CDR 2 has the amino acid sequence RVSNLAS (SEQ ID NO:22), and the VL CDR 3 has the amino acid sequence AQLLELPYT (SEQ ID NO:23);
(ii) the VL CDR 1 has the amino acid sequence LHSNGITYLYWY (SEQ ID NO:49), the VL CDR 2 has the amino acid sequence LLISRVSNLA (SEQ ID NO:50), and the VL CDR 3 has the amino acid sequence AQLLELPY (SEQ ID NO:51); or
(iii) the VL CDR 1 has the amino acid sequence KNLLHSNGITY (SEQ ID NO: 147), the VL CDR 2 has the amino acid sequence RVS, and the VL CDR 3 has the amino acid sequence AQLLELPYT (SEQ ID NO:23).

In one aspect, described herein is a humanized antibody or a fragment thereof that specifically binds to HDM2, said antibody or fragment comprising:
(a) a heavy chain variable region (VH) comprising VH complementarity determining region ("CDR") 1, VH CDR 2, and VH CDR 3, wherein:
(i) the VH CDR 1 has the amino acid sequence GFTFTHY (SEQ ID NO: 18), the VH CDR 2 has the amino acid sequence RNKAKGYT (SEQ ID NO: 19), and the VH CDR 3 has the amino acid sequence DIGDN (SEQ ID NO:20);
(ii) the VH CDR 1 has the amino acid sequence GFTFTHYYMS (SEQ ID NO:42), the VH CDR 2 has the amino acid sequence FIRNKAKGYTAE (SEQ ID NO:45), and the VH CDR 3 has the amino acid sequence DIGDN (SEQ ID NO:20);
(iii) the VH CDR 1 has the amino acid sequence HYYMS (SEQ ID NO:43), the VH CDR 2 has the amino acid sequence FIRNKAKGYTAEYSASVKG (SEQ ID NO:46), and the VH CDR 3 has the amino acid sequence DIGDN (SEQ ID NO:20);
(iv) the VH CDR 1 has the amino acid sequence THYYMS (SEQ ID NO:44), the VH CDR 2 has the amino acid sequence WLGFIRNKAKGYTAE (SEQ ID NO:47), and the VH CDR 3 has the amino acid sequence ARDIGD (SEQ ID NO:48); or
(v) the VH CDR 1 has the amino acid sequence FTFTHYY (SEQ ID NO: 144), the VH CDR 2 has the amino acid sequence IRNKAKGYTA (SEQ ID NO: 145), and the VH CDR 3 has the amino acid sequence ARDIGDN (SEQ ID NO: 146); and
(b) a light chain variable region (VL) comprising VL complementarity determining region ("CDR") 1, VL CDR 2, and VL CDR 3, wherein:
(i) the VL CDR 1 has the amino acid sequence RSSKNLLHSNGITYLY (SEQ ID NO:21), the VL CDR 2 has the amino acid sequence RVSNLAS (SEQ ID NO:22), and the VL CDR 3 has the amino acid sequence AQLLELPYT (SEQ ID NO:23);
(ii) the VL CDR 1 has the amino acid sequence LHSNGITYLYWY (SEQ ID NO:49), the VL CDR 2 has the amino acid sequence LLISRVSNLA (SEQ ID NO:50), and the VL CDR 3 has the amino acid sequence AQLLELPY (SEQ ID NO:51); or
(iii) the VL CDR 1 has the amino acid sequence KNLLHSNGITY (SEQ ID NO: 147), the VL CDR 2 has the amino acid sequence RVS, and the VL CDR 3 has the amino acid sequence AQLLELPYT (SEQ ID NO:23).

In one aspect, described herein is an antibody or a fragment thereof that specifically binds to HDM2, said antibody or fragment comprising a heavy chain variable region (VH) comprising VH complementarity determining region ("CDR") 1, VH CDR 2, and VH CDR 3, wherein:
(i) the VH CDR 1 has the amino acid sequence GDTLSGS (SEQ ID NO:24), the VH CDR 2 has the amino acid sequence HLNRGT (SEQ ID NO:25), and the VH CDR 3 has the amino acid sequence SPGFAY (SEQ ID NO:26);
(ii) the VH CDR 1 has the amino acid sequence GDTLSGSWMH (SEQ ID NO:52), the VH CDR 2 has the amino acid sequence EIHLNRGTTN (SEQ ID NO: 55), and the VH CDR 3 has the amino acid sequence SPGFAY (SEQ ID NO:26);
(iii) the VH CDR 1 has the amino acid sequence GSWMH (SEQ ID NO:53), the VH CDR 2 has the amino acid sequence EIHLNRGTTNYNEKFKG (SEQ ID NO:56), and the VH CDR 3 has the amino acid sequence SPGFAY (SEQ ID NO:26);
(iv) the VH CDR 1 has the amino acid sequence SGSWMH (SEQ ID NO: 54), the VH CDR 2 has the amino acid sequence WIGEIHLNRGTTN (SEQ ID NO:57), and the VH CDR 3 has the amino acid sequence ARSPGFA (SEQ ID NO: 58); or
(v) the VH CDR 1 has the amino acid sequence GDTLSGSW (SEQ ID NO: 148), the VH CDR 2 has the amino acid sequence IHLNRGTT (SEQ ID NO: 143), and the VH CDR 3 has the amino acid sequence ARSPGFA (SEQ ID NO:58).

In one aspect, described herein is an antibody or a fragment thereof that specifically binds to HDM2, said antibody or fragment comprising a VH, wherein the VH comprises VH CDR1, VH CDR2, and VH CDR 3, wherein:
(i) the VH CDR 3 has the amino acid sequence SPGFAY (SEQ ID NO:26); or
(ii) the VH CDR 3 has the amino acid sequence ARSPGFA (SEQ ID NO:58).

In one aspect, described herein is an antibody or a fragment thereof that specifically binds to HDM2, said antibody or fragment comprising a light chain variable region (VL) comprising a VL complementarity determining region ("CDR") 1, VL CDR 2, and VL CDR 3, wherein:
(i) the VL CDR 1 has the amino acid sequence RSSKSLLHSNGNSYLY (SEQ ID NO:27), the VL CDR 2 has the amino acid sequence RMSNLAS (SEQ ID NO:28), and the VL CDR 3 has the amino acid sequence MQHLEYPFT (SEQ ID NO:29);
(ii) the VL CDR 1 has the amino acid sequence LHSNGNSYLYWF (SEQ ID NO:59), the VL CDR 2 has the amino acid sequence LLIYRMSNLA (SEQ ID NO: 60), and the VL CDR 3 has the amino acid sequence MQHLEYPF (SEQ ID NO:61); or
(iii) the VL CDR 1 has the amino acid sequence KSLLHSNGNSY (SEQ ID NO: 141), the VL CDR 2 has the amino acid sequence RMS, and the VL CDR 3 has the amino acid sequence MQHLEYPFT (SEQ ID NO:29).

In one aspect, described herein is an antibody or a fragment thereof that specifically binds to HDM2, said antibody or fragment comprising:
(a) a heavy chain variable region (VH) comprising VH complementarity determining region ("CDR") 1, VH CDR 2, and VH CDR 3, wherein:
(i) the VH CDR 1 has the amino acid sequence GDTLSGS (SEQ ID NO:24), the VH CDR 2 has the amino acid sequence HLNRGT (SEQ ID NO:25), and the VH CDR 3 has the amino acid sequence SPGFAY (SEQ ID NO:26);
(ii) the VH CDR 1 has the amino acid sequence GDTLSGSWMH (SEQ ID NO:52), the VH CDR 2 has the amino acid sequence EIHLNRGTTN (SEQ ID NO: 55), and the VH CDR 3 has the amino acid sequence SPGFAY (SEQ ID NO:26);
(iii) the VH CDR 1 has the amino acid sequence GSWMH (SEQ ID NO:53), the VH CDR 2 has the amino acid sequence EIHLNRGTTNYNEKFKG (SEQ ID NO:56), and the VH CDR 3 has the amino acid sequence SPGFAY (SEQ ID NO:26);
(iv) the VH CDR 1 has the amino acid sequence SGSWMH (SEQ ID NO: 54), the VH CDR 2 has the amino acid sequence WIGEIHLNRGTTN (SEQ ID NO:57), and the VH CDR 3 has the amino acid sequence ARSPGFA (SEQ ID NO: 58); or
(v) the VH CDR 1 has the amino acid sequence GDTLSGSW (SEQ ID NO: 148), the VH CDR 2 has the amino acid sequence IHLNRGTT (SEQ ID NO: 143), and the VH CDR 3 has the amino acid sequence ARSPGFA (SEQ ID NO: 58); and
(b) a light chain variable region (VL) comprising VL complementarity determining region ("CDR") 1, VL CDR 2, and VL CDR 3, wherein:
(i) the VL CDR 1 has the amino acid sequence RSSKSLLHSNGNSYLY (SEQ ID NO:27), the VL CDR 2 has the amino acid sequence RMSNLAS (SEQ ID NO:28), and the VL CDR 3 has the amino acid sequence MQHLEYPFT (SEQ ID NO:29);
(ii) the VL CDR 1 has the amino acid sequence LHSNGNSYLYWF (SEQ ID NO:59), the VL CDR 2 has the amino acid sequence LLIYRMSNLA (SEQ ID NO: 60), and the VL CDR 3 has the amino acid sequence MQHLEYPF (SEQ ID NO:61); or
(iii) the VL CDR 1 has the amino acid sequence KSLLHSNGNSY (SEQ ID NO: 141), the VL CDR 2 has the amino acid sequence RMS, and the VL CDR 3 has the amino acid sequence MQHLEYPFT (SEQ ID NO:29).

In one aspect, described herein is an antibody or a fragment thereof that specifically binds to HDM2, said antibody or fragment comprising a heavy chain variable region (VH) comprising VH complementarity determining region ("CDR") 1, VH CDR 2, and VH CDR 3, wherein:
(i) the VH CDR 1 has the amino acid sequence GYTFTSY (SEQ ID NO:30), the VH CDR 2 has the amino acid sequence NPRNGG (SEQ ID NO:31), and the VH CDR 3 has the amino acid sequence SGYYAMDY (SEQ ID NO:32);
(ii) the VH CDR 1 has the amino acid sequence GYTFTSYYMY (SEQ ID NO:62), the VH CDR 2 has the amino acid sequence GINPRNGGTN (SEQ ID NO: 65), and the VH CDR 3 has the amino acid sequence SGYYAMDY (SEQ ID NO:32);
(iii) the VH CDR 1 has the amino acid sequence SYYMY (SEQ ID NO:63), the VH CDR 2 has the amino acid sequence GINPRNGGTNFNEKFKN (SEQ ID NO: 66), and the VH CDR 3 has the amino acid sequence SGYYAMDY (SEQ ID NO:32); or
(iv) the VH CDR 1 has the amino acid sequence TSYYMY (SEQ ID NO:64), the VH CDR 2 has the amino acid sequence WIGGINPRNGGTN (SEQ ID NO: 67), and the VH CDR 3 has the amino acid sequence TRSGYYAMD (SEQ ID NO:68).

In one aspect, described herein is an antibody or a fragment thereof that specifically binds to HDM2, said antibody or fragment comprising a VH, wherein the VH comprises VH CDR1, VH CDR2, and VH CDR 3, wherein:
(i) the VH CDR 3 has the amino acid sequence SGYYAMDY (SEQ ID NO:32); or
(ii) the VH CDR 3 has the amino acid sequence TRSGYYAMD (SEQ ID NO: 68).

In one aspect, described herein is an antibody or fragment further comprises a light chain variable region (VL) comprising VL complementarity determining region ("CDR") 1, VL CDR 2, and VL CDR 3, wherein:
(i) the VL CDR 1 has the amino acid sequence RASQDISNFLN (SEQ ID NO:33), the VL CDR 2 has the amino acid sequence YTSRLHS (SEQ ID NO:34), and the VL CDR 3 has the amino acid sequence QQGNTLPRT (SEQ ID NO: 35); or
(ii) the VL CDR 1 has the amino acid sequence SNFLNWY (SEQ ID NO: 69), the VL CDR 2 has the amino acid sequence LLIYYTSRLH (SEQ ID NO: 70), and the VL CDR 3 has the amino acid sequence QQGNTLPR (SEQ ID NO:71).

In one aspect, described herein is an antibody or a fragment thereof that specifically binds to HDM2, said antibody or fragment comprising:
(a) a heavy chain variable region (VH) comprising VH complementarity determining region ("CDR") 1, VH CDR 2, and VH CDR 3, wherein:
(i) the VH CDR 1 has the amino acid sequence GYTFTSY (SEQ ID NO:30), the VH CDR 2 has the amino acid sequence NPRNGG (SEQ ID NO:31), and the VH CDR 3 has the amino acid sequence SGYYAMDY (SEQ ID NO:32);
(ii) the VH CDR 1 has the amino acid sequence GYTFTSYYMY (SEQ ID NO:62), the VH CDR 2 has the amino acid sequence GINPRNGGTN (SEQ ID NO: 65), and the VH CDR 3 has the amino acid sequence SGYYAMDY (SEQ ID NO:32);

(iii) the VH CDR 1 has the amino acid sequence SYYMY (SEQ ID NO:63), the VH CDR 2 has the amino acid sequence GINPRNGGTNFNEKFKN (SEQ ID NO: 66), and the VH CDR 3 has the amino acid sequence SGYYAMDY (SEQ ID NO:32); or (iv) the VH CDR 1 has the amino acid sequence TSYYMY (SEQ ID NO:64), the VH CDR 2 has the amino acid sequence WIGGINPRNGGTN (SEQ ID NO: 67), and the VH CDR 3 has the amino acid sequence TRSGYYAMD (SEQ ID NO: 68); and (b) a light chain variable region (VL) comprising VL complementarity determining region ("CDR") 1, VL CDR 2, and VL CDR 3, wherein:

(i) the VL CDR 1 has the amino acid sequence RASQDIS-NFLN (SEQ ID NO:33), the VL CDR 2 has the amino acid sequence YTSRLHS (SEQ ID NO:34), and the VL CDR 3 has the amino acid sequence QQGNTLPRT (SEQ ID NO:35); or (ii) the VL CDR 1 has the amino acid sequence SNFLNWY (SEQ ID NO: 69), the VL CDR 2 has the amino acid sequence LLIYYTSRLH (SEQ ID NO: 70), and the VL CDR 3 has the amino acid sequence QQGNTLPR (SEQ ID NO:71).

In one aspect, described herein is an antibody or fragment thereof that specifically binds to HDM2 comprising a VH having the amino acid sequence of SEQ ID NO:36, or a VH having at least 90%, at least 95%, at least 98%, or at least 99% sequence identity to the amino acid sequence of SEQ ID NO:36.

In one aspect, described herein is an antibody or fragment thereof that specifically binds to HDM2 comprising a VL having the amino acid sequence of SEQ ID NO:37, or a VL having at least 90%, at least 95%, at least 98%, or at least 99% sequence identity to the amino acid sequence of SEQ ID NO:37 (and, optionally, comprising a VH having the amino acid sequence of SEQ ID NO:36, or a VH having at least 90%, at least 95%, at least 98%>, or at least 99% sequence identity to the amino acid sequence of SEQ ID NO:36).

In one aspect, described herein is an antibody or fragment thereof that specifically binds to HDM2 comprising a VH having the amino acid sequence of SEQ ID NO:38, or a VH having at least 90%, at least 95%, at least 98%>, or at least 99% sequence identity to the amino acid sequence of SEQ ID NO:38.

In one aspect, described herein is an antibody or fragment thereof that specifically binds to HDM2 comprising a VL having the amino acid sequence of SEQ ID NO:39, or a VL having at least 90%, at least 95%, at least 98%, or at least 99% sequence identity to the amino acid sequence of SEQ ID NO:39 (and, optionally, comprising a VH having the amino acid sequence of SEQ ID NO:38, or a VH having at least 90%, at least 95%, at least 98%, or at least 99% sequence identity to the amino acid sequence of SEQ ID NO:38).

In one aspect, described herein is an antibody or fragment thereof that specifically binds to HDM2 comprising a VH having the amino acid sequence of SEQ ID NO:40, or a VH having at least 90%, at least 95%, at least 98%, or at least 99% sequence identity to the amino acid sequence of SEQ ID NO:40.

In one aspect, described herein is an antibody or fragment thereof that specifically binds to HDM2 comprising a VL having the amino acid sequence of SEQ ID NO:41, or a VL having at least 90%, at least 95%, at least 98%, or at least 99% sequence identity to the amino acid sequence of SEQ ID NO:41 (and, optionally, comprising a VH having the amino acid sequence of SEQ ID NO:40, or a VH having at least 90%, at least 95%, at least 98%, or at least 99% sequence identity to the amino acid sequence of SEQ ID NO:40).

In preferred embodiments, the anti-M(H)DM2/4 antibody described herein is a monoclonal antibody. In certain embodiments, the anti-M(H)DM2/4 antibody described herein is a human, humanized, or a chimeric antibody (e.g., a human, humanized or chimeric monoclonal antibody). In one embodiment, the anti-M(H)DM2/4 antibody described herein is a human antibody. In one embodiment, the anti-M(H)DM2/4 antibody described herein is a humanized antibody. In one embodiment, the anti-M(H)DM2/4 antibody described herein is a chimeric antibody.

In certain embodiments, the anti-M(H)DM2/4 antibody described herein is a purified antibody.

In certain embodiments, the anti-M(H)DM2/4 antibody described herein is an immunoglobulin (e.g., IgG or IgM). In one embodiment, the immunoglobulin is an IgG. In one embodiment, the immunoglobulin is an IgM. In certain embodiments, the immunoglobulin is of IgG1 isotype. In other embodiments, the immunoglobulin is of IgG3 isotype. In other embodiments, the immunoglobulin is of IgG2 isotype. In certain embodiments, the anti-M(H)DM2/4 antibody described herein comprises an Fc region, wherein the Fc region is a human IgG Fc region or a human IgM Fc region. In specific embodiments, the anti-M(H)DM2/4 antibody described herein comprises an Fc region, which is a human IgG1 Fc region, a human IgG2 Fc region, or a human IgG3 Fc region. In one embodiment, the anti-M(H)DM2/4 antibody described herein comprises a human IgG1 Fc region. In one embodiment, the anti-M(H)DM2/4 antibody described herein comprises a human IgG3 Fc region. In one embodiment, the anti-M(H)DM2/4 antibody described herein comprises a human IgG2 Fc region. In one embodiment, the anti-M(H)DM2/4 antibody described herein comprises a human IgM Fc region. In one embodiment, the anti-M(H)DM2/4 antibody described herein comprises a human IgE Fc region.

In certain embodiments, the anti-M(H)DM2/4 antibody or fragment described herein is an antigen-binding fragment of an anti-M(H)DM2/4 antibody. In certain embodiments, the antibody or fragment described herein is an Fv fragment, a Fab fragment, a Fab' fragment, a F(ab')2 fragment, a single chain antibody molecule, or a single chain Fv (scFv). In one embodiment, the antibody or fragment described herein is an Fv fragment. In one embodiment, the antibody or fragment described herein is a Fab fragment. In one embodiment, the antibody or fragment described herein is a Fab' fragment. In one embodiment, the antibody or fragment described herein is a F(ab')2 fragment. In one embodiment, the antibody or fragment described herein is a single chain antibody molecule. In one embodiment, the antibody or fragment described herein is a single chain Fv (scFv).

In certain embodiments, the anti-M(H)DM2/4 antibody or antigen-binding fragment described herein mediates complement-dependent cytotoxicity (CDC) or antibody-dependent cell-mediated cytoxicity (ADCC). In one embodiment, the anti-M(H)DM2/4 antibody or antigen-binding fragment mediates complement-dependent cytotoxicity (CDC).

In certain embodiments, the anti-M(H)DM2/4 antibody described herein is a bispecific antibody that also specifically binds to a cell surface antigen of an effector cell (e.g., a T cell, a B lymphocyte, a neutrophil, a macrophage, a natural killer cell, or a dendritic cell).

In one embodiment, the antibody or fragment described herein specifically binds to an extracellularly accessible epitope of M(H)DM2 (e.g., HDM2) and does not bind to M(H)DM4 (e.g., HDM4). In another embodiment, the antibody or fragment described herein specifically binds to extracellularly accessible epitopes of both M(H)DM2 (e.g., HDM2) and M(H)DM4 (e.g., HDM4). In one embodiment, the antibody or fragment described herein specifically binds to an extracellularly accessible epitope of HDM2, and optionally, may also bind to an extracellularly accessible epitope of MDM2.

In a specific embodiment, the anti-HDM2 antibody or fragment described herein specifically binds HDM2 within amino acids of SEQ ID NO: 1 (which are amino acids 1 to 15 of HDM2 (SEQ ID NO:4)). In another specific embodiment, the anti-HDM2 antibody described herein specifically binds HDM2 within amino acids of SEQ ID NO: 2 (which are amino acids 15 to 25 of HDM2 (SEQ ID NO:4)). In another specific embodiment, the anti-HDM2 antibody described herein specifically binds HDM2 within amino acids of SEQ ID NO: 3 (which are amino acids 475-491 of HDM2 (SEQ ID NO:4)). In another specific embodiment, the anti-HDM2 antibody described herein specifically binds within amino acids 19 to 50 of SEQ ID NO: 4. In another specific embodiment, the anti-HDM2 antibody described herein specifically binds within amino acids 154 to 167 of SEQ ID NO: 4. In yet another specific embodiment, the anti-HDM2 antibody described herein specifically binds within amino acids 1 to 60 of SEQ ID NO: 4. In yet another specific embodiment, the anti-HDM2 antibody described herein specifically binds within amino acids 1 to 100 of SEQ ID NO: 4. In another specific embodiment, the anti-HDM2 antibody described herein specifically binds within amino acids 100 to 110 of SEQ ID NO: 4. In another specific embodiment, the anti-HDM2 antibody described herein specifically binds within amino acids 50 to 60 of SEQ ID NO: 4. In yet another specific embodiment, the anti-HDM2 antibody described herein specifically binds within amino acids 1 to 109 of SEQ ID NO: 4. In another specific embodiment, the anti-HDM2 antibody described herein specifically binds within amino acids 26 to 60 of SEQ ID NO: 4. In one specific embodiment, the anti-HDM2 antibody described herein specifically binds within the terminal 60 amino acids at the C-terminus of the HDM2 on the plasma membrane of the cancer cells. In another specific embodiment, the anti-HDM2 antibody described herein specifically binds within the terminal 100 amino acids at the C-terminus of the HDM2 on the plasma membrane of the cancer cells.

In one embodiment, the anti-M(H)DM2/4 antibody described herein does not bind within amino acids 101 to 200 of SEQ ID NO:4. In one embodiment, the anti-M(H)DM2/4 antibody described herein does not bind to the epitope of HDM2 or MDM2 to which "MDM2 monoclonal antibody (MO1), clone 1A7" (Abnova, Cat. No. H00004193-M01) binds. In one embodiment, the anti-M(H)DM2/4 antibody described herein does not compete with "MDM2 monoclonal antibody (MO1), clone 1A7" (Abnova, Cat. No. H00004193-M01) for binding to HDM2.

In another embodiment, the anti-M(H)DM2/4 antibody described herein binds within amino acids 101 to 200 of SEQ ID NO:4. In one embodiment, the anti-M(H)DM2/4 antibody described herein binds to the epitope of HDM2 or MDM2 to which "MDM2 monoclonal antibody (MO1), clone 1A7" (Abnova, Cat. No. H00004193-M01) binds. In one embodiment, the anti-M(H)DM2/4 antibody described herein competes with "MDM2 monoclonal antibody (MO1), clone 1A7" (Abnova, Cat. No. H00004193-M01) for binding to HDM2.

In one embodiment, the anti-M(H)DM2/4 antibody described herein does not bind within amino acids 153 to 222 of SEQ ID NO:4. In one embodiment, the anti-M(H)DM2/4 antibody described herein does not bind within amino acids 26 to 169 of SEQ ID NO:4. In a specific embodiment, the anti-M(H)DM2/4 antibody described herein does not bind within amino acids 26 to 222 of SEQ ID NO:4.

In certain embodiments, the M(H)DM2/4 exposed on the surface of cancer cells being targeted by the antibodies or fragments described herein is an M(H)DM2/4 variant that lacks one or more nuclear localization signal domains. In specific embodiments, the HDM2 exposed on the surface of cancer cells being targeted by the antibodies or fragments described herein is an HDM2 variant that lacks the sequence of amino acids 179 to 185 of SEQ ID NO: 4 and/or the sequence of amino acids 464 to 471 of SEQ ID NO: 4. In one embodiment, the HDM2 exposed on the surface of cancer cells being targeted by the antibodies or fragments described herein is an HDM2 variant that lacks the sequence of amino acids 181 to 185 of SEQ ID NO: 4.

In one aspect, provided herein are antibodies or fragments thereof that compete for binding to M(H)DM2/4 with an anti-M(H)DM2/4 (e.g., anti-HDM2) antibody or fragment thereof described herein. Preferably, such antibodies or fragments that compete for binding are monoclonal antibodies or fragments thereof.

In one aspect, provided herein are antibodies or fragments thereof that compete for binding to M(H)DM2/4 with a mouse anti-HDM2 immunoglobulin (preferably IgG) antibody selected from the group consisting of: (i) an antibody comprising a heavy chain variable region (VH) having the amino acid sequence of SEQ ID NO: 36, and a light chain variable region (VL) having the amino acid sequence of SEQ ID NO:37; (ii) an antibody comprising a VH having the amino acid sequence of SEQ ID NO: 38, and a VL having the amino acid sequence of SEQ ID NO:39; and (iii) an antibody comprising a VH having the amino acid sequence of SEQ ID NO:40, and a VL having the amino acid sequence of SEQ ID NO:41.

In one aspect, provided herein are antibodies or fragments thereof that: (i) compete for binding to a peptide of sequence SEQ ID NO: 1 with a mouse anti-HDM2 IgG1 antibody comprising a heavy chain variable region (VH) having the amino acid sequence of SEQ ID NO: 36, and a light chain variable region (VL) having the amino acid sequence of SEQ ID NO: 37; or (ii) compete for binding to a peptide of SEQ ID NO:2 with a mouse anti-HDM2 IgG3 antibody comprising a VH having the amino acid sequence of SEQ ID NO:38, and a VL having the amino acid sequence of SEQ ID NO:39; or (iii) compete for binding to a peptide of SEQ ID NO:3 with a mouse IgM antibody comprising a VH having the amino acid sequence of SEQ ID NO:40, and a VL having the amino acid sequence of SEQ ID NO:41.

In one aspect, provided herein are antibody-drug conjugates comprising any antibody or fragment described herein (e.g., an antibody-drug conjugate in which an anti-M(H)DM2/4 antibody or fragment described herein is covalently bound to a cytotoxic drug).

In one aspect, provided herein are pharmaceutical compositions comprising a therapeutically effective amount of any antibody or fragment described herein.

In one aspect, provided herein are methods for treating cancer in a subject in need thereof, said method comprising administering to the subject: (i) any anti-M(H)DM2/4 antibody described herein; (ii) an antibody or a fragment thereof that specifically binds to an extracellularly accessible epitope of M(H)DM2/4, wherein said antibody or fragment is not bound to a cell-penetrating peptide (e.g., a membrane resident peptide); or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein are methods for treating cancer in a subject in need thereof, said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein are methods for treating cancer in a subject in need thereof, said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for treating cancer in a subject in need thereof, said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMS VPTDGAVT (SEQ ID NO:1), TTSQIPASEQE (SEQ ID NO:2), or CPVCRQPIQMIVLTYFP (SEQ ID NO:3). In one embodiment, provided herein is a method for treating cancer in a subject in need thereof, said method comprising administering to the subject an anti-M(H)DM2/4 antibody or fragment thereof that specifically binds to an extracellularly accessible epitope of M(H)DM2/4 contained within a peptide of SEQ ID NCvl, SEQ ID NO:2, or SEQ ID NO:3.

In one aspect, provided herein are methods for inhibiting tumor growth in a subject in need thereof, said method comprising administering to the subject: (i) any anti-M(H)DM2/4 antibody or fragment described herein; (ii) an antibody or a fragment thereof that specifically binds to an extracellularly accessible epitope of M(H)DM2/4, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein are methods for inhibiting tumor growth in a subject in need thereof, said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein are methods for inhibiting tumor growth in a subject in need thereof, said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetraitng peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for inhibiting tumor growth in a subject in need thereof, said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMSVPTDGAVT (SEQ ID NO:1), TTSQIPASEQE (SEQ ID NO:2), or CPVCRQPIQMIVLTYFP (SEQ ID NO:3). In one embodiment, provided herein is a method for inhibiting tumor growth in a subject in need thereof, said method comprising administering to the subject an anti-M(H)DM2/4 antibody or fragment thereof that specifically binds to an extracellularly accessible epitope of M(H)DM2/4 contained within a peptide of SEQ ID NO:1, SEQ ID NO:2, or SEQ ID NO:3.

In one aspect, provided herein are methods for inhibiting tumor progression in a subject in need thereof, said method comprising administering to the subject: (i) any anti-M(H)DM2/4 antibody or fragment described herein; (ii) an antibody or a fragment thereof that specifically binds to an extracellularly accessible epitope of M(H)DM2/4, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein are methods for inhibiting tumor progression in a subject in need thereof, said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein are methods for inhibiting tumor progression in a subject in need thereof, said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for inhibiting tumor progression in a subject in need thereof, said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMSVPTDGAVT (SEQ ID NO:1), TTSQIPASEQE (SEQ ID NO:2), or CPVCRQPIQMIVLTYFP (SEQ ID NO:3). In one embodiment, provided herein is a method for inhibiting tumor progression in a subject in need thereof, said method comprising administering to the subject an anti-M(H)DM2/4 antibody or fragment thereof that specifically binds to an extracellularly accessible epitope of M(H)DM2/4 contained within a peptide of SEQ ID NO:1, SEQ ID NO:2, or SEQ ID NO:3.

In one aspect, provided herein is a method for preventing cancer recurrence or relapse in a subject in need thereof (e.g., a subject who is in remission from cancer), said method comprising administering to the subject: (i) any anti-M(H)DM2/4 antibody or fragment described herein; (ii) an antibody or a fragment thereof that specifically binds to an extracellularly accessible epitope of M(H)DM2/4, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein is a method for preventing cancer recurrence or relapse in a subject in need thereof (e.g., a subject who is in remission from cancer), said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein is a method for preventing cancer recurrence or relapse in a subject in need thereof (e.g., a subject who is in remission from cancer), said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for preventing cancer recurrence or relapse in a subject in need thereof (e.g., a subject who is in remission from cancer), said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMSVPTDGAVT (SEQ ID NO:1), TTSQIPASEQE (SEQ ID NO:2), or CPVCRQPIQMIVLTYFP (SEQ ID NO:3).

In one embodiment, provided herein is a method for preventing cancer recurrence or relapse in a subject in need thereof (e.g., a subject who is in remission from cancer), said method comprising administering to the subject an anti-M(H)DM2/4 antibody or fragment thereof that specifically binds to an extracellularly accessible epitope of M(H)DM2/4 contained within a peptide of SEQ ID NCv1, SEQ ID NO:2, or SEQ ID NO:3.

In one aspect, provided herein is a method for increasing survival in a subject having a cancer (e.g., relative to a subject not treated with anti-M(H)DM2/4 antibody or fragment), said method comprising administering to the subject: (i) any anti-M(H)DM2/4 antibody or fragment described herein; (ii) an antibody or a fragment thereof that specifically binds to an extracellularly accessible epitope of M(H)DM2/4, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein is a method for increasing survival in a subject having a cancer (e.g., relative to a subject not treated with anti-M(H)DM2/4 antibody or fragment), said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein is a method for increasing survival in a subject a cancer (e.g., relative to a subject not treated with anti-M(H)DM2/4 antibody or fragment), said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for increasing survival in a subject having a cancer (e.g., relative to a subject not treated with anti-M(H)DM2/4 antibody or fragment), said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMSVPTDGAVT (SEQ ID NO:1), TTSQIPASEQE (SEQ ID NO:2), or CPVCRQPIQMIVLTYFP (SEQ ID NO:3). In one embodiment, provided herein is a method for increasing survival in a subject having a cancer (e.g., relative to a subject not treated with anti-M(H)DM2/4 antibody or fragment), said method comprising administering to the subject an anti-M(H)DM2/4 antibody or fragment thereof that specifically binds to an extracellularly accessible epitope of M(H)DM2/4 contained within a peptide of SEQ ID NO: 1, SEQ ID NO:2, or SEQ ID NO:3.

In one aspect, provided herein are methods for preventing metastasis in a subject having a cancer, said method comprising administering to the subject: (i) any anti-M(H)DM2/4 antibody or fragment described herein; (ii) an antibody or a fragment thereof that specifically binds to an extracellularly accessible epitope of M(H)DM2/4, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein are methods for preventing metastasis in a subject in need thereof, said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein are methods for preventing metastasis in a subject having a cancer, said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for preventing metastasis in a subject having a cancer, said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMSVPTDGAVT (SEQ ID NO:1), TTSQIPASEQE (SEQ ID NO:2), or CPVCRQPIQMIVLTYFP (SEQ ID NO:3). In one embodiment, provided herein is a method for preventing metastasis in a subject having a cancer, said method comprising administering to the subject an anti-M(H)DM2/4 antibody or fragment thereof that specifically binds to an extracellularly accessible epitope of M(H)DM2/4 contained within a peptide of SEQ ID NO:1, SEQ ID NO:2, or SEQ ID NO:3.

In one aspect, provided herein are methods for inhibiting metastasis (e.g., reducing the number, size or invasiveness of metastases) in a subject having a metastatic cancer, said method comprising administering to the subject: (i) any anti-M(H)DM2/4 antibody or fragment described herein; (ii) an antibody or a fragment thereof that specifically binds to an extracellularly accessible epitope of M(H)DM2/4 exposed, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one aspect, provided herein are methods for inhibiting metastasis in a subject in need thereof, said method comprising administering to the subject: an antibody or a fragment thereof that specifically binds to an extracellularly accessible epitope of M(H)DM2/4 (e.g., HDM2), wherein said antibody or fragment is not bound to a cytotoxic component. In one aspect, provided herein are methods for inhibiting metastasis (e.g., reducing the number, size or invasiveness of metastases) in a subject having a metastatic cancer, said method comprising administering to the subject: (i) any anti-HDM2 antibody or fragment described herein; (ii) an antibody or a fragment thereof that specifically binds to an extracellularly accessible epitope of HDM2, wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) any pharmaceutical composition described herein, or (iv) any antibody-drug conjugate described herein. In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide. In one embodiment, provided herein is a method for inhibiting metastasis (e.g., reducing the number, size or invasiveness of metastases) in a subject having a metastatic cancer, said method comprising administering to the subject an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of MCNTNMS VPTDGAVT (SEQ ID NO:1), TTSQIPASEQE (SEQ ID NO:2), or CPVCRQPIQMIVLTYFP (SEQ ID NO:3). In one embodiment, provided herein is a method for inhibiting metastasis (e.g., reducing the number, size or invasiveness of metastases) in a subject having a metastatic cancer, said method comprising administering to the subject an anti-M(H)DM2/4 antibody or fragment thereof that specifically binds to an extracellularly accessible epitope of M(H)DM2/4 contained within a peptide of SEQ ID NCvl, SEQ ID NO:2, or SEQ ID NO:3.

In one aspect, provided herein are methods of selecting and treating a subject (e.g., a human) having a cancer, said method comprising: (a) identifying a subject having a cancer wherein an antibody or a fragment thereof (e.g., a labeled antibody or fragment) that specifically binds to an extracellularly accessible epitope of M(H)DM2/4 (e.g., HDM2) binds to the surface of an intact cell of the cancer; and (b) administering to the subject (i) any M(H)DM2/4 (e.g., anti-HDM2) antibody or fragment described herein or an antibody-drug conjugate comprising said antibody or fragment (e.g., an anti-M(H)DM2/4 antibody or fragment thereof that specifically binds to an extracellularly accessible epitope of M(H)DM2/4, wherein the antibody or fragment specifically binds to a peptide, wherein the sequence of the peptide consists of SEQ ID NO: 1, SEQ ID NO:2, or SEQ ID NO:3); (ii) an antibody or a fragment thereof that specifically binds to an extracellularly accessible epitope of M(H)DM2/4 (e.g., HDM2), wherein said antibody or fragment is not bound to a cell-penetrating peptide (e.g., a membrane resident peptide), or an antibody-drug conjugate comprising the antibody or fragment (i.e., said antibody or fragment that is not bound to a cell-penetrating peptide) bound to a cytotoxic drug, (iii) an antibody or a fragment thereof that specifically binds to an extracellularly accessible epitope of M(H)DM2/4 (e.g., HDM2), wherein said antibody or fragment is not bound to a cytotoxic component, (iv) any pharmaceutical composition described herein, or (v) any antibody-drug conjugate described herein. The antibody or fragment thereof in step (b) can be the same or different from the antibody or fragment thereof in step (a). In certain embodiments, provided herein are methods that further comprise, before step (b), a step of determining whether the antibody or fragment binds to the surface of the intact cell of the cancer (e.g., using FACS or cell-based ELISA analysis) (using any anti-M(H)DM2/4 antibody described herein). In one embodiment, provided herein are methods that further comprise, before the determining step, the step of obtaining intact cells of the cancer (e.g., by biopsy of the cancerous tumor in the subject, or by obtaining a blood sample with circulating cancer cells from the subject). In one embodiment, the method comprises administering to the subject an antibody-drug conjugate comprising the antibody or a fragment thereof that specifically binds to an extracellularly accessible epitope of M(H)DM2/4 bound to a cytotoxic drug, wherein said antibody or fragment is not bound to a cell-penetrating peptide.

In one aspect, provided herein are methods for selecting a subject (e.g., a human) for treatment and treating cancer in the subject, said method comprising: (a) selecting a subject having a cancer for treatment by: (i) obtaining an intact cancer cell from the subject (e.g., by biopsy of the cancerous tumor in the subject, or by obtaining a blood sample with circulating cancer cells from the subject), and (ii) determining whether an antibody or a fragment thereof (e.g., a labeled antibody or fragment) that specifically binds to M(H)DM2/4 (e.g., an antibody or fragment that specifically binds to an extracellularly accessible epitope of M(H)DM2/4, such as any anti-M(H)DM2/4 antibody or fragment described herein) binds to the surface of the intact cancer cell obtained from the subject (e.g., using FACS or cell-based ELISA analysis), and (b) if the binding is detected in step (a), administering to the subject said antibody or fragment, wherein said antibody or fragment is not bound to a cell-penetrating peptide. In one aspect, provided herein are methods for selecting a subject for treatment and treating cancer in the subject, said method comprising: (a) selecting a subject having a cancer for treatment by: (i) obtaining an intact cancer cell from the subject (e.g., by biopsy of the cancerous tumor in the subject, or by obtaining a blood sample with circulating cancer cells from the subject), and (ii) determining whether an antibody or a fragment thereof that specifically binds to HDM2 (e.g., an antibody or fragment that specifically binds to an extracellularly accessible epitope of HDM2, such as any anti-M(H)DM2/4 antibody or fragment described herein) binds to the surface of the intact cancer cell obtained from the subject (e.g., using FACS or cell-based ELISA analysis), and (b) if the binding is detected in step (a), administering to the subject said antibody or fragment, wherein said antibody or fragment is not bound to a cell-penetrating peptide.

In certain embodiments, the cancer treated in accordance with the methods described herein is a type of cancer that is known to metastasize. In some embodiments, the cancer treated in accordance with the methods described herein is an advanced stage cancer. In other embodiments, the cancer treated in accordance with the methods described herein is an early stage cancer. In specific embodiments, the cancer treated in accordance with the methods described herein is a metastatic cancer. The cancer being treated can be a solid cancer or a non-solid cancer (e.g., leukemia).

In certain embodiments, the cancer treated in accordance with the methods described herein is a cervical cancer, an endometrial cancer, an ovarian cancer, a pancreatic cancer, a melanoma (e.g., a uveal melanoma), a breast cancer, a colorectal cancer (e.g. a colon cancer), a bladder cancer, an astrocytic neoplasm, a glioblastoma, a pediatric Rhabdomyosarcoma, or a lung cancer (e.g., a non-small cell lung carcinoma). In specific embodiments, the cancer treated in accordance with the methods described herein is a melanoma, a pancreatic cancer, a breast cancer, or an ovarian cancer. In one embodiment, the cancer treated in accordance with the methods described herein is a lung cancer. In one embodiment, the cancer treated in accordance with the methods described herein is a colorectal cancer. In one embodiment, the cancer treated in accordance with the methods described herein is a colon cancer. In one embodiment, the cancer treated in accordance with the methods described herein is a melanoma. In one embodiment, the cancer treated in accordance with the methods described herein is a pancreatic cancer. In one embodiment, the cancer treated in accordance with the methods described herein is a breast cancer. In one embodiment, the cancer treated in accordance with the methods described herein is an ovarian cancer.

The subject treated in accordance with the methods described herein can be a human or a non-human animal (such as a mammal). In a preferred embodiment, the subject is a human.

In certain embodiments, the anti-M(H)DM2/4 antibodies or fragments described herein are administered intravenously, intraperitoneally, intramuscularly, subcutaneously, or intratumorally. In other embodiments, the anti-M(H)DM2/4 antibodies or fragments described herein are administered orally.

In certain embodiments, the subject being treated in accordance with the methods described herein is further administered an additional anti-cancer therapy that is different from said antibody or fragment or antibody-drug conjugate (e.g., vaccine, targeted therapy, chemotherapy, radiotherapy, surgery, or immunotherapy). In one embodiment, the additional therapy is a vaccine. In one embodiment, the additional therapy is a targeted therapy. In one embodiment, the additional therapy is a chemotherapy (e.g., gemcitabine, paclitaxel, nab-paclitaxel, or a combination of gemcitabine and nab-paclitaxel). In one embodiment, the additional therapy is an immunotherapy. In one embodiment, the additional therapy is a radiotherapy. In one embodiment, the additional therapy is a surgery (e.g., to remove part or all of the cancerous tumor being treated). In specific embodiments, the additional therapy is an inhibitor of the function of one or more checkpoint inhibitory molecules (e.g., an inhibitor, such as an inhibitory antibody to, one or more of: CTLA-4, PD-1, PD-L1, PD-L2, TIM-3, OX40, and LAG-3). In certain embodiments, the additional therapy is not a cell cycle inhibitor. In a specific embodiment, the subject treated using the methods described herein is not administered a cell cycle inhibitor during the course of treatment with said antibody or fragment. In certain embodiments, the anti-M(H)DM2/4 antibodies or fragments described herein are administered alone, without any additional anti-cancer therapy (e.g., the subject treated using the methods described herein is not administered an additional anti-cancer therapy during the course of treatment with said antibody or fragment).

In certain embodiments, the subject being treated in accordance with the methods described herein is further administered chemotherapy, wherein the chemotherapy is cisplatin. In certain embodiments, the subject being treated in accordance with the methods described herein is further administered chemotherapy, wherein the chemotherapy is 5-FU. In certain embodiments, the subject being treated in accordance with the methods described herein is further administered chemotherapy, wherein the chemotherapy is paclitaxel. In certain embodiments, the subject being treated in accordance with the methods described herein is further administered chemotherapy, wherein the chemotherapy is paclitaxel formulated as albumin-bound particles (e.g., ABRAXANE®). In certain embodiments, the subject being treated in accordance with the methods described herein is further administered chemotherapy, wherein the chemotherapy is gemcitabine (e.g., where the cancer being treated is a pancreatic cancer). In certain embodiments, the subject being treated in accordance with the methods described herein is further administered chemotherapy, wherein the chemotherapy is nab-paclitaxel (e.g., where the cancer being treated is a pancreatic cancer). In certain embodiments, the cancer is a pancreatic cancer, and the subject being treated in accordance with the methods described herein is further administered chemotherapy, wherein the chemotherapy is a combination of gemcitabine and nab-paclitaxel. In certain embodiments, the gemcitabine and/or nab-paclitaxel are administered in doses that are lower than doses used when gemcitabine and/or nab-paclitaxel are administered not in combination with an anti-cancer antibody (such as an anti-M(H)DM2/4 antibody or fragment described herein). In certain embodiments, wherein the subject is human, gemcitabine is administered in a dose that is less than 1,500 mg/m$^2$, and/or nab-paclitaxel is administered in a dose that is less than 300 mg/m$^2$. In one embodiment, wherein the subject is human, gemcitabine is administered in a dose that is equal to or less than 1,000 mg/m$^2$ and/or the nab-paclitaxel is administered in a dose that is equal to or less than 125 mg/m$^2$. In one embodiment, wherein the subject is human, gemcitabine is administered in a dose that is equal to or less than 500 mg/m$^2$ and/or the nab-paclitaxel is administered in a dose that is equal to or less than 62.5 mg/m$^2$. In certain embodiments, the combination of gemcitabine and nab-paclitaxel is administered with a frequency of every 2 weeks or less.

In certain embodiments, the subject being treated in accordance with the methods described herein is resistant to other cancer therapies (e.g., vaccine, targeted therapy, chemotherapy, radiotherapy, surgery, or immunotherapy). In specific embodiments, the subject being treated in accordance with the methods described herein is resistant to chemotherapy. In one embodiment, the subject being treated in accordance with the methods described herein has a chemotherapy-resistant ovarian cancer. In other embodiments, the subject being treated in accordance with the methods described herein is resistant to one or more inhibitor of an inhibitory immune checkpoint molecule. In other embodiments, the subject being treated in accordance with the methods described herein is resistant to radiotherapy.

In a specific embodiment, the anti-M(H)DM2/4 antibody or fragment used in the methods described herein specifically binds within amino acids 19 to 50 of SEQ ID NO:4. In another specific embodiment, the anti-M(H)DM2/4 antibody used in the methods described herein specifically binds within amino acids 154 to 167 of SEQ ID NO:4. In yet another specific embodiment, the anti-M(H)DM2/4 antibody used in the methods described herein specifically binds within amino acids 1 to 60 of SEQ ID NO:4. In yet another specific embodiment, the anti-M(H)DM2/4 antibody used in the methods described herein specifically binds within amino acids 1 to 100 of SEQ ID NO:4. In yet another specific embodiment, the anti-M(H)DM2/4 antibody used in the methods described herein specifically binds within amino acids 1 to 109 of SEQ ID NO:4. In another specific embodiment, the anti-M(H)DM2/4 antibody used in the methods described herein specifically binds within amino acids 26 to 60 of SEQ ID NO: 4. In one specific embodiment, the anti-M(H)DM2/4 antibody used in the methods described herein specifically binds within the terminal 60 amino acids at the C-terminus of the HDM2 on the plasma membrane of cancer cells. In another specific embodiment, the anti-M(H)DM2/4 antibody used in the methods described herein specifically binds within the terminal 100 amino acids at the C-terminus of the HDM2 on the plasma membrane of cancer cells. In one specific embodiment, the anti-M(H)DM2/4 antibody used in the methods described herein specifically binds within amino acids 101 to 200 of SEQ ID NO:4.

In particular embodiments, the anti-M(H)DM2/4 antibody or fragment used in the methods described herein competes for binding to M(H)DM2/4 with mouse anti-HDM2 antibody OP145 (which is described herein, see, e.g., Table 10). In other particular embodiments, the anti-M(H)DM2/4 antibody or fragment used in the methods described herein competes for binding to M(H)DM2/4 with mouse anti-HDM2 antibody 965 (SMP14) (which is described herein, see, e.g., Tables 3 and 10). In yet other particular embodiments, the anti-M(H)DM2/4 antibody or fragment used in the methods described herein competes for binding to M(H)DM2/4 with rabbit anti-HDM2 antibody sc-813 (N-20) (which is described herein, see, e.g., Table 10). In another embodiment, the anti-M(H)DM2/4 antibody or fragment used in the methods described herein competes for binding to M(H)DM2/4 with rabbit anti-HDM2 antibody sc-812 (C-18) (which is described herein, see, e.g., Table 10). In another embodiment, the anti-M(H)DM2/4 antibody or fragment used in the methods described herein competes for binding to M(H)DM2/4 with mouse anti-HDM2 antibody M01, clone 1A7 (which is described herein, see, e.g., Table 3).

In certain aspects, provided herein are methods for treating cancer or preventing metastases in a subject in need thereof, said method comprising administering to the subject any anti-M(H)DM2/4 antibody described herein (such as an antibody that specifically binds to an extracellularly accessible epitope of M(H)DM2/4 on the surface of cells of said cancer), wherein the antibody comprises a human IgGFc region that mediates complement-dependent cytotoxicity (CDC) and/or antibody-dependent cell-mediated cytotoxicity (ADCC). In some of these embodiments, the extracellular region of HDM2 targeted by the anti-HDM2 antibodies or fragments used herein is within one of the following amino acid regions of HDM2: amino acids of SEQ ID NO: 1 (which are amino acids 1 to 15 of SEQ ID NO:4), amino acids of SEQ ID NO: 2 (which are amino acids 15 to 25 of SEQ ID NO:4), amino acids of SEQ ID NO: 3 (which are amino acids 475 to 491 of SEQ ID NO:4), amino acids 19 to 50 of SEQ ID NO: 4, amino acids 50 to 60 of SEQ ID NO: 4, amino acids 100 to 110 of SEQ ID NO: 4, amino acids 154 to 167 of SEQ ID NO: 4, amino acids 1 to 60 of SEQ ID NO: 4, or the terminal 60 amino acids at the C-terminus of the HDM2 on the plasma membrane of the cancer cells. In specific embodiments of the methods described in this paragraph, the cancer is a leukemia, a lung cancer, a colon cancer, a melanoma, a pancreatic cancer, a breast cancer, or an ovarian cancer.

In one aspect, provided herein are methods of diagnosing cancer in a subject (e.g., a human), said method comprising: (a) detecting whether an antibody or a fragment thereof (e.g., a labeled antibody or fragment) that specifically binds to M(H)DM2/4 (e.g., HDM2) binds to the surface of intact cells of the subject, wherein the antibody or fragment is any anti-M(H)DM2/4 antibody or fragment described herein (in a preferred example, wherein the antibody or fragment is any anti-M(H)DM2/4 antibody or fragment that specifically binds to a peptide of SEQ ID NO"1, SED ID NO:2, or SEQ ID NO:3); and (b) diagnosing the subject with cancer if binding is detected in step (a). In one embodiment, the method of diagnosing is an ex vivo method. In one embodiment, the method of diagnosing further comprises, before step (a), obtaining intact cells from the subject. In one embodiment, the method of diagnosing comprises administering the antibody or fragment to the subject before the detecting in step (a), and wherein the detecting is performed by in vivo imaging of the subject.

5.1 Terminology

As used herein, the term "HDM2" refers to the human E3 ubiquitin-protein ligase of UniProt Accession Number Q00987 (SEQ ID NO:4) (i.e., full-length HDM2 protein) or a protein product of any splice variant of the full-length HDM2 protein known in the art or described herein. The amino acid sequences of exemplary splice variants of the full-length HDM2 protein are shown as SEQ ID NO:8, SEQ ID NO:9, SEQ ID NO: 10, SEQ ID NO11, SEQ ID NO: 12, SEQ ID NO:13, SEQ ID NO:14, SEQ ID NO: 15, SEQ ID NO: 16 and SEQ ID NO: 17.

As used herein, the term "MDM2" refers to the mouse E3 ubiquitin-protein ligase of UniProt Accession Number P23804 (SEQ ID NO:5) (i.e., full-length MDM2 protein) or a protein product of any splice variant of the full-length MDM2 protein known in the art or described herein.

As used herein, the term "M(H)DM2" refers to HDM2, MDM2, or an E3 ubiquitin-protein ligase from species other than human and mouse that is a homolog of HDM2 or MDM2.

As used herein, the term "HDM4" refers to the human protein of UniProt Accession Number 015151 (SEQ ID NO:6) (i.e., full-length HDM4 protein) or a protein product of any splice variant of the full-length HDM4 protein known in the art or described herein.

As used herein, the term "MDM4" refers to the mouse protein of UniProt Accession Number 035618 (i.e., full-length MDM4 protein) or a protein product of any splice variant of the full-length MDM4 protein known in the art or described herein. The amino acid sequence of an exemplary splice variant of the full-length MDM4 protein is shown as SEQ ID NO:6. Other splice variants of the full length MDM4 protein known in the art include, without limitation MDM4-S, MDM4-A, MDM4-G, MDM4-X ALT1/XALT2 and MDM4-211.

As used herein, the term "M(H)DM4" refers to HDM4 (also called HDMX), MDM4 (also called MDMX), or a protein from a species other than human and mouse that is a homolog of HDM4 or MDM4.

As used herein, the term "M(H)DM2/4" refers to HDM2, MDM2, HDM4, MDM4, or a protein from a species other than human and mouse that is a homolog of HDM2, MDM2, HDM4 or MDM4.

As used herein, the term "about," when used to modify a numeric value, indicate that deviations of up to 10% above and below the numeric value remain within the intended meaning of the recited value.

As used herein, the term "intact" with reference to a cell refers to a cell that is viable or fixed but not permeabilized.

As used herein, the term "extracellularly accessible" with reference to an epitope of M(H)DM2/4, refers to an epitope of M(H)DM2/4 that, when the M(H)DM2/4 is expressed by an intact cell, the epitope is available for binding with an extracellular antibody (without a need for intracellular transport of the antibody). An antibody or a fragment thereof can be determined to bind to an extracellularly accessible epitope of M(H)DM2/4, when the antibody, when extracellular, binds to M(H)DM2/4 expressed by an intact cell.

As used herein, the term "VL" refers to the light chain variable region of an antibody.

As used herein, the term"VH" refers to the heavy chain variable region of an antibody.

As used herein, the term "percent (%) amino acid sequence identity" or "percent sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity. Alignment for purposes of determining percent amino acid sequence identity can be achieved in various ways that are known in the art, for instance, using publicly available computer software such as BLASTp, BLAST-2, ALIGN (e.g., ALIGN-2) or Megalign (DNASTAR) software.

6. BRIEF DESCRIPTION OF FIGURES

FIGS. 1A-D show that monoclonal antibodies NMC-103, NMC-204 and NMC-303 specifically bound to NMC-P1 (SEQ ID NO: 1), NMC-P2 (SEQ ID NO:2) and NMC-P3 (SEQ ID NO:3) peptide antigens, respectively, in peptide-ELISA experiments. (A) NMC-103 bound to NMC-P1 peptide while NMC-204 did not show binding to NMC-P1. (B) NMC-204 bound to NMC-P2 peptide while NMC-103 did not bind to NMC-P2. (C) NMC-303 bound to NMC-P3 peptide while NMC-204 did not bind to NMC-P3. (D) While NMC-103 bound to NMC-P1, pre-incubation of NMC-P1 peptide with NMC-103 abolished the binding of NMC-103 to NMC-P1 peptide on the plate. In contrast, pre-incubation of NMC-103 with either NMC-P2 or NMC-P3 did not affect the binding of NMC-103 to NMC-P1.

FIG. 2 shows that monoclonal antibodies NMC-103, NMC-204, NMC-303 bound to HDM2 recombinant protein.

FIGS. 3A-B show that monoclonal antibody NMC-103 bound to an extracellularly accessible epitope of HDM2 on intact human (A) and murine (B) cancer cells.

FIGS. 4A-B show that monoclonal antibody NMC-204 bound to an extracellularly accessible epitope of HDM2 on intact human (A) and murine (B) cancer cells.

FIGS. 5A-B show that monoclonal antibody NMC-303 bound to an extracellularly accessible epitope of HDM2 on intact human (A) and murine (B) cancer cells.

FIG. 6 shows that monoclonal antibody NMC-204 bound to an extracellularly accessible epitope of HDM2 on intact human cancer cells but did not bind to intact normal human peripheral blood mononuclear cells.

FIGS. 7A-B depict the binding curves of the binding of monoclonal antibodies NMC-103 (A) and NMC-204 (B) to intact MIA PaCa-2 cells.

FIGS. 8A-C show that the binding of monoclonal antibody NMC-103 to its extracellularly accessible epitope of HDM2 on the plasma membrane of intact human pancreatic cancer MIA PaCa-2 cells was competed by the NMC-P1 peptide (A), the binding of monoclonal antibody NMC-204 to its extracellularly accessible epitope of HDM2 on the plasma membrane of intact human pancreatic cancer MIA PaCa-2 cells was competed by the NMC-P2 peptide (B), and the binding of monoclonal antibody NMC-303 to its extracellularly accessible epitope of HDM2 on the plasma membrane of intact human pancreatic cancer MIA PaCa-2 cells was competed by the NMC-P3 peptide (C).

Figures 11A, 11B, 11C:
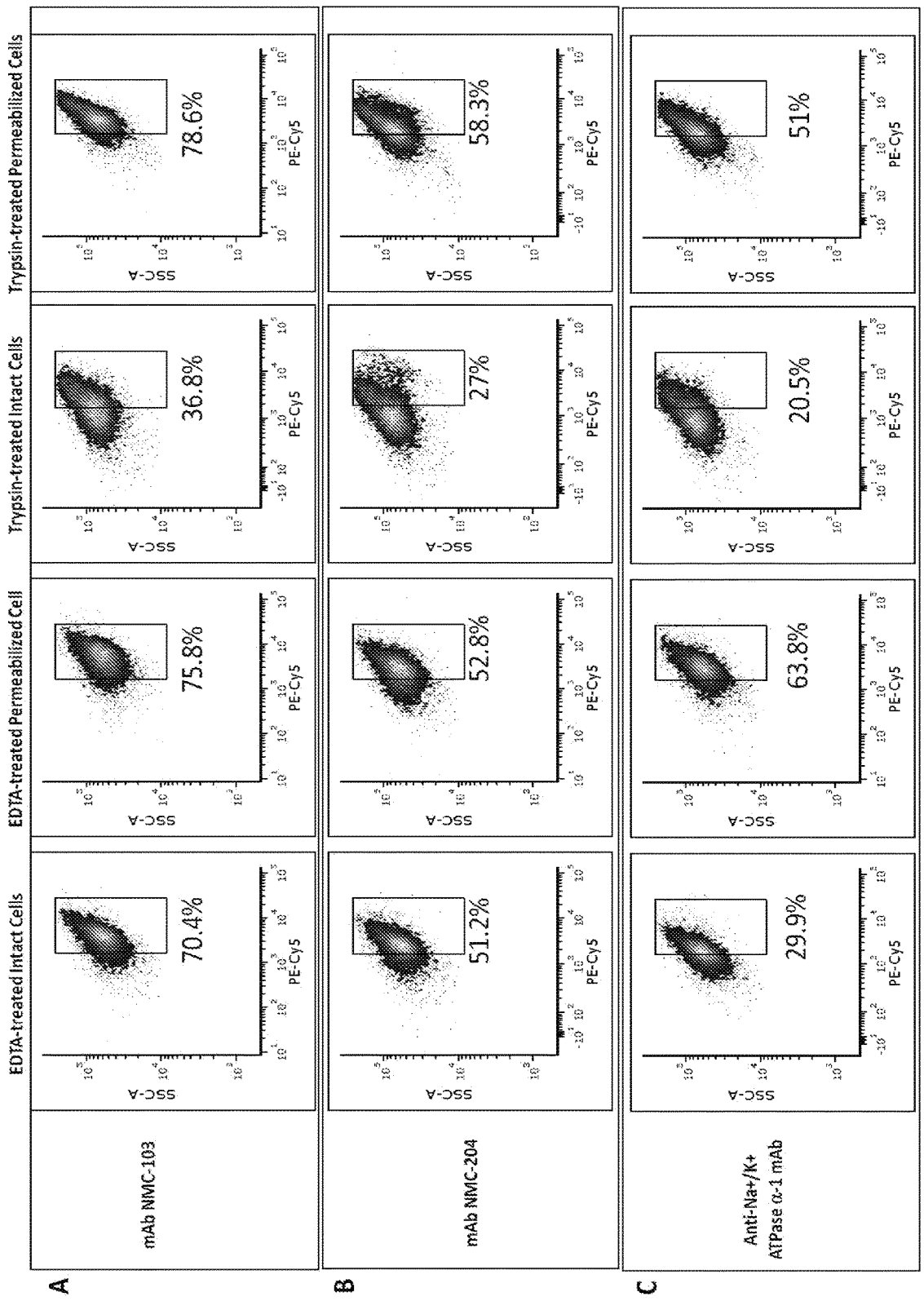

FIGS. 11A-C present flow cytometry data on % cells stained with monoclonal antibodies NMC-103 (A), NMC-204 (B), and anti-Na+/K+ ATPase a-1 (C), respectively.

FIGS. 12A-D show that monoclonal antibodies NMC-103 (A and D) and NMC-204 (B and D), but not an anti-Cytochrome-C antibody (C and D), inhibited cell proliferation of intact human pancreatic MIAPaCa-2 cells.

Figures 13A, 13B:
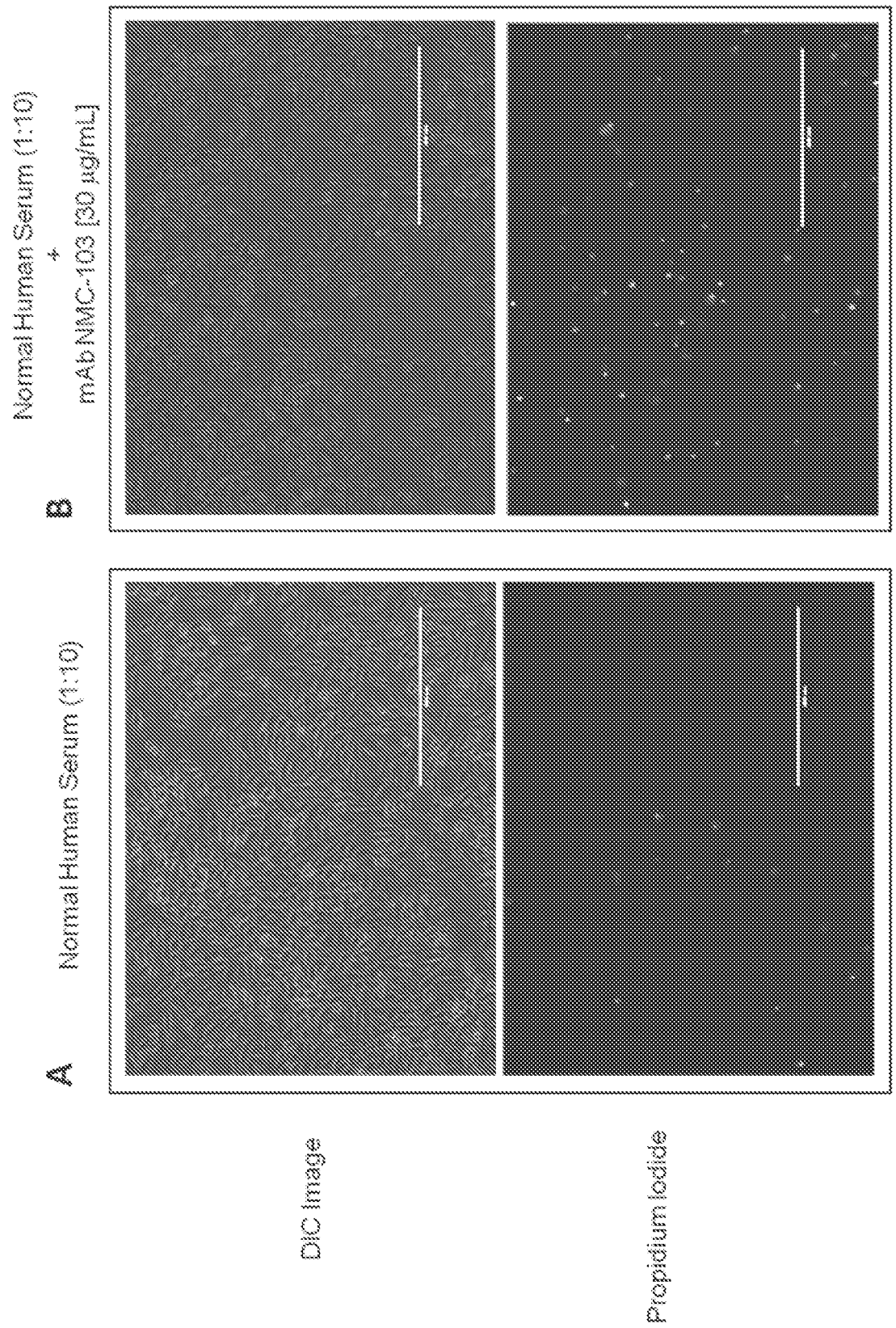
Figure 13C:
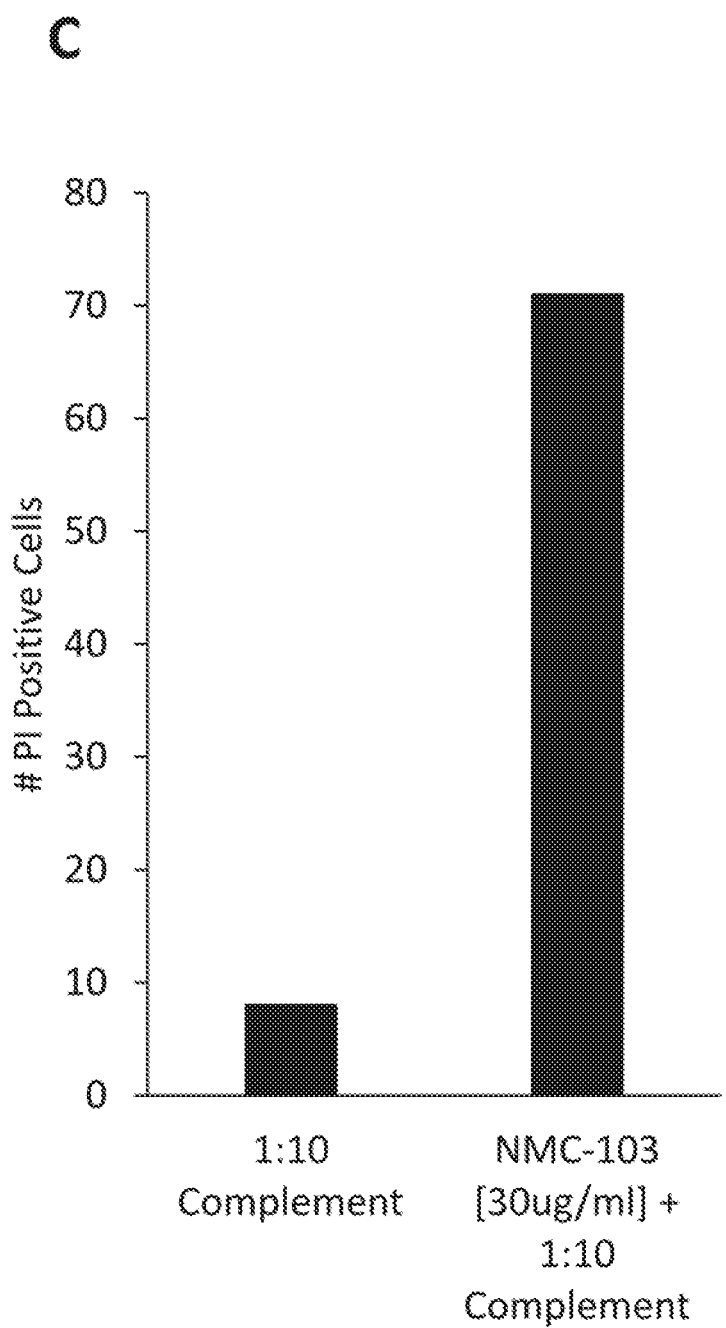

FIGS. 13A-C show that monoclonal antibody NMC-103 (B and C) in the presence of normal human serum induces complement-mediated cytotoxicity against human pancreatic MIAPaCa-2 cells as compared with cells treated with normal human serum in the absence of any antibody (A).

Figures 14A, 14B:
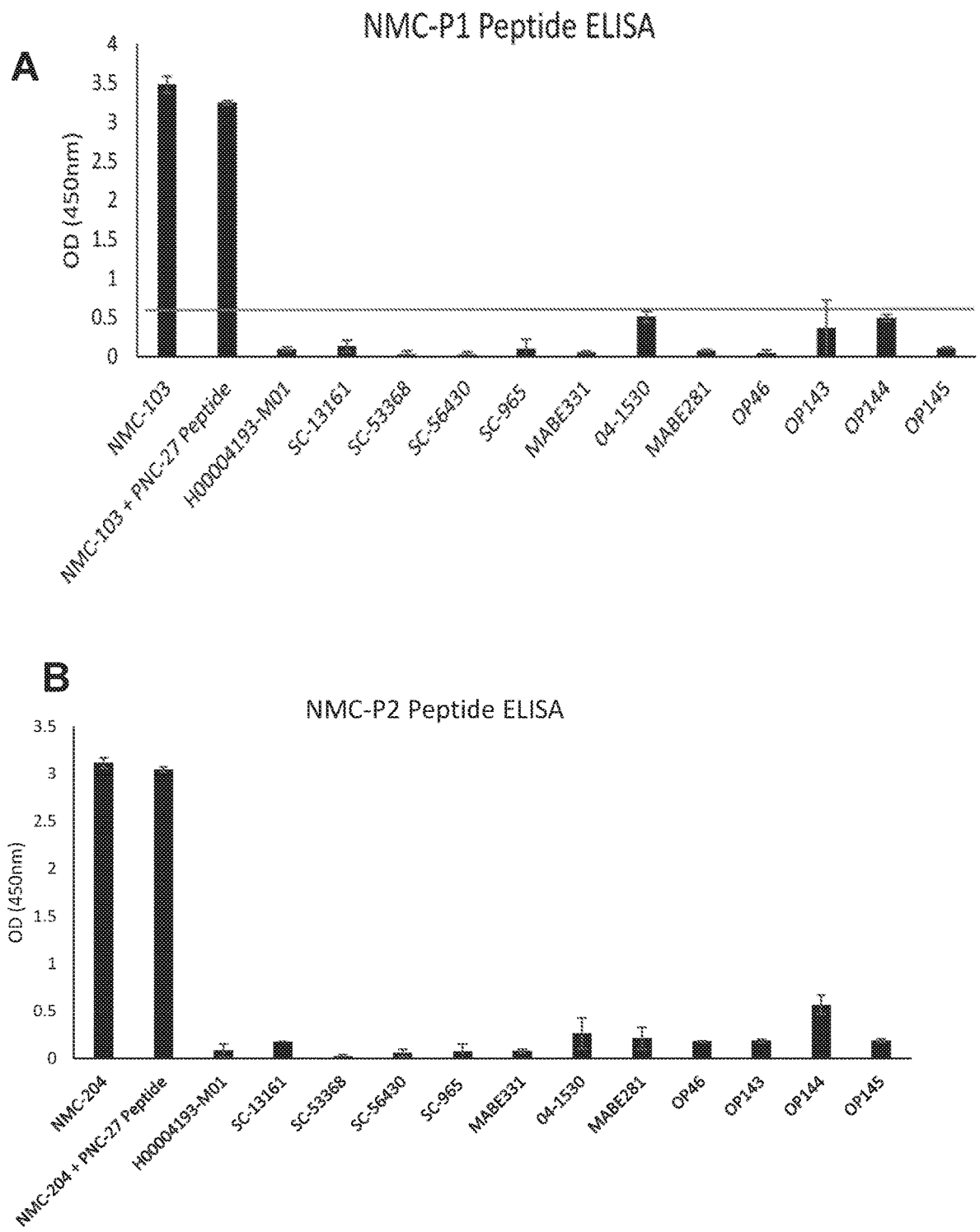

FIGS. 14A-B show the lack of binding of many commercially available monoclonal antibodies to either NMC-P1 (A) or NMC-P2 (B).

Figure 15A:
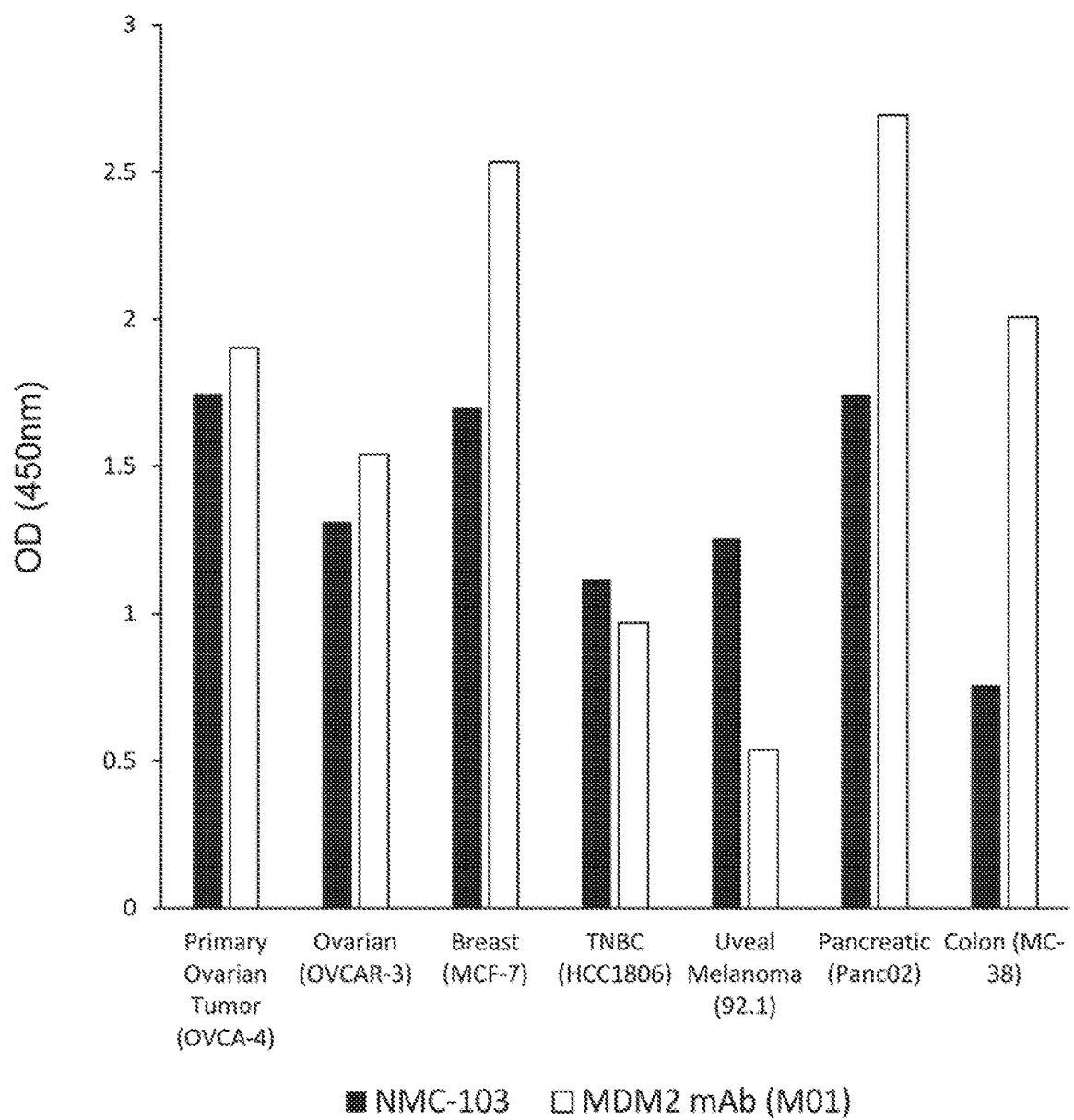
Figure 15B:
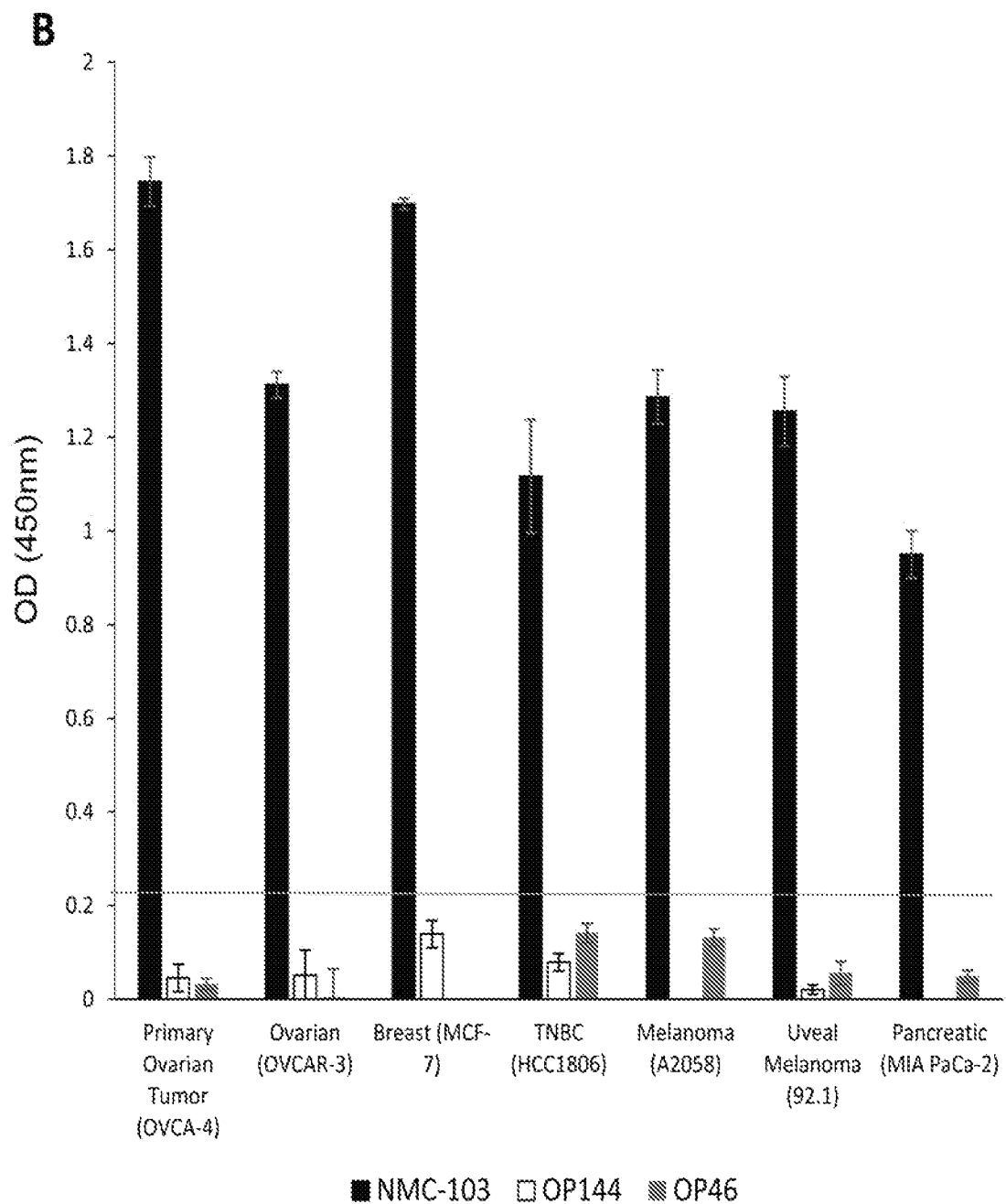

FIGS. 15A-B show that an anti-HDM2 antibody termed "MDM2 monoclonal antibody (M01), clone 1A7" (Abnova, Cat. No. H00004193-M01) reacted with intact cancer cells (A), but an anti-HDM2 antibody termed "Anti-MDM2 (Ab-4) Mouse mAb (2A9C1.18)" (EMD Millipore, Cat. No. OP 144) and an anti-HDM2 antibody termed "Anti-MDM2 (Ab-1) Mouse mAb (IF2)" (EMD Millipore, Cat. No. OP46) did not react with intact cancer cells (B).

Figure 16:
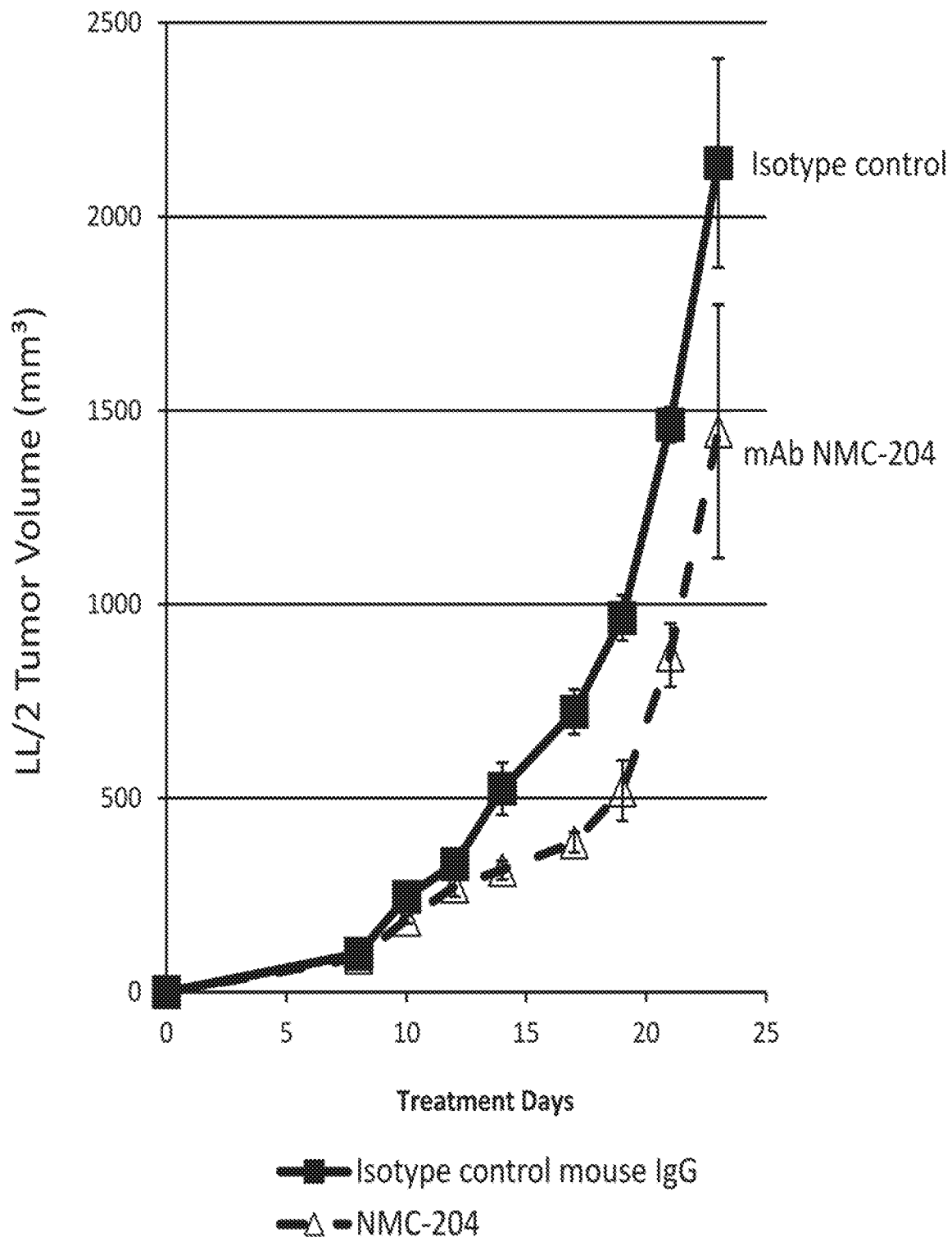

FIG. 16 depicts the effect of monoclonal antibody NMC-204 on tumor volume of the LL/2 syngeneic mouse model of lung cancer.

Figures 17A, 17B:
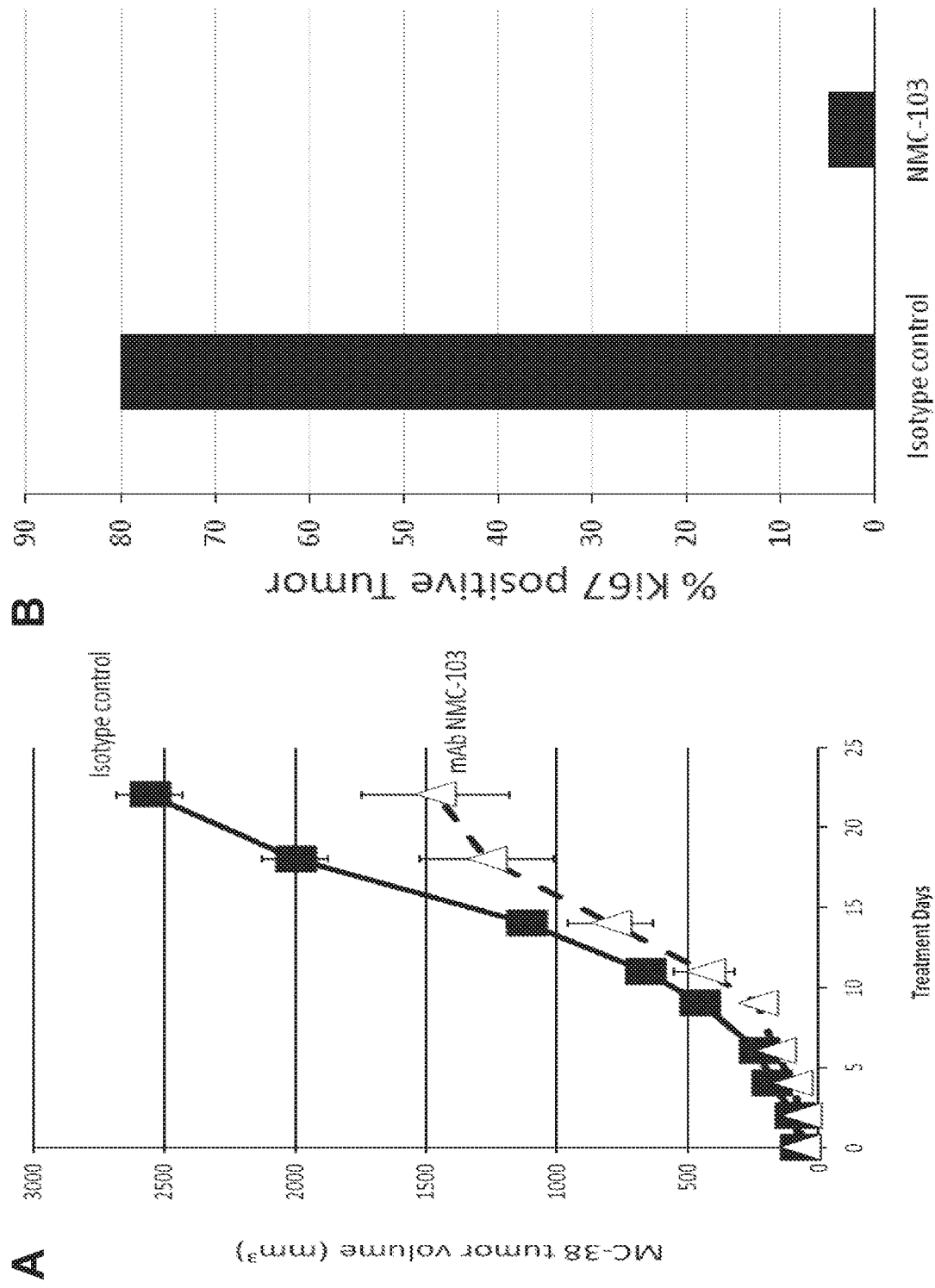

FIGS. 17A-B depict the effect of monoclonal antibody NMC-103 on tumor volume (A) and tumor cell proliferation (B) of the MC-38 syngeneic mouse model of colon cancer.

Figures 18A, 18B:
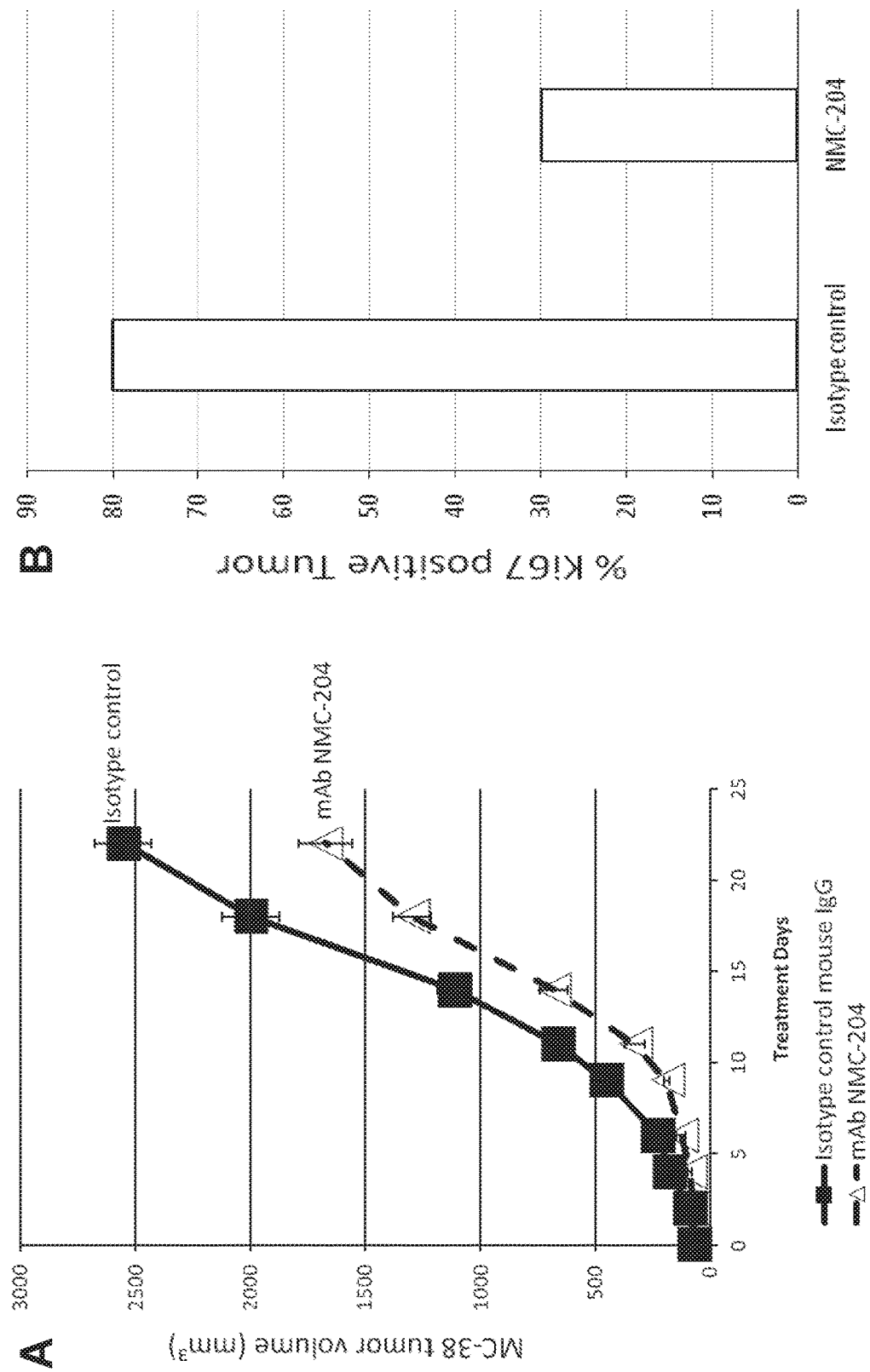

FIGS. 18A-B depict the effect of monoclonal antibody NMC-204 on tumor volume (A) and tumor cell proliferation (B) of the MC-38 syngeneic mouse model of colon cancer.

Figure 19:
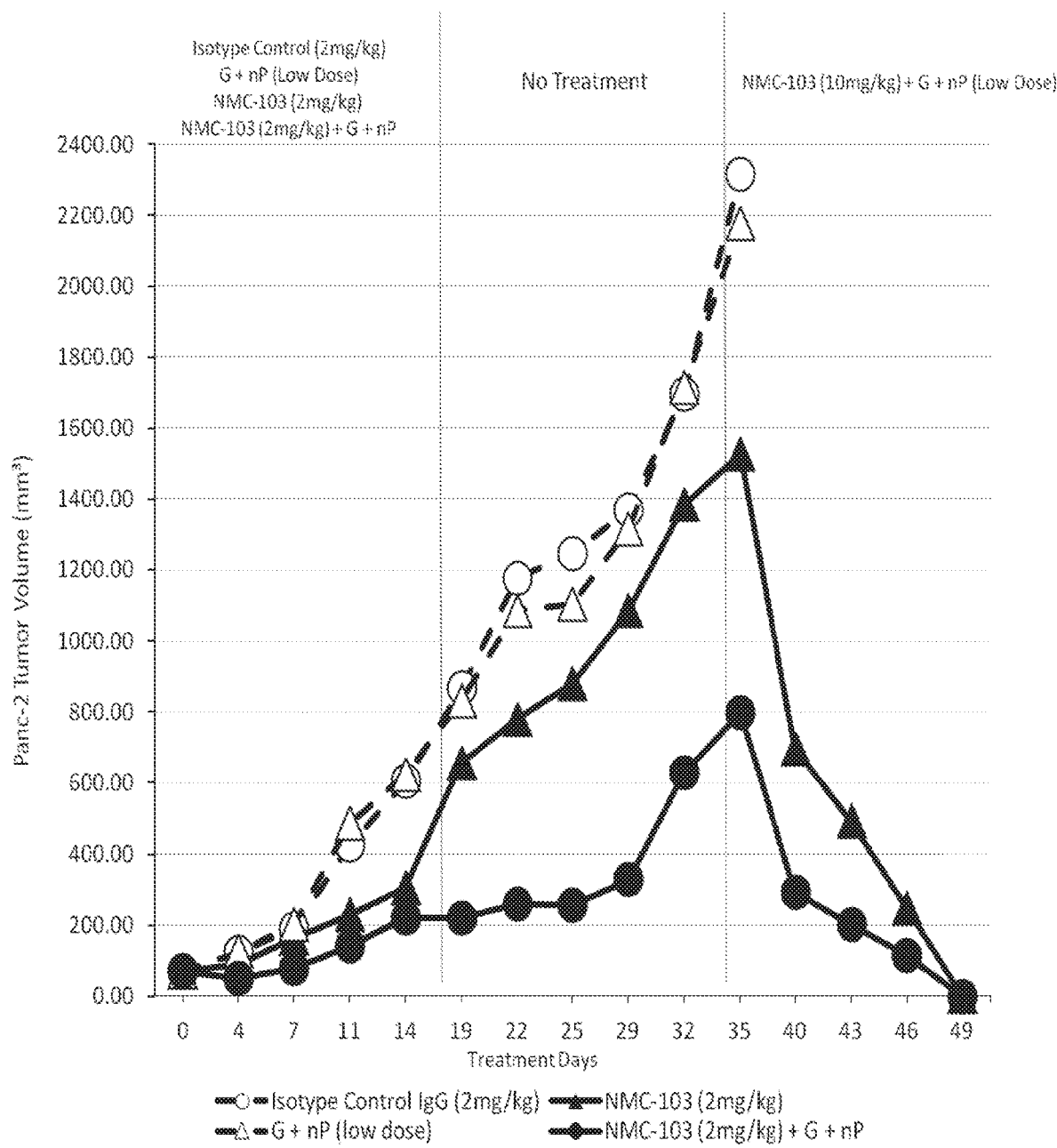

FIG. 19 depicts the effect of monoclonal antibody NMC-103 alone (2 mg/kg), a combination of low dose Gemcitabine (25 mg/kg) and nab-Paclitaxel (5 mg/kg), a combination of low dose Gemcitabine (25 mg/kg), nab-Paclitaxel (5 mg/kg) and NMC-103 (2 mg/kg), and isotype control mouse IgG1 (2 mg/kg), respectively, on tumor volume of the Panc-2 syngeneic mouse model of pancreatic cancer. Treatment started when tumors in mice reached approximately 70 mm$^3$.

FIG. 20 depicts the DNA sequence and protein sequence of the heavy chain variable region and the light chain variable region, respectively, of monoclonal antibody NMC-103.

FIG. 21 depicts the DNA sequence and protein sequence of the heavy chain variable region and the light chain variable region, respectively, of monoclonal antibody NMC-204.

FIG. 22 depicts the DNA sequence and protein sequence of the heavy chain variable region and the light chain variable region, respectively, of monoclonal antibody NMC-303. The leader sequence before the DNA and protein sequences of the heavy chain variable region and the light chain variable region is in bold (but not underlined).

Figure 23:
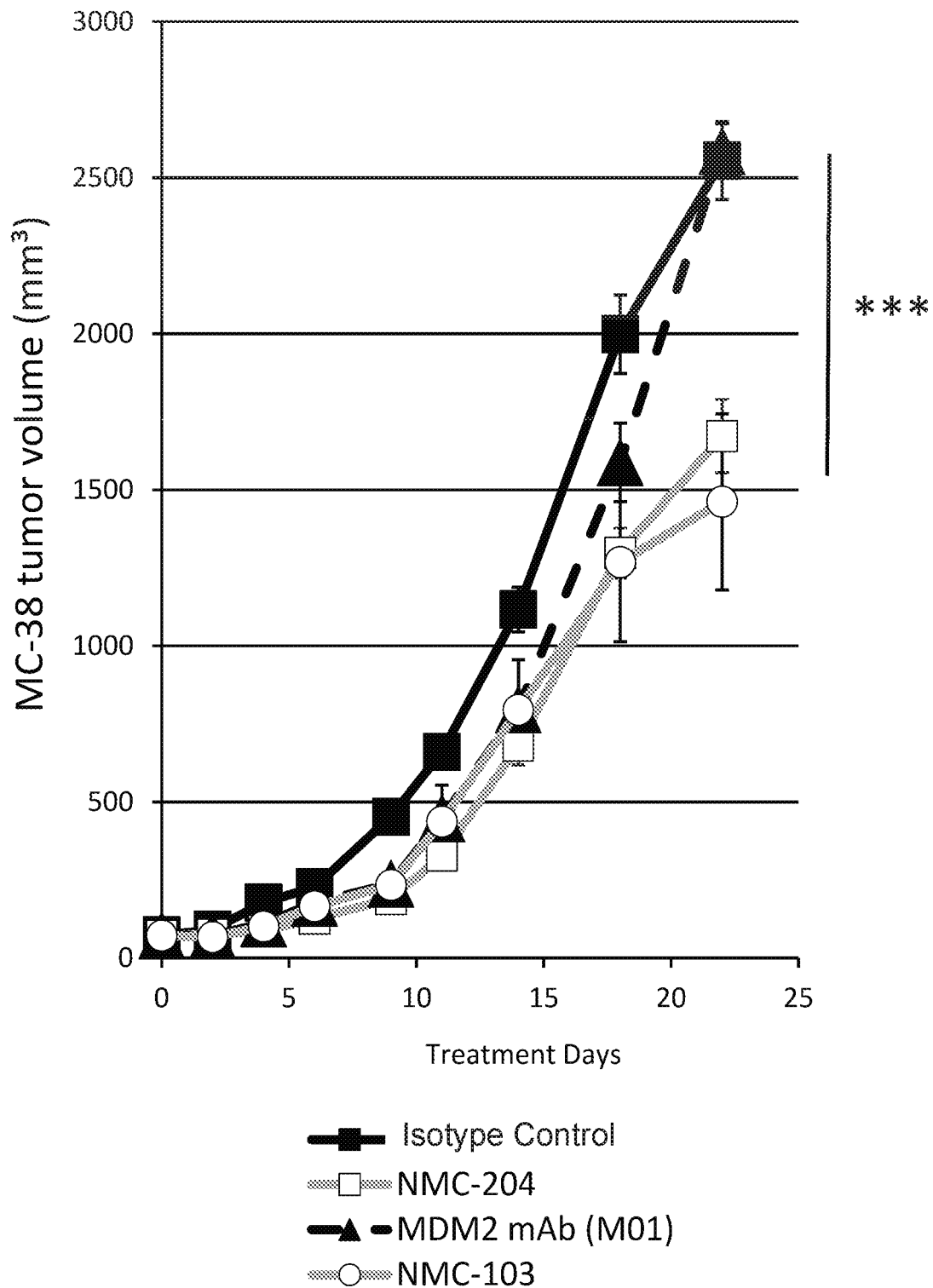

FIG. 23 shows the tumor size of mice treated with the anti-HDM2 antibody termed "MDM2 monoclonal antibody (M01), clone 1A7" (Abnova, Cat. No. H00004193-M01), the tumor size of mice treated with NMC-103, the tumor size of mice treated with NMC-204, and the tumor size of mice treated with isotype control.

Figures 24A, 24B:
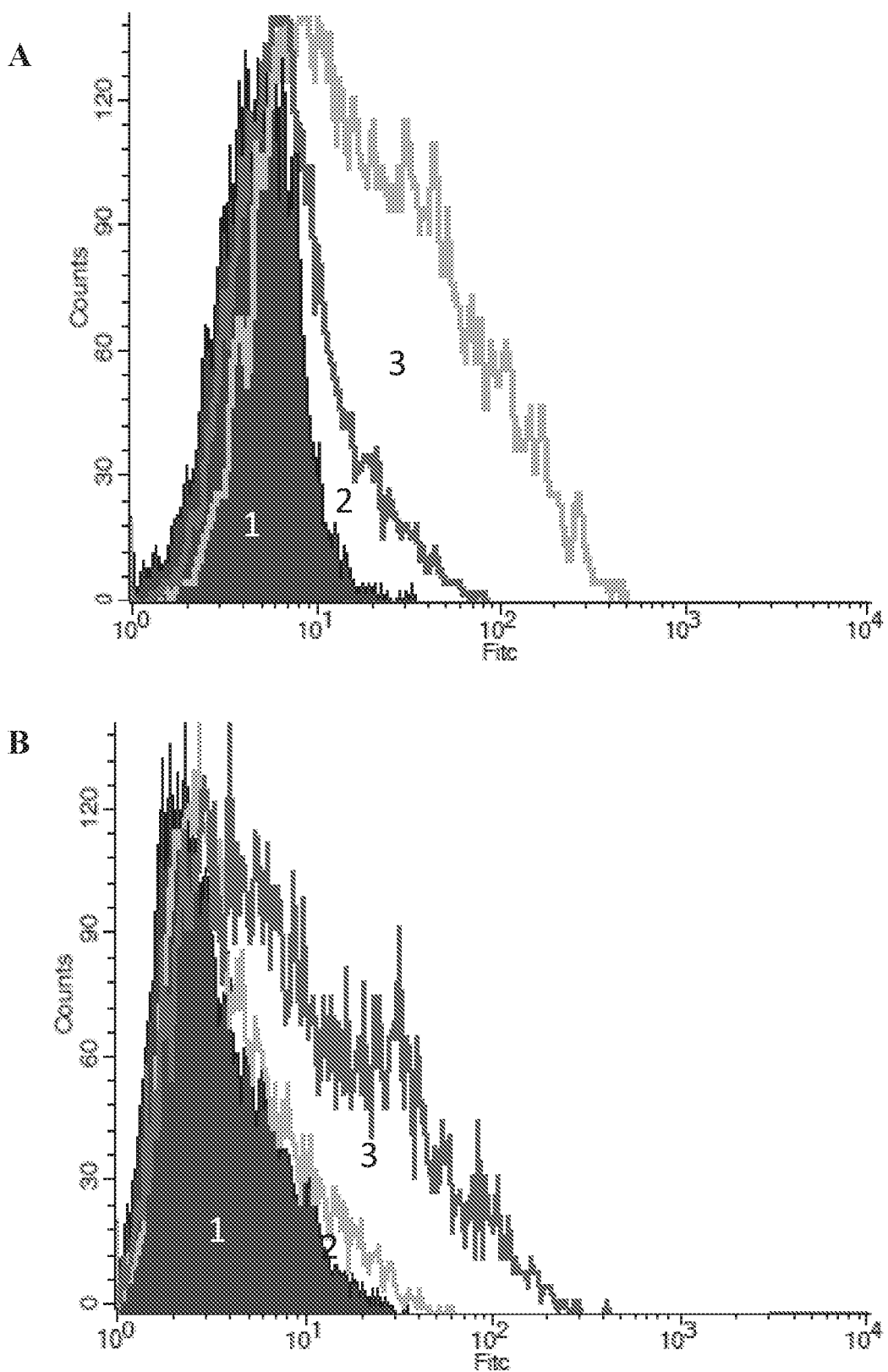
Figures 24C, 24D:
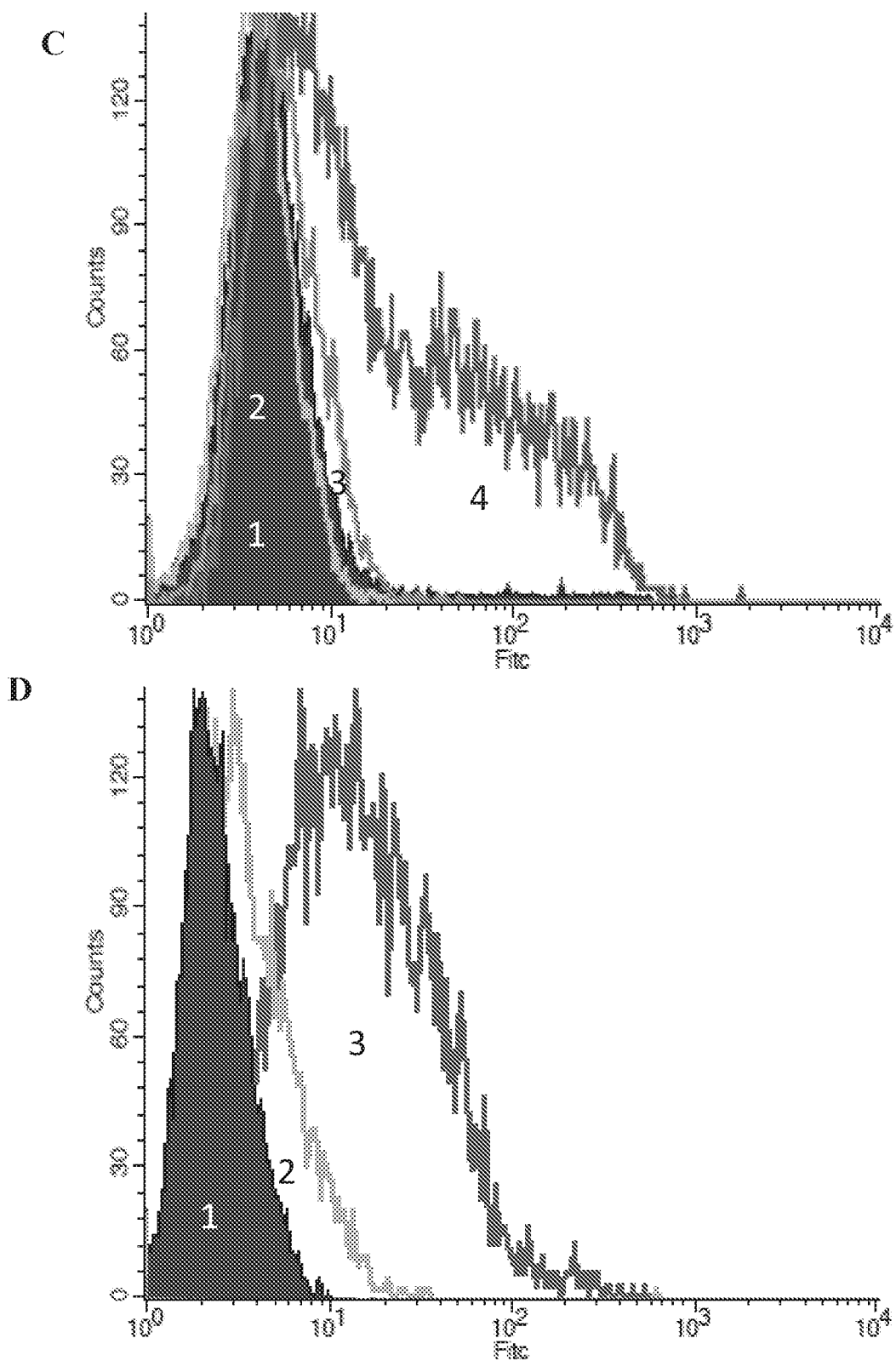
Figures 24E, 24F:
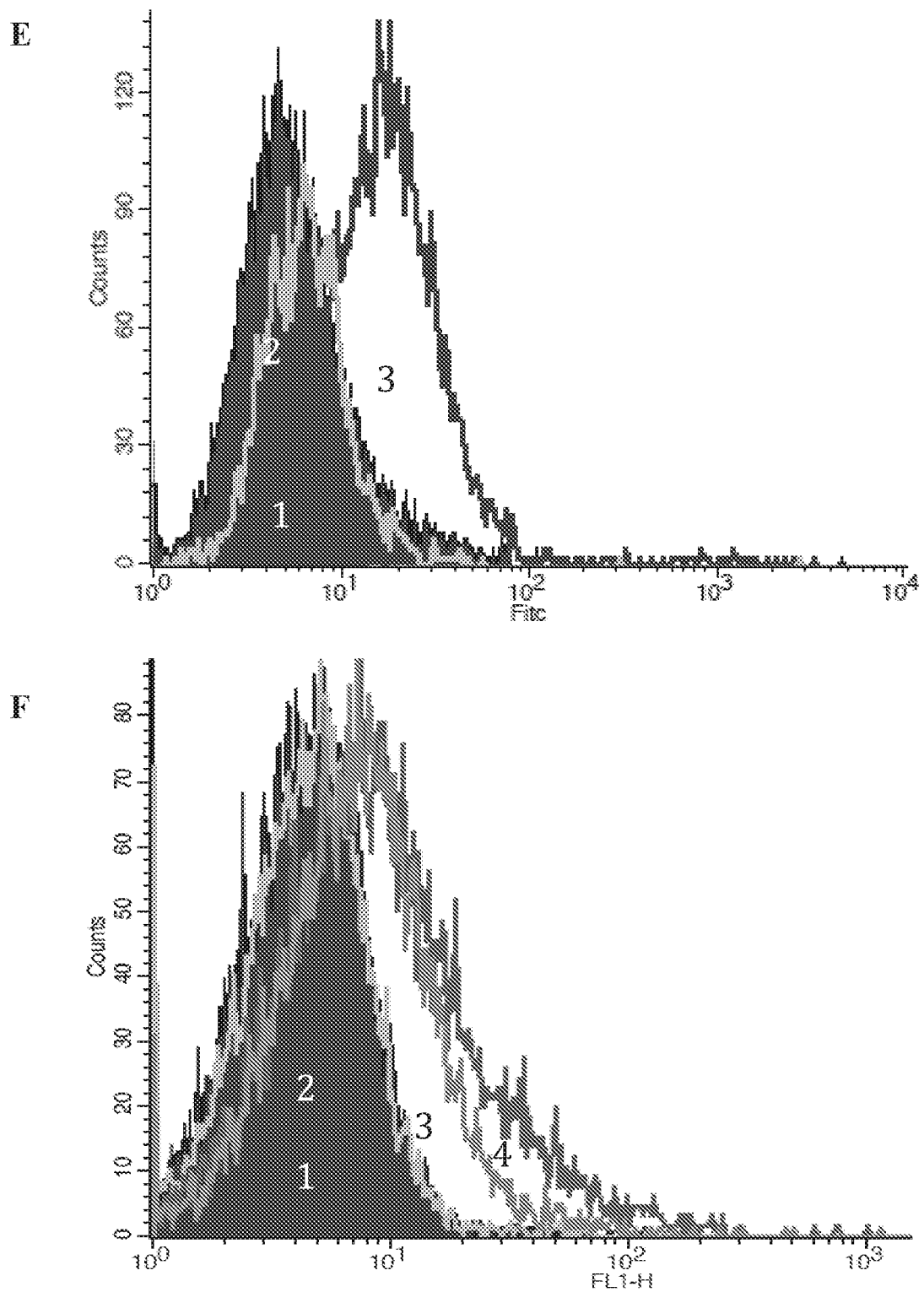

FIGS. 24A-F. Anti-HDM2-specific antibodies stain the surface of cancer cells but not normal cells. Intact cells released either with either EDTA or Trypsin were blocked with 5% human serum albumin. Cells were then incubated with either polyclonal N-20 M(H)DM2-specific antibody (sc-813, N-20, rabbit IgG; from Santa Cruz; "N-20") or monoclonal M(H)DM2-specific OP145 antibody (OP145, mouse IgG1; from Calbiochem; "OP145") for 90 min. on ice. Another set of cells prepared under the same conditions were incubated with the same antibodies that were pre-incubated with their corresponding blocking peptides before incubation with cells. Following primary antibody incubation, cells were washed 3 times with ice-cold PBS followed by FITC-secondary antibody incubation for 60 min Cells were then washed 3 times with PBS and were subjected to FACS analyzer. Human melanoma cells (24A, 24B, and 24C), primary human ovarian cancer cells (24D and 24E), and normal mouse splenocytes (24F). FIG. 24A: area under curve #1 represents cells incubated with goat anti-rabbit secondary antibody only; area under curve #2 represents cells incubated with anti-FIDM2 polyclonal antibody N-20 pre-incubated with its blocking peptide followed by goat anti-rabbit secondary antibody; area under curve #3 represents cells incubated with anti-HDM2 polyclonal antibody N-20 followed by goat anti-rabbit secondary antibody. FIG. 24B: area under curve #1 represents cells incubated with goat anti-mouse secondary antibody only; area under curve #2 represents cells incubated with anti-HDM2 monoclonal antibody OP 145 pre-incubated with its blocking peptide followed by goat anti-rabbit secondary antibody; area under curve #3 represents cells incubated with anti-FIDM2 monoclonal antibody OP145 followed by goat anti-mouse secondary antibody. FIG. 24C: area under curve #1 represents cells incubated with goat anti-rabbit secondary antibody only; area under curve #2 represents trypsin-released cells incubated with anti-HDM2 polyclonal antibody N-20 followed by goat anti-rabbit secondary antibody; area under curve #3 represents EDTA-released cells incubated with anti-FIDM2 polyclonal antibody N-20 pre-incubated with its blocking peptide followed by goat anti-rabbit secondary antibody; area under curve #4 represents EDTA-released cells incubated with anti-FIDM2 polyclonal antibody N-20 followed by goat anti-rabbit secondary antibody. FIGS. 24D & E: area under curve #1 represents cells incubated with goat anti-rabbit secondary antibody only; area under curve #2 represents cells incubated with anti-FIDM2 polyclonal antibody N-20 pre-incubated with its blocking peptide followed by goat anti-rabbit secondary antibody; area under curve #3 represents cells incubated with anti-FIDM2 polyclonal antibody N-20 followed by goat anti-rabbit secondary antibody. FIG. 24F: area under curve #1 represents cells incubated with goat anti-rabbit secondary antibody only; area under curve #2 represents trypsin-released cells incubated with anti-FIDM2 polyclonal antibody N-20 followed by goat anti-rabbit secondary antibody; area under curve #3 represents EDTA-released cells incubated with anti-FIDM2 polyclonal antibody N-20 pre-incubated with its blocking peptide followed by goat anti-rabbit secondary antibody; area under curve #4 represents EDTA-released cells incubated with anti-ffDM2 polyclonal antibody N-20 followed by goat anti-rabbit secondary antibody.

Figure 25A:
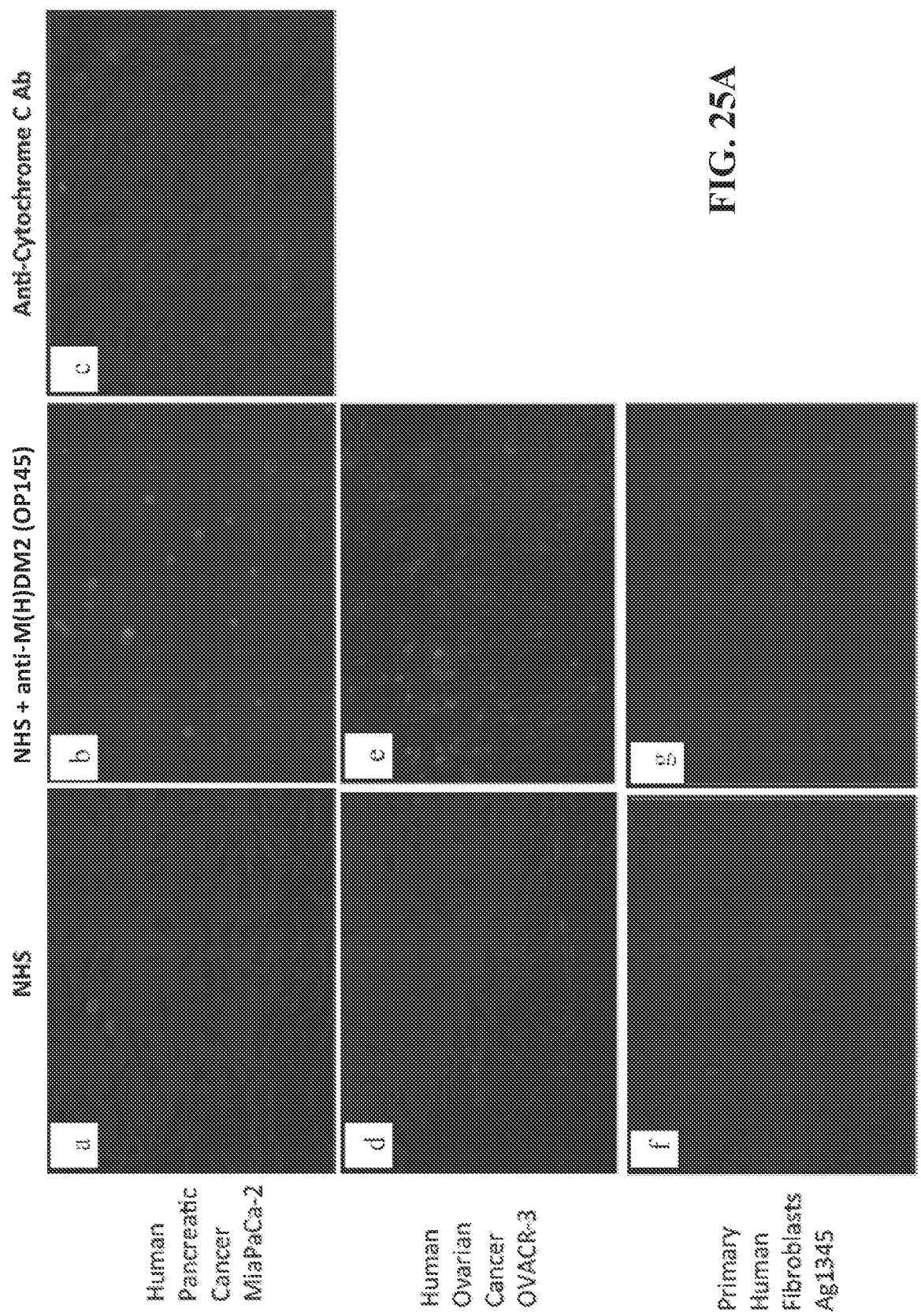
Figure 25B:
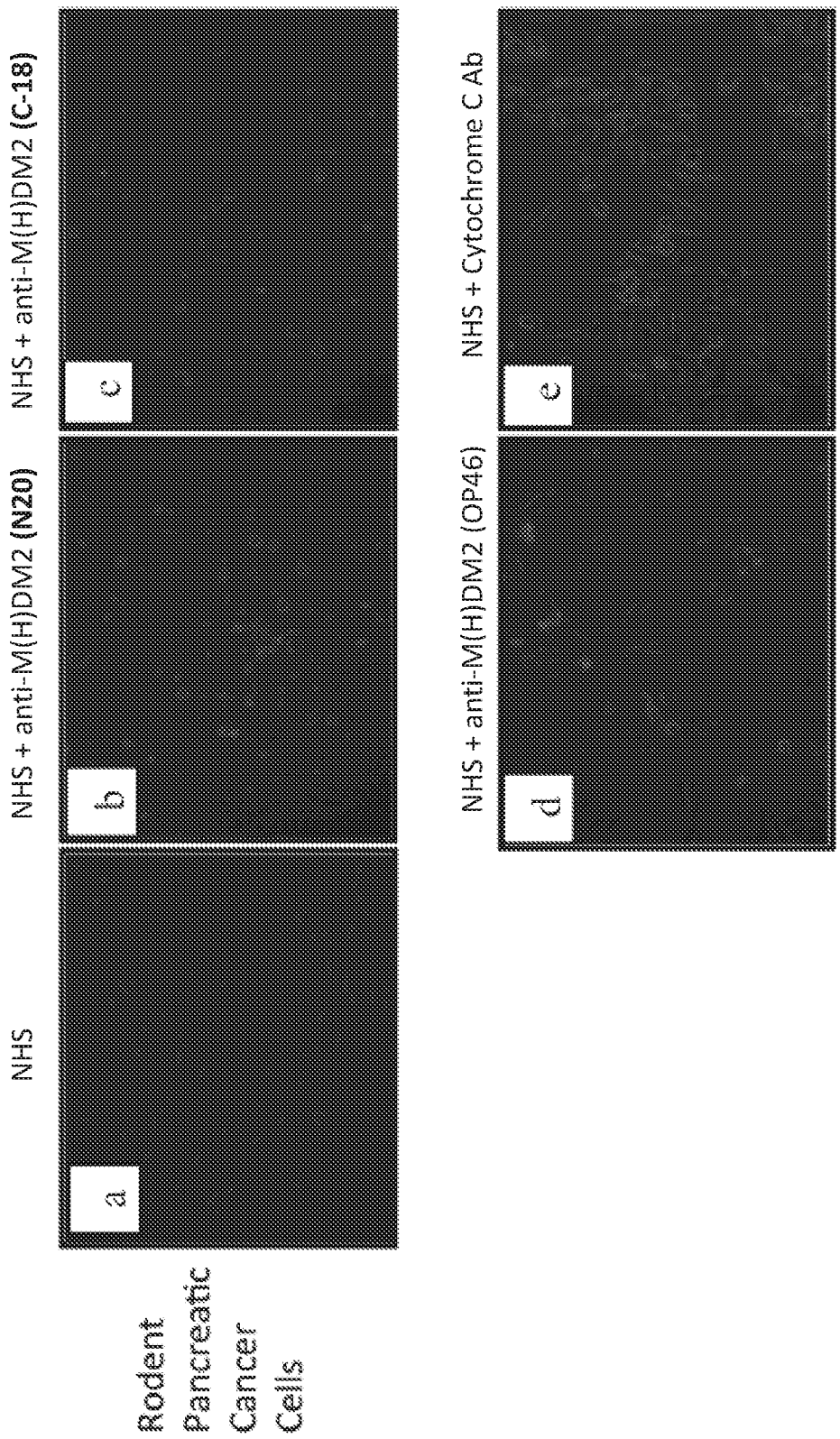
Figure 25C:
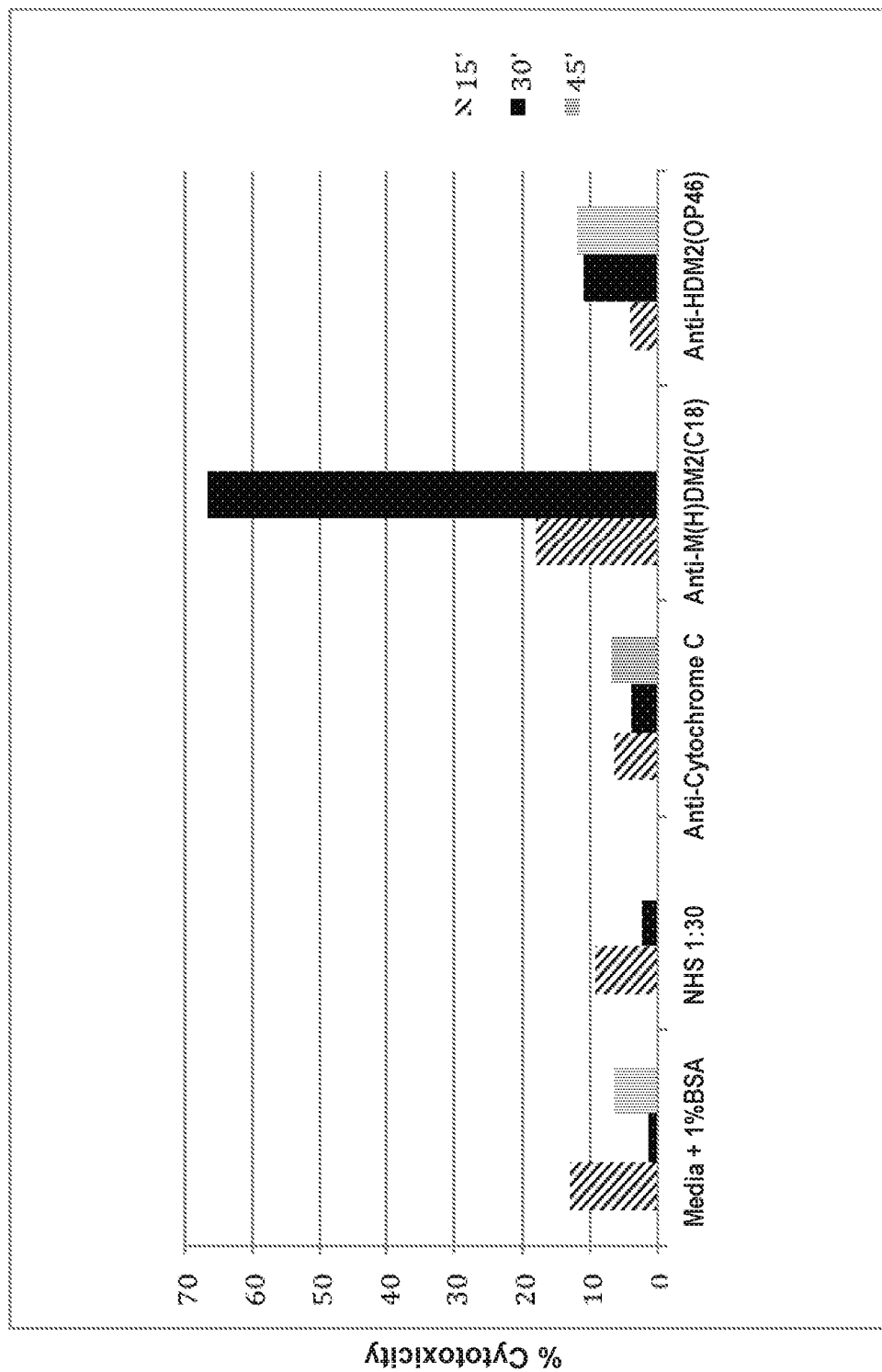

FIGS. 25A-C. (A) Human pancreatic or ovarian cancer cells and normal human fibroblasts were treated with normal human serum (NHS) alone, NHS+anti-HDM2 OP 145 monoclonal antibody (mouse IgG1, from Calbiochem, "OP 145") or control antibody (NHS+ Cytochrome C). Extensive cell death as evident by Propidium Iodide (PI) staining was observed when cancer cells were treated with the OP145 antibody (see panels b and e) in the presence of NHS, whereas the same antibody had no effect on the viability of normal human fibroblasts (see panel g). Control antibody to Cytochrome C shows no cytotoxicity (see panel c) beyond that observed in untreated cells (see panel a). Lack of cell death is manifested by no or little PI staining in panels a, c, d, f and g. The cell death marker PI was visualized using Olympus FluoView FV 1000 Confocal Laser Scanning Biological Microscope built on the Olympus 1X81 Inverted Microscope. (B) Rodent pancreatic cancer cells were treated with anti-HDM2 antibodies and control cytochrome C antibody. Extensive cell death as evident by Propidium Iodide (PI) staining was observed when cells were treated with anti-HDM2 antibodies, N-20 (polyclonal, sc-813 N-20, rabbit IgG, from Santa Cruz, "N-20") or C-18 (polyclonal, sc-812 C-18, rabbit IgG; from Santa Cruz; "C-18") (see panels b and e), whereas, no cytotoxicity was observed when cells were treated with anti-HDM2 monoclonal OP46 antibody (OP46 (Ab-1); mouse IgG1; from Calbiochem; "OP46") (see panel d) or control Cytochrome C antibody (see panel e). (C) M(H)DM2-specific antibodies are cytotoxic to pancreatic cancer MiaPaCa-2 cells in the presence of NHS. Quantitative representations of M(H)DM2-specific antibody-dependent complement cytotoxicity against human pancreatic cancer cells. Cells treated with anti-M(H)DM2 (C-18) antibody in the presence of NHS demonstrated cytotoxicity over 15-30 min post-treatment, whereas anti-HDM2 OP46 shows no cytotoxic effect beyond that observed when cells were treated with control anti-Cytochrome C antibody or when cells were treated with NHS in the absence of anti-M(H)DM2 antibodies.

Figure 26:
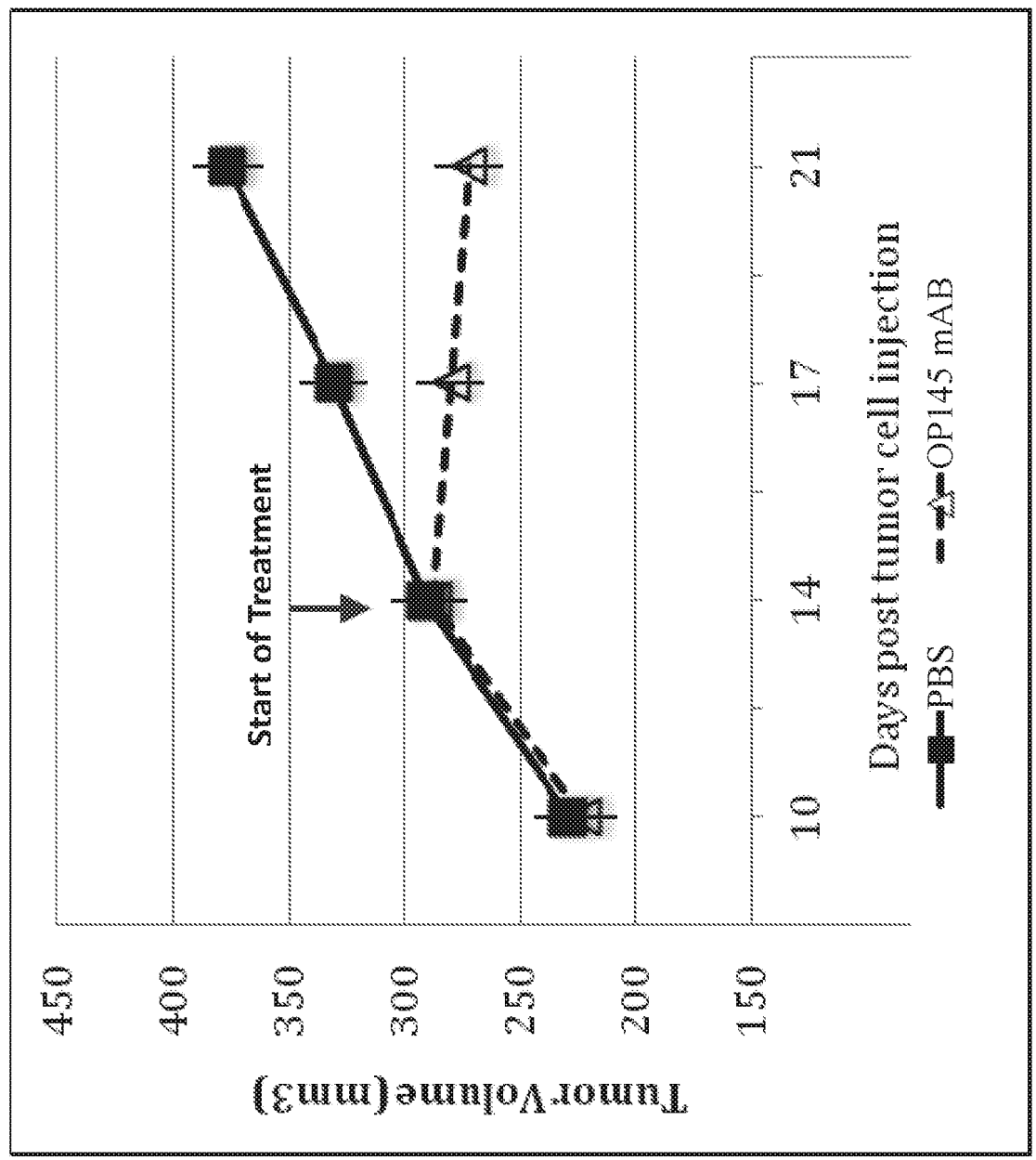

FIG. 26 shows the tumor size of mice treated with anti-HDM2 antibody OP145 and the tumor size of mice treated with PBS control (in Panc02 syngeneic mouse model of pancreatic cancer). The x axis shows days after tumor cell injection into the mice. The y axis shows tumor volume in mm³. The arrow shows the day on which the treatment was started.

Figure 27:
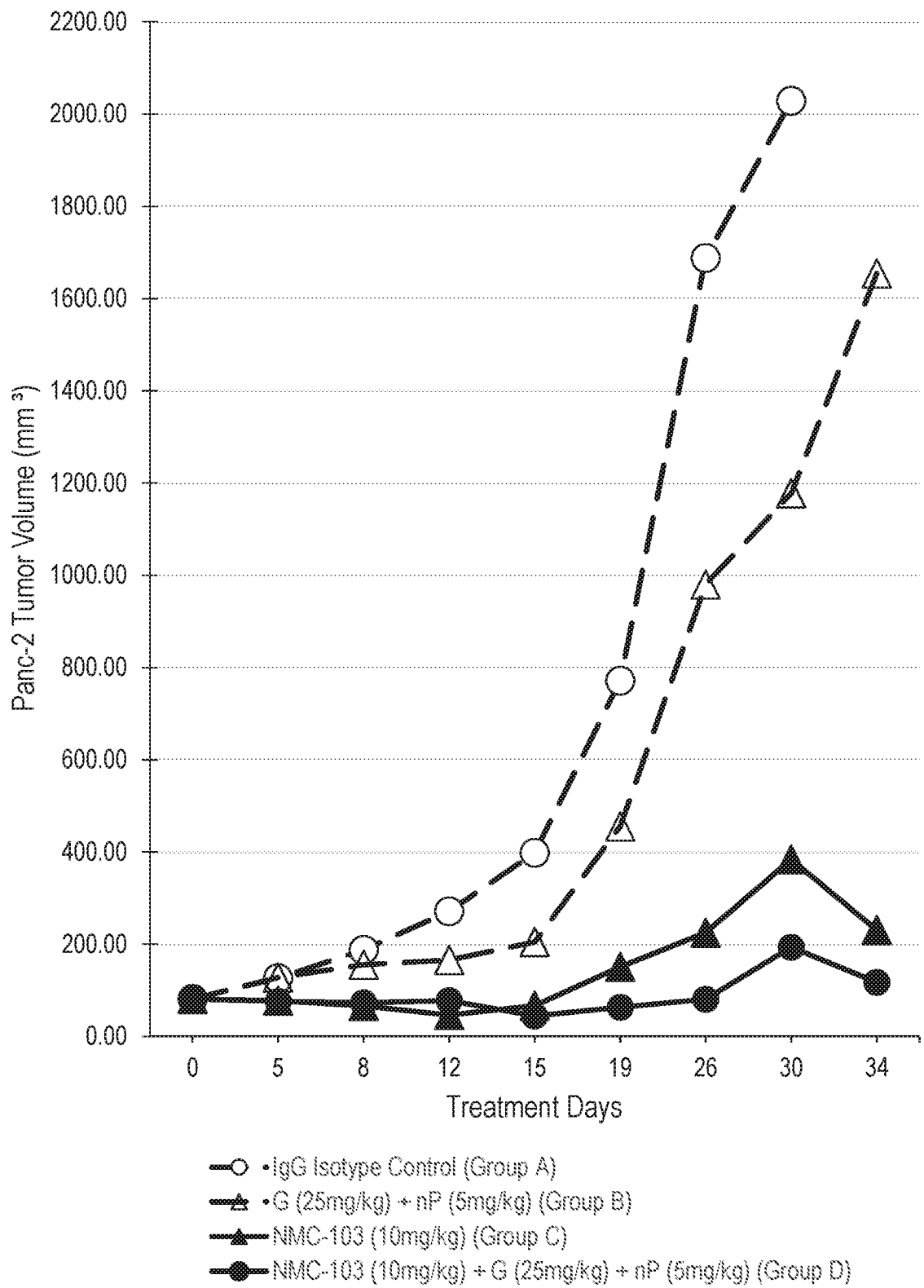

FIG. 27 depicts the effect of monoclonal antibody NMC-103 alone (10 mg/kg), a combination of low dose Gemcitabine (25 mg/kg) and nab-Paclitaxel (5 mg/kg), a combination of low dose Gemcitabine (25 mg/kg), nab-Paclitaxel (5 mg/kg) and NMC-103 (10 mg/kg), and isotype control mouse IgG1 (10 mg/kg), respectively, on tumor volume of the Panc-2 syngeneic mouse model of pancreatic cancer (number of mice/group=8). Treatment in this study started when tumors in mice reached approximately 80-100 mm³.

Figure 28:
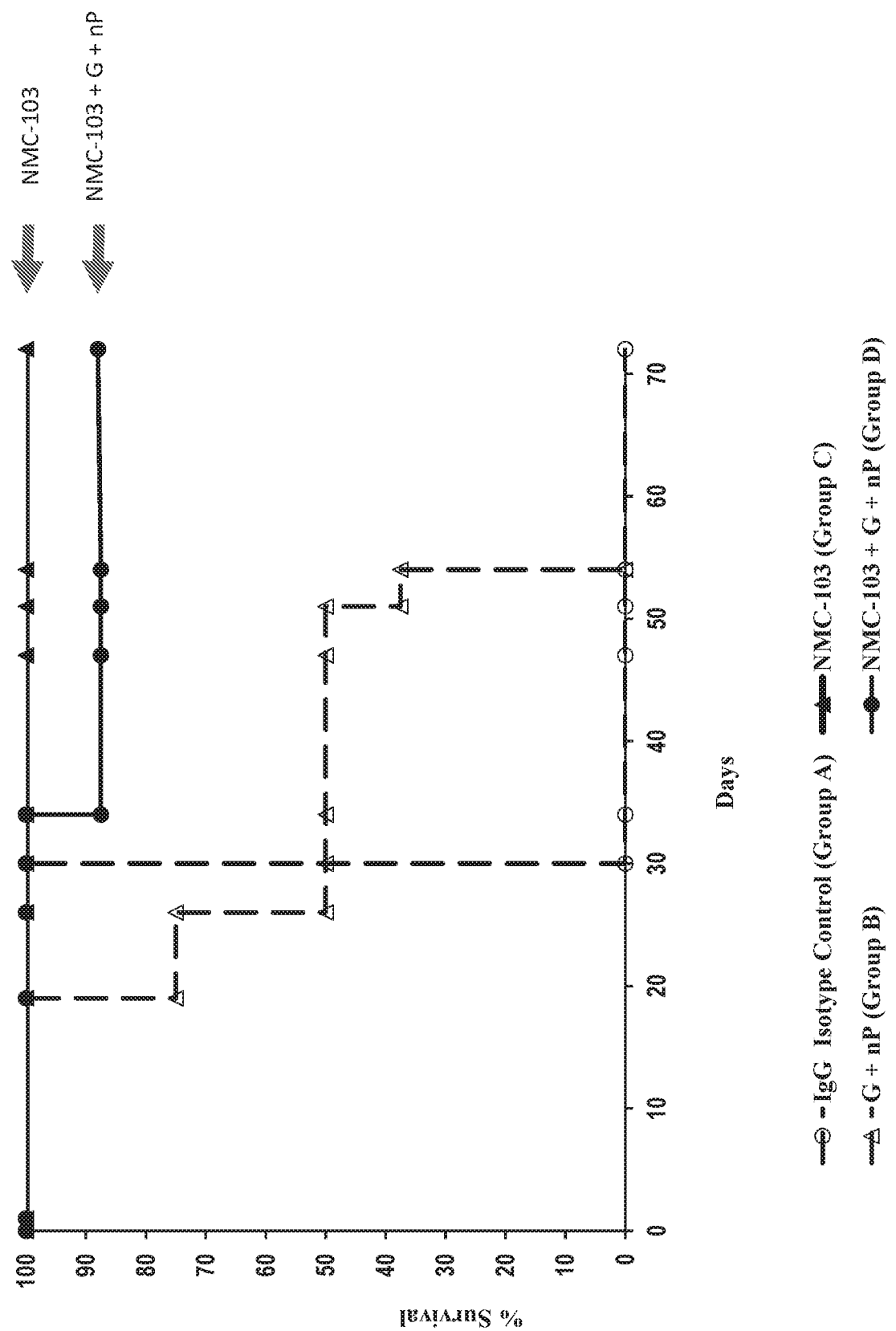

FIG. 28 depicts a Kaplan Meier survival analysis demonstrating survival benefit in mice that received NMC-103 alone or in combination with chemotherapy when compared to chemotherapy alone or control antibody under the experimental conditions described in FIG. 27.

Figure 29:
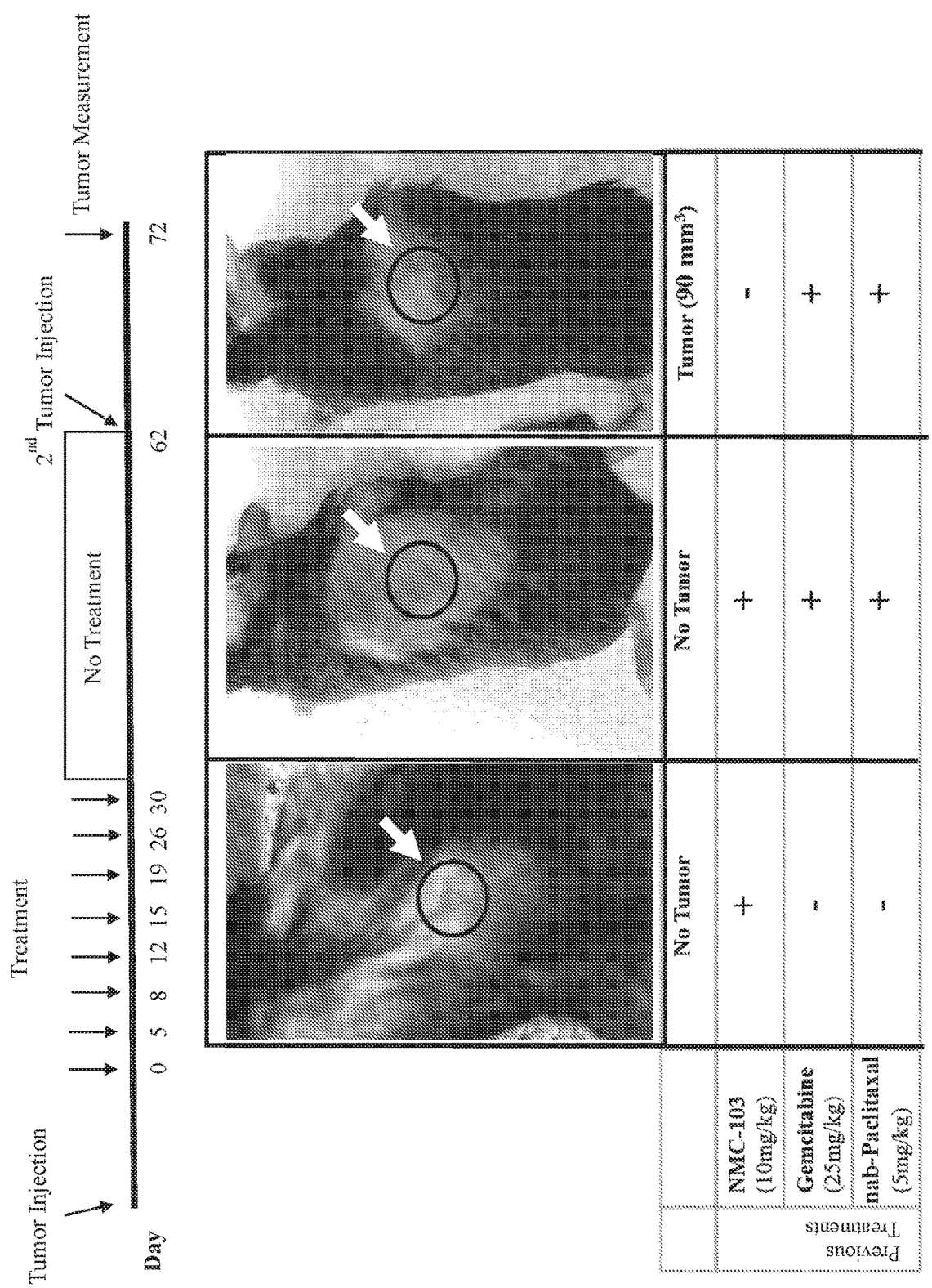

FIG. 29 shows that mice previously treated with NMC-103 as described in FIG. 27, become immune to tumor re-challenging after drug withdrawal. To evaluate the long-term anti-tumor effect of NMC-103, at 62 days after the start of the study, mice that had previously received with a combination of G+nP, mice in group C (mice that had been previously treated with NMC-103) and group D (mice that had been previously treated with a combination of NMC-103+G+nP) were re-challenged by a second round of Panc-2 inoculation (subcutaneous injection of 2×10⁶ cells/mouse), on the left dorsal flank. Tumor growth was monitored for 10 days at which point, a tumor of 90 mm³ was measured in the mice from group B. No tumor was observed in mice from the two groups that had previously received NMC-103 antibody (Groups C and D).

Figure 30:
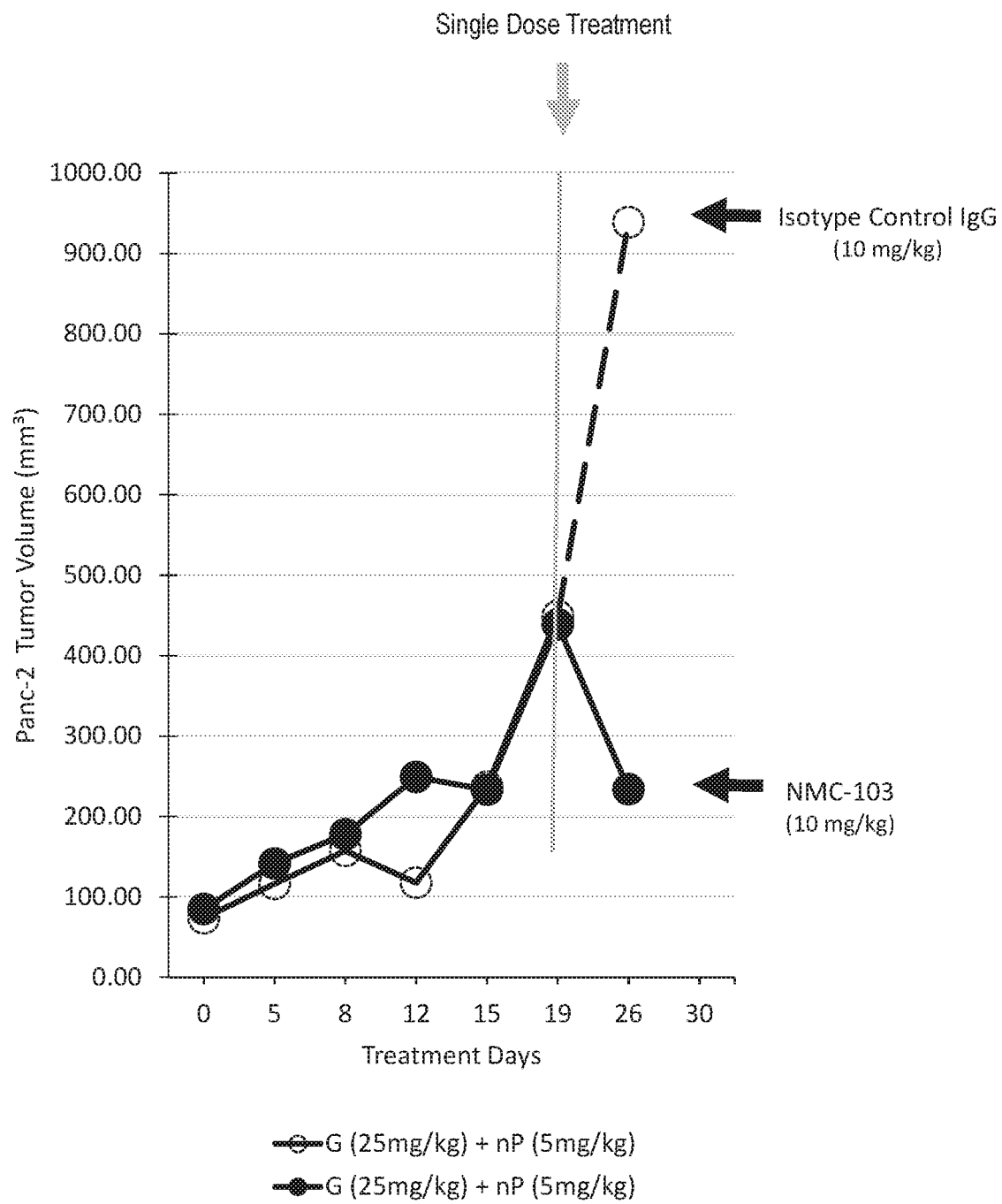

FIG. 30 depicts the effect of a single dose of monoclonal antibody NMC-103 (10 mg/kg) or isotype control mouse IgG1 (10 mg/kg), when added to a treatment regimen of a combination of low dose Gemcitabine (25 mg/kg) and nab-Paclitaxel (5 mg/kg), in the treatment of large size tumors (i.e. advanced cancers) on tumor volume of the Panc-2 syngeneic mouse model of pancreatic cancer. Mice were treated with pancreatic cancer standard of care (Gemcitabine (25 mg/kg)+nab-Paclitaxel (5 mg/kg)) for 19 days at which point they reached a tumor size of approximately 450 mm³. Mice were then randomly divided in 2 groups that received a single dose of an isotype control mouse IgG1 (10 mg/kg) or NMC-103 (10 mg/kg). As shown in this figure, a single i.p. injection of NMC-103 reduced the tumor size by almost half 6 days post treatment (from 438 mm³ to 233 mm³).

Figure 31:
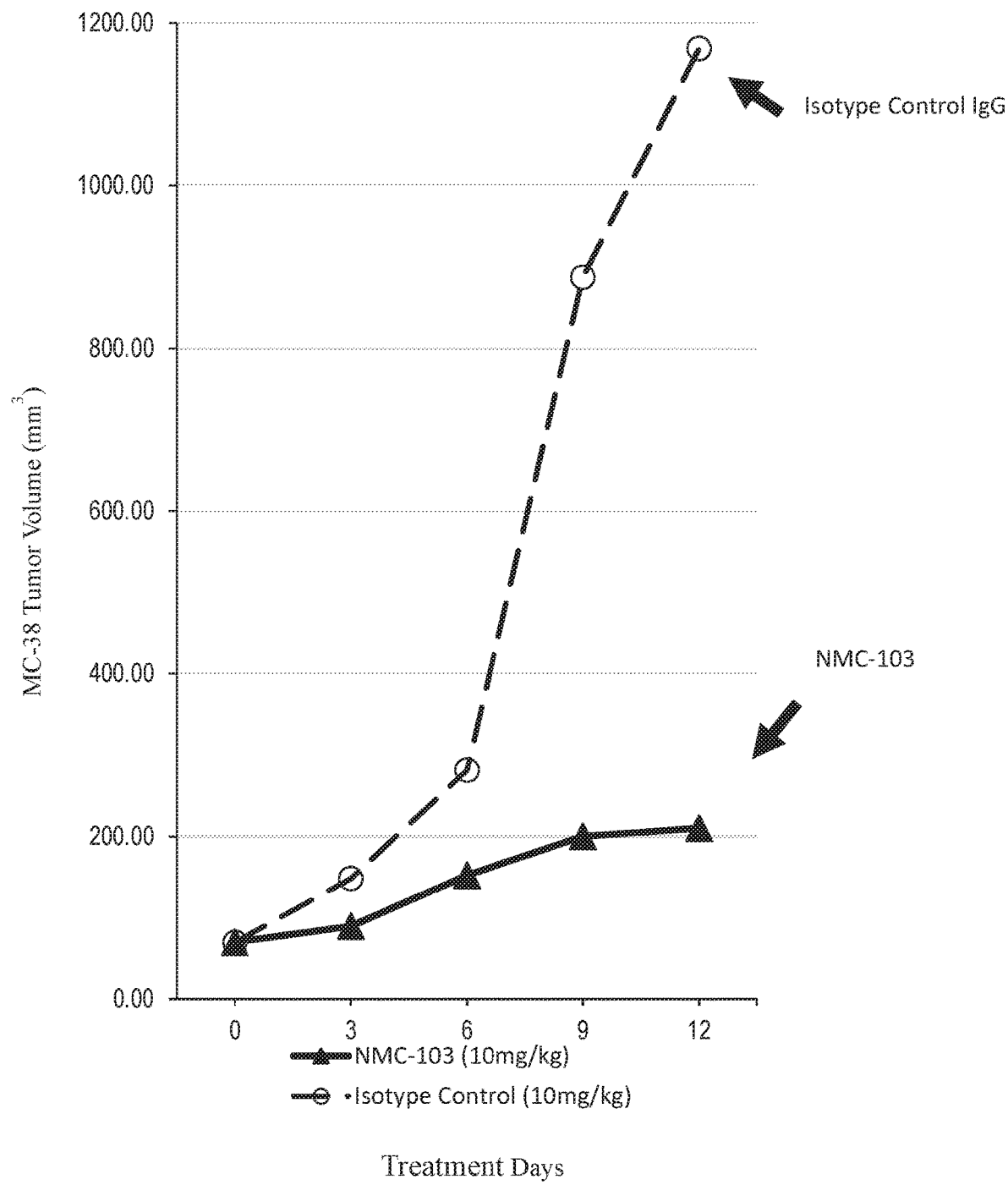

FIG. 31 depicts the effect of monoclonal antibody NMC-103 on tumor volume of the MC-38 syngeneic mouse model of colon cancer. As shown in this figure, mice treated with NMC-103 at 10 mg/kg, 2 times per week for 2 weeks reached an average tumor size of 210 mm³, while mice in the group that were treated with isotype control antibody at 10 mg/kg grew rapidly and reached 1168 mm³ by day 12. When compared to mice treated with NMC-103 at 0.4 mg/kg (FIG. 17), these data support the dose-dependent anti-tumor effect of NMC-103 antibody.

Figure 32A:
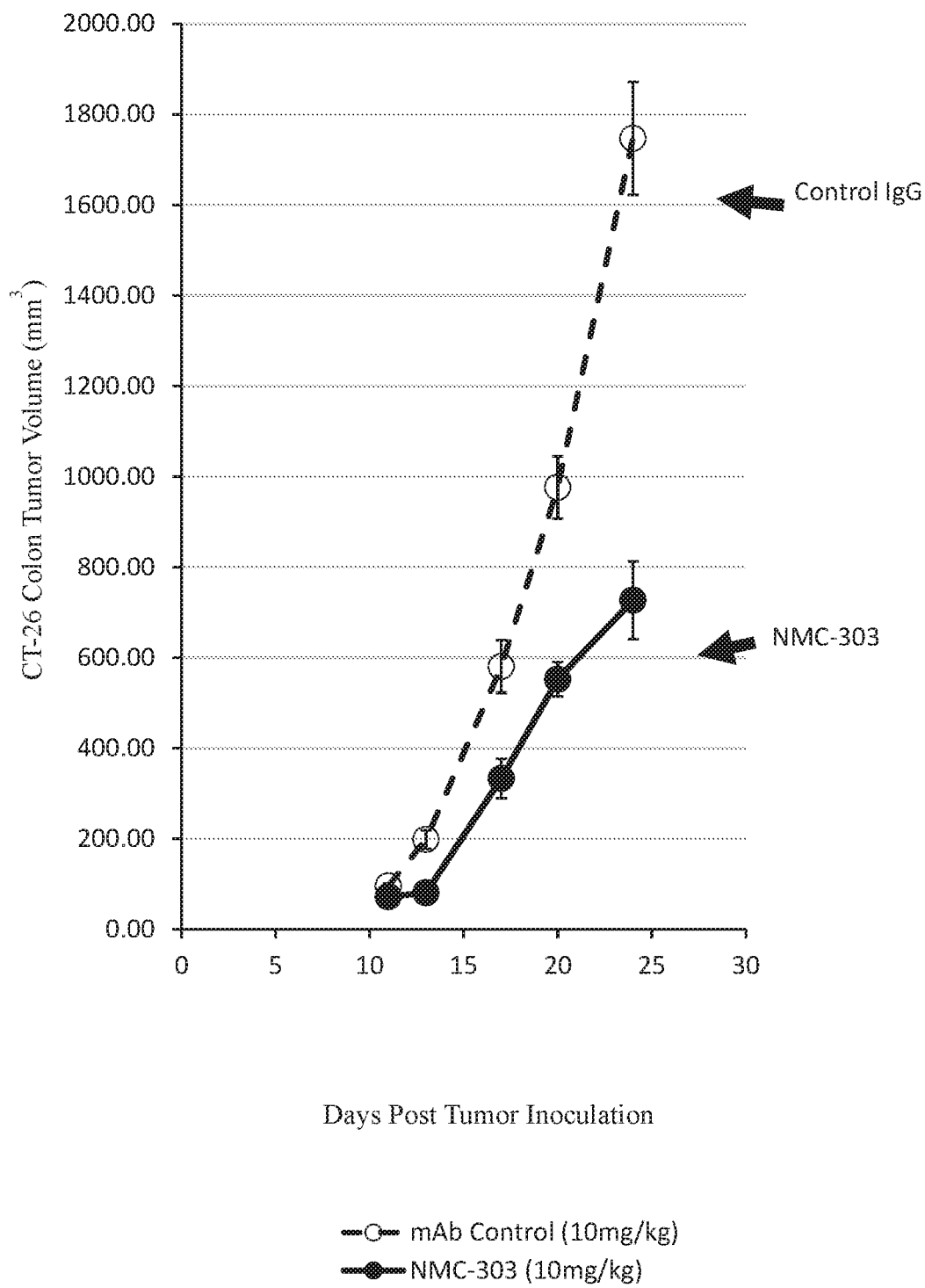
Figure 32B:
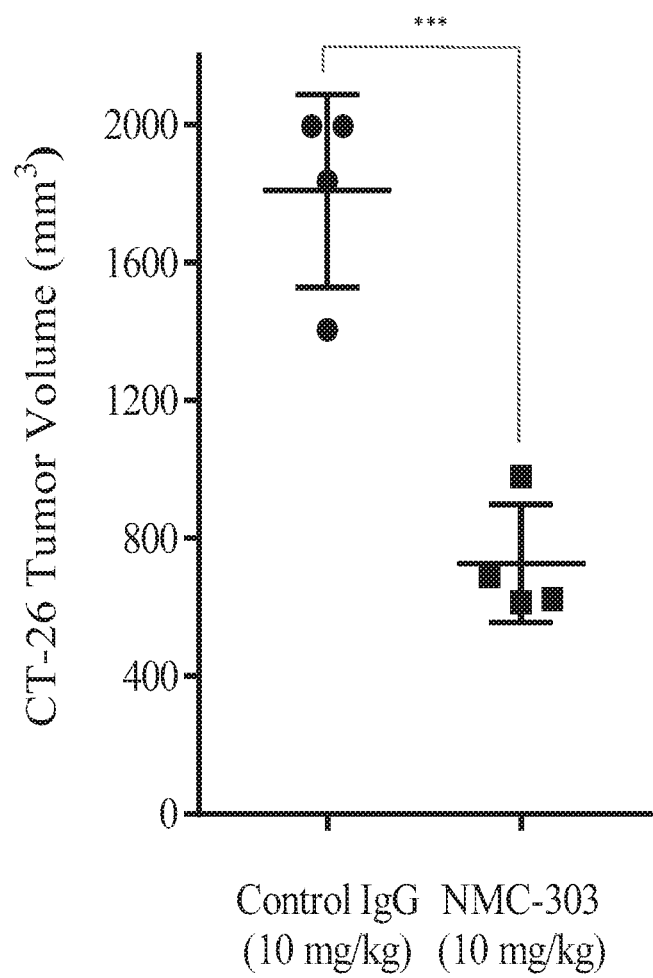

FIGS. 32A and 32B depict the effect of a chimeric version of monoclonal antibody NMC-303. Isotype class-switching was performed on a mouse NMC-303 to convert it from a mouse IgM to a chimeric IgG1. The mouse Heavy and Light chain variable regions were cloned into a human Ig gamma-1 chain and human Ig kappa chain as constant region. A total of eight (8) BALB/c mice were injected subcutaneously with CT-26. Mice were then divided into two groups (n=4) that received: A) control antibody (10 mg/kg) or B) chimeric version of NMC-303 antibody (10 mg/kg) two times a week for 3 weeks. FIG. 32A shows that by day 24 post tumor inoculation, mice treated with chimeric version of NMC-303 (10 mg/kg) reached an average tumor size of 726 mm3, while mice treated with control antibody (10 mg/kg) had an average tumor size of 1746 mm3. Furthermore, FIG. 32B shows the individual mouse tumor sizes on day 24 post tumor inoculation.

7. DETAILED DESCRIPTION

Provided herein are antibodies or antigen-binding fragments thereof that specifically bind to an extracellularly accessible epitope of M(H)DM2/4 (e.g., HDM2). In a specific embodiment, the extracellularly accessible epitope is contained within SEQ ID NO:1, SEQ ID NO:2, or SEQ ID NO:3. Antibodies provided herein are described in Section 5.1, below. Also provided herein are antibody-drug conjugates comprising an antibody or fragment that specifically binds to an extracellularly accessible epitope of M(H) DM2/4 (e.g., HDM2) described herein bound (e.g., covalently) to a cytotoxic drug. Also provided herein are antibodies or antigen-binding fragments thereof that specifically bind to an extracellularly accessible epitope of M(H)DM2/4 (e.g., HDM2), wherein said antibodies or fragments are not bound to a cytotoxic component.

Also provided herein are pharmaceutical compositions comprising an antibody or fragment that specifically binds to an extracellularly accessible epitope of M(H)DM2/4 (e.g., HDM2) described herein. In certain embodiments, such pharmaceutical compositions comprise a therapeutically effective amount of such antibody or fragment (i.e., an amount that can be used to treat a cancer in a subject, e.g. by achieving one or more anti-tumor effects described herein).

Also provided herein are nucleic acids encoding the antibodies and antigen-binding fragments described herein. In certain embodiments, provided herein are vectors and cells comprising nucleic acids encoding such antibodies or antigen-binding fragments thereof. Cells recombinantly producing the antibodies or antigen-binding fragments thereof described herein are also provided.

Chimeric antigen receptors (CARs) are engineered receptors that provide both antigen binding and immune cell activation functions (Sadelain et al., 2013, Cancer Discovery 3:388-398). Also provided herein are CARs comprising a single-chain variable fragment (scFv) that specifically binds to an extracellularly accessible epitope of M(H)DM2/4, such as a scFv comprising the VH and VL of an anti-M(H)DM2/4 antibody described herein, fused via a linker to a transmembrane domain (e.g., of CD3 zeta) fused to an intracellular T cell activation domain such as CD3 zeta intracellular domain, optionally further fused to a co-stimulatory domain (e.g., CD28 intracellular domain). T cells expressing such CARs are also provided.

Also provided herein is a peptide, the amino acid sequence of which is MCNTNMSVPTDGAVT (SEQ ID NO:1), TTSQIPASEQE (SEQ ID NO:2), or CPVCRQPIQMIVLTYFP (SEQ ID NO:3). The peptide can be, for example, synthetic or recombinant. In some embodiments, the peptide is purified. In some embodiments, the peptide is labeled with a detectable marker (e.g., a fluorescent marker or an isotope). In some embodiments, the peptide is tagged (e.g., with a GST, His, Strep, myc, FLAG, or HA tag). In some embodiments, a cysteine is added at one of the ends of the peptide (which may allow for linkage to a carrier protein). In some embodiments, the peptide is linked to a carrier protein (e.g., linked to Keyhole limpet hemocyanin (KLH), bovine serum albumin (BSA), ovalbumin, thyroglobulin, tetanus toxoid, or diphtheria toxoid). Also provided herein are nucleic acids encoding a peptide described herein. Also provided herein are vectors and cells comprising a nucleic acid encoding a peptide described herein. Cells recombinantly producing a peptide described herein are also provided. Also provided herein are uses of the peptides described herein as immunogens. The peptides of SEQ ID NO: 1, SEQ ID NO:2, and SEQ ID NO: 3 described herein contain extracellularly accessible epitopes of MDM2 and HDM2. In particular, provided herein are methods of making an anti-M(H)DM2/4 antibody (e.g., an antibody that specifically binds to M(H)DM2/4) by immunizing an animal (e.g., a mouse or a rabbit) with a peptide described herein. Also provided herein are methods of screening antibodies for binding to one or more of the peptides described herein (for example, using ELISA with a plate-bound peptide). Also provided herein are methods of identifying an anti-M(H)DM2/4 antibody suitable for therapeutic use in treating cancer or preventing metastasis, or suitable for use in diagnosis of cancer, by contacting an anti-M(H)DM2/4 antibody with a peptide described herein under conditions suitable for binding between the antibody and the peptide, and detecting or measuring binding between the antibody and the peptide that occurs, where the detection of binding between the antibody and the peptide indicates that the antibody is suitable for the therapeutic or diagnostic use. For example, provided herein are methods of identifying an anti-M(H)DM2/4 antibody suitable for therapeutic use by contacting an anti-M(H)DM2/4 antibody with a peptide described herein under conditions suitable for binding between the antibody and the peptide, and detecting or measuring binding between the antibody and the peptide that occurs, and, if the binding between the antibody and the peptide is detected, using the antibody in the methods of treating cancer described herein. In another example, provided herein are methods of identifying an anti-M(H)DM2/4 antibody suitable for diagnostic use by contacting an anti-M(H)DM2/4 antibody with a peptide described herein under conditions suitable for binding between the antibody and the peptide, and detecting or measuring binding between the antibody and the peptide that occurs, and, if the binding between the antibody and the peptide is detected, using the antibody in the methods of diagnosing cancer described herein.

Also provided herein are methods for treating cancer, inhibiting tumor growth or proliferation, inhibiting tumor progression, and/or preventing metastases in a subject by administering to the subject an anti-M(H)DM2/4 antibody or fragment described herein, in particular, an antibody or a fragment thereof that specifically binds to an extracellularly accessible epitope of M(H)DM2/4 (in particular, a region exposed on the plasma membrane surface of cancer cells). Preferably the antibody or fragment thereof specifically binds to an extracellularly accessible epitope of HDM2 (in particular, a region exposed on the plasma membrane surface of cancer cells). In certain embodiments, the antibody or fragment (e.g., for use in the methods described herein) does not bind or only minimally binds to the plasma membrane surface of normal cells of the tissue type from which the cancer in the subject originates.

Where the subject being treated is a human, in certain embodiments, an antibody or a fragment thereof used herein specifically binds to an extracellularly accessible epitope of HDM2 and/or HDM4 (a region exposed on the plasma membrane surface of cancer cells). In one embodiment of treating a human, an antibody or a fragment thereof used herein specifically binds to an extracellularly accessible epitope of HDM2 (a region exposed on the plasma membrane surface of cancer cells) (optionally, such antibody or fragment that does not bind to HDM4). In one embodiment of treating a human, an antibody or a fragment thereof used herein specifically binds to an extracellularly accessible epitope of HDM4 (a region exposed on the plasma membrane surface of cancer cells) (optionally, such antibody or fragment that does not bind to HDM2).

Where the subject is a non-human animal (e.g., a mammal such as a dog or a cat), an antibody or a fragment thereof used herein binds to an extracellularly accessible epitope of M(H)DM2/4 (a region exposed on the plasma membrane surface of cancer cells), where the M(H)DM2/4 is a homologue of HDM2 and/or HDM4 expressed in such animal. In one embodiment, an antibody or a fragment thereof used herein binds to an extracellularly accessible epitope of M(H)DM2 (a region exposed on the plasma membrane surface of cancer cells), where the M(H)DM2 is a homologue of HDM2 expressed in such animal (optionally, such antibody or fragment does not bind to M(H)DM4). In one embodiment, an antibody or a fragment thereof used herein binds to an extracellularly accessible of M(H)DM4 (a region exposed on the plasma membrane surface of cancer cells), where the M(H)DM4 is a homologue of HDM4 expressed in such animal (optionally, such antibody or fragment does not bind to M(H)DM2).

The description of the invention that follows is largely in terms of HDM2 and antibodies and antibody fragments thereto, which shall be understood to be for use in treating a human; it will be clear to one skilled in the art that the description also should be deemed applicable to: (i) HDM4 and antibodies and antibody fragments thereto, and use thereof for treatment of humans (unless indicated otherwise explicitly or by context), and (ii) M(H)DM2/4 and antibodies and antibody fragments thereto, and use thereof for treatment of non-human animals, e.g., mammals (unless indicated otherwise explicitly or by context). In preferred embodiments, the patients or subjects being treated using the methods described herein are human.

In preferred embodiments, the anti-HDM2 antibody or a fragment thereof used in accordance with the methods described herein mediates complement-dependent cytotoxicity (CDC), mediates antibody-dependent cell-mediated cytotoxicity (ADCC), and/or is bound to a cytotoxic drug or drugs (e.g., is an antibody-drug conjugate). In preferred embodiments, the invention provides for the use of antibodies that mediate complement-dependent cytotoxicity (CDC) and antibody-dependent cell-mediated cytotoxicity (ADCC).

In certain embodiments, the anti-HDM2 antibody or a fragment thereof used in accordance with the methods described herein is not bound to a cell-penetrating peptide. Cell penetrating peptides can insert into a cell plasma membrane and transport molecules to which they are attached into the cell. Such cell-penetrating peptides include, without limitation, a membrane resident peptide (MRP), Membrane Transduction Domain of Antennapedia, trans-activating transcriptional activator (TAT), and a Penetratin peptide. In certain embodiments, the anti-HDM2 antibody or a fragment thereof used in accordance with the methods described herein is not attached to a membrane resident peptide (MRP), Membrane Transduction Domain of Antennapedia, TAT, and/or a Penetratin peptide. In certain embodiments, the anti-HDM2 antibody or a fragment thereof used in accordance with the methods described herein is not attached to any peptide sequence that can insert into the lipid bilayer of the plasma membrane of cells. In one embodiment, the anti-HDM2 antibody or a fragment thereof used in accordance with the methods described herein is not attached to an MRP. In one embodiment, the anti-HDM2 antibody or a fragment thereof used in accordance with the methods described herein is not attached to a Penetratin peptide.

The examples set forth herein demonstrate that HDM-2 targeting antibodies alone are selectively cytotoxic to cancer cells. Further, as set forth in the examples herein, it has been demonstrated that extracellularly accessible epitopes of HDM2 are appropriate therapeutic targets for anti-HDM2 antibodies, and that cancer cells expressing HDM2 on their surface can be successfully targeted and destroyed with antibodies to such extracellular regions of HDM2. In particular, the data presented in the examples demonstrate that select HDM2-specific antibodies can bind to the extracellularly accessible sequences of HDM2 on the surface membrane of intact cancer cells, while exhibiting minimal binding to the surface membrane of normal human blood mononuclear cells. In addition, the data presented in the examples show that such HDM2-specific antibodies can inhibit the growth of cancer cells in vitro and in vivo, strongly suggesting that they can be used as therapeutic agents in vivo. Further, the data presented in the examples show that such HDM2-specific antibodies can have a synergistic anti-tumor effect when combined with chemotherapeutic drugs.

7.1 Antibodies

Provided herein are antibodies or antigen-binding fragments thereof that (immuno) specifically bind to an extracellularly accessible epitope of M(H)DM2/4 (e.g., HDM2) (a region exposed on the plasma membrane surface of cells). "Specifically bind[s]/binding" as those terms are used herein does not exclude cross-reactivity of the antibody or antigen-binding fragment; thus, for example, antibodies or antigen-binding fragments thereof that (immuno) specifically bind to an extracellularly accessible epitope of HDM2 exposed on the plasma membrane surface of cells may also specifically bind to (cross-react with) MDM2. In particular, provided herein are anti-M(H)DM2/4 antibodies and fragments thereof that (immuno) specifically bind to an extracellularly accessible epitope of M(H)DM2/4 and that have an anti-tumor effect (e.g., inhibit tumor growth in vivo). In specific embodiments, an antibody or an antigen-binding fragment thereof specifically binds an epitope of M(H)DM2/4 that is extracellularly accessible on cancer cells but not on non-cancer cells (e.g., non-cancerous cells of the same organ type or tissue type as the cancer cells). In other specific embodiments, an antibody or an antigen-binding fragment thereof specifically binds an epitope of M(H)DM2/4, exposure or accessibility of which on the plasma membrane surface of cancer cells is increased relative to its exposure or accessibility on the plasma membrane surface of non-cancer cells (e.g., non-cancerous cells of the organ or tissues of the host). Also provided herein are antibodies or antigen-binding fragments thereof that (immuno) specifically bind to an extracellularly accessible epitope of M(H)DM2/4 (e.g., HDM2), which are not bound to a cell-penetrating peptide (e.g., a membrane resident peptide).

Also provided herein are antibodies or antigen-binding fragments thereof that (immuno) specifically bind to M(H)DM2/4 (e.g., HDM2), in particular to an extracellularly accessible epitope of M(H)DM2/4, wherein the antibody or fragment specifically binds to a peptide the sequence of which peptide consists of MCNTNMS VPTDGAVT (SEQ ID NO:1), TTSQIPASEQE (SEQ ID NO:2), or CPVCRQPIQMIVLTYFP (SEQ ID NO:3). In certain embodiments, provided herein are antibodies or antigen-binding fragments thereof that (immuno) specifically bind to M(H)DM2/4 (e.g., HDM2), in particular to an extracellularly accessible epitope of M(H)DM2/4 wherein the antibody or fragment specifically binds to a peptide the sequence of which peptide consists of MCNTNMSVPTDGAVT (SEQ ID NO:1), TTSQIPASEQE (SEQ ID NO:2), or CPVCRQPIQMIVLTYFP (SEQ ID NO:3); and wherein such antibodies or fragments have an anti-tumor effect in vivo, and/or wherein such antibodies or fragments are not bound to a cell-penetrating peptide.

Also provided herein are anti-M(H)DM2/4 antibodies and fragments having heavy chain variable regions and/or light chain variable regions described herein (see, e.g., having sequences of heavy chain variable regions and/or light chain variable regions of antibodies NMC-103, NMC-204 and NMC-303 provided herein, see, e.g., Section 8 and FIGS. 20-22). Also provided herein are anti-M(H)DM2/4 antibodies and fragments having one or more complementarity determining regions (CDRs) described herein (see, e.g., CDRs provided in Tables 4-9 and FIGS. 20-22).

CDRs are defined in various ways in the art, including the Kabat, Chothia, AbM, Contact, and IMGT. In certain aspects, the CDRs of an antibody can be defined according to the Kabat system, which is based on sequence variability (see, e.g., Kabat E A & Wu T T (1971) Ann NY Acad Sci 190: 382-391; Kabat E A et al, (1991) Sequences of Proteins of Immunological Interest, Fifth Edition, U.S. Department of Health and Human Services, NIH Publication No. 91-3242. In a specific embodiment, with respect to the Kabat system, (i) the VH CDR1 is present at amino acid positions 31 to 35 of the heavy chain; (ii) the VH CDR2 is present at amino acid positions 50 to 68 or 50 to 66 of the heavy chain; and (iii) the VH CDR3 is present at amino acid positions 101 to 105 or 99 to 104 or 99 to 106 of the heavy chain. In a specific embodiment, with respect to the Kabat system, (i) the VL CDR1 is present at amino acid positions 24 to 39 or 24 to 34 of the light chain; (ii) the VH CDR2 is present at amino acid positions 55 to 61 or 50 to 56 of the light chain; and (iii) the V H CDR3 is present at amino acid positions 94 to 102 or 89 to 97 of the light chain. As is well known to those of skill in the art, with respect to the Kabat system, the actual linear amino acid sequence of the antibody variable domain can contain fewer or additional amino acids due to a shortening or lengthening of a framework region (FR) and/or CDR and, as such, an amino acid's Kabat number is not necessarily the same as its linear amino acid number. The Kabat CDR positions may vary depending on the antibody, and may be determined according to methods known in the art. In a specific embodiment, the CDRs of the antibodies described herein are determined using the Kabat system.

In certain aspects, the CDRs of an antibody can be defined according to the Chothia system, which is based on the location of immunoglobulin structural loop regions (see, e.g., Chothia C & Lesk A M, (1987), J Mol Biol 196: 901-917; Al-Lazikani B et al., (1997) J Mol Biol 273: 927-948; Chothia C et al, (1992) J Mol Biol 227: 799-817; Tramontano A et al, (1990) J Mol Biol 215(1): 175-82; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Dübel, eds., Chapter 31, pp. 422-439, Springer-Verlag, Berlin (2001)). In a specific embodiment, with respect to the Chothia system, using the Kabat numbering system of numbering amino acid residues in the VH region, (i) the VH CDR1 is present at amino acid positions 26 to 32 of the heavy chain; (ii) the VH CDR2 is present at amino acid positions 52 to 59 or 52 to 57 of the heavy chain; and (iii) the VH CDR3 is present at amino acid positions 101 to 105 or 99 to 104 or 99 to 106 of the heavy chain. In a specific embodiment, with respect to the Chothia system, using the Kabat numbering system of numbering amino acid residues in the VL region, (i) the VL CDR1 is present at amino acid positions 24 to 39 or 24 to 34 of the light chain; (ii) the VL CDR2 is present at amino acid positions 55 to 61 or 50 to 56 of the light chain; and (iii) the VL CDR3 is present at amino acid positions 94 to 102 or 89 to 97 of the light chain. The Chothia CDR positions may vary depending on the antibody, and may be determined according to methods known in the art. In a specific embodiment, the CDRs of the antibodies described herein are determined using the Chothia system.

In certain aspects, the CDRs of an antibody can be defined according to the AbM system, which is based on AbM hypervariable regions that represent a compromise between the Kabat CDRs and Chothia structural loops, and where CDRs are determined using Oxford Molecular's AbM antibody modeling software (Oxford Molecular Group, Inc.). In a specific embodiment, with respect to the AbM system, using the Kabat numbering system of numbering amino acid residues in the VH region, (i) the VH CDR1 is present at amino acid positions 26 to 35 of the heavy chain; (ii) the VH CDR2 is present at amino acid positions 50 to 61 or 50 to 59 of the heavy chain; and (iii) the VH CDR3 is present at amino acid positions 101 to 105 or 99 to 104 or 99 to 106 of the heavy chain. In a specific embodiment, with respect to the AbM system, using the Kabat numbering system of numbering amino acid residues in the VL region, (i) the VL CDR1 is present at amino acid positions 24 to 39 or 24 to 34 of the light chain; (ii) the VH CDR2 is present at amino acid positions 55 to 61 or 50 to 56 of the light chain; and (iii) the VH CDR3 is present at amino acid positions 94 to 102 or 89 to 97 of the light chain. The AbM CDR positions may vary depending on the antibody, and may be determined according to methods known in the art. In a specific embodiment, the CDRs of the antibodies described herein are determined using the AbM numbering system.

In certain aspects, the CDRs of an antibody can be defined according to the EVIGT system (see "IMGT®, the international ImMunoGeneTics information system® website imgt.org, founder and director: Marie-Paule Lefranc, Montpellier, France; see, e.g., Lefranc, M.-P., 1999, The Immunologist, 7:132-136 and Lefranc, M.-P. et al., 1999, Nucleic Acids Res., 27:209-212, both of which are incorporated herein by reference in their entirety). In a specific embodiment, with respect to the IMGT system, (i) the VH CDR1 is present at amino acid positions 27 to 33 or 26 to 33 of the heavy chain; (ii) the VH CDR2 is present at amino acid positions 51 to 60 or 51 to 58 of the heavy chain; and (iii) the VH CDR3 is present at amino acid positions 99 to 105 or 97 to 103 of the heavy chain. In a specific embodiment, with respect to the IMGT system, (i) the VL CDR1 is present at amino acid positions 27 to 37 of the light chain; (ii) the VH CDR2 is present at amino acid positions 55 to 57 of the light chain; and (iii) the VH CDR3 is present at amino acid positions 94 to 102 of the light chain. The IMGT CDR positions may vary depending on the antibody, and may be determined according to methods known in the art. In a specific embodiment, the CDRs of the antibodies described herein are determined using the IMGT system.

In certain aspects, the CDRs of an antibody can be defined according to the Contact system. The Contact definition is based on an analysis of the available complex crystal structures (bioinf.org.uk/abs) (see MacCallum R M et al., (1996) J Mol Biol 5: 732-745; see also, e.g., Martin A. "Protein Sequence and Structure Analysis of Antibody Variable Domains," in Antibody Engineering, Kontermann and Düebel, eds., Chapter 31, pp. 422-439, Springer-Verlag, Berlin (2001)). In a specific embodiment, with respect to the Contact system, using the Kabat numbering system of numbering amino acid residues in the VH region, (i) the VH CDR1 is present at amino acid positions 30 to 35 of the heavy chain; (ii) the VH CDR2 is present at amino acid positions 47 to 61 or 47 to 59 of the heavy chain; and (iii) the VH CDR3 is present at amino acid positions 99 to 104 or 97 to 103 or 97 to 105 of the heavy chain. In a specific embodiment, with respect to the Contact system, using the Kabat numbering system of numbering amino acid residues in the VL region, (i) the VL CDR1 is present at amino acid positions 30 to 41 or 30 to 36 of the light chain; (ii) the VH CDR2 is present at amino acid positions 51 to 60 or 46 to 55 of the light chain; and (iii) the VH CDR3 is present at amino acid positions 94 to 101 or 89 to 96 of the light chain. The Contact CDR positions may vary depending on the antibody, and may be determined according to methods known in the art. In a specific embodiment, the CDRs of the antibodies described herein are determined using the Contact system.

In a particular embodiment, provided herein are antibodies or fragments thereof that specifically bind to M(H)DM2/4 {e.g., HDM2) and comprise CDRs of any one of the antibodies described herein (any one of antibodies NMC-103, NMC-204, and NMC-303), which are defined according to any of the above-described systems.

In certain embodiments, provided herein are antibodies or antigen-binding fragments thereof that specifically bind to an extracellularly accessible epitope of M(H)DM2/4 (e.g., HDM2) and comprise a heavy chain variable region (VH) having one, two or all three VH CDRs (preferably all three VH CDRs) of any anti-HDM2 antibody described herein (such as NMC-103, NMC-204, or NMC-303). As is known in the art, VHs contain VH CDRs surrounded by framework regions (the CDR and FR sequences appear in the following sequence in the VH: FR1-VH CDR 1-FR2-VH CDR 2-FR3-VH CDR 3-FR4), optionally the framework regions are human framework regions. In certain embodiments, provided herein are antibodies or antigen-binding fragments thereof that specifically bind to an extracellularly accessible epitope of M(H)DM2/4 (e.g., HDM2) and comprise a heavy chain variable region (VH) having one, two or all three VH CDRs of a VH having the amino acid sequence of SEQ ID NO:36 (which is the VH of NMC-103). In certain embodiments, provided herein are antibodies or antigen-binding fragments thereof that specifically bind to an extracellularly accessible epitope of M(H)DM2/4 (e.g., HDM2) and comprise a heavy chain variable region (VH) having one, two or all three VH CDRs of a VH having the amino acid sequence of SEQ ID NO:38 (which is the VH of NMC-204). In certain embodiments, provided herein are antibodies or antigen-binding fragments thereof that specifically bind to an extracellularly accessible epitope of M(H)DM2/4 (e.g., HDM2) and comprise a heavy chain variable region (VH) having one, two or all three VH CDRs of a VH having the amino acid sequence of SEQ ID NO:40 (which is the VH of NMC-303). In certain embodiments, such antibody or fragment is a humanized antibody or fragment.

In certain embodiments, provided herein are antibodies or antigen-binding fragments thereof that specifically bind to an extracellularly accessible epitope of M(H)DM2/4 (e.g., HDM2) and comprise a light chain variable region (VL) having one, two or all three VL CDRs (preferably all three VL CDRs) of any anti-HDM2 antibody described herein (such as NMC-103, NMC-204, or NMC-303). As is known in the art, VLs contain VL CDRs surrounded by framework regions (the CDR and FR sequences appear in the following sequence in the VL: FR1-VL CDR 1-FR2-VL CDR 2-FR3-VL CDR 3-FR4); optionally the framework regions are human framework regions. In certain embodiments, provided herein are antibodies or antigen-binding fragments thereof that specifically bind to an extracellularly accessible epitope of M(H)DM2/4 (e.g., HDM2) and comprise a light chain variable region (VL) having one, two or all three VL CDRs of a VL having the amino acid sequence of SEQ ID NO:37 (which is the VL of NMC-103). In certain embodiments, provided herein are antibodies or antigen-binding fragments thereof that specifically bind to an extracellularly accessible epitope of M(H)DM2/4 (e.g., HDM2) and comprise a light chain variable region (VL) having one, two or all three VL CDRs of a VL having the amino acid sequence of SEQ ID NO:39 (which is the VL of NMC-204). In certain embodiments, provided herein are antibodies or antigen-binding fragments thereof that specifically bind to an extracellularly accessible epitope of M(H)DM2/4 (e.g., HDM2) and comprise a light chain variable region (VL) having one, two or all three VL CDRs of a VL having the amino acid sequence of SEQ ID NO:40 (which is the VL of NMC-303). In certain embodiments, such antibody or fragment is a humanized antibody or fragment.

In certain embodiments, provided herein are antibodies or antigen-binding fragments thereof that specifically bind to an extracellularly accessible epitope of M(H)DM2/4 (e.g., HDM2) and comprise a heavy chain variable region (VH) having one, two or all three VH CDRs (preferably all three VH CDRs) of any anti-HDM2 antibody described herein (such as NMC-103, NMC-204, or NMC-303) and comprise a light chain variable region (VL) having one, two or all three VL CDRs (preferably all three VL CDRs) of such anti-HDM2 antibody.

In certain embodiments, provided herein is an antibody or a fragment thereof that specifically binds to HDM2 and comprises a heavy chain variable region (VH) having one, two or all three VH CDRs identified in Table 4 (providing VH CDRs of NMC-103). In one embodiment, provided herein is an antibody or a fragment thereof that specifically binds to HDM2 and comprises a VH CDR3 ("CDR-H3") identified in Table 4. In certain embodiments, provided herein is an antibody or a fragment thereof that specifically binds to HDM2 and comprises a light chain variable region (VL) having one, two or all three VL CDRs identified in Table 5 (providing VL CDRs of NMC-103). In certain embodiments, provided herein is an antibody or a fragment thereof that specifically binds to HDM2 and comprises a heavy chain variable region (VH) having one, two or all three VH CDRs identified in Table 4; and comprises a light chain variable region (VL) having one, two or all three VL CDRs identified in Table 5.

In certain embodiments, provided herein is an antibody or a fragment thereof that specifically binds to HDM2 and comprises a heavy chain variable region (VH) having one, two or all three VH CDRs identified in Table 6 (providing VH CDRs of NMC-204). In one embodiment, provided herein is an antibody or a fragment thereof that specifically binds to HDM2 and comprises a VH CDR3 ("CDR-H3") identified in Table 6. In certain embodiments, provided herein is an antibody or a fragment thereof that specifically binds to HDM2 and comprises a light chain variable region (VL) having one, two or all three VL CDRs identified in Table 7 (providing VL CDRs of NMC-204). In certain embodiments, provided herein is an antibody or a fragment thereof that specifically binds to HDM2 and comprises a heavy chain variable region (VH) having one, two or all three VH CDRs identified in Table 6; and comprises a light chain variable region (VL) having one, two or all three VL CDRs identified in Table 7.

In certain embodiments, provided herein is an antibody or a fragment thereof that specifically binds to HDM2 and comprises a heavy chain variable region (VH) having one, two or all three VH CDRs identified in Table 8 (providing VH CDRs of NMC-303). In one embodiment, provided herein is an antibody or a fragment thereof that specifically binds to HDM2 and comprises a VH CDR3 ("CDR-H3") identified in Table 8. In certain embodiments, provided herein is an antibody or a fragment thereof that specifically binds to HDM2 and comprises a light chain variable region (VL) having one, two or all three VL CDRs identified in Table 9 (providing VL CDRs of NMC-303). In certain embodiments, provided herein is an antibody or a fragment thereof that specifically binds to HDM2 and comprises a heavy chain variable region (VH) having one, two or all three VH CDRs identified in Table 8; and comprises a light chain variable region (VL) having one, two or all three VL CDRs identified in Table 9.

In certain embodiments, provided herein is an antibody or fragment thereof that specifically binds to HDM2 comprising a VH of any antibody described herein, such as a VH of any antibody provided in Section 8 or FIGS. 20-22 (e.g., the VH of NMC-103, the VH of NMC-204, or the VH of NMC-303), or a VH having at least 75%, 80%, 85%, 90%, 95%, 98%, or 99% sequence identity thereto. In certain embodiments, provided herein is an antibody or fragment thereof that specifically binds to HDM2 comprising a VL of any antibody described herein, such as a VL of any antibody provided in Section 8 or FIGS. 20-22 (e.g., the VL of NMC-103, the VL of NMC-204, or the VL of NMC-303), or a VL having at least 75%, 80%, 85%, 90%, 95%, 98%, or 99% sequence identity thereto. In certain embodiments, substitutions, insertions, or deletions in these sequences occur in regions outside the CDRs (i.e., in the FRs).

In certain embodiments, provided herein is an antibody or fragment thereof that specifically binds to HDM2 comprising a VH and a VL of any antibody described herein, such as a VH and VL of any antibody provided in Section 8 or FIGS. 20-22 (e.g., the VH and VL of NMC-103, the VH and VL of NMC-204, or the VH and VL of NMC-303), or a VH and VL having at least 75%, 80%, 85%, 90%, 95%, 98%, or 99% sequence identity thereto.

In certain embodiments, provided herein is an antibody or fragment thereof that specifically binds to HDM2 comprising: (i) a VH having the amino acid sequence of SEQ ID NO:36, or a VH having at least 70%, 75%, 80%, 85%, 90%, 95%, 98%, 99% sequence identity thereto; and/or (ii) a VL having the amino acid sequence of SEQ ID NO:37, or a VL having at least 70%, 75%, 80%, 85%, 90%, 95%, 98%, 99% sequence identity thereto.

In certain embodiments, provided herein is an antibody or fragment thereof that specifically binds to HDM2 comprising: (i) a VH having the amino acid sequence of SEQ ID NO:38, or a VH having at least 70%, 75%, 80%, 85%, 90%, 95%, 98%, 99% sequence identity thereto; and/or (ii) a VL having the amino acid sequence of SEQ ID NO:39, or a VL having at least 70%, 75%, 80%, 85%, 90%, 95%, 98%, 99% sequence identity thereto.

In certain embodiments, provided herein is an antibody or fragment thereof that specifically binds to HDM2 comprising: (i) a VH having the amino acid sequence of SEQ ID NO:40, or a VH having at least 70%, 75%, 80%, 85%, 90%, 95%, 98%, 99% sequence identity thereto; and/or (ii) a VL having the amino acid sequence of SEQ ID NO:41, or a VL having at least 70%, 75%, 80%, 85%, 90%, 95%, 98%, 99% sequence identity thereto.

In certain aspects, provided herein are antibodies or fragments thereof that specifically bind to M(H)DM2/4 (e.g., HDM2) and comprise one or more Kabat VL CDRs of a VL of any one of the antibodies described herein (any one of NMC-103, NMC-204, and NMC-303) and/or one or more Kabat VH CDRs of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise Kabat VH CDR 3 of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise three Kabat VL CDRs of a VL of any one of the antibodies described herein (any one of NMC-103, NMC-204, and NMC-303) and/or three Kabat VH CDRs of a VH of any one of the antibodies described herein (any one of antibodies NMC-103, NMC-204, and NMC-303).

In certain aspects, provided herein are antibodies or fragments thereof that specifically bind to M(H)DM2/4 (e.g., HDM2) and comprise one or more Chothia VL CDRs of a VL of any one of the antibodies described herein (any one of NMC-103, NMC-204, and NMC-303) and/or one or more Chothia VH CDRs of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise Chothia VH CDR 3 of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise three Chothia VL CDRs of a VL of any one of the antibodies described herein (any one of NMC-103, NMC-204, and NMC-303) and/or three Chothia VH CDRs of a VH of any one of the antibodies described herein (any one of antibodies NMC-103, NMC-204, and NMC-303).

In certain aspects, provided herein are antibodies or fragments thereof that specifically bind to M(H)DM2/4 (e.g., HDM2) and comprise one or more AbM VL CDRs of a VL of any one of the antibodies described herein (any one of NMC-103, NMC-204, and NMC-303) and/or one or more AbM VH CDRs of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise AbM VH CDR 3 of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise three AbM VL CDRs of a VL of any one of the antibodies described herein (any one of NMC-103, NMC-204, and NMC-303) and/or three AbM VH CDRs of a VH of any one of the antibodies described herein (any one of antibodies NMC-103, NMC-204, and NMC-303).

In certain aspects, provided herein are antibodies or fragments thereof that specifically bind to M(H)DM2/4 (e.g., HDM2) and comprise one or more Contact VL CDRs of a VL of any one of the antibodies described herein (any one of NMC-103, NMC-204, and NMC-303) and/or one or more Contact VH CDRs of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise Contact VH CDR 3 of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise three Contact VL CDRs of a VL of any one of the antibodies described herein (any one of NMC-103, NMC-204, and NMC-303) and/or three Contact VH CDRs of a VH of any one of the antibodies described herein (any one of antibodies NMC-103, NMC-204, and NMC-303).

In certain aspects, provided herein are antibodies or fragments thereof that specifically bind to M(H)DM2/4 (e.g., HDM2) and comprise one or more IMGT VL CDRs of a VL of any one of the antibodies described herein (any one of NMC-103, NMC-204, and NMC-303) and/or one or more IMGT VH CDRs of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise IMGT VH CDR 3 of a VH of any one of the antibodies described herein (any one of antibodies NMC-103, NMC-204, and NMC-303). In one embodiment, provided herein are antibodies or fragments thereof that specifically bind to M(H)DM2/4 (e.g., HDM2) and comprise three IMGT VL CDRs of a VL of any one of the antibodies described herein (any one of NMC-103, NMC-204, and NMC-303) and/or three IMGT VH CDRs of a VH of any one of the antibodies described herein (any one of antibodies NMC-103, NMC-204, and NMC-303).

In certain embodiments, provided herein are antibodies or fragments thereof that specifically bind to M(H)DM2/4 (e.g., HDM2) and comprise combinations of Kabat CDRs, Chothia CDRs, AbM CDRs, IMGT CDRs, and Contact CDRs (or a combination of CDRs defined by any two, three, four or five of these CDR defining systems).

In a specific embodiment, the position of one or more CDRs along the VH (e.g., CDR1, CDR2, or CDR3) and/or VL (e.g., CDR1, CDR2, or CDR3) region of an antibody described herein may vary by one, two, three, four, five, or six amino acid positions so long as immunospecific binding to M(H)DM2/4 (e.g., HDM2) is maintained (e.g., substantially maintained, for example, at least 50%, at least 60%>, at least 70%, at least 80%>, at least 90%, at least 95%). For example, in one embodiment, the position defining a CDR of any of antibody described herein (any one of antibodies NMC-103, NMC-204, and NMC-303) may vary by shifting the N-terminal and/or C-terminal boundary of the CDR by one, two, three, four, five, or six amino acids, so long as immunospecific binding to M(H)DM2/4 (e.g., HDM2) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody described herein may vary (e.g., be shorter or longer) by one, two, three, four, five, or more amino acids, so long as immunospecific binding to M(H)DM2/4 (e.g., HDM2) is maintained (e.g., substantially maintained, for example, at least 50%, at least 60%>, at least 70%, at least 80%, at least 90%, at least 95%).

In specific embodiments, an anti-M(H)DM2/4 (e.g., HDM2) antibody described herein is a humanized immunoglobulin (e.g., an IgG) that comprises the 3 VH CDRs and the 3 VL CDRs (i.e., VH CDR1, VH CDR2, VH CDR3, VL CDR1, VL CDR2, and VL CDR3) of any of the antibodies described herein (any one of murine antibodies NMC-103, NMC-204, and NMC-303), respectively, human or human-derived framework regions, and human or human-derived constant regions; antigen-binding fragments of such humanized antibodies are also provided by the present invention. Non-limiting examples of human framework regions are described in the art, e.g., see Kabat et al. (1991) Sequences of Proteins of Immunological Interest Fifth Edition, U.S. Department of Health and Human Services, NIH Publication No. 91-3242). In certain embodiments, a humanized anti-M(H)DM2/4 {e.g., HDM2) antibody or antigen-binding fragment thereof comprises a VH with VH CDR1, VH CDR2, and VH CDR3 as described herein (e.g., those of MNC-103, NMC-204, or NMC-303), surrounded by VH framework regions that are human framework regions or derived from human framework regions. In certain embodiments, an anti-M(H)DM2/4 {e.g., HDM2) antibody or antigen-binding fragment thereof comprises a VL with VL CDR1, VL CDR2, and VL CDR3 as described herein (e.g., those of MNC-103, NMC-204, or NMC-303), surrounded by VL framework regions that are human framework regions or derived from human framework regions. In certain embodiments, an anti-M(H)DM2/4 {e.g., HDM2) antibody or antigen-binding fragment thereof comprises (i) a VH with VH CDR1, VH CDR2, and VH CDR3 as described herein (e.g., those of MNC-103, NMC-204, or NMC-303), surrounded by VH framework regions that are human framework regions or derived from human framework regions; and (ii) a VL with VL CDR1, VL CDR2, and VL CDR3 as described herein (e.g., those of MNC-103, NMC-204, or NMC-303), surrounded by VL framework regions that are human framework regions or derived from human framework regions.

Human framework regions that may be used include, without limitation: (i) framework regions selected using the "best-fit" method (see, e.g., Sims et al. J. Immunol. 151: 2296 (1993)); (ii) framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); (iii) human mature (somatically mutated) framework regions or human germline framework regions (see, e.g., Almagro and Fransson, Front. Biosci. 13:1619-1633 (2008)); and (iv) framework regions derived from screening FR libraries (see, e.g., Baca et al., J. Biol. Chem. 272:10678-10684 (1997) and Rosok et al., J. Biol. Chem. 271:22611-22618 (1996)). See, e.g., Chothia et al., J. Mol. Biol. 278: 457-479 (1998) for a listing of human framework regions.

In a specific embodiment, using routine recombinant DNA techniques, one or more of the CDRs of an anti-M(H) DM2/4 (e.g., HDM2) or antigen-binding fragment thereof described herein may be inserted within known framework regions. The framework regions may be naturally occurring or consensus framework regions, and preferably human framework regions.

In certain embodiments, described herein are polynucleotides comprising combinations of the framework regions and CDRs that encode an anti-M(H)DM2/4 (e.g., HDM2) or antigen-binding fragment thereof that specifically binds M(H)DM2/4 (e.g., HDM2). One or more (e.g., one or two or three) amino acid substitutions may be made within the framework regions, preferably, one or more (e.g, one or two or three) amino acid substitutions may be made that improve binding of the antibody to M(H)DM2/4 (e.g., HDM2).

In an alternative embodiment wherein the antibody or fragment thereof is not humanized, the framework regions in the variable domains can be those of the native (e.g., murine) antibody.

Antibodies provided herein include immunoglobulin molecules and immunologically active fragments of immunoglobulin molecules (i.e., molecules that possess an antigen-binding site) that specifically bind to an extracellular region (epitope) of M(H)DM2/4 accessible on the plasma membrane surface of cancer cells (for example, an epitope that is expressed or exposed on the plasma membrane of cancer cells at greater levels than on non-cancer cells (e.g., when such cancer and non-cancer cells originated from the same tissue)).

In a preferred embodiment, anti-M(H)DM2/4 antibodies described herein are monoclonal antibodies or fragments thereof. The antibodies and fragments described herein are preferably human, humanized or chimeric. A human antibody can be a human immunoglobulin, which may be isolated from a human immunoglobulin library or isolated from mice or other animals that express antibodies from human genes. In one embodiment, an antibody provided herein is human (or a fragment of a human antibody). In one embodiment, an antibody provided herein is humanized (or a fragment of a humanized antibody). In one embodiment, an antibody provided herein is chimeric (or a fragment of a chimeric antibody) (where a chimeric antibody is an antibody with a variable region of one species (e.g., murine) and a constant region of another species (e.g., human)). Preferably, an antibody provided herein is a human, humanized or chimeric monoclonal antibody (which is particularly suitable for treatment of human subjects). In one embodiment, an antibody provided herein is a synthetic antibody. In one embodiment, an antibody provided herein is a multi-specific antibody (e.g., a bi-specific antibody). In one embodiment, an antibody provided herein is a single chain antibody, e.g., a single chain Fv (scFv). In one embodiment, an antigen-binding fragment of an anti-M(H)DM2/4 antibody is provided herein wherein the fragment can be, without limitation, an Fv fragment, a Fab fragment, a F(ab') fragment, a F(ab')$_2$ fragment, or a disulfide-linked Fv (sdFv). In one embodiment, an antigen-binding fragment provided herein is an Fv fragment. In one embodiment, an antigen-binding fragment provided herein is a Fab fragment. In one embodiment, an antigen-binding fragment provided herein is a F(ab')$_2$ fragment. In one embodiment, an antigen-binding fragment provided herein is a F(ab') fragment.

In a specific embodiment, an antibody provided herein is a multispecific antibody (such as a bi-specific antibody) that specifically binds to an extracellularly accessible epitope of M(H)DM2/4 exposed on the plasma membrane surface of cancer cells and specifically binds to a second antigen, wherein such binding allows re-targeting of effector cells towards tumor cells (as an example of such engineered bi-specific antibodies directed to a different target see Chames et al., 2009, MAbs 1:539-547, describing an antibody termed catumaxomab, a T-cell targeting agent). In one embodiment, an antibody provided herein is a multispecific antibody (such as a bi-specific antibody) that specifically binds to an extracellularly accessible epitope of M(H)DM2/4 exposed on the plasma membrane surface of cancer cells, and also binds to an antigen exposed on the plasma membrane surface of an effector cell. Effector cells include but are not limited to T cells, natural killer cells, neutrophils, macrophages, dendritic cells and B lymphocytes. In one embodiment, an antibody provided herein is a multispecific antibody (e.g., a bi-specific antibody) that specifically binds to an extracellularly accessible epitope of M(H)DM2/4 exposed on the plasma membrane surface of cancer cells, and also specifically binds to an antigen exposed on the surface of T cells (e.g., cytotoxic T cells). In one embodiment, an antibody provided herein is a multispecific antibody (e.g., a bi-specific antibody) that specifically binds to an extracellularly accessible epitope of M(H)DM2/4 exposed on the plasma membrane surface of cancer cells, and also specifically binds to CD3. In specific embodiments, an antibody provided herein is a multispecific antibody (e.g., a bi-specific antibody) that specifically binds to an extracellularly accessible epitope of M(H)DM2/4 exposed on the plasma membrane surface of cancer cells, and also specifically binds to an antigen exposed on the surface of natural killer cells, neutrophils, macrophages, dendritic cells, and/or B-lymphocytes. In specific embodiments, an antibody provided herein is a multispecific antibody (e.g., a bi-specific antibody) that specifically binds to an extracellularly accessible epitope of M(H)DM2/4 exposed on the plasma membrane surface of cancer cells, and also specifically binds to an antigen exposed on the surface of neutrophils, macrophages, dendritic cells, and/or B-lymphocytes. In specific embodiments, an antibody provided herein is a multispecific antibody (e.g., a bi-specific antibody) that specifically binds to an extracellularly accessible epitope of M(H)DM2/4 exposed on the plasma membrane surface of cancer cells, and also specifically binds to an antigen exposed on the surface of natural killer cells, macrophage and/or dendritic cells.

In a preferred embodiment, wherein a human subject is treated, the antibody used is a monoclonal antibody or an antigen-binding fragment thereof that is human, humanized or chimeric.

In certain embodiments, for example where non-human subjects are being treated, such as cats, dogs, cows, and other domestic, farm and wild animals, the antibody can be an antibody or fragment appropriate for use in the treated species (i.e., of that species). The antibodies described herein can be from any animal species, such as mammals (e.g., mouse, donkey, sheep, rabbit, goat, guinea pig, camel, horse, dog, cat) or birds (e.g., chicken).

In specific embodiments, wherein the antibody is an immunoglobulin, the immunoglobulin molecules that can be used are of any type (e.g., IgG, IgE, IgM, IgD, IgA, IgY), class (e.g., IgG1, IgG2, IgG3, IgG4, IgA1, IgA2) or subclass of immunoglobulin molecule. In a preferred embodiment, the antibody is an immunoglobulin, and, in particular, an IgG. In another embodiment, the antibody is an IgM.

In preferred embodiments, the anti-M(H)DM2/4 antibodies or fragments described herein are antibodies or fragments that mediate complement-dependent cytotoxicity (CDC), antibody-dependent cell-mediated cytoxicity (ADCC), and/or cytotoxicity due to a cytotoxic drug bound to the antibody or fragment.

In specific embodiments, the anti-M(H)DM2/4 antibodies or fragments described herein are antibodies or fragments that are capable of inducing cytotoxicity against the cancer cells being targeted by such antibodies or fragments, where the cytotoxicity can be due to complement-dependent cytotoxicity (CDC), antibody-dependent cell-mediated cytotoxicity (ADCC), or due to cytotoxicity of a drug bound to the antibody (where the antibody used is in a form of an antibody-drug conjugate).

In a specific embodiment, the anti-M(H)DM2/4 antibodies or fragments described herein are antibodies or fragments that mediate complement-dependent cytotoxicity (CDC). Methods of making an antibody that has CDC function are known in the art. In some embodiments, in which the CDC activity is desired, the Fc region of the antibody described herein is of a human IgG (e.g., IgG1, IgG2, IgG3, IgG4) type or a human IgM type. In some embodiments, in which the CDC activity is desired, the Fc region of the antibody described herein is of a mouse IgG (e.g., IgG1, IgG2a, IgG2b, IgG3) or mouse IgM type. In one embodiment, the Fc region of the antibody described herein is of a human IgG1 isotype. In one embodiment, the Fc region of the antibody described herein is of a human IgG3 isotype. In one embodiment, the Fc region of the antibody described herein is of a human IgG2 isotype. In one embodiment, the Fc region of the antibody described herein is bioengineered (e.g., mutated) to increase its CDC activity. In one embodiment, the antibody or fragment is a bispecific antibody or fragment that specifically binds to two distinct extracellular epitopes on M(H)DM2/4 (which may, e.g., lead to the amplification of complement activation, the increased deposition of fragments (C3b, iC3b, C3d, C3g, C4b) on the cancer cell surface membrane, and/or the increased cancer cell killing by the MAC). In another embodiment, the antibody or fragment is a bispecific antibody or fragment that specifically binds to an extracellular epitope of M(H)DM2/4 and specifically binds to an extracellular epitope of a complement regulatory protein (CRP) (which may, e.g., prevent the degradation of the freshly deposited immunologically active fragments (C3b, iC3b, C3d, C3g, C4b) by CRPs, amplify the activation of the complement cascade, and/or amplify MAC induced cancer cell lysis). Such bispecific anti-M(H)DM2/4 antibodies or fragments may increase CDC activity, increase ADCC activity, increase antibody-dependent cellular phagocytosis (ADCP) by neutrophils and macrophages, or increase CDC, ADCC and ADCP.

In a specific embodiment, the anti-M(H)DM2/4 antibodies or fragments described herein are antibodies or fragments that mediate antibody-dependent cell-mediated cytoxicity (ADCC) and/or antibody-dependent cellular phagocytosis (ADCP).

Methods of making an antibody that has ADCC function are known in the art.

Methods of making an antibody that has ADCP function are known in the art. Generally, the Fc region of the antibody mediates its binding to an Fc receptor, FcR, on neutrophils, macrophages, natural killer cells, eosinophils and mast cells, which leads to ADCC and on neutrophils, macrophages and dendritic cells resulting in ADCP. In some embodiments, in which the ADCC and/or ADCP activity is desired, the Fc region of the antibody described herein is of a human IgG (e.g., IgG1, IgG2, IgG3) type or a human IgE type. In one embodiment, the Fc region of the antibody described herein is of a human IgG1 isotype.

In one embodiment, the Fc region of the antibody described herein is bioengineered (e.g., via cross-linking, via di-sulfide bond formation, via oligosaccharide addition, or via mutation) to increase its ADCC and/or ADCP activity. In one embodiment, the Fc region of the antibody described herein is mutated to increase the lifespan of the intact antibody (e.g., in accordance with the methods described in Vaccaro et al., 2005, Nat Biotechnol. 23:1283-8128, the disclosure of which is incorporated by reference herein). In another embodiment, amino acid substitutions in the Fc CH2 and CH3 domains can be employed to direct the efficacy towards ADCC/ADCP and away from CDC or to increase the efficiency of all three cytotoxic activities (i.e., ADCC, ADCP and CDC). In another embodiment, CH2 and/or CH3 domains of the Fc region of the antibody described herein are modified at their glycosylation sites to remove/reduce fucose residues in order to improve ADCC and/or ADCP function, e.g., in accordance with the methods described in, e.g., Satoh et al., 2006, Expert Opin Biol Ther. 6:1161-1173 and/or Liu et al., 2015, Ca Immunol Res. 3:173-183, the disclosures of which are incorporated by reference herein).

In a specific embodiment, the anti-M(H)DM2/4 antibodies described herein having an IgG Fc region are bioengineered at their Fc region to change the N-glycan structure at their glycosylation site to the G0 glycan type terminating in GlcNAc (N-acetylglucosamine), and without fucose and sialic acid residues (which may result in, e.g., the activation of both the classic and alternate pathway of complement pathways and in increased binding to lectins including the mannose-binding lectins secreted during inflammatory responses).

In one embodiment, the Fc region of the antibody described herein is of a human IgG1 isotype and has alanine substitution at position 333 of its CH2 domain. In one embodiment, the Fc region of the antibody described herein is of a human IgG1 isotype and has a triple mutation S239D/I332E/A330L (which leads to a higher affinity for FcγRIIIa and a lower affinity for FcγRIIb resulting in enhanced ADCC) (such Fc modification can be made, e.g., in accordance with the methods described in Lazar et al., 2006, PNAS 103:4005-4010). In one embodiment, the Fc region of the antibody described herein is of a human IgG1 isotype and has a triple mutation S239D/I332E/G236A (which leads to improved FcγRIIIa affinity and FcYRIIa/FcγRIIb ratio that mediates enhanced phagocytosis of target cells by macrophages) (such Fc modification can be made, e.g., in accordance with the methods described in Richards et al., 2008, Mol. Cancer Ther. 7:2517-27).

In a specific embodiment, the anti-M(H)DM2/4 antibodies or fragments described herein are antibodies or fragments that mediate both complement-dependent cytotoxicity (CDC) and antibody-dependent cell-mediated cytotoxicity (ADCC). In a specific embodiment, the anti-M(H)DM2/4 antibodies or fragments described herein are antibodies or fragments that mediate complement-dependent cytotoxicity (CDC), antibody-dependent cell-mediated cytoxicity (ADCC) and antibody-dependent cellular phagocytosis (ADCP). In other embodiments, contemplated herein is an antibody or fragment that mediates only CDC or only ADCC activity. The CDC and ADCC function of the antibodies described herein can be tested by any in vitro and/or in vivo cytotoxicity assays known in the art. In certain embodiments, an antibody or fragment used herein comprises one or more amino acid mutations or substitutions in the Fc region that improve its CDC or ADCC activity (e.g., any mutations or substitutions described herein or known in the art (see, e.g., Idusogie et al., 2001. J Immunol. 166(4):2571-5; Strohl, 2009, Curr Opin Biotechnol. 20(6):685-91; Lazar et al., 2006, PNAS 103(11): 4005-4010, the disclosures of which are incorporated by reference herein)).

In a specific embodiment, the anti-M(H)DM2/4 antibodies or fragments are unconjugated, for example, are not conjugated to a cytotoxic drug).

In certain embodiments, the anti-M(H)DM2/4 antibodies or fragments described herein are not bound (e.g., not conjugated) to a drug (e.g., to a cytotoxic drug). In some of these embodiments, the anti-M(H)DM2/4 antibodies or fragments mediate CDC and/or ADCC.

In one embodiment, an anti-M(H)DM2/4 antibody or fragment thereof specifically binds to an extracellularly accessible segment (i.e. epitope) within amino acids 1 to 15, 15 to 25 or 475 to 491 of HDM2 (SEQ ID NO:4).

In one embodiment, an anti-HDM2 antibody or fragment thereof specifically binds to HDM2 within amino acids of SEQ ID NO: 1 (which are amino acids 1 to 15 of HDM2 (SEQ ID NO:4)). Amino acids of SEQ ID NO: 1 (which are amino acids 1 to 15 of SEQ ID NO:4) are in an extracellularly accessible epitope of HDM2.

In one embodiment, an anti-HDM2 antibody or fragment thereof specifically binds to HDM2 within amino acids of SEQ ID NO:2 (which are amino acids 15 to 25 of HDM2 (SEQ ID NO:4)). Amino acids of SEQ ID NO:2 (which are amino acids 15 to 25 of SEQ ID NO:4) are in an extracellularly accessible epitope of HDM2.

In one embodiment, an anti-HDM2 antibody or fragment thereof specifically binds to HDM2 within amino acids of SEQ ID NO: 3 (which are amino acids 475 to 491 of HDM2 (SEQ ID NO:4)). Amino acids of SEQ ID NO:3 (which are amino acids 475 to 491 of SEQ ID NO:4) are in an extracellularly accessible epitope of HDM2.

In one embodiment, anti-M(H)DM2/4 antibodies or fragments thereof specifically bind to an extracellularly accessible epitope of HDM2 within amino acids 50 to 60 of M(H)DM2/4 (SEQ ID NO:4 or SEQ ID NO:6).

In one embodiment, anti-M(H)DM2/4 antibodies or fragments thereof specifically bind to an extracellularly accessible epitope of M(H)DM2/4 within amino acids 100 to 110 of M(H)DM2/4 (SEQ ID NO:4 or SEQ ID NO:6).

In one embodiment, anti-M(H)DM2/4 antibodies or fragments thereof specifically bind to an extracellular epitope of M(H)DM2/4 within amino acids 1 to 126 of M(H)DM2/4 (SEQ ID NO:4 or SEQ ID NO:6).

In one embodiment, anti-M(H)DM2/4 antibodies or fragments thereof specifically bind to an extracellularly accessible epitope of M(H)DM2/4 within amino acids 436 to 482 of M(H)DM2/4 (SEQ ID NO:4 or SEQ ID NO:6).

In one embodiment, anti-M(H)DM2/4 antibodies or fragments thereof specifically bind to an extracellularly accessible epitope of M(H)DM2/4 within the terminal 100 amino acids at the C-terminus of the M(H)DM2/4 (e.g., M(H) DM2/4 protein variant (splice variant) known or expected to be expressed on the plasma membrane of cells of the cancer type being treated, or M(H)DM2/4 protein variant (splice variant) determined to be expressed on the plasma membrane of cancer cells of the subject being treated).

The invention also provides anti-M(H)DM2/4 antibodies or fragments thereof that compete for binding to HDM2 with an antibody that specifically binds to HDM2 within the amino acid sequence of SEQ ID NO:1 (e.g., NMC-103 antibody described herein, or any antibody or fragment having the VH of NMC-103 (i.e., the VH of SEQ ID NO:36) and the VL of NMC-103 (i.e., the VL of SEQ ID NO:37), or any antibody or fragment having the VH and VL CDRs of NMC-103). The invention also provides anti-M(H)DM2/4 antibodies or fragments thereof that compete for binding to HDM2 with an antibody that specifically binds to HDM2 within the amino acid sequence of SEQ ID NO:2 (e.g., NMC-204 antibody described herein, or any antibody or fragment having the VH of NMC-204 (i.e., the VH of SEQ ID NO:38) and the VL of NMC-204 (i.e., the VL of SEQ ID NO:39), or any antibody or fragment having the VH and VL CDRs of NMC204). The invention also provides anti-M(H) DM2/4 antibodies or fragments thereof that compete for binding to HDM2 with an antibody that specifically binds to HDM2 within the amino acid sequence of SEQ ID NO:3 (e.g., NMC-303 antibody described herein, or any antibody or fragment having the VH of NMC-303 (i.e., the VH of SEQ ID NO:40) and the VL of NMC-303 (i.e., the VL of SEQ ID NO:41), or any antibody or fragment having the VH and VL CDRs of NMC-303).

Any competition assay known in the art can be used to identify an antibody that competes with an antibody described herein for binding to M(H)DM2/4 (see Harlow and Lane (1988) Antibodies: A Laboratory Manual ch.14 (Cold Spring Harbor Laboratory, Cold Spring Harbor, N.Y.)). In an exemplary competition assay, immobilized M(H)DM2/4 (e.g., immobilized on a microtiter plate or well) is incubated in a solution comprising a first labeled antibody that binds to M(H)DM2/4 and a second unlabeled antibody that is being tested for its ability to compete with the first antibody for binding to M(H)DM2/4. As a control, immobilized M(H)DM2/4 can be incubated in a solution comprising the first labeled antibody but without the second unlabeled antibody. After incubation, excess unbound antibody is removed, and the amount of label associated with immobilized M(H)DM2/4 is measured. The substantial reduction of the amount of label in the test sample relative to the control sample indicates that the second antibody is competing with the first antibody for binding to M(H)DM2/4.

In specific embodiments, an antibody that competes with an antibody described herein (e.g., antibodies having the VH and VL of NMC-103, NMC-204 or NMC-303) for binding to M(H)DM2/4 also binds to the same peptide derived from M(H)DM2/4 that is bound by such antibody (e.g., the peptide of SEQ ID NO: 1, SEQ ID NO:2 or SEQ ID NO:3). In specific embodiments, an antibody that competes with an antibody described herein (e.g., antibodies having the VH and VL of NMC-103, NMC-204 or NMC-303) for binding to M(H)DM2/4 also binds to the same epitope in M(H) DM2/4 that is bound by such antibody.

In one embodiment, an anti-M(H)DM2/4 antibody or fragment thereof binds to the same epitope of M(H)DM2/4 as an antibody or fragment having a VH of SEQ ID NO:36 and a VL of SEQ ID NO:37. In one embodiment, an anti-M(H)DM2/4 antibody or fragment thereof described herein binds to the same epitope of M(H)DM2/4 as an antibody or fragment having a VH of SEQ ID NO:38 and a VL of SEQ ID NO:39. In one embodiment, an anti-M(H) DM2/4 antibody or fragment thereof described herein binds to the same epitope of M(H)DM2/4 as an antibody or fragment having a VH of SEQ ID NO:40 and a VL of SEQ ID NO:41.

In one embodiment, an anti-M(H)DM2/4 antibody or fragment thereof for use in the methods described herein specifically binds to an extracellularly accessible epitope within amino acids 19 to 50 of HDM2 (SEQ ID NO:4).

In one embodiment, an anti-M(H)DM2/4 antibody or fragment thereof for use in the methods described herein specifically binds to an extracellularly accessible epitope within amino acids 19 to 108 of HDM2 (SEQ ID NO:4).

In one embodiment, an anti-M(H)DM2/4 antibody or fragment thereof for use in the methods described herein specifically binds to an extracellularly accessible epitope within amino acids 154 to 167 of HDM2 (SEQ ID NO:4).

In one embodiment, an anti-M(H)DM2/4 antibody or fragment thereof for use in the methods described herein specifically binds to an extracellularly accessible epitope within amino acids 1 to 60 of HDM2 (SEQ ID NO:4).

In one embodiment, an anti-M(H)DM2/4 antibody or fragment thereof for use in the methods described herein specifically binds to an extracellularly accessible epitope within amino acids 1 to 100 of HDM2 (SEQ ID NO:4).

In one embodiment, an anti-M(H)DM2/4 antibody or fragment thereof for use in the methods described herein specifically binds to an extracellularly accessible epitope within amino acids 1 to 108 of HDM2 (SEQ ID NO:4).

In one embodiment, an anti-M(H)DM2/4 antibody or fragment thereof for use in the methods described herein specifically binds to an extracellularly accessible epitope within amino acids 26 to 60 of HDM2 (SEQ ID NO:4).

In one embodiment, an anti-M(H)DM2/4 antibody or fragment thereof for use in the methods described herein specifically binds to an extracellularly accessible epitope within the terminal 60 amino acids at the C-terminus of the HDM2 (e.g., HDM2 protein variant (splice variant) known or expected to be expressed on the plasma membrane of cells of the cancer type being treated, or HDM2 protein variant (splice variant) determined to be expressed on the plasma membrane of cancer cells of the subject being treated).

In one embodiment, an anti-M(H)DM2/4 antibody or fragment thereof for use in the methods described herein specifically binds to an extracellularly accessible epitope within the terminal 100 amino acids at the C-terminus of the HDM2 (e.g., HDM2 protein variant (splice variant) known or expected to be expressed on the plasma membrane of cells of the cancer type being treated, or HDM2 protein variant (splice variant) determined to be expressed on the plasma membrane of cancer cells of the subject being treated).

In one embodiment, an anti-M(H)DM2/4 antibody or fragment thereof for use in the methods described herein specifically binds to an extracellularly accessible epitope within amino acids 101 to 200 of HDM2 (SEQ ID NO:4).

In one embodiment, an anti-M(H)DM2/4 antibody or fragment thereof for use in the methods described herein competes for binding to HDM2 with antibody OP 145 (monoclonal antibody commercially available from Calbiochem, Catalogue No. OP145-100UG; see Table 10, below, for further details regarding OP145). In one embodiment, an anti-M(H)DM2/4 antibody or fragment thereof for use in the methods described herein competes for binding to HDM2 with antibody 965 (SMP14) (monoclonal antibody commercially available from Santa Cruz, Catalogue No. Sc-965; see Tables 3 and 10, below, for further details regarding 965 (SMP14)). In one embodiment, an anti-M(H)DM2/4 antibody or fragment thereof for use in the methods described herein competes for binding to HDM2 with antibody sc-813 (N-20) (polyclonal antibody commercially available from Santa Cruz, Catalogue No. Sc-813; see Table 10, below, for further details regarding sc-813 (N-20)). In one embodiment, an anti-M(H)DM2/4 antibody or fragment thereof for use in the methods described herein competes for binding to HDM2 with antibody sc-812 (C-18) (polyclonal antibody commercially available from Santa Cruz, Catalogue No. Sc-812; see Table 10, below, for further details regarding sc-812 (C-18)). In one embodiment, an anti-M(H)DM2/4 antibody or fragment thereof for use in the methods described herein competes for binding to HDM2 with antibody MO1, clone 1A7 (monoclonal antibody commercially available from Abnova, Catalogue No. H00004193-M01; see Table 3, below, for further details regarding MO1, clone 1A7).

Any competition assay known in the art can be used to identify an antibody that competes with antibody OP145, SMP14, N-20, C-18, or MO1, clone 1A7 for binding to M(H)DM2/4 (e.g., HDM2) (see Harlow and Lane (1988) Antibodies: A Laboratory Manual ch. 14 (Cold Spring Harbor Laboratory, Cold Spring Harbor, N.Y.)).

In specific embodiments, an antibody that competes with antibody OP145, SMP14, N-20, C-18, or MO1, clone 1A7 for binding to M(H)DM2/4 also binds to the same epitope that is bound by such antibodies.

In one embodiment, an anti-M(H)DM2/4 antibody or fragment thereof for use in the methods described herein binds to the same epitope of HDM2 as antibody OP 145 (see Table 10, below, for further details regarding OP145). In one embodiment, an anti-M(H)DM2/4 antibody or fragment thereof for use in the methods described herein binds to the same epitope of HDM2 as antibody 965 (SMP14) (see Tables 3 and 10, below, for further details regarding 965 (SMP14)). In one embodiment, an anti-M(H)DM2/4 antibody or fragment thereof for use in the methods described herein binds to one of the same epitope(s) of HDM2 as polyclonal antibody sc-813 (N-20) (see Table 10, below, for further details regarding 813 (N-20)). In one embodiment, an anti-M(H)DM2/4 antibody or fragment thereof for use in the methods described herein binds to one of the same epitope(s) of HDM2 as polyclonal antibody sc-812 (C-18) (see Table 10, below, for further details regarding sc-812 (C-18)). In one embodiment, an anti-M(H)DM2/4 antibody or fragment thereof for use in the methods described herein binds to the same epitope of HDM2 as antibody MOL clone 1A7 (i.e., monoclonal antibody commercially available from Abnova, Catalogue No. H00004193-M01; see Table 3, below, for further details regarding MOL clone 1A7).

In a specific embodiment, the anti-M(H)DM2/4 antibody or fragment thereof described herein is purified. In certain embodiments, an antibody or fragment is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods (see Flatman et al., J. Chromatogr. B 848:79-87 (2007) for review of methods for assessment of antibody purity).

The anti-M(H)DM2/4 antibody or fragment described herein can be fused or conjugated (e.g., covalently or non-covalently linked) to a detectable label or substance. Such labeled antibodies or fragments can be used to detect M(H)DM2/4 on the plasma membrane surface of cells.

Examples of detectable labels or substances include enzyme labels, radioisotopes (e.g., iodine, carbon, sulfur, tritium, indium, and technetium), luminescent labels, fluorescent labels, and biotin. This methodology can be used to determine whether cells of a certain cancer (e.g., cells of cancer in a patient) express M(H)DM2/4, or a certain splice variant of M(H)DM2/4, on the plasma membrane, where the detection of M(H)DM2/4 using the antibody (or fragment) may indicate that the antibody (or fragment) (with or without the detectable label or substance) can be used in the diagnosis and treatment of the cancer or preventing metastases of the cancer.

7.2 Antibody-Drug Conjugates

In a specific embodiment, the invention provides antibody-drug conjugates comprising an anti-M(H)DM2/4 antibody or fragment described herein bound (e.g., covalently bound) to a cytotoxic drug. In such embodiments, the antibody-drug conjugates are intended to mediate cytotoxicity by delivery of a cytotoxic drug to the cells of the cancer.

Accordingly, an anti-M(H)DM2/4 antibody or an antigen-binding fragment described herein can be bound or conjugated to one or more cytotoxic agents. The cytotoxic agent can be any agent that inhibits or prevents a vital cellular function (e.g., cell division) and/or causes cell death or destruction. The cytotoxic agents that can be bound or conjugated to an anti-M(H)DM2/4 antibody or fragment include, without limitation, chemotherapeutic agents (e.g., any chemotherapeutic agent known in the art or described herein), toxins (e.g., protein toxins, enzymatically active toxins of bacterial, fungal, plant or animal origin, or fragments thereof), radioactive isotopes, growth inhibitory agents, and nucleolytic enzymes. The antibody-drug conjugates and their methods of making (including the types of antibodies that can be used in such conjugates, drugs that can be used in such conjugates, and linkers that can be used to link the antibody to the drug) are known in the art (see, e.g., Peters & Brown, 2015, Biosci. Rep. 35, e00225, doi:10.1042/BSR20150089).

Examples of the cytotoxic agents that can be conjugated to an anti-M(H)DM2/4 antibody or fragment described herein include, without limitation, anthracyclin, doxorubicin, methotreaxate, an anti-metabolite agent, an anti-folate agent, an auristatin (e.g., MMAE or MMAF), a maytansine, a calicheamicin, a duocarymucin, and a pyrrolobenzodiazepine (PBD) dimer.

In specific embodiments, an M(H)DM2/4 antibody or fragment described herein is conjugated to one or more of the following drugs: a maytansinoid, an auristatin (such as monomethylauristatin drug moieties DE and DF (MMAE and MMAF)), a dolastatin, a calicheamicin or derivative thereof, an anthracycline (such as daunomycin or doxorubicin), methotrexate, vindesine, a taxane (such as docetaxel), paclitaxel, larotaxel, tesetaxel, ortataxel, and a trichothecene.

In another embodiment, an M(H)DM2/4 antibody or fragment described herein is conjugated to a toxin or a fragment thereof (e.g., diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, Phytolaca americana proteins, *Momordica charantia* inhibitor, curcin, crotin, sapaonaria *officinalis* inhibitor, gelonin, mitogellin, restrictocin, phenomycin, enomycin, or atricothecene).

In another embodiment, an M(H)DM2/4 antibody or fragment described herein is conjugated to a radioactive isotope (e.g., $At_{211}$, $I^{131}$, $I^{125}$, $Y^{90}$, $Re^{186}$, $Re^{188}$, $Sm^{153}$, $Bi^{212}$, $P^{32}$, $Pb^{212}$, or a radioactive isotope of Lu).

In another embodiment, an M(H)DM2/4 antibody or fragment thereof described herein is conjugated to nanoparticles or other targeting tools to promote concentrated delivery to and retention of the antibodies at the tumor site.

7.3 Making of Antibodies

The anti-M(H)DM2/4 antibodies or fragments described herein can be produced by any method known in the art.

Methods for producing polyclonal antibodies are known in the art (see, for example, Chapter 11 in: Short Protocols in Molecular Biology, (2002) 5th Ed., Ausubel F M et al, eds., John Wiley and Sons, New York).

Methods for producing monoclonal antibodies are also known in the art, and include the use of hybridoma, recombinant and phage display technologies, and the use of humanized mice. For example, monoclonal antibodies can be produced using hybridoma techniques as taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or in Kohler G & Milstein C (1975) Nature 256: 495. In another example, human monoclonal antibodies can be produced using humanized mice as taught, for example, in Laffleur et al., 2012, Methods Mol. Biol. 901:149-59.

Methods for producing specific antibodies using hybridoma technology are routine and well known in the art.

In particular, a mouse or another appropriate host animal can be immunized to elicit lymphocytes that produce or are capable of producing antibodies that will specifically bind to the target protein (i.e., extracellular region of M(H)DM2/4) used for immunization. Lymphocytes then are fused with myeloma cells to form a hybridoma cell (see Goding J W (Ed), Monoclonal Antibodies: Principles and Practice, pp. 59-103 (Academic Press, 1986); see also Kozbor D (1984) J Immunol 133: 3001-5; Brodeur et al, Monoclonal Antibody Production Techniques and Applications, pp. 51-63 (Marcel Dekker, Inc., New York, 1987)). The hybridoma cells are then grown in a suitable culture medium, which can be assayed for production of monoclonal antibodies directed against M(H)DM2/4. The binding specificity of monoclonal anti-M(H)DM2/4 antibodies produced by this method can be determined by methods known in the art, e g, immunoprecipitation or an in vitro assay, such as radioimmunoassay (RIA) or enzyme-linked immunoabsorbent assay (ELISA). The hybridoma clones thus selected are then grown by standard methods (see Goding J W (Ed), Monoclonal Antibodies: Principles and Practice, supra). The monoclonal antibodies can then be separated from the culture medium and purified.

Further, the antibodies or fragments described herein can also be made using various phage display technologies known in the art (see Brinkman U et al, (1995) J Immunol Methods 182: 41-50; Ames R S et al, (1995) J Immunol Methods 184: 177-186; Kettleborough C A et al., (1994) Eur J Immunol 24: 952-958; Persic L et al., (1997) Gene 187: 9-18; and Burton D R & Barbas C F (1994) Advan Immunol 57: 191-280).

Methods for producing chimeric antibodies (i.e., antibody with a variable region of one species (e.g., murine) and a constant region of another species (e.g., human)) are known in the art (see Morrison S L (1985) Science 229: 1202-7; Oi V T & Morrison S L (1986) BioTechniques 4: 214-221; Gillies S D et al, (1989) J Immunol Methods 125: 191-202; and U.S. Pat. Nos. 5,807,715, 4,816,567, 4,816,397, and 6,331,415).

Methods of making antibody fragments are known in the art. For example, Fab and F(ab')₂ fragments can be produced by proteolytic cleavage of immunoglobulin molecules, using enzymes such as papain (to produce Fab fragments) or pepsin (to produce F(ab')₂ fragments).

Methods of making humanized antibodies are also known in the art (see International Publication No. WO 91/09967; Padlan E A (1991) Mol Immunol 28(4/5): 489-498; Studnicka G M et al, (1994) Prot Engineering 7(6): 805-814; and Roguska M A et al, (1994) PNAS 91: 969-973; International Publication No. WO 93/17105; Tan P et al, (2002) J Immunol 169: 1119-25; Caldas C et al, (2000) Protein Eng. 13(5): 353-60; Morea V et al, (2000), Methods 20(3): 267-79; Baca M et al, (1997) J Biol Chem 272(16): 10678-84; Roguska M A et al, (1996) Protein Eng 9(10): 895 904; Couto J R et al, (1995) Cancer Res. 55 (23 Supp): 5973s-5977s; Couto J R et al, (1995) Cancer Res 55(8): 1717-22; Sandhu J S (1994) Gene 150(2): 409-10 and Pedersen J T et al, (1994) J Mol Biol 235(3): 959-73). In a specific embodiment, a humanized antibody is made by CDR grafting.

Methods of making human antibodies are known in the art and include phage display methods using antibody libraries derived from human immunoglobulin sequences (see U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741). In some embodiments, human antibodies can be produced using mouse-human hybridomas (see Shinmoto H et al, (2004) Cytotechnology 46: 19-23; Naganawa Y et al, (2005) Human Antibodies 14: 27-31).

Methods of making single domain antibodies, for example, antibodies lacking the light chains, are also known in the art (see Riechmann L & Muyldermans S (1999) J Immunol 23 1: 25-38; Nuttall S D et al, (2000) Curr Pharm Biotechnol 1(3): 253-263; Muyldermans S, (2001) J Biotechnol 74(4): 277-302).

Methods of making single chain Fv (scFv) antibodies are also known in the art (see Ahmad et al., 2012, Clinical and Developmental Immunology, doi:10. 1155/2012/980250; Wang et al., 2006, Anal. Chem. 78, 997-1004; Pansri et al., 2009, BMC Biotechnology 9:6). For example, scFv antibodies can be constructed by fusing variable domains of heavy and light chains of immunoglobulins via short polypeptide linkers (using recombinant expression techniques), and scFv antibodies having desired antigen-binding properties can be selected by phage display technology.

Methods of producing bispecific antibodies are well known in the art (Konterman, 2012, MAbs 4:182-197; Gramer et al., 2013, MAbs 5:962-973).

Methods of conferring CDC or ADCC activity on an antibody (such as an antibody that does not have CDC or ADCC activity to begin with) are known in the art (see Kellner et al., 2014, Methods 65:105-113; International Publication No. WO 2012010562; Natsume et al., 2009, Drug Design, Development and Therapy 3(3):7-16). Such methods include, without limitation, Fc region isotype shuffling, amino acid mutations in the Fc region conferring enhanced or optimized CDC and/or ADCC activity, and changes in the Fc region glycosylation profile conferring enhanced or optimized CDC and/or ADCC activity).

7.4 Antibody Selection

If a candidate antibody or fragment for use in the therapeutic and diagnostic methods provided herein is not yet known or has not yet been demonstrated to bind to a region of M(H)DM2/4 exposed on the surface of cancer cells, the antibody or fragment may optionally be tested by any of the following methods:

In certain aspects, provided herein is a method for identifying an anti-M(H)DM2/4 antibody or a fragment thereof for use in the methods described herein (e.g., for diagnosis of cancer, treating cancer or for preventing metastases) comprising: (a) contacting intact cancer cells (e.g., cancer cells expected, known, or determined to express M(H)DM2/4) with an anti-M(H)DM2/4 antibody or a fragment thereof; and (b) determining whether the antibody or fragment binds to the intact cancer cells, in particular on the extracellular surface of the cancer cells (e.g., relative to intact cancer cells not contacted by said antibody or fragment), wherein the binding of the anti-M(H)DM2/4 antibody or fragment to the intact cancer cells contacted with such antibody or fragment indicates that said antibody or fragment is suitable for use in the methods described herein. In a specific embodiment, the cancer cells are from the patient proposed to be treated with the antibody or fragment thereof.

In certain aspects, provided herein is a method for identifying an anti-M(H)DM2/4 antibody or a fragment thereof for use in the methods described herein (e.g., for diagnosis of cancer, treating cancer or for preventing metastases) comprising: (a) contacting intact cancer cells (e.g., cancer cells expected, known, or determined to express M(H)DM2/4) with an anti-M(H)DM2/4 antibody or a fragment thereof; and (b) determining whether the antibody or fragment binds to the intact cancer cells (in particular on the extracellular surface of the cancer cells) at an increased level relative to binding to intact normal cells (e.g., non-cancerous cells of the same tissue or organ type as the cancer cells), wherein increased binding of the anti-M(H)DM2/4 antibody or fragment to the intact cancer cells relative to normal cells indicates that said antibody or fragment is suitable for use in the methods described herein.

In certain aspects, provided herein is a method for identifying an anti-M(H)DM2/4 antibody or a fragment thereof for use in the methods described herein (e.g., for treating cancer or for preventing metastases) comprising: (a) contacting intact cancer cells (e.g., cancer cells known, expected or determined to express M(H)DM2/4) with an anti-M(H) DM2/4 antibody or a fragment thereof; and (b) determining whether the contacting step results in an increased amount of cell death or destruction of the intact cancer cells (e.g., as determined by cell-death markers such as Propidium Iodide staining) relative to the amount of death or destruction of intact cancer cells not contacted by said antibody or fragment and/or relative to the amount of death or destruction of intact normal cells (e.g., non-cancerous cells of the same tissue or organ as the cancer cells) contacted by said antibody or fragment, wherein increased amount of cell death or destruction of the intact cancer cells contacted with the antibody or fragment indicates that said antibody or fragment is suitable for use in the methods described herein.

In certain aspects, provided herein is a method for identifying an anti-M(H)DM2/4 antibody or a fragment thereof for use in the methods described herein (e.g., for treating cancer or for preventing metastases) comprising: (a) contacting intact cancer cells (e.g., cells known, expected or determined to express M(H)DM2/4) with an anti-M(H) DM2/4 antibody or fragment; and (b) determining whether the contacting step results in an increased level of complement-dependent cytotoxicity (CDC) or antibody-dependent cell-mediated cytotoxicity (ADCC) (as determined by one or more cytotoxicity assays) towards the intact cancer cells relative to the level of CDC or ADCC towards intact cancer cells not contacted by said antibody or fragment and/or relative to the level of CDC or ADCC towards intact normal cells (e.g., non-cancerous cells of the same tissue or organ as the cancer cells) contacted by said antibody or fragment, wherein increased level of CDC or ADCC towards the intact cancer cells indicates that said antibody or fragment is suitable for use in the methods described herein.

In certain aspects, provided herein is a method for identifying an anti-M(H)DM2/4 antibody or a fragment thereof for use in the methods described herein (e.g., for treating cancer or for preventing metastases) comprising: (a) contacting intact cancer cells (e.g., cells known, expected or determined to express M(H)DM2/4) with an anti-M(H) DM2/4 antibody or a fragment thereof; and (b) determining whether the contacting step results in increased inhibition of growth and proliferation of the intact cancer cells relative to the inhibition of growth and proliferation of intact cancer cells not contacted by said antibody or fragment and/or relative to the inhibition of growth and proliferation of intact normal cells (e.g., non-cancerous cells of the same tissue or organ as the cancer cells) contacted by said antibody or fragment, wherein increased inhibition of growth and proliferation of the intact cancer cells contacted with the antibody or fragment indicates that said antibody or fragment is suitable for use in the methods described herein.

7.5 Pharmaceutical Compositions

Provided herein are pharmaceutical compositions comprising an anti-M(H)DM2/4 antibody or an antigen-binding fragment thereof and a pharmaceutically acceptable carrier. Also provided herein are pharmaceutical compositions comprising an antibody-drug conjugate as described herein and a pharmaceutically acceptable carrier. Appropriate pharmaceutically acceptable carriers including, but not limited to, excipients and stabilizers) are known in the art (see, e.g., Remington's Pharmaceutical Sciences (1990)Mack Publishing Co., Easton, Pa.). The anti-M(H)DM2/4 antibody or fragment, or antibody-drug conjugate, in the pharmaceutical compositions described herein can be purified.

Pharmaceutically acceptable carriers may include an isotonic agent, a buffer, a suspending agent, a dispersing agent, an emulsifying agent, a wetting agent, a sequestering or chelating agent, a pH buffering agent, a solubility enhancer, an antioxidant, an anesthetic, and/or an antimicrobial agent. Suitable excipients include, without limitation, water, saline, glycerol, ethanol, starch, lactose, sucrose, gelatin, malt, propylene, silica gel, sodium stearate, base cream and dextrose. If administered parenterally, suitable pharmaceutically acceptable carriers may include physiological saline or phosphate buffered saline (PBS), and solutions containing such agents as glucose, polyethylene glycol, polypropylene glycol or other agents.

In specific embodiments, pharmaceutical compositions provided herein comprise an anti-M(H)DM2/4 antibody or an antigen-binding fragment thereof, or antibody-drug conjugate, described herein, and optionally one or more other therapeutic (e.g., anti-cancer) agents, in a pharmaceutically acceptable carrier.

A pharmaceutical composition may be formulated for any route of administration to a subject. Formulations for injections can be prepared as liquid solutions, suspensions, emulsions, or solid forms suitable for making into a solution or suspension prior to injection.

The anti-M(H)DM2/4 antibody or fragment thereof, or antibody-drug conjugate, can be used or present in the pharmaceutical composition in a therapeutically effective amount. The therapeutically effective amount of the antibody or conjugate can be determined by standard clinical techniques.

In a specific embodiment, a pharmaceutical composition contemplated for use in the therapeutic methods described herein comprises an anti-M(H)DM2/4 antibody or an antigen-binding fragment thereof, or antibody-drug conjugate described herein, and does not comprise any additional anti-cancer agent or therapy. In another specific embodiment, a pharmaceutical composition contemplated for use in the therapeutic methods described herein comprises an anti-M(H)DM2/4 antibody or an antigen-binding fragment thereof, or antibody-drug conjugate described herein, and further comprises an additional anti-cancer agent or therapy (e.g., any one, two or more additional anti-cancer agents or therapies described herein).

7.6 Therapeutic Methods

In one aspect, the invention provides for treating cancer (e.g., inhibiting cancer proliferation, inhibiting cancer progression) in a subject in need thereof comprising administering to the subject any anti-M(H)DM2/4 (e.g., anti-HDM2) antibody or fragment described herein. In a specific embodiment, the invention provides a method of treating cancer in a subject in need thereof, said method comprising administering to the subject: an antibody or a fragment thereof that specifically binds to an extracellularly accessible epitope of M(H)DM2/4. In another specific embodiment, the invention provides a method of preventing metastasis in a subject in need thereof, said method comprising administering to the subject: an antibody or a fragment thereof that specifically binds to an extracellularly accessible epitope of M(H)DM2/4. In a specific embodiment of the methods described herein, the antibody or fragment is not bound to a cell-penetrating peptide.

In one aspect, the invention provides for treating cancer (e.g., inhibiting cancer proliferation, inhibiting cancer progression) in a subject in need thereof comprising administering to the subject an antibody or a fragment thereof that specifically binds to an extracellularly accessible epitope of HDM2 exposed on the surface of cancer cells (e.g., where the cells of the type of cancer being treated are known or expected to have such extracellular region of HDM2 exposed on their plasma membrane surface), preferably wherein the antibody or fragment is not bound to a cell-penetrating peptide. In one embodiment, the method of treating cancer encompasses preventing metastasis of the cancer. In one embodiment, the method of treating cancer is a method for reducing tumor size (as measured, e.g., by tumor volume or diameter), inhibiting the growth of the tumor, reducing the growth of the tumor, or eradicating the tumor.

In another aspect, the invention provides for preventing metastases in a subject that has cancer comprising administering to the subject any anti-M(H)DM2/4 (e.g., anti-HDM2) antibody or fragment described herein. In another aspect, the invention provides for preventing metastases in a subject that has cancer comprising administering to the subject an antibody or a fragment thereof that specifically binds to an extracellular region of HDM2 exposed on the surface of cancer cells (e.g., where the cells of the type of cancer being treated are known or expected to have such extracellular region of HDM2 exposed on their plasma membrane surface).

In another aspect, the invention provides for reducing the number, size or invasiveness of metastases, or eradicating metastases, in a subject that has a metastatic cancer comprising administering to the subject any anti-M(H)DM2/4 (e.g., anti-HDM2) antibody or fragment described herein. In another aspect, the invention provides for reducing the number, size or invasiveness of metastases, or eradicating metastases, in a subject that has a metastatic cancer comprising administering to the subject an antibody or a fragment thereof that specifically binds to an extracellularly accessible epitope of HDM2 exposed on the surface of cancer cells (e.g., where the cells of the type of cancer being treated are known or expected to have such extracellularly accessible epitope of HDM2 exposed on their plasma membrane surface).

In one aspect, the invention provides for treatment of a cancer that is resistant to another cancer therapy or therapies (e.g., vaccine, targeted therapy (such as small molecule targeted therapy), chemotherapy, radiotherapy, or immunotherapy (such as treatment with another monoclonal antibody)). In one embodiment, the invention provides for treating a cancer resistant to chemotherapy (i.e., resistant to one or more chemotherapeutic drugs). In one embodiment, the invention provides for treating a cancer resistant to treatment with another monoclonal antibody or antibodies. In one embodiment, the invention provides for treating a cancer resistant to radiotherapy. In one embodiment, the invention provides for treating a cancer resistant to small molecule targeted therapy or therapies.

Disclosed herein is therapeutic use of an anti-M(H)DM2/4 (e.g., anti-HDM2) antibody or antigen-binding fragment thereof in a patient who has cancer (e.g., has been diagnosed with cancer). In preferred embodiments, disclosed herein is therapeutic use of an anti-HDM2 antibody (or a fragment thereof) in a patient who has cancer that is known to metastasize (i.e., is a type of cancer that is commonly known to become metastatic cancer). In some embodiments, the patient being treated has metastatic cancer. In other embodiments, a patient with a cancer that has not metastasized is treated in accordance with a method described herein in order to prevent metastasis of the cancer. In some embodiments, the patient being treated has been previously treated with other cancer therapies (e.g. vaccine, targeted therapy, chemotherapy, immunotherapy). In a specific embodiment, the patient with a cancer that has metastasized is treated in accordance with a method described herein in order to reduce, slow down or stop metastases, or decrease the number or size of metastases of the cancer.

The methods described herein are suitable for treating cancers that are expected, known or determined to express anti-M(H)DM2/4 (e.g., HDM2) on the surface of their cells. The HDM2 on the surface of cancer cells targeted by the methods described herein can be one of the splice variants of HDM2 protein known in the art or described herein. Without intending to be bound by a mechanism of action, it is believed that HDM2 on the surface of cancer cells is usually a splice variant of the HDM2 protein that lacks at least one or all nuclear localization signals (e.g., the nuclear localization sequence at the N-terminal portion of HDM2, the nuclear localization signal at the C-terminal portion of HDM2, or both nuclear localization signals). In a specific embodiment, HDM2 on the surface of cancer cells is a splice variant of the HDM2 protein that lacks at least one or all nuclear localization signals, and further lacks a nuclear export signal. In one embodiment, the HDM2 on the surface of cancer cells is HDM2 that lacks the nuclear localization signal at amino acids 179-185 of SEQ ID NO: 4 (i.e., lacks amino acids 179 to 185 of SEQ ID NO: 4). In one embodiment, the HDM2 on the surface of cancer cells is HDM2 that lacks the nuclear localization signal at amino acids 466-473 of SEQ ID NO: 4 (i.e., lacks amino acids 466 to 473 of SEQ ID NO: 4). In one embodiment, the HDM2 on the surface of cancer cells is HDM2 that lacks the nuclear localization signals at amino acids 179-185 and amino acids 466-473 of SEQ ID NO: 4 (i.e., lacks amino acids 179 to 185 and 466 to 473 of SEQ ID NO: 4). In some embodiments, the HDM2 on the surface of cancer cells is HDM2 that lacks the nuclear export signal, such as the nuclear export signal at amino acids 190-202 of SEQ ID NO: 4 (i.e., lacks amino acids 190 to 202 of SEQ ID NO: 4).

In certain embodiments, the HDM2 on the surface of cancer cells targeted by the methods described herein is a splice variant of the HDM2 protein, such as one of the splice variants known in the art or described herein (see Table 1 and Table 2, and Section 8, for the list of HDM2 variants). In some embodiments, the HDM2 on the surface of cancer cells targeted by the methods described herein is a splice variant of the HDM2 protein known as MDM2-A (SEQ ID NO: 8), which lacks amino acids 28-222 of SEQ ID NO: 4. In some embodiments, the HDM2 on the surface of cancer cells targeted by the methods described herein is a splice variant of the HDM2 protein known as MDM2-A1 (SEQ ID NO: 9), which lacks amino acids 28-222 and 275-300 of SEQ ID NO: 4. In some embodiments, the HDM2 on the surface of cancer cells targeted by the methods described herein is a splice variant of the HDM2 protein known as MDM2-B (SEQ ID NO: 10), which lacks amino acids 28-300 of SEQ ID NO: 4. In some embodiments, the HDM2 on the surface of cancer cells targeted by the methods described herein is a splice variant of the HDM2 protein known as MDM2-C(SEQ ID NO: 11), which lacks amino acids 53-222 of SEQ ID NO: 4. In some embodiments, the HDM2 on the surface of cancer cells targeted by the methods described herein is a splice variant of the HDM2 protein known as MDM2-D (SEQ ID NO: 12), which lacks amino acids 30-388 of SEQ ID NO: 4. In some embodiments, the HDM2 on the surface of cancer cells targeted by the methods described herein is a splice variant of the HDM2 protein known as MDM2-E (SEQ ID NO: 13), which lacks amino acids 76-102 and 103-491 of SEQ ID NO: 4. In some embodiments, the HDM2 on the surface of cancer cells targeted by the methods described herein is a splice variant of the HDM2 protein known as MDM2-F (SEQ ID NO: 14), which lacks amino acids 53-97 of SEQ ID NO: 4. In some embodiments, the HDM2 on the surface of cancer cells targeted by the methods described herein is a splice variant of the HDM2 protein known as MDM2-G (SEQ ID NO: 15), which lacks amino acids 115-169 of SEQ ID NO: 4. In some embodiments, the HDM2 on the surface of cancer cells targeted by the methods described herein is a splice variant of the HDM2 protein known as MDM2-11 (SEQ ID NO: 16), in which amino acid M has been substituted with M→MVRSRQM in SEQ ID NO: 4. In some embodiments, the HDM2 on the surface of cancer cells targeted by the methods described herein is a splice variant of the HDM2 protein known as MDM2-KB2 (SEQ ID NO: 17), which lacks amino acids 157-248 of SEQ ID NO: 4. In some embodiments, the methods described herein target a splice variant of M(H)DM4 on the surface of cancer cells, for example, target one or more of the following splice variants: MDMX-S, MDM4-S, MDM4-A, MDM4-G, MDM4-XALT1/XALT2 and MDM4-211 (or a human equivalent of the listed splice variants).

In a specific embodiment, the anti-M(H)DM2/4 (e.g., anti-HDM2) antibody or a fragment thereof for use in the methods described herein has been tested and determined to be expected to bind to HDM2 exposed on the surface of the cells of the cancer to be treated. This binding to HDM2 can be shown by, for example, the ability of the anti-HDM2 antibody or fragment to bind to an intact cancer cell of the tissue type of the tissue of origin of the cancer being treated (which can be but does not need to be from the subject being treated). In one embodiment, an anti-HDM2 antibody or a fragment thereof is tested and determined to be expected to bind to the intact cells of the cancer of a subject, before administering the antibody or fragment to the subject. This testing can be done, e.g., by showing binding of the anti-HDM2 antibody or fragment to the surface of intact cancer cells obtained by biopsy or to a cancer cell line of the appropriate tissue type.

Optionally, the cancer cells of the prospective patient to be treated can be tested for expression of M(H)DM2/4 (e.g., HDM2) on their surface using techniques known in the art in order to determine whether the subject is an appropriate candidate for anti-HDM2 therapy described herein; however, such ordinarily would not be deemed necessary if the patient has a cancer of a tissue type that is known or expected to have an extracellularly accessible epitope of M(H)DM2/4. In a specific embodiment, the cells of the cancer in the subject being treated have been tested and determined to have an extracellularly accessible epitope of HDM2 (targeted by the anti-HDM2 antibody or fragment thereof) exposed on their plasma membrane surface (e.g., determined to express a variant of HDM2 that is known to have this extracellular region exposed on the plasma membrane surface). In certain embodiments, the cancer being treated using the methods described herein is a cancer that is known or determined to express a splice variant of HDM2 (for example, MDM2-A (SEQ ID NO: 8), MDM2-A1 (SEQ ID NO: 9), MDM2-B (SEQ ID NO: 10), MDM2-C(SEQ ID NO: 11), MDM2-D (SEQ ID NO: 12), MDM2-E (SEQ ID NO: 13), MDM2-F (SEQ ID NO: 14), MDM2-G (SEQ ID NO: 15), MDM2-11 (SEQ ID NO: 16) or MDM-KB2 (SEQ ID NO: 17)), on the plasma membrane surface of its cells. Such can be detected using techniques known in the art (e.g., RT-PCR on a nucleic acid sample from cancer biopsy).

In specific embodiments, the administration of an anti-M(H)DM2/4 (e.g., anti-HDM2) antibody or an antigen-binding fragment thereof in accordance with the methods described herein can be carried out to achieve, or found to result in achieving, at least one, two, three, four or more of the following effects (e.g., in a subject with a cancerous tumor): (i) a decrease in tumor size (e.g., volume or diameter), (ii) a reduction in the growth of the tumor, (iii) inhibition of the progression of tumor growth, (iv) the regression of the tumor, (v) inhibition of a recurrence of the tumor, (vi) eradication of the tumor (e.g., primary tumor or metastatic tumor), (vii) prevention of metastasis of the tumor, (vii) reduction in the number, size or invasiveness of the metastases of the tumor, (viii) reduction or amelioration of the severity or duration of one or more symptoms of the tumor, (ix) the inhibition of the development or onset of one or more symptoms associated with cancer, (x) the enhancement or improvement of the therapeutic effect of another therapy, (xi) reduction in hospitalization (e.g., length of the hospitalization) in the subject, (xii) improvement in subject's quality of life, (xiii) a reduction in mortality, (xiv) an increase in a relapse free survival or the length of remission in the subject. Any of these effects can be assessed by any method known in the art. For example, the tumor size can be assessed using magnetic resonance imaging (MRI), dynamic contrast-enhanced MRI (DCE-MRI), X-ray, computed tomography (CT) scan, or positron emission tomography (PET) scan.

In certain embodiments, the administration of an anti-M(H)DM2/4 (e.g., anti-HDM2) antibody or an antigen-binding fragment thereof in accordance with the methods described herein is effective to treat cancer in a subject (e.g., reduces tumor volume or diameter, reduces tumor growth, reduce tumor proliferation, eradicates the tumor, or improves one or more symptoms of cancer), when used alone or in combination with another therapy. In certain embodiments, the administration of an anti-HDM2 antibody or an antigen-binding fragment thereof in accordance with the methods described herein is effective to prevent metastases in a subject that has cancer, when used alone or in combination with another therapy. In certain embodiments, the administration of an anti-HDM2 antibody or an antigen-binding fragment thereof in accordance with the methods described herein is effective to treat a metastatic cancer (e.g., reduces the number, size or invasiveness of metastases, or eradicates metastases), when used alone or in combination with another therapy.

In particular embodiments, the administration of an anti-M(H)DM2/4 (e.g., anti-HDM2) antibody or an antigen-binding fragment thereof in accordance with the methods described herein is effectiveto treat cancer or prevent metastasis in a subject when used alone (i.e., without an additional therapy). In other particular embodiments, the administration of an anti-HDM2 antibody or an antigen-binding fragment thereof in accordance with the methods described herein is effective to treat cancer or prevent metastasis in a subject when used in combination with one or more of the additional therapies described herein.

The effectiveness of therapies described herein can be assessed by evaluating a parameter (e.g., tumor size) before and after administration of the therapies described herein to the subject being treated. Alternatively, the effectiveness of therapy can be assessed by evaluating a parameter (e.g., tumor size) before and after administration of the therapies described herein to an animal model (e.g., in an animal model, such as a mouse model, a rat model, or a hamster model, of the cancer being treated). Any assay known in the art can be used to evaluate the therapeutic effectiveness of the therapies described herein.

In the therapeutic methods described herein using an anti-M(H)DM2/4 (e.g., anti-HDM2) antibody or an antigen-binding fragment thereof, it will be understood that an antibody-drug conjugate described herein can alternatively be used.

7.6.1 Cancers to be Treated

Examples of cancers that can be treated in accordance with the methods described herein include, but are not limited to, breast cancer, cervical cancer, ovarian cancer, endometrial cancer, uterine cancer, pancreatic cancer, skin cancer (e.g., melanoma), prostate cancer (e.g., hormone refractory, such as castration resistant, prostate cancer), lung cancer (e.g., small-cell lung cancer, or non-small cell lung cancer), colorectal cancer (e.g., colon cancer, or rectal cancer), gastrointestinal cancer, stomach cancer, small bowel cancer, appendix cancer, esophageal cancer, gastric cancer, renal cancer, bladder cancer, gallbladder cancer, kidney cancer (e.g., renal cell carcinoma, or Wilms tumor)), liver cancer (e.g., hepatic carcinoma, or hepatoma), central nervous system cancer (e.g., brain cancer), peripheral nervous system cancer, bronchial cancer, cancer of the oral cavity or pharynx (e.g., oropharyngeal cancer, laryngeal cancer), thyroid cancer, biliary tract cancer, salivary gland cancer, thyroid gland cancer, adrenal gland cancer, vulvar cancer, testicular cancer, urethral cancer, vaginal cancer, penile cancer, bone cancer, eye cancer (e.g. retinoblastoma or uveal melanoma), and head and neck cancer (e.g., head and neck squamous cell carcinoma). In specific embodiments, the cancer is cervical cancer, endometrial cancer, ovarian cancer, pancreatic cancer, melanoma, breast cancer, or colon cancer. In one embodiment, the cancer is a pancreatic cancer. In one embodiment, the cancer is a melanoma. In one embodiment, the cancer is a breast cancer. In one embodiment, the cancer is an ovarian cancer.

In certain embodiments, the cancer that can be treated in accordance with the methods described herein is resistant to another cancer therapy or therapies (e.g., vaccine, targeted therapy (such as small molecule targeted therapy), chemotherapy, radiotherapy, or immunotherapy (such as treatment with another monoclonal antibody)). In one embodiment, the cancer that can be treated in accordance with the methods described herein is resistant to chemotherapy. In one embodiment, the cancer that can be treated in accordance with the methods described herein is resistant to treatment with another monoclonal antibody or antibodies. In one embodiment, the cancer that can be treated in accordance with the methods described herein is resistant to radiation. In one embodiment, the cancer that can be treated in accordance with the methods described herein is resistant to small molecule targeted therapy.

In a specific embodiment, the cancer treated in accordance with the methods described herein is a solid cancer. In another specific embodiment, the cancer treated in accordance with the methods described herein is a non-solid cancer (e.g., hematologic cancer).

In specific embodiments, the cancer treated in accordance with the invention is leukemia (e.g., acute leukemia (such as acute lymphocytic leukemia or acute myelocytic leukemia), chronic leukemia (such as chronic myelocytic leukemia or chronic lymphocytic leukemia), or hairy cell leukemia), lymphoma (e.g., Hodgkin's lymphoma, non-Hodgkin's lymphoma, B-cell lymphoma, Burkitt's lymphoma, follicular lymphoma, lymphoblastic lymphoma, mantle cell lymphoma, or T-cell lymphoma).

In specific embodiments, the cancer treated in accordance with the invention is carcinoma (e.g., adenocarcinoma, basal cell carcinoma, renal cell carcinoma, squamous cell carcinoma, osteocarcinoma, thyoma/thymic carcinoma, or choriocarcinoma), blastoma, sarcoma (e.g., soft tissue sarcoma, osteosarcoma, chondrosarcoma, rhabdomyosarcoma, or synovia sarcoma), lymphoma, leukemia, a germ cell tumor, myeloma (e.g., multiple myeloma), squamous cell cancer, mesothelioma, glioblastoma (e.g., glioblastoma multiforme), glioma, neuroblastoma, melanoma, astrocytoma, medulloblastoma, hepatoma, seminoma, craniopharyngioma, ependymoma, pinealoma, hemangioblastoma, neuroma, oligodendroglioma, meningioma, or retinoblastoma.

In specific embodiments, the cancer treated in accordance with the methods described herein is a sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, endometrial stromal sarcoma, mast cell sarcoma, adult soft tissue sarcoma, uterine sarcoma, Kaposi sarcoma, merkel cell carcinoma, urothelial carcinoma, colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, embryonal carcinoma, lung carcinoma (e.g., small cell lung carcinoma), bladder carcinoma, or epithelial carcinoma.

In certain embodiments, the cancer treated in accordance with the methods of the invention is metastatic. In some embodiments, the cancer treated in accordance with the methods described herein is a metastatic melanoma, a metastatic ovarian cancer, a metastatic cervical cancer, a metastatic endometrial cancer, a metastatic pancreatic cancer, a metastatic breast cancer, a metastatic colon cancer, or a metastatic brain cancer.

7.6.2 Methods of Administration

The anti-M(H)DM2/4 (e.g., anti-HDM2) antibodies or fragments described herein (and pharmaceutical compositions comprising such antibodies) can be administered to a subject by any suitable means which include, but are not limited to, parenteral (e.g., intravenous, intraarterial, intramuscular, intraosseous, intracerebral, intracerebroventricular, intrathecal, subcutaneous), intraperitoneal, intratumoral, intrapulmonary, intradermal, transdermal, conjunctival, intraocular, intranasal, intratracheal, oral and local intralesional routes of administration. In certain embodiments, the anti-HDM2 antibodies or fragments described herein are administered intravenously, intraarterially, intramuscularly, intraperitoneally, intratumorally, or subcutaneously. In one embodiment, the anti-HDM2 antibodies or fragments described herein are administered intravenously. In one embodiment, the anti-HDM2 antibodies or fragments described herein are administered intraperitoneally. In one embodiment, the anti-HDM2 antibodies or fragments described herein are administered intramuscularly. In one embodiment, the anti-HDM2 antibodies or fragments described herein are administered subcutaneously. In one embodiment, the anti-HDM2 antibodies or fragments described herein are administered intratumorally (such as by an injection into the tumor of the cancer being treated). In particular embodiments, the anti-HDM2 antibodies or fragments described herein are administered intravenously, intraperitoneally, or intratumorally.

In a specific embodiment, nano-particles coated with an anti-M(H)DM2/4 (e.g., anti-HDM2) antibody or a fragment thereof described herein are used for tumor targeting and treatment (see, for example, Cardoso et al., 2012, Curr. Med. Chem. 19(19):3103-27 and Arruebo et al., 2009, 7. of Nanomater. 2009:Article ID 439389, regarding nano-particle coating with antibodies). In one embodiment, provided herein are methods for treating cancer or preventing metastasis in a subject having a cancer comprising administering to the subject nano-particles coated with an an anti-M(H)DM2/4 (e.g., anti-HDM2) antibody or a fragment thereof.

Various dosing schedules of the anti-M(H)DM2/4 (e.g., anti-HDM2) antibodies or fragments described herein (and pharmaceutical compositions comprising such antibodies) are contemplated including single administration or multiple administrations over a period of time. The methods of administration include, without limitation, bolus administration, pulse infusions, and continuous infusions.

The therapeutic regimen for use in the methods described herein may include administration of anti-M(H)DM2/4 (e.g., anti-HDM2) antibodies or fragments thereof (and compositions comprising such antibodies) once every week, once every two weeks, once every three weeks, once every four weeks, once every six weeks, once every eight weeks or once every twelve weeks (e.g., such that the subject receives from at least two, at least three, at least four, at least five, at least six, at least eight, or at least ten doses of the antibody, or from two to twenty doses of the antibody). In certain embodiments, anti-HDM2 antibodies or fragments thereof (and compositions comprising such antibodies) are administered daily, every other day, or two, three, or four times a week (e.g., for a period of time, such as one week, two weeks, three weeks, four weeks, six weeks, two months or three months). The treatment regimens contemplated herein include regimens wherein the initial higher dose of the antibody may be followed by one or more lower doses, or wherein the initial lower dose of the antibody is followed by one or more higher doses. An exemplary treatment course (in which the anti-HDM2 antibody or fragment is administered) may last for one week, two weeks, three weeks, four weeks, six weeks, two months, three months, four months, five months, six months, one year, or over several years.

In some embodiments, the initial treatment period (where the antibody is administered, e.g., once a month, once in two weeks, once a week, twice a week or three times a week) is followed by a withdrawal period in which the antibody is not administered (for, e.g., a week, two weeks, three weeks, four weeks, six weeks, two months, three months, four months, six months or one year), and then followed by a second treatment period (where the antibody is administered, e.g., once a month, once in two weeks, once a week, twice a week or three times a week). Such initial treatment and such second treatment periods can last, for example, two weeks, three weeks, four weeks, six weeks, two months, three months, four months, or six months (where the initial treatment period can be the same or different from the second treatment period). This course of treatment (having the initial treatment period, a withdrawal period and a second treatment period) can be repeated twice, three times, four times, five times, six times, ten times or more than ten times.

In some embodiments, two or more antibodies or fragments thereof with different binding specificities for M(H)DM2/4 (e.g., HDM2) are administered simultaneously or sequentially to the subject being treated.

The appropriate dosage of anti-M(H)DM2/4 (e.g., anti-HDM2) antibodies or fragments for use in the methods described herein will depend on the type of antibody used, the type of cancer being treated, the severity of the cancer being treated, the route of administration, the target site, the condition of the patient (e.g., age, body weight, health), the responsiveness of the patient to the antibody, other medications used by the patient, and other factors to be considered at the discretion of the medical practitioner performing the treatment.

In certain embodiments, the dosage of an anti-M(H)DM2/4 (e.g., anti-HDM2) antibody or fragment described herein which is administered to the subject can be from about 1 µg/kg to 200 mg/kg of the patient's body weight. In certain embodiments, the dosage of an anti-M(H)DM2/4 (e.g., anti-HDM2) antibody or fragment described herein which is administered to the subject can be from about 1 µg/kg to 100 mg/kg of the patient's body weight (e.g., from about 0.01 mg/kg to about 100 mg/kg, from about 0.05 mg/kg to about 100 mg/kg, or from about 0.5 mg/kg to about 100 mg/kg). In certain embodiments, the dosage of an anti-M(H)DM2/4 (e.g., anti-HDM2) antibody or fragment described herein which is administered to the subject can be from about 1 mg/kg to 200 mg/kg of the patient's body weight. In one embodiment, the dosage of an anti-HDM2 antibody or fragment described herein which is administered to the subject is from 0.025 mg/kg to about 5 mg/kg. In one embodiment, the dosage of an anti-HDM2 antibody or fragment described herein which is administered to the subject is from 0.05 mg/kg to about 2 mg/kg. In one embodiment, the dosage of an anti-HDM2 antibody or fragment described herein which is administered to the subject is from 5 mg/kg to about 30 mg/kg. In specific embodiments, doses (e.g., one or more doses) of about 0.025 mg/kg, 0.05 mg/kg, 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/kg, 7.5 mg/kg, 10 mg/kg, 20 mg/kg, 30 mg/kg, 40 mg/kg, 50 mg/kg, 75 mg/kg, or 100 mg/kg of an anti-HDM2 antibody or fragment described herein can be administered to the subject being treated. In one embodiment, a dose (e.g., one or more doses) of about 0.1 mg/kg of an anti-HDM2 antibody or fragment described herein can be administered to the subject being treated (e.g., when the antibody is administered intratumorally).

7.7 Diagnostic, Companion Diagnostic and Prognostic Methods

In one aspect, provided herein are methods of diagnosing cancer in a subject (e.g., a human), said method comprising: (a) detecting whether an antibody or a fragment thereof (e.g., a labeled antibody or fragment) that specifically binds to M(H)DM2/4 (e.g., HDM2) binds to the surface of an intact cell of the subject, wherein the antibody or fragment is any anti-M(H)DM2/4 antibody or fragment described herein (in particular, any antibody or fragment that specifically binds to SEQ ID NO: 1, SEQ ID NO:2, or SEQ ID NO:3); and (b) diagnosing the subject with cancer if the binding is detected in step (a). In one embodiment, the method of diagnosing further comprises, before the detecting in step (a), obtaining the intact cell from the subject, and then performing the detecting by, e.g., determining whether a labeled antibody or fragment binds to the intact cell from the subject using, e.g., FACS or cell-based ELISA analysis. In one embodiment, the method of diagnosing comprises administering the antibody or fragment to the subject before the detecting in step (a), and wherein the detecting is performed by in vivo imaging of the subject.

In one aspect, a patient is selected for treatment using an anti-M(H)DM2/4 (e.g., anti-HDM2) antibody or antibody fragment described herein based on the detection of binding of such antibody or fragment to the surface of intact cancer cells obtained from the patient. In certain embodiments, provided herein is a method of selecting a patient having a cancer for treatment with an antibody or fragment that specifically binds to an extracellularly accessible epitope of HDM2 comprising: obtaining an intact cancer cell from the patient (e.g., by biopsy of the cancerous tumor in the patient, or by obtaining a blood sample with circulating cancer cells from the patient), and determining whether the antibody or fragment binds to the surface of the intact cancer cell of the patient (using any method known in the art or described herein, e.g., using cell-based ELISA or FACS analysis), wherein the detection of binding indicates that the patient can be treated with the antibody or fragment. In specific embodiments, provided herein is a method of selecting a patient having a cancer for treatment with an antibody or fragment that specifically binds to an extracellularly accessible epitope of HDM2 comprising: obtaining an intact cancer cell from the patient (e.g., by biopsy of the cancerous tumor in the patient, or by obtaining a blood sample with circulating cancer cells from the patient), determining whether the antibody or fragment binds to the surface of the intact cancer cell of the patient (using any method known in the art or described herein, e.g., using cell-based ELISA or FACS analysis), and, if the binding is detected, administering the antibody or fragment to the patient. The antibody or fragment administered to the patient can be the same or different from the antibody or fragment used for selection of the patient to be treated. In one embodiment, provided herein is a method of selecting a patient having an ovarian cancer for treatment with an antibody or fragment that specifically binds to an extracellularly accessible epitope of HDM2 comprising: obtaining an intact ovarian cancer cell from the patient, determining whether the antibody or fragment binds to the surface of the intact cancer cell of the patient, and, if the binding is detected, administering the antibody or fragment to the patient. In one embodiment, any antibody or a fragment thereof that specifically binds to SEQ ID NO: 1, SEQ ID NO:2, or SEQ ID NO:3 is used for such patient selection and/or treatment. In one embodiment, any antibody or a fragment thereof that specifically binds to an extracellularly accessible epitope of M(H)DM2/4, which is not bound to a cell-penetrating peptide is used for such patient selection and/or treatment. In one embodiment, any antibody or a fragment thereof that specifically binds to an extracellularly accessible epitope of M(H)DM2/4, which is not bound to a cell-penetrating peptide is used for such patient selection, and any antibody or a fragment thereof that specifically binds to SEQ ID NO: 1, SEQ ID NO: 2, or SEQ ID NO:3 is used for the treatment of the patient.

Non-limiting exemplary samples that can be used for in diagnostic or patient selection methods using an anti-M(H)DM2/4 antibody (e.g., anti-HDM2 antibody) or fragment thereof described herein include: tissue biopsies, intact cells obtained from malignant tissues, and circulating cancer cells isolated from blood. For example, a tissue sample can be obtained from a patient and immunohistochemistry can be performed to detect whether a labeled anti-M(H)DM2/4 antibody (e.g., anti-HDM2 antibody) or fragment thereof binds to the tissue sample. Alternatively, intact cells (known or suspected to be malignant) can be isolated from a patient and FACS or cell-based ELISA analysis can be performed to detect whether a labeled anti-M(H)DM2/4 antibody (e.g., anti-HDM2 antibody) or fragment thereof binds to such cell. In yet another example, a blood sample with circulating cancer cells can be obtained from a patient and FACS or cell-based ELISA analysis can be performed to detect whether a labeled anti-M(H)DM2/4 antibody (e.g., anti-HDM2 antibody) or fragment thereof binds to such cells.

In one aspect, the duration of treatment and/or dosage of an anti-M(H)DM2/4 (e.g., anti-HDM2) antibody or antibody fragment described herein to be used in the treatment of a patient is determined based on the detection of binding of such antibody or fragment to the surface of intact cancer cells obtained from the patient. In certain embodiments, provided herein is a method of determining whether to continue the treatment of a patient having a cancer with an antibody or fragment that specifically binds to an extracellularly accessible epitope of HDM2 comprising: administering the antibody or fragment to the patient for a first period of time (e.g., where the patient had been selected for treatment as described above), obtaining an intact cancer cell from the patient (e.g., by biopsy of the cancerous tumor in the patient, or by obtaining a blood sample with circulating cancer cells from the patient), and determining whether the antibody or fragment binds to the surface of the intact cancer cell of the patient (using any method known in the art or described herein, e.g., using cell-based ELISA or FACS analysis), and, if the binding is detected, continuing administering the antibody or fragment to the patient for a second period of time (but, e.g., if the binding is not detected, discontinuing the treatment). In certain embodiments, provided herein is a method of determining whether to increase the dose of an antibody or fragment that specifically binds to an extracellularly accessible epitope of HDM2 for use in the treatment of a patient having a cancer comprising: administering a dose the antibody or fragment to the patient for a period of time (e.g., where the patient had been selected for treatment as described above), obtaining an intact cancer cell from the patient (e.g., by biopsy of the cancerous tumor in the patient, or by obtaining a blood sample with circulating cancer cells from the patient), and determining whether the antibody or fragment binds to the surface of the intact cancer cell of the patient (using any method known in the art or described herein, e.g., using cell-based ELISA or FACS analysis), and, if the binding is detected, administering a dose of the antibody or fragment to the patient for a second period of time, wherein the dose administered during the second period of time is higher than the dose administered during the first period of time (e.g., two times, or three times higher) (but, e.g., if the binding is not detected, discontinuing the treatment or administering a lower dose of the antibody or fragment during the second period of time).

In another specific embodiment, treatment with an anti-M(H)DM2/4 (e.g., anti-HDM2) antibody or an antibody fragment described herein is monitored in a patient by determining the amount of HDM2 expressed on the surface of cancer cells obtained from the patient, before and after treatment, wherein a decrease in the amount is a positive prognosis.

7.8 Patient Populations

The patients or subjects being treated in accordance with the methods described herein include, but are not limited to, humans and non-human vertebrates. In certain embodiments, the subject being treated is a mammal, e.g., a human, a dog, a cat, a monkey, a rabbit, a cow, a horse, a goat, a sheep, or a pig. In a preferred embodiment, the subject being treated is a human.

In certain embodiments, the subject being treated in accordance with the methods described herein has been diagnosed with a cancer (e.g., using a biopsy or any another method known in the art). In particular embodiments, the subject being treated has been diagnosed with an early stage cancer. In other embodiments, the subject being treated has been diagnosed with an advanced stage cancer. In particular embodiments, the subject being treated has been diagnosed with a high-grade tumor. In other embodiments, the subject being treated has been diagnosed with a low-grade tumor. In certain embodiments, the subject being treated has been diagnosed with a cancer that can metastasize. In specific embodiments, the subject being treated has been diagnosed with a metastatic cancer.

In specific embodiments, the subject being treated in accordance with the methods described herein has been diagnosed with a cervical cancer, an endometrial cancer, an ovarian cancer, a pancreatic cancer, a melanoma, a breast cancer, a colorectal cancer (e.g., a colon cancer), a bladder cancer, an astrocytic neoplasm, a glioblastoma, a pediatric Rhabdomyosarcoma, or a lung cancer (e.g., non-small cell lung carcinoma). In specific embodiments, the subject being treated in accordance with the methods described herein has been diagnosed with a melanoma, a pancreatic cancer, a breast cancer, or an ovarian cancer. In one embodiment, the subject being treated in accordance with the methods described herein has been diagnosed with a melanoma. In one embodiment, the subject being treated in accordance with the methods described herein has been diagnosed with a pancreatic cancer. In one embodiment, the subject being treated in accordance with the methods described herein has been diagnosed with a breast cancer. In one embodiment, the subject being treated in accordance with the methods described herein has been diagnosed with an ovarian cancer. In one embodiment, the subject being treated in accordance with the methods described herein has been diagnosed with a lung cancer.

In certain embodiments, the subject being treated has previously undergone one or more other cancer therapies (e.g., vaccine, targeted therapy (such as small molecule targeted therapy), chemotherapy, radiotherapy, or immunotherapy (such as treatment with another monoclonal antibody)), and the subject's cancer has developed resistance to the one or more other cancer therapies. In one embodiment, the subject being treated is resistant to chemotherapy. In one embodiment, the subject being treated is resistant to radiotherapy. In one embodiment, the subject being treated is resistant to a small molecule targeted therapy. In one embodiment, the subject being treated is resistant to treatment with another monoclonal antibody.

In certain embodiments, the subject being treated has a type of a cancer that is known or expected to have M(H)DM2/4 (e.g., HDM2) on the surface of its cells. In specific embodiments, the subject being treated has a type of cancer, the cells of which express one or more of splice variants of HDM2 on their cell surface, for example (and without limitation), one or more of the following splice variants: MDM2-A (SEQ ID NO: 8), MDM2-A1 (SEQ ID NO: 9), MDM2-B (SEQ ID NO: 10), MDM2-C(SEQ ID NO: 11), MDM2-D (SEQ ID NO: 12), MDM2-E (SEQ ID NO: 13), MDM2-F (SEQ ID NO: 14), MDM2-G (SEQ ID NO: 15), MDM2-11 (SEQ ID NO: 16) or MDM-KB2 (SEQ ID NO: 17).

In certain embodiments, the subject being treated has a cancer that has been tested and determined (using any assay known in the art) to carry M(H)DM2/4 (e.g., HDM2) on the plasma membrane of its cells. In particular embodiments, the subject being treated has a cancer, the cells of which have been tested and determined (by any method known in the art) to expose on their plasma membrane surface an extracellular region of HDM2 that can be targeted by an anti-HDM2 antibody or fragment (and such antibody can then be administered to the subject). In specific embodiments, the subject being treated has a cancer, the cells of which have been tested and determined (by any method known in the art) to express one or more of splice variants of HDM2 on their cell surface, for example (and without limitation), one or more of the following splice variants: MDM2-A (SEQ ID NO: 8), MDM2-A 1 (SEQ ID NO: 9), MDM2-B (SEQ ID NO: 10), MDM2-C(SEQ ID NO: 11), MDM2-D (SEQ ID NO: 12), MDM2-E (SEQ ID NO: 13), MDM2-F (SEQ ID NO: 14), MDM2-G (SEQ ID NO: 15), MDM2-11 (SEQ ID NO: 16) or MDM-KB2 (SEQ ID NO: 17).

7.9 Combination Therapies and Kits

In certain embodiments, an anti-M(H)DM2/4 antibody or fragment thereof described herein is administered to a subject in combination with one or more anti-cancer therapies different from said antibody or fragment, e.g., a chemotherapy, a surgery, a radiation therapy, another antibody with an anti-cancer activity, a cytokine, a T cell therapy, a vaccine (e.g., a cellular vaccine), a small molecule with an anti-cancer activity, an anti-hormonal agent, or any other anti-cancer therapy known in the art.

In a specific embodiment, an anti-M(H)DM2/4 antibody or fragment thereof described herein is administered to a subject in combination with chemotherapy. Examples of types of chemotherapeutic agents that can be used in the methods described herein include, without limitation, an alkylating agent, a nitrosourea agent, an antimetabolite, a topoisomerase inhibitor, an aromatase inhibitor, an antitumor antibiotic, an alkaloid derived from a plant, a hormone antagonist, a P-glycoprotein inhibitor, and a platinum complex derivative. Specific examples of chemotherapeutic drugs that can be used in the methods described herein include, without limitation, taxol, paclitaxel, nab-paclitaxel, 5-fluorouracil (5-FU), gemcitabine, doxorubicin, daunorubicin, colchicin, mitoxantrone, tamoxifen, cyclophosphamide, mechlorethamine, melphalan, chlorambucil, busulfan, uramustine, mustargen, ifosamide, bendamustine, carmustine, lomustine, semustine, fotemustine, streptozocin, thiotepa, mitomycin, diaziquone, tetrazine, altretamine, dacarbazine, mitozolomide, temozolomide, procarbazine, hexamethylmelamine, altretamine, hexalen, trofosfamide, estramustine, treosulfan, mannosulfan, triaziquone, carboquone, nimustine, ranimustine, azathioprine, sulfanilamide, fluoropyrimidine, thiopurine, thioguanine, mercaptopurine, cladribine, capecitabine, pemetrexed, fludarabine, methotrexate, hydroxyurea, nelarabine or clofarabine, cytarabine, decitabine, pralatrexate, floxuridine, thioquanine, azacitidine, cladribine, pentostatin, mercaptopurine, imatinib, dactinomycin, cerubidine, bleomycin, actinomycin, luteomycin, epirubicin, idarubicin, plicamycin, vincristin, vinblastine, vinorelbine, vindesine, vinflunine, paclitaxel, docetaxel, etoposide, teniposide, periwinkle, *vinca*, taxane, irinotecan, topotecan, camptothecin, teniposide, pirarubicin, novobiocin, merbarone, aclarubicin, amsacrine, antiandrogen, antiestrogen, bicalutamide, medroxyprogesterone, fluoxymesterone, diethylstilbestrol, estrace, octreotide, megestrol, raloxifene, toremifene, fulvestrant, prednisone, flutamide, leuprolide, goserelin, aminoglutethimide, testolactone, anastrozole, letrozole, exemestane, vorozole, formestane, fadrozole, androstene, resveratrol, myosmine, catechin, apigenin eriodictyol isoliquiritigenin, mangostin, amiodarone, azithromycin, captopril, clarithromycin, cyclosporine, piperine, quercetine, quinidine, quinine, reserpine, ritonavir, tariquidar, verapamil, cisplatin, carboplatin, oxaliplatin, transplatin, nedaplatin, satraplatin, triplatin and carboplatin. In specific embodiments, an anti-M(H)DM2/4 antibody or fragment thereof described herein is administered to a subject in combination with one or more of the following chemotherapeutic agents: gemcitabine, nab-paclitaxel, capecitabine, irinotecan, and celecoxib. In specific embodiments, an anti-M(H)DM2/4 antibody or fragment thereof described herein is administered to a subject in combination with one or more of the following chemotherapeutic agents: gemcitabine, nab-paclitaxel, cisplatin, 5-FU, and paclitaxel (e.g., paclitaxel formulated as albumin-bound particles such as ABRAXANE®). In specific embodiments, the cancer treated using a combination therapy described herein is a pancreatic cancer, a breast cancer, a lung cancer or an ovarian cancer.

In one embodiment, an anti-M(H)DM2/4 antibody or fragment thereof described herein is administered to a subject in combination with gemcitabine (e.g., for treatment of a non-small cell lung cancer, a pancreatic cancer or an ovarian cancer). In one embodiment, an anti-M(H)DM2/4 antibody or fragment thereof described herein is administered to a subject in combination with capecitabine. In one embodiment, an anti-M(H)DM2/4 antibody or fragment thereof described herein is administered to a subject in combination with irinotecan. In one embodiment, an anti-M(H)DM2/4 antibody or fragment thereof described herein is administered to a subject in combination with celecoxib. In one embodiment, an anti-M(H)DM2/4 antibody or fragment thereof described herein is administered to a subject in combination with paclitaxel (e.g., paclitaxel formulated as albumin-bound particles such as ABRAXANE®) (e.g., for treatment of a metastatic breast cancer). In one embodiment, an anti-M(H)DM2/4 antibody or fragment thereof described herein is administered to a subject in combination with nab-paclitaxel. In one embodiment, an anti-M(H)DM2/4 antibody or fragment thereof described herein is administered to a subject in combination with cisplatin. In one embodiment, an anti-M(H)DM2/4 antibody or fragment thereof described herein is administered to a subject in combination with 5-FU (e.g., for treatment of a colorectal cancer such as a colon cancer). In one embodiment, an anti-M(H)DM2/4 antibody or fragment thereof described herein is administered to a subject in combination with carboplatin. In one embodiment, an anti-M(H)DM2/4 antibody or fragment thereof described herein is administered to a subject in combination with gemcitabine and nab-paclitaxel (e.g., for treatment of a pancreatic cancer). In one embodiment, an anti-M(H)DM2/4 antibody or fragment thereof described herein is administered to a subject in combination with gemcitabine and carboplatin (e.g., for treatment of an ovarian cancer). In one embodiment, an anti-M(H)DM2/4 antibody or fragment thereof described herein is administered to a subject in combination with paclitaxel (e.g., paclitaxel formulated as albumin-bound particles such as ABRAXANE®) and gemcitabine (e.g., for treatment of a breast cancer, or a pancreatic cancer such as adenocarcinoma of the pancreas or metastatic adenocarcinoma of the pancreas). In one embodiment, an anti-M(H)DM2/4 antibody or fragment thereof described herein is administered to a subject in combination with gemcitabine and cisplatin (e.g., for treatment of anon-small cell lung cancer). In one embodiment, an anti-M(H)DM2/4 antibody or fragment thereof described herein is administered to a subject in combination with gemcitabine and 5-FU. In one embodiment, an anti-M(H)DM2/4 antibody or fragment thereof described herein is administered to a subject in combination with paclitaxel (e.g., paclitaxel formulated as albumin-bound particles such as ABRAXANE and carboplatin (e.g., for treatment of a non-small cell lung cancer).

In certain embodiments, wherein the subject is human, gemcitabine is administered in a dose of 1,500 mg/m$^2$. In certain embodiments, wherein the subject is human, nab-paclitaxel is administered in a dose of 300 mg/m$^2$. In certain embodiments, wherein the subject is human, gemcitabine is administered in a dose of 1,000 mg/m$^2$. In certain embodiments, wherein the subject is human, nab-paclitaxel is administered in a dose of 125 mg/m$^2$.

In certain embodiments, the gemcitabine and/or nab-paclitaxel are administered in doses that are lower than doses used when gemcitabine and/or nab-paclitaxel are administered not in combination with an anti-cancer antibody (such as an anti-M(H)DM2/4 antibody or fragment described herein). In certain embodiments, wherein the subject is human, gemcitabine is administered in a dose that is less than 1,500 mg/m$^2$, and/or nab-paclitaxel is administered in a dose that is less than 300 mg/m$^2$. In certain embodiments, wherein the subject is human, gemcitabine is administered in a dose that is less than 1,000 mg/m$^2$, and/or nab-paclitaxel is administered in a dose that is less than 125 mg/m$^2$. In one embodiment, wherein the subject is human, gemcitabine is administered in a dose that is equal to or less than 500 mg/m$^2$, 400 mg/m$^2$, 300 mg/m$^2$ or 200 mg/m$^2$, and/or the nab-paclitaxel is administered in a dose that is equal to or less than 62.5 mg/m$^2$, 50 mg/m$^2$, 40 mg/m$^2$, 30 mg/m$^2$, or 20 mg/m$^2$. In one embodiment, wherein the subject is human, gemcitabine is administered in a dose that is equal to or less than 900 mg/m$^2$, 800 mg/m$^2$, 700 mg/m$^2$ or 600 mg/m$^2$, and/or the nab-paclitaxel is administered in a dose that is equal to or less than 110 mg/m$^2$, 100 mg/m$^2$, 90 mg/m$^2$, 80 mg/m$^2$, or 70 mg/m$^2$. In certain embodiments, gemcitabine and/or nab-paclitaxel are administered with a frequency of every 2 weeks or less (e.g., every 3 weeks, every 4 weeks, every 6 weeks, or every 8 weeks, or less). In certain embodiments, gemcitabine is administered with a frequency of once a day, 4 times per week, 3 times per week, 2 times per week, or once per week. In certain embodiments, nab-paclitaxel is administered with a frequency of once a day, 4 times per week, 3 times per week, 2 times per week, or once per week. In certain embodiments, gemcitabine and nab-paclitaxel are administered with a frequency of once a day, 4 times per week, 3 times per week, 2 times per week, or once per week. In one embodiment, gemcitabine and/or nab-paclitazel is administered once a week. In certain embodiments, the total duration of treatment with gemcitabine and/or nab-paclitaxel is, or is more than, 2 weeks, 3 weeks, 4 weeks, 5 weeks, 6 weeks, 7 weeks, 8 weeks, 9 weeks, 10 weeks, 11 weeks, or 12 weeks.

In certain embodiments, an anti-M(H)DM2/4 antibody or fragment thereof described herein is administered to a subject with a cancer in combination with the chemotherapy drug(s) indicated for said cancer, which chemotherapy drug(s) can be optionally administered in the dosage and/or regime of administration indicated for said cancer. Non-limiting examples of chemotherapy drugs as well as their dosage and regime of administration indicated for various cancers are provided below.

Ovarian Cancer: The following information is taken from Gemzar® (gemcitabine for injection), Eli Lilly and Company, Highlights of Prescribing Information, revised March 2017, http://pi.lilly.com/us/gemzar.pdf (last accessed on Jul. 27, 2017). Gemcitabine (Gemzar®) in combination with carboplatin is indicated for the treatment of patients with advanced ovarian cancer that has relapsed at least 6 months after completion of platinum-based therapy. The recommended dose of Gemzar® is 1000 mg/m$^2$ as an intravenous infusion over 30 minutes on Days 1 and 8 of each 21-day cycle, in combination with carboplatin (AUC 4) intravenously after Gemzar® administration on Day 1 of each 21-day cycle.

Breast Cancer: The following information is taken from Gemzar® (gemcitabine for injection), Eli Lilly and Company, Highlights of Prescribing Information, revised March 2017, http://pi.lilly.com/us/gemzar.pdf (last accessed on Jul. 27, 2017). Gemcitabine (Gemzar®) in combination with paclitaxel is indicated for the first-line treatment of patients with metastatic breast cancer after failure of prior anthracycline-containing adjuvant chemotherapy, unless anthracyclines were clinically contraindicated. The recommended dose of Gemzar® is 1250 mg/m$^2$ intravenously over 30 minutes on Days 1 and 8 of each 21-day cycle that includes paclitaxel. Paclitaxel can be administered at 175 mg/m2 on Day 1 as a 3 hour intravenous infusion before Gemzar® administration.

Non-Small Cell Lung Cancer: The following information is taken from Gemzar® (gemcitabine for injection), Eli Lilly and Company, Highlights of Prescribing Information, revised March 2017, http://pi.lilly.com/us/gemzar.pdf (last accessed on Jul. 27, 2017). Gemcitabine (Gemzar®) is indicated in combination with cisplatin for the first-line treatment of patients with inoperable, locally advanced (Stage IIIA or III 3), or metastatic (Stage IV) non-small cell lung cancer. Every 4-week schedule: the recommended dose of Gemzar® is 1000 mg/m$^2$ intravenously over 30 minutes on Days 1, 8, and 15 in combination with cisplatin therapy; cisplatin can be administered intravenously at 100 mg/m$^2$ on Day 1 after the infusion of Gemzar®. Every 3-week schedule: the recommended dose of Gemzar® is 1250 mg/m$^2$ intravenously over 30 minutes on Days 1 and 8 in combination with cisplatin therapy; cisplatin can be administered intravenously at 100 mg/m$^2$ on Day 1 after the infusion of Gemzar®.

Pancreatic Cancer: The following information is taken from Gemzar® (gemcitabine for injection), Eli Lilly and Company, Highlights of Prescribing Information, revised March 2017, http://pi.lilly.com/us/gemzar.pdf (last accessed on Jul. 27, 2017). Gemcitabine (Gemzar®) is indicated as first-line treatment for patients with locally advanced (non-resectable Stage II or Stage III) or metastatic (Stage IV) adenocarcinoma of the pancreas. Gemzar® is indicated for patients previously treated with 5-FU. The recommended dose of Gemzar® is 1000 mg/m$^2$ over 30 minutes intravenously. The recommended treatment schedule is as follows: weeks 1-8—weekly dosing for the first 7 weeks followed by one week rest; after week 8—weekly dosing on Days 1, 8, and 15 of 28-day cycles.

Metastatic Breast Cancer: The following information is taken from ABRAXANE® (paclitaxel protein-bound particles for injectable suspension, albumin-bound), Celgene Corporation, Highlights of Prescribing Information, revised July 2015, http://www.abraxane.com/wp-content/pi/prescribing-info.html (last accessed Jul. 27, 2017). ABRAXANE® is indicated for the treatment of breast cancer after failure of combination chemotherapy for metastatic disease or relapse within 6 months of adjuvant chemotherapy. Prior therapy should have included an anthracycline unless clinically contraindicated. After failure of combination chemotherapy for metastatic breast cancer or relapse within 6 months of adjuvant chemotherapy, the recommended regimen for ABRAXANE® is 260 mg/m$^2$ administered intravenously over 30 minutes every 3 weeks.

Non-Small Cell Lung Cancer: The following information is taken from ABRAXANE® (paclitaxel protein-bound particles for injectable suspension, albumin-bound), Celgene Corporation, Highlights of Prescribing Information, revised July 2015, http://www.abraxane.com/wp-content/pi/prescribing-info.html (last accessed Jul. 27, 2017). ABRAXANE® is indicated for the first-line treatment of locally advanced or metastatic non-small cell lung cancer, in combination with carboplatin, in patients who are not candidates for curative surgery or radiation therapy. The recommended dose of ABRAXANE® is 100 mg/m$^2$ administered as an intravenous infusion over 30 minutes on Days 1, 8, and 15 of each 21-day cycle. Carboplatin can be administered on Day 1 of each 21 day cycle immediately after ABRAXANE®.

Adenocarcinoma of the Pancreas: The following information is taken from ABRAXANE® (paclitaxel protein-bound particles for injectable suspension, albumin-bound), Celgene Corporation, Highlights of Prescribing Information, revised July 2015, http://www.abraxane.com/wp-content/pi/prescribing-info.html (last accessed Jul. 27, 2017). ABRAXANE is indicated for the first-line treatment of patients with metastatic adenocarcinoma of the pancreas, in combination with gemcitabine. The recommended dose of ABRAXANE is 125 mg/m$^2$ administered as an intravenous infusion over 30-40 minutes on Days 1, 8 and 15 of each 28-day cycle. Gemcitabine can be administered immediately after ABRAXANE® on Days 1, 8 and 15 of each 28-day cycle.

In a specific embodiment, an anti-M(H)DM2/4 antibody or fragment thereof described herein is administered to a subject in combination with an immunomodulator (e.g., a cytokine, an antigen, or a checkpoint targeting agent). In one embodiment, an anti-M(H)DM2/4 antibody or fragment thereof described herein is administered to a subject in combination with a checkpoint targeting agent such as, without limitation, an antagonist of PD-1, an antagonist of PD-L1, an antagonist of PD-L2, an antagonist of CTLA-4, an antagonist of TIM-3, an antagonist of GITR, an antagonist of OX40, an antagonist of LAG-3 (e.g., the antagonist of any of the above-mentioned checkpoint molecules can be an antibody, such as an inhibitory antibody to these molecules, an antibody fragment, or a small molecule). In one embodiment, an anti-M(H)DM2/4 antibody or fragment thereof described herein is administered to a subject in combination with an inhibitor of PD-1, an inhibitor of PD-L1, or an inhibitor of CTLA-4 (where the inhibitor can be an antagonistic antibody, an antibody fragment, or a small molecule).

In a specific embodiment, an anti-M(H)DM2/4 antibody or fragment thereof described herein is administered to a subject in combination with radiation therapy (e.g., x-rays, gamma-rays or another source of radiation).

In a specific embodiment, an anti-M(H)DM2/4 antibody or fragment thereof described herein is administered to a subject in combination with surgery (such as a surgery to remove part or all of the cancerous tumor being treated).

In a specific embodiment, an anti-M(H)DM2/4 antibody or fragment thereof described herein is administered to a subject in combination with a Treg-inhibitory agent.

In a specific embodiment, an anti-M(H)DM2/4 antibody or fragment thereof described herein is administered to a subject in combination with a T-cell therapy.

In a specific embodiment, an anti-M(H)DM2/4 antibody or fragment thereof described herein is administered to a subject in combination with a tumor vaccine.

In a specific embodiment, an anti-M(H)DM2/4 antibody or fragment thereof described herein is administered to a subject in combination with EGFR inhibitor (e.g., erlotinib).

In certain embodiments, an anti-M(H)DM2/4 antibody or fragment thereof described herein is used to treat a subject that is not treated with a cell cycle inhibitor (i.e., the additional therapy is not an agent that inhibits cell cycle). In one embodiment, an anti-M(H)DM2/4 antibody or fragment thereof described herein is used to treat a subject that is not concurrently (during the same treatment period) treated with a cell cycle inhibitor (i.e., the subject is not treated with an anti-M(H)DM2/4 antibody or fragment thereof and a cell cycle inhibitor during the same period of time, e.g., day or week). In one embodiment, an anti-M(H)DM2/4 antibody or fragment thereof described herein is used to treat a subject that has not been previously treated and is not concurrently treated with a cell cycle inhibitor.

In particular embodiments, an anti-M(H)DM2/4 antibody or fragment thereof described herein can be used before, during, or after the second therapy (e.g., a chemotherapy, a radiation therapy, a surgery, or any other therapy described herein or known in the art).

In certain embodiments, the subject being treated in accordance with the methods described herein has not received an anti-cancer therapy prior to the administration of an anti-M(H)DM2/4 antibody or fragment thereof. In other embodiments, an anti-M(H)DM2/4 antibody or fragment thereof is administered to a subject that has received an anti-cancer therapy prior to administration of the antibody or fragment. In particular, embodiments, anti-M(H)DM2/4 antibody or fragment thereof is administered to a subject recovering from or receiving an immunosuppressive therapy.

In certain embodiments, provided herein are kits comprising an anti-M(H)DM2/4 antibody or a fragment thereof, and one or more additional anti-cancer agents. In one embodiment, provided herein are kits comprising (i) an anti-M(H)DM2/4 antibody or a fragment thereof (e.g., in a therapeutically effective amount), and (ii) one or more of chemotherapeutic drugs, for example, gemcitabine, paclitaxel, or gemcitabine and nab-paclitaxel (e.g., in therapeutically effective amounts, such as any amounts described herein, which may be less than the therapeutically effective amount of the drug or drugs when the drug or drugs are used without the anti-M(H)DM2/4 antibody or fragment).

The following examples are offered by way of illustration and not by way of limitation. Various other embodiments of the invention may be practiced, given the general description provided herein.

8. EXAMPLES

The data presented herein demonstrate that specific segments (i.e., epitopes) of HDM2 are extracellularly accessible on the plasma membrane surface of intact {i.e., viable and non-permeabilized) cancer cells. Three (3) different extracellularly accessible epitopes have been identified. Specific segments of HDM2 that are extracellularly accessible include but are not limited to epitopes present in the NMC-P1, NMC-P2 and NMC-P3 peptide sequences (SEQ ID NO:1, SEQ ID NO:2, and SEQ ID NO:3, respectively). These extracellularly accessible sequences are appropriate therapeutic and diagnostic targets for anti-HDM2 antibodies. Therefore, cancer cells expressing HDM2 on their surface membrane can be targeted with antibodies to HDM2 for diagnostic and therapeutic {i.e., anti-tumor cytotoxic and inhibitory effect) purposes.

In particular, the data presented herein demonstrated that select HDM2-specific antibodies bound to the extracellularly accessible sequences of M(H)DM2/4 on the surface membrane of intact cells of several rodent and human cancer cell lines as well as primary tumor cells from human patients. In contrast, the same HDM2-specific antibodies exhibited minimal binding to the surface membrane of normal human blood mononuclear cells. It was found that these HDM2-specific antibodies selectively bound to various cancer cells such as: intact human melanoma, uveal melanoma, pancreatic, breast, colon, lung and ovarian cancer cells in vitro. In addition, the data presented herein showed that HDM2-specific antibodies inhibited the growth of cancer cells in vitro and in vivo, strongly indicating that they can be used as therapeutic agents in vivo. Data from in vivo studies and described herein showed that select HDM2-specific antibodies inhibited tumor growth and were cytotoxic against tumors in rodent tumor models. The examples below demonstrated that select HDM2-specific antibodies were not only cytotoxic to tumor cells but also inhibited tumor growth in mouse models of pancreatic cancer, lung cancer and colon cancer. Data herein further demonstrated that only select antibodies recognized extracellularly accessible epitopes of HDM2.

Methods of Making of Antibodies Used in the Examples

Anti-HDM2 antibodies that specifically bind to (i) NMC-P1, i.e., the peptide of SEQ ID NO:1 ("NMC-100s series of monoclonal antibodies)", (ii) NMC-P2, i.e., the peptide of SEQ ID NO:2 ("NMC-200s series of monoclonal antibodies"), and (iii) NMC-P3, i.e., the peptide of SEQ ID NO: 3 ("NMC-300s series of monoclonal antibodies") were generated using the hybridoma approach. NMC-P1, NMC-P2 and NMC-P3 peptides were conjugated to Keyhole limpet hemocyanin (KLH) using Sulfo-SMCC method (Thermo Scientific, Cat. No. 22122). Briefly, Protein-NH2 was made in Conjugation Buffer (provided by manufacturer). Twenty-fold molar excess of crosslinker was added to the protein solution and the reaction mixture was incubated for 30 minutes at room temperature. Excess cross linker was then removed using desalting column equilibrated with Conjugation Buffer. Protein-SH and desalted Protein-NH2 were then combined, mixed and incubated for 30 minutes at room temperature. The conjugation reaction was then stopped by addition of buffer containing reduced cysteine at a concentration several times greater than the sulfhydryls of Protein-SH. Following peptide conjugation, mice (BALB/c female) were immunized with the peptide NMC-P1, NMC-P2 or NMC-P3 by intraperitoneal injection at 100 ng/mouse. Boosters were injected 5-7 times to provoke immune response. Specific-antibody production was then evaluated by peptide-ELISA of the mice serum for antibody titration. Spleens of mice with high antibody titer were then harvested from each mice and single cell suspension of splenocytes were prepared. Splenocytes were then fused with SP2/0 myeloma cells (1:5 ratio). Briefly, 250 µl of EDTA was added to the mixture of splenocytes and myeloma cells. Cells were then span down and supernatant was removed. Cell pellet was then loosened and 1 mL of PEG was dispensed alongside the tube slowly over 1 min and the mixture was incubated for 5 min in 37° C. water bath. 1 mL of 100×FBS and 10 mL of IMDM medium (10% FBS) was then added and kept in the incubator for 1 hour. Cells were then centrifuged and supernatant was removed. Cell pellet was then re-suspended in IMDM (20% FBS)-containing HAT Fusion medium (hypoxanthine-aminopterin-thymidine medium). Cells were then plated in 96-well dishes and incubated for roughly 10 to 14 days. After 10-14 days when clones became visible, media supernatant from each well was tested by ELISA for its binding to their corresponding specific immunogenic peptide (NMC-P1, NMC-P2 or NMC-P3). ELISA-positive wells were then selected for further clone selection, single-cell sub-cloning and monoclonal antibody purification. Monoclonal antibody selection was done by peptide-ELISA using NM C-P1, NMC-P2 or NMC-P3 peptide antigen. To further select antibodies that react with the peptide antigen as well as with plasma membrane HDM2, binding assays were also performed for mAb selection by cell-ELISA on intact cancer cells.

Predicted Reactivities of the Generated Antibodies

Predicted reactivities of the NMC-100s series, NMC-200s series, and NMC-300s series of monoclonal antibodies with different HDM2 isoforms/variants are presented in Table 1 and Table 2. Predictions were made based on whether the respective isoform contains the sequence corresponding to the sequence of PI, P2 or P3 (and knowledge of to which peptide (PI, P2, or P3) the respective NMC series mAb binds, based on which peptide was used as immunogen for which series).

TABLE 1

Predicted reactivities of the NMC-1OOs series, NMC-200s series, and NMC-300s series of monoclonal antibodies with different HDM2 isoforms/variants.

| Uniprot Accession # | Isoform | Amino acid residues of HDM2 (SEQ ID NO: 4) that are missing in the isoform | Reactivity with mAb NMC-1OOs series | Reactivity with mAb NMC-200s series | Reactivity with mAb NMC-300s series |
|---|---|---|---|---|---|
| Q00987-2 | Mdm2-A | 28-222 | + | + | + |
| Q00987-3 | Mdm2-A1 | 28-222; 275-300 | + | + | + |
| Q00987-4 | Mdm2-B | 28-300 | + | + | + |
| Q00987-5 | Mdm2-C | 53-222 | + | + | + |

TABLE 1-continued

Predicted reactivities of the NMC-1OOs series, NMC-200s series, and NMC-300s series of monoclonal antibodies with different HDM2 isoforms/variants.

| Uniprot Accession # | Isoform | Amino acid residues of HDM2 (SEQ ID NO: 4) that are missing in the isoform | Reactivity with mAb NMC-1OOs series | Reactivity with mAb NMC-200s series | Reactivity with mAb NMC-300s series |
|---|---|---|---|---|---|
| Q00987-6 | Mdm2-D | 30-388 | + | + | + |
| Q00987-7 | Mdm2-E | 76-102: YCSNDLLGDLFGVPSFSVKEHRKIYTM → NDCANLFPLVDLSIRELYISNYITLGI; 103-491 | + | + | − |
| Q00987-9 | Mdm2-F | 53-97 | + | + | + |
| Q00987-10 | Mdm2-G | 115-169 | + | + | + |
| Q00987-11 | Isoform 11 | 1-1: M → MVRSRQM | + | + | + |
|  | MDM2-KB2 | 157-248 | + | + | + |
| Q00987-8 | Mdm2-alpha | 1-61 | − | − | + |
| Q00987 | Canonical | 1-491 | + | + | + |

TABLE 2

Predicted reactivities of the NMC-1OOs series, NMC-200s series, and NMC-300s series of monoclonal antibodies with different HDM2 isoforms/variants.

| NCBI Accession # | Reactivity with mAb NMC-100 series | Reactivity with mAb NMC-200 series | Reactivity with mAb NMC-300 series |
|---|---|---|---|
| EAW97204.1 | + | + | − |
| EAW97206.1 | + | + | + |
| EAW97213.1 | + | + | + |
| EAW97210.1 | + | + | + |
| EAW97201.1 | + | + | − |
| EAW97202.1 | + | + | + |
| EAW97203.1 | + | + | + |
| EAW97212.1 | + | + | + |
| EAW97209.1 | + | + | + |
| EAW97205.1 | + | + | + |
| AFM80534.1 | − | − | + |
| CAP16722.1 | + | + | − |
| CAP16731.1 | + | + | − |
| AAA75518.1 | + | + | − |
| CAD36961.1 | + | + | − |
| CAP16717.1 | + | + | − |
| AFM80529.1 | + | + | + |
| AFM80530.1 | + | + | + |
| CAC07811.1 | + | + | + |
| AAA75517.1 | + | + | + |
| AFM80531.1 | + | + | + |
| CAP16743.1 | + | + | − |
| CAC07810.1 | + | − | + |
| CAP16730.1 | + | + | − |
| AAL13247.1 | + | + | + |
| AFM80533.1 | + | + | + |
| CAD36959.1 | + | + | − |
| CAP16712.1 | + | + | − |
| CAD23252.1 | + | + | + |
| CAP16721.1 | + | + | − |
| CAP16716.1 | + | + | − |
| AFM80535.1 | + | + | + |
| CAP16728.1 | + | + | − |
| CAP16734.1 | + | + | − |
| AAL13243.1 | + | + | − |
| AFM80536.1 | + | + | + |
| AFM80537.1 | + | + | + |
| AAA75515.1 | + | + | + |
| AFM80538.1 | + | + | − |
| AFM80539.1 | + | + | + |
| CAC07809.1 | + | + | + |
| CAD23251.1 | + | + | + |
| NP_001138812.1 | + | + | + |
| AAA75514.1 | + | + | + |
| CAP16729.1 | + | + | − |
| CAP16733.1 | + | + | − |
| AFM80540.1 | + | + | + |
| XP_006719463.1 | − | − | + |
| CAP16735.1 | + | + | − |
| CAP16708.1 | + | + | + |
| XP_006719462.1 | − | − | + |
| AAL40179.1 | + | + | + |
| NP_001138811.1 | + | + | + |
| NP_001138809.1 | + | + | + |
| AAL40180.1 | + | + | + |
| CAP16705.1 | + | + | + |
| ACX31156.1 | + | + | + |
| CAP16732.1 | + | + | + |
| CAP16703.1 | + | + | − |
| CAP16738.1 | + | + | − |
| XP_005268929.1 | + | + | + |
| NP_002383.2 | + | + | + |
| CAD36962.1 | + | + | − |
| CAP16704.1 | + | + | + |
| CAP16715.1 | + | + | − |
| CAD79459.1 | + | + | − |
| CAP16707.1 | + | + | − |
| AAL13242.1 | + | + | − |
| CAP16718.1 | + | + | − |
| CAP16727.1 | + | + | − |
| CAD79456.1 | + | + | − |
| AAL13244.1 | + | + | − |
| CAP16739.1 | + | + | − |
| CAD79457.1 | + | + | − |
| CAD36960.1 | + | + | − |
| CAD79458.1 | + | + | − |
| CAP16725.1 | + | + | − |
| CAP16719.1 | + | + | − |
| CAP16740.1 | + | + | − |
| CAP16736.1 | + | + | − |
| AFM80527.1 | + | + | − |
| AAL13245.1 | + | + | − |
| CAP16737.1 | + | + | − |
| AFM80528.1 | + | + | + |
| AAL13246.1 | + | + | + |
| CAC07812.1 | + | + | + |
| AAF42995.1 | − | + | + |

Antibodies Used in the Examples

Monoclonal antibody NMC-103 is an antibody that binds to NMC-P1 (SEQ ID NO: 1) (it is one of the NMC-100s series of antibodies). Monoclonal antibody NMC-204 is an antibody that binds to NMC-P2 (SEQ ID NO:2) (it is one of the NMC-200s series of antibodies). Monoclonal antibody NMC-303 is an antibody that binds to NMC-P3 (SEQ ID NO:3) (it is one of the NMC-3005 series of antibodies). The heavy chain/light chain frame work region sequences, complementarity determining region (CDR) sequences, and variable region sequences of these antibodies are listed in Section 8, below.

The following anti-HDM2 antibodies were used in the experiments described in Examples 1-9: (i) purified NMC-103 mouse monoclonal antibody (mAb) of the IgG1 isotype (NMC-103 mAbs produced by single-cell cloned hybridoma cells were purified on protein G/A columns), (ii) purified NMC-204 mouse mAb of the IgG3 isotype (NMC-204 mAbs produced by single-cell cloned hybridoma cells were purified on protein G/A columns); (iii) purified NMC-303 mouse mAb of the IgM isotype (NMC-303 mAbs produced by single-cell cloned hybridoma cells were purified on protein G/A columns); (iv) an anti-HDM2 antibody termed "MDM2 monoclonal antibody (M01), clone 1A7" (Abnova, Cat. No. H00004193-M01); (v) an anti-HDM2 antibody termed "MDM2 Antibody (D-7)" (Santa Cruz, Cat. No. sc-13161); (vi) an anti-HDM2 antibody termed "p-MDM2 Antibody (2G2)" (Santa Cruz, Cat. No. sc-53368); (vii) an anti-HDM2 antibody termed "MDM2 Antibody (SPM344)" (Santa Cruz, Cat. No. sc-56430); (viii) an anti-HDM2 antibody termed "MDM2 Antibody (SMP14)" (Santa Cruz, Cat. No. sc-965); (ix) an anti-HDM2 antibody termed "Anti-MDM2 clone 4B2C1.11" (EMD Millipore, Cat. No. MABE331); (x) an anti-HDM2 antibody termed "Anti-MDM2 clone 3G9" (EMD Millipore, Cat. No. 04-1530); (xi) an anti-HDM2 antibody termed "Anti-MDM2 clone 2A10" (EMD Millipore, Cat. No. MABE281); (xii) an anti-HDM2 antibody termed "Anti-MDM2 (Ab-1) Mouse mAb (IF2)" (EMD Millipore, Cat. No. OP46); (xiii) an anti-HDM2 antibody termed "Anti-MDM2 (Ab-3) Mouse mAb (4B11)" (EMD Millipore, Cat. No. OP143); (xiv) an anti-HDM2 antibody termed "Anti-MDM2 (Ab-4) Mouse mAb (2A9C1.18)" (EMD Millipore, Cat. No. OP 144); (xv) an anti-HDM2 antibody termed "Anti-MDM2 (Ab-5) Mouse mAb (4B2C1.11)" (EMD Millipore, Cat. No. OP 145); (xvi) an anti-HDM2 antibody termed "MDM2 Antibody (C-18): sc-812" (Santa Cruz, polyclonal, Cat No. sc-812); and (xvii) n anti-HDM2 antibody termed "MDM2 Antibody (N-20): sc-813" (Santa Cruz, polyclonal, Cat No. sc-813).

8.1 Example 1: Selection of HDM2-Specific mAhs to Extracellularly Accessible Enitones of HΩM2

Utilizing enzyme-linked immunosorbent assay (ELISA) the data presented herein showed that mAb NMC-103 specifically bound to peptide NMC-P1 (SEQ ID NO: 1) corresponding to amino acids 1-15 of HDM2, while mAb NMC-204 specifically bound to NMC-P2 peptide (SEQ ID NO:2) corresponding to amino acids 15-25 of HDM2, and mAb NMC-303 specifically bound to NMC-P3 peptide (SEQ ID NO:3) corresponding to amino acids 475-491 of HDM2. Moreover, immunoblot analysis presented here shows that mAbs NMC-103, NMC-204 and NMC-303 recognized the full-length recombinant HDM2 protein.

Peptide-ELISA Methodology: 5 µg/ml of NMC-P1, NMC-P2 or NMC-P3 peptide antigen was dried onto a 96-well ELISA plate overnight. Plates were then blocked with 5% BSA in 1× phosphate-buffered saline (PBS) (100 µℓ/well) for 2 hours at room temperature. Microplate wells were then washed 5 times with 300 µℓ of ice cold 1× PBS. Appropriate dilutions of monoclonal antibodies NMC-103, NMC-204 or NMC-303 in 1% bovine serum albumin (BSA) in PBS solution were then incubated with their corresponding peptides (NMC-P1, NMC-P2 or NMC-P3, respectively) at room temperature. After 2 hours, wells were washed 5 times with 300 µℓ µℓ ice-cold PBS/well and 100 µℓ secondary antibody (HRP-labeled Goat anti-Mouse F(ab')2 H&L cross-adsorbed secondary antibody (HRP-GaM F(ab')2), ThermoFisher, Cat. No. A24524) diluted 1:2500 to 1:5000 in PBS-1% BSA solution were added and the incubation continued at room temperature. After 1 hour, the wells were washed again 5 times with 200 µℓ of ice-cold PBS and 50 µiL of the TMB Substrate Solution (1-StepTM Ultra TMB-ELISA, ThermoFisher, Cat. No. 34028) were added to each well and color was allowed to develop for 30 minutes at room temperature. The reaction was stopped by addition of 50 µµℓ ␣ of stop solution (ThermoFisher, Cat. No. SSO4) to each well and absorbance of each well was read immediately for optical density (OD) at 450 nm.

Competition assays: As for peptide antigen binding competition experiments, 1 µℓ/ml of mAb NMC-103 was pre-incubated with 10 µℓ/ml of NMC-P1, NMC-P2 or NMC-P3 for 1 hour at room temperature. MAb NMC-103 was then incubated with ELISA plates coated with NMC-P1 as described above.

Western Blot: As for immunoblots, 1 µg/well of recombinant FlDM2 protein (GST tagged, Abeam, Cat. No. ab188727) was separated on 8-16% sodium dodecyl sulfate (SDS) polyacrylamide gel and proteins were then transferred to polyvinylidene difluoride (PVDF) membrane. The membrane was blocked with 5% milk followed by incubation with monoclonal antibody NMC-103, NMC-204 or NMC-303 at 1 µg/πιµℓ in 1% milk in PBS for 2 hours. The membrane was then washed×3 times (10 minutes each) and incubated for 1 hour with corresponding HRP-conjugated secondary antibody (Goat anti-Mouse IgG (H&L), F(ab')2 Frag Cross-adsorbed HRP (HRP-GaM F(ab')2), ThermoFisher, Cat. No. A24524) diluted 1:5000 in 1% BSA-PBS. The membrane was then washed×3 times and incubated with Pierce ECL Plus Western Blotting Substrate (ThermoFisher, Cat. No. #32132) for 10 min before developing on a LICOR Scanner.

Figures 1A, 1B, 1C, 1D:
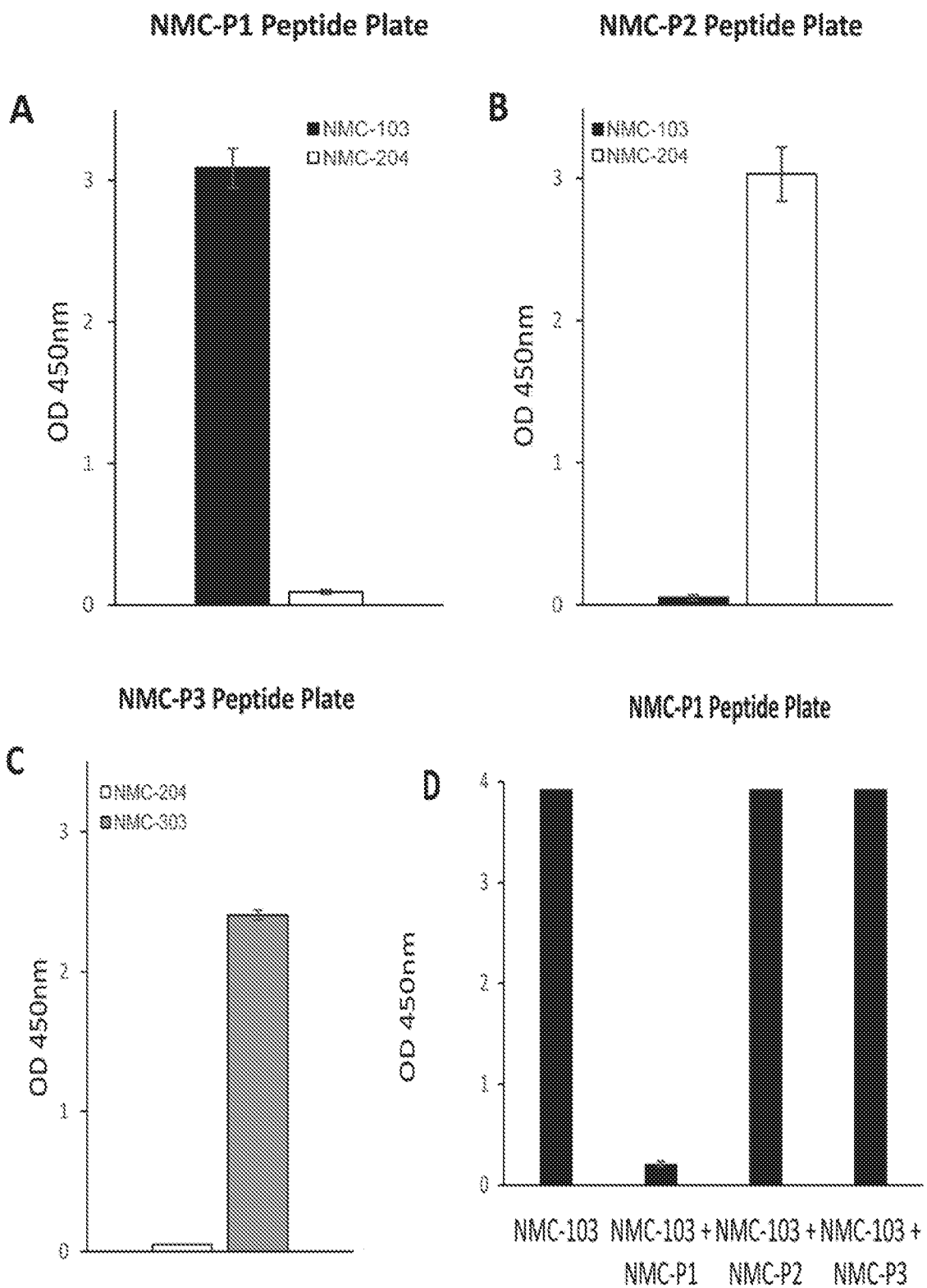

The peptide-ELISA experiments shown in FIG. 1 demonstrated selective and specific binding of monoclonal antibodies (mAb) NMC-103, NMC-204 and NMC-303 to their corresponding peptide antigens. FIG. 1A shows that NMC-103 bound to NMC-P1 peptide while NMC-204 did not bind to NMC-P1. FIG. IB shows that mAb NMC-204 bound to NMC-P2 peptide while mAb NMC-103 did not bind to NMC-P2. FIG. 1C shows that mAb NMC-303 bound to NMC-P3 peptide while NMC-204 did not bind to NMC-P3. Thus, the Peptide-ELISA results demonstrated that each of the mAbs NMC-103, NMC-204 and NMC-303 selectively bound to their corresponding antigen peptides on the ELISA-plate and not to other peptides. Figure ID shows that while mAb NMC-103 bound to NMC-P1, pre-incubation of NMC-P1 peptide with mAb NMC-103 abolished the binding of NMC-103 to NMC-P1 peptide on the plate. In contrast, pre-incubation of mAb NMC-103 with either NMC-P2 or NMC-P3 did not affect the binding of mAb NMC-103 to NMC-P1. These experiments demonstrate the specificity of mAbs NMC-103, NMC-204 and NMC-303 for their corresponding peptide antigens.

Figure 2:
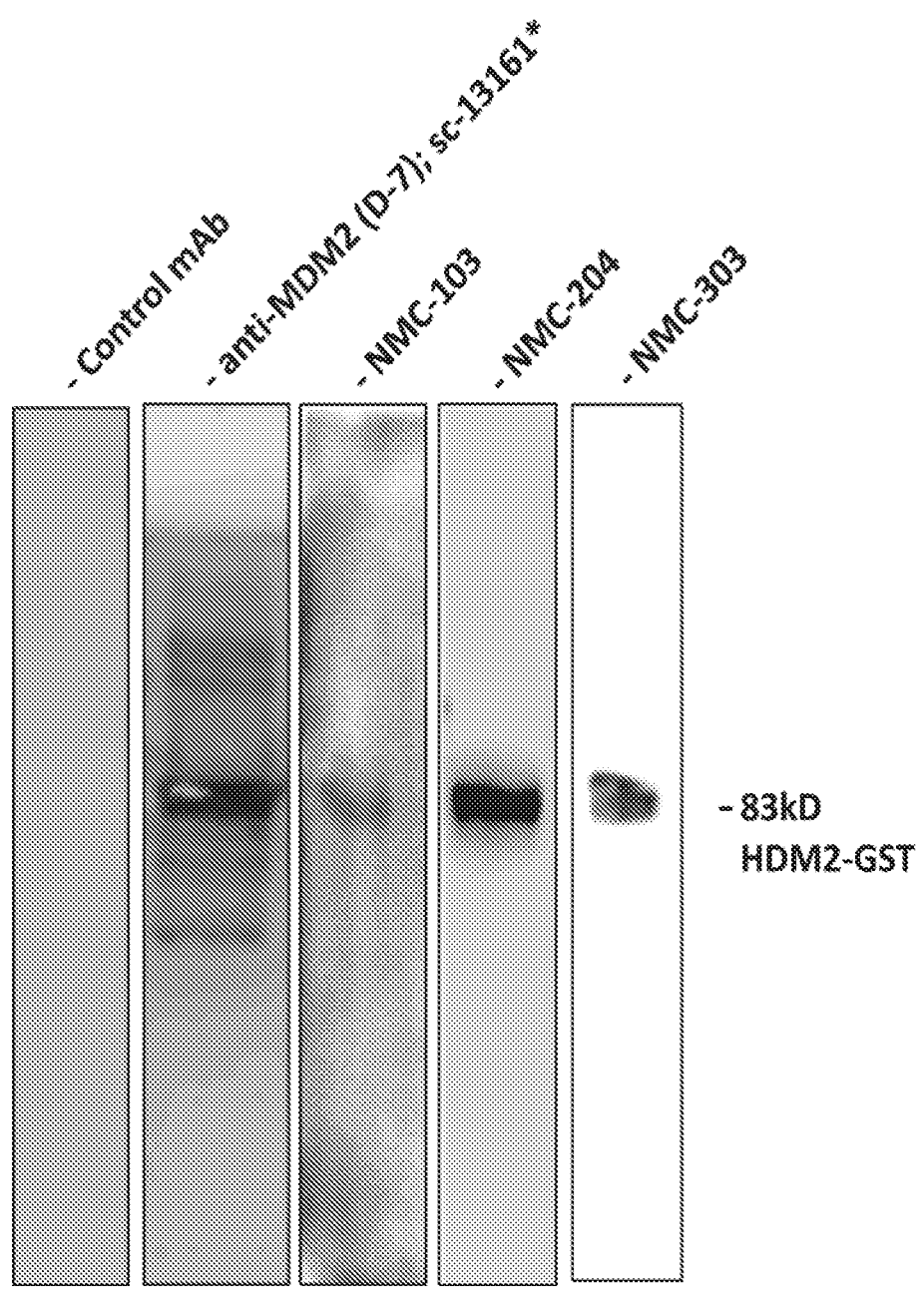

The results of the immunoblot experiments in FIG. 2 demonstrated that mAbs NMC-103, NMC-204 and NMC-303 reacted with the recombinant full-length HDM2 protein. The recombinant protein has a GST tag at its N-terminal which brings the molecular weight to approximately 83 kD. Lane 2 of the immunoblot shows the reactivity of a commercially available antibody raised against amino acids 100-320 of MDM2 of human origin (MDM2 (D-7); Santa Cruz, Cat. No. sc-13161) to the full-length recombinant HDM-2 protein. Lane 3 of the immunoblot shows the reactivity of mAb NMC-103 with a single band at approximately 83 kD, corresponding to the recombinant HDM2-GST protein. Lane 4 of the immunoblot shows the binding of mAb NMC-204 to a single band at approximately 83 kD, corresponding to the recombinant HDM2-GST protein. Lane 5 of the immunoblot shows reactivity of mAb NMC-303 with the recombinant HDM2-GST protein at 83 kD. In contrast, in Lane 1, control mouse IgG (Abeam, Cat. No. ab 18447) did not react with the recombinant HDM2-GST protein. The data presented here further demonstrated that mAbs NMC-103, NMC-204 and NMC-303 recognized full-length HDM2.

8.2 Example 2: HDM2-Specific Antibodies Hound to Extracelliilarly Accessible Enitones of MfH)DM2/4 on Intact Cancer Cells from Different Rodent and Human Cancer Cell Lines and Freshly Isolated Primary Human Cancer Cells Hut not to Normal Cells General description: Utilizing ELISA, the data presented herein demonstrated the binding of mAbs NMC-103, NMC-204 and NMC-303 to extracellularly accessible epitopes of M(H)DM2/4 within the NMC-P1, NMC-P2 and NMC-P3 sequences, respectively, on the plasma membrane of human breast cancer cells, human triple negative breast cancer cells, human melanoma cells, chemo-resistant human ovarian cancer cells as well as primary patient-derived human ovarian cancer cells, human and mouse pancreatic cancer cells, mouse colon cancer cells and mouse lung cancer cells. Data presented herein also demonstrated the selective binding of these mAb to cancer cells and not to normal untransformed cells. Moreover, peptide-antigen competition results showed that each of these mAbs specifically bound to their corresponding NMC-P1, NMC-P2 or NMC-P3 regions of the plasma membrane M(H)DM2/4.

Cell-ELISA Methodology: 8,000-10,000 cells/well of a 96-well microplate were grown overnight. The next day, unbound cells were washed off with sterile 1× PBS. The cells in each well were fixed with freshly prepared 4% buffered paraformaldehyde (pH 7.2) for 1 hour followed by 3 washes with 1× PBS. The wells were then blocked with 5% BSA in PBS (100 µl /well) for 2 hours at room temperature. Microplate wells were then washed 5 times with 300 µl of ice cold 1× PBS. MAbs NMC-103, NMC-204 or NMC-303 at 1 µg/mL in 1% BSA/PBS were then incubated with various cancer or normal untransformed cells for 2 hours at room temperature. Wells were then washed with 300 µl of ice-cold 1× PBS for 5 times and corresponding secondary antibody HRP-GaM F(ab')2 diluted 1:2500 or 1:5000 in PBS with 1% BSA were added at 100 µl /well for 1 hour at room temperature followed by washing 5 times with 300 µl of ice-cold 1× PBS. TMB Substrate Solution (1-StepTM Ultra TMB-ELISA, ThermoFisher, Cat. No. 34028) was then added at 50 µl ⌐ to each microplate well and incubated at room temperature for 30 minutes. The reaction was stopped by addition of 50 µL, of stop solution (ThermoFisher, Cat. No. SSO4) to each well and absorbance of each well was measured at OD450 nm. The absorbance value of each experimental well was corrected for the absorbance value obtained from wells treated with isotype-identical mAbs included in each experiment. The results are thus expressed as "relative binding".

Figures 3A, 3B:
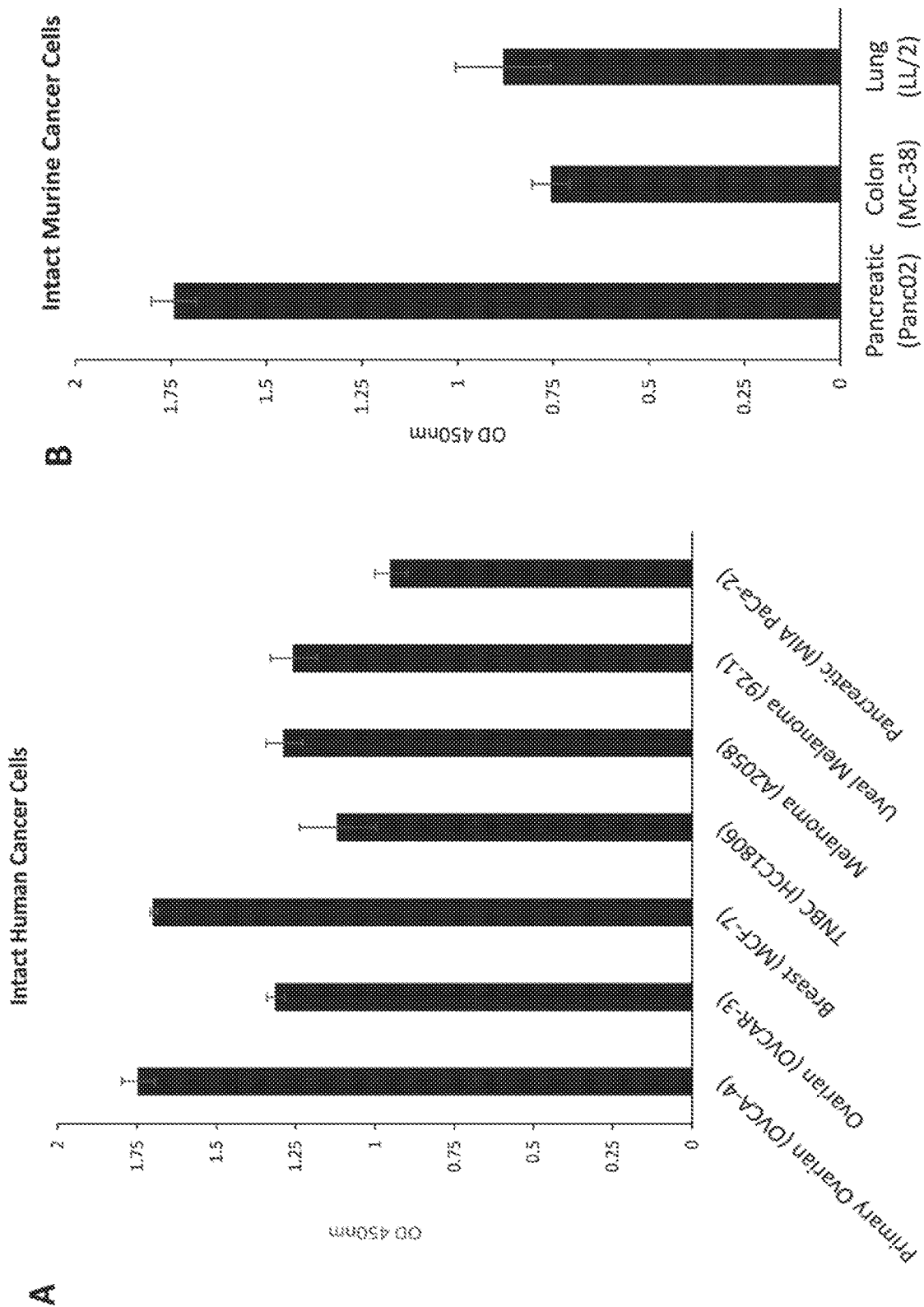
Figures 4A, 4B:
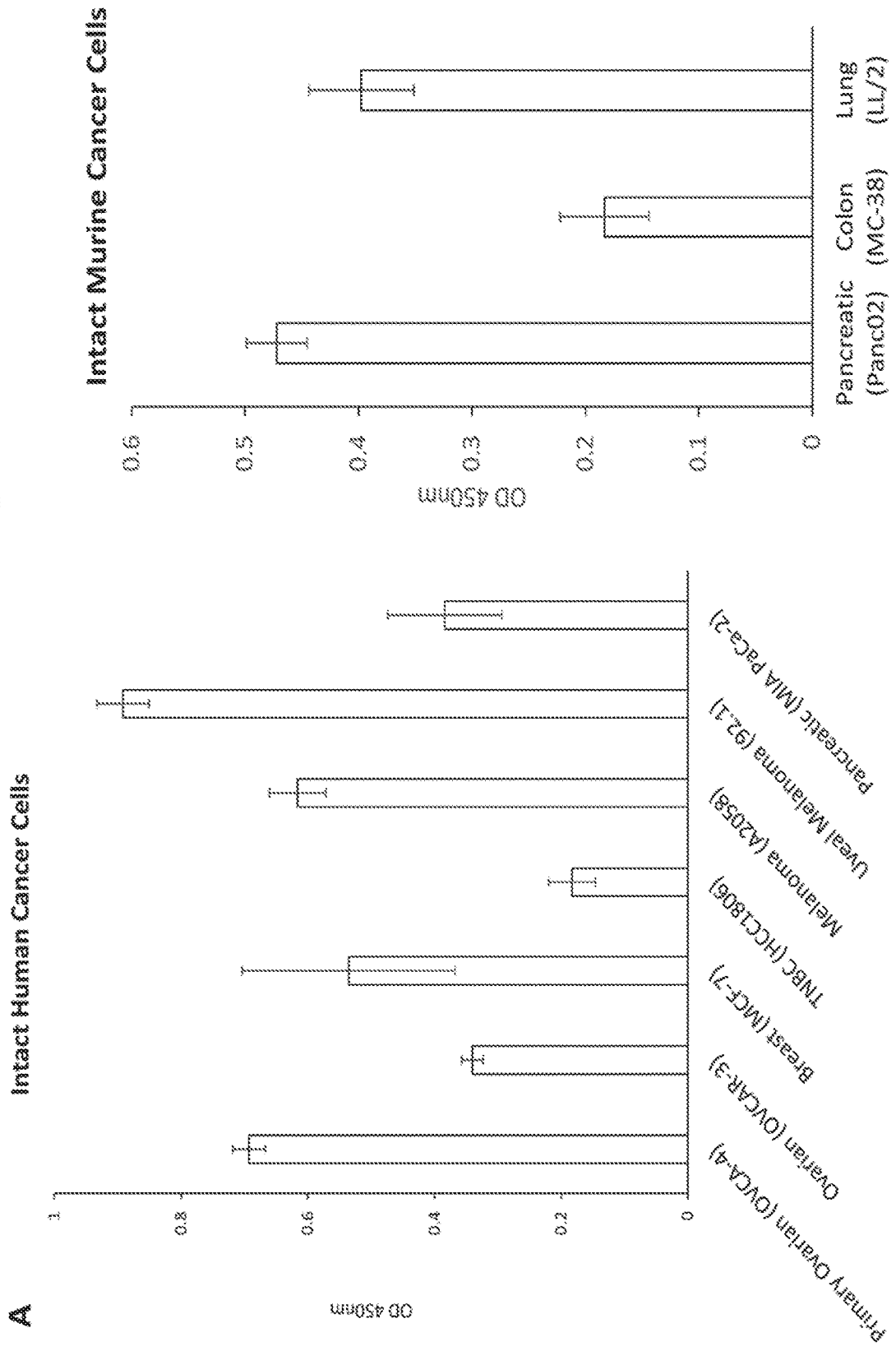
Figures 5A, 5B:
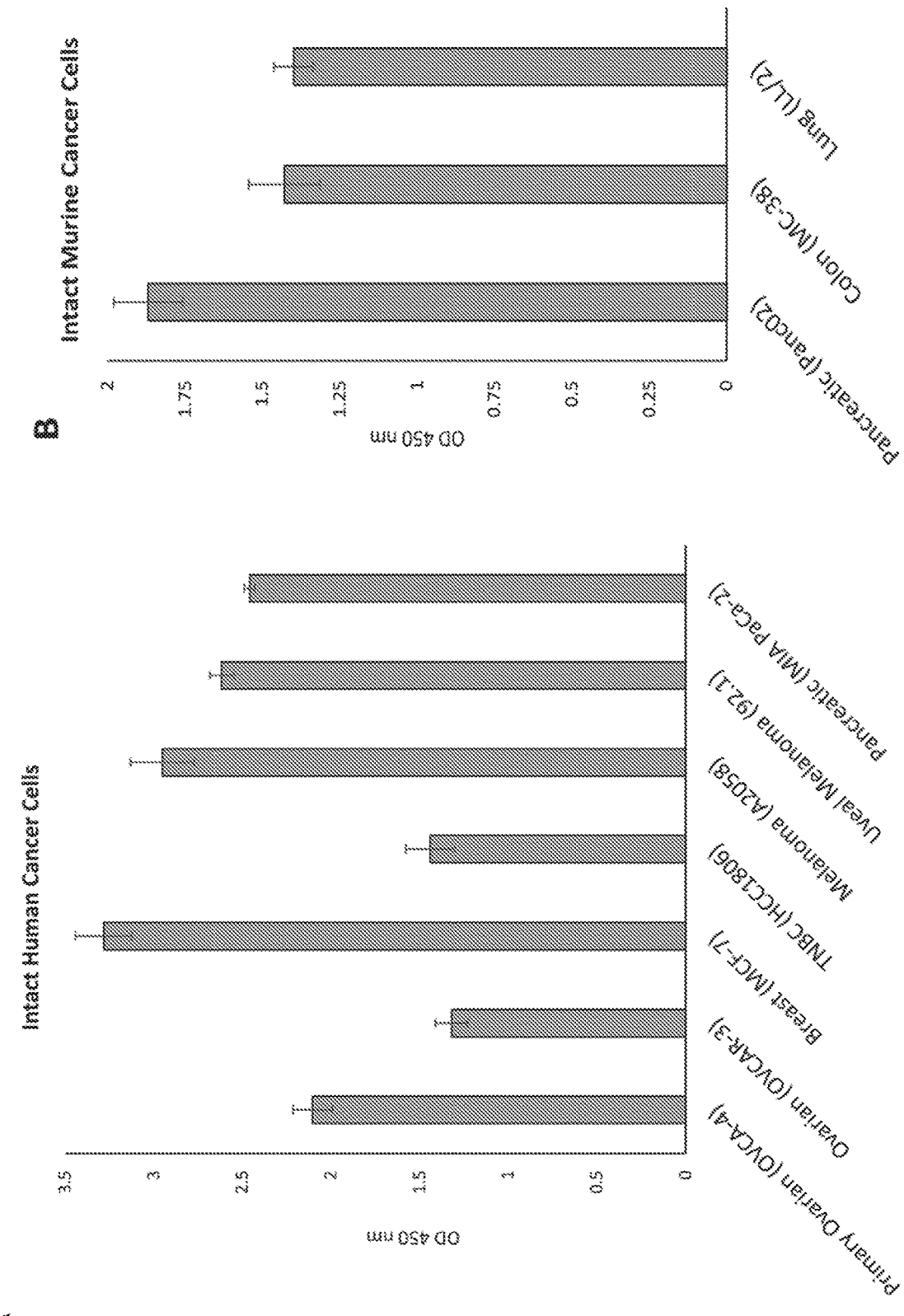

FIGS. 3-5 show the relative binding of mAbs NMC-103, NMC-204 and NMC-303 to intact cells of different types of human (A) and rodent (B) cancers. FIG. 3 shows reactivity of mAb NMC-103 to human breast cancer MCF-7 cells, human triple negative breast cancer HCC1806 cells, human pancreatic cancer MIA PaCa-2 cells, human ovarian cancer OVCAR-3 cells that are resistant to adriamycin, melphalan, and cisplatin, primary patient-derived human ovarian cancer OVCA4 cells, human melanoma A2058 cells, human uveal melanoma 92.1 cells, mouse colon cancer MC-38 cells, mouse Lewis Lung LL/2 cells and mouse pancreatic Panc02 cells. FIG. 4 presents the reactivity of NMC-204 monoclonal antibody to human breast cancer MCF-7 cells, human triple negative breast cancer HCC1806 cells, human pancreatic cancer MIA PaCa-2 cells, human ovarian cancer OVCAR-3 cells, primary patient-derived human ovarian cancer OVCA.4 cells, human melanoma A2058 cells, human uveal melanoma 92.1 cells, mouse colon cancer MC-38 cells, mouse Lewis Lung LL/2 cells and mouse pancreatic Panc02 cells. FIG. 5 shows reactivity of NMC-303 monoclonal antibody to human breast cancer MCF-7 cells, human triple negative breast cancer HCC1806 cells, human pancreatic cancer MIA PaCa-2 cells, human ovarian cancer OVCAR-3 cells, primary patient-derived human ovarian cancer OVCA.4 cells, human melanoma A2058 cells, human uveal melanoma 92.1 cells, mouse colon cancer MC-38 cells, mouse Lewis Lung LL/2 cells and mouse pancreatic Panc02 cells.

Figure 6:
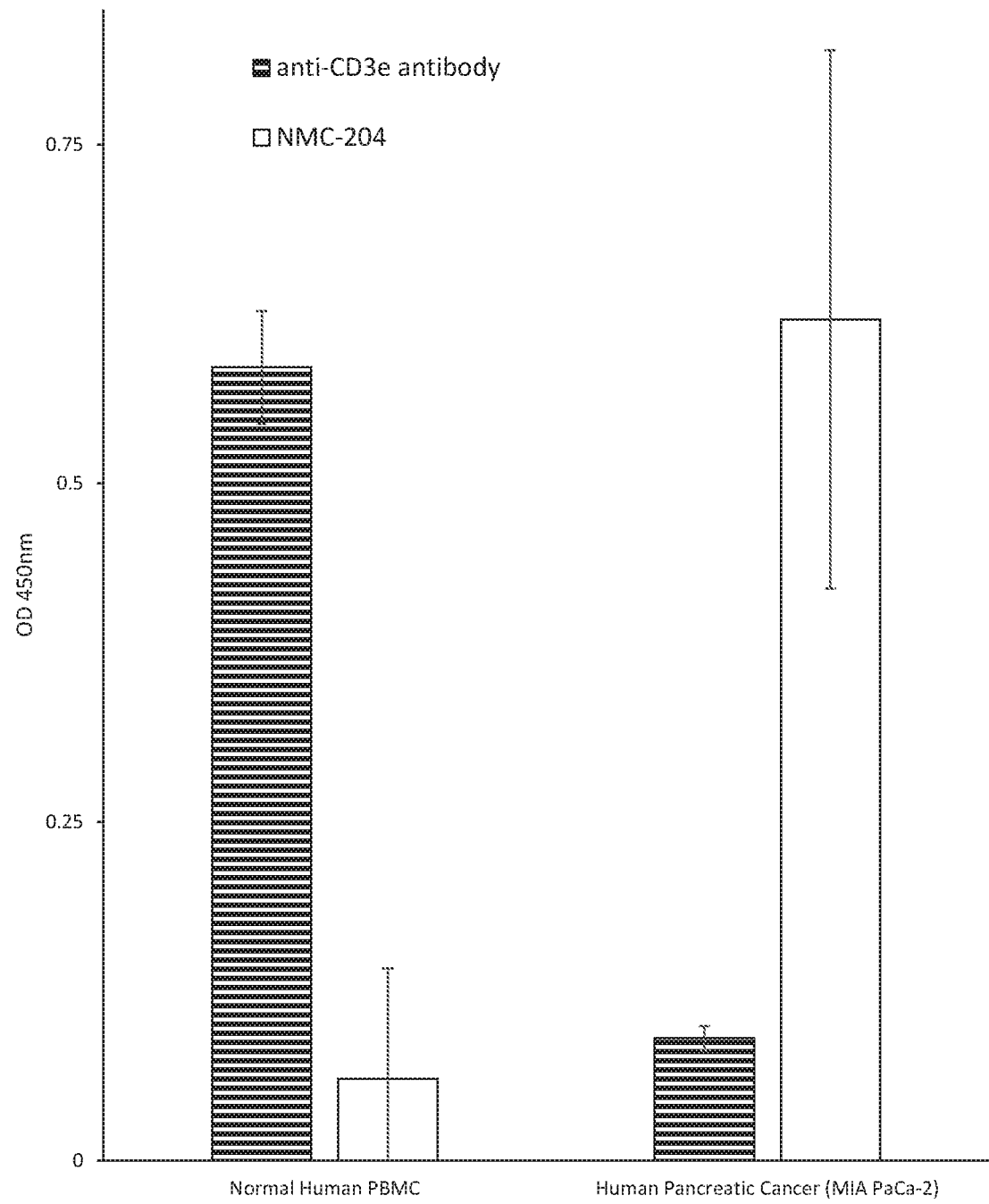

FIG. 6 demonstrates that NMC-204 did not react with normal human PBMCs. In contrast to cancer cells, neither mAb NMC-103, NMC-204 nor NMC-303 bound to normal intact cells (the data for NMC-103 and NMC-303 is not shown). Data presented herein show that, while mAb NMC-204 reacted with human pancreatic cancer MIA PaCa-2 cells, no binding was seen above the background when mAb NMC-204 was incubated with freshly isolated normal human peripheral blood mononuclear cells (PBMCs). Moreover, FIG. 6 demonstrates that while mAb NMC-204 did not react with normal human PBMCs (FIG. 6 left; white bar graph), these cells showed strong reactivity with an mAb against CD3e, a cell surface marker for T cells (FIG. 6 left; shaded bar graph).

Figures 7A, 7B:
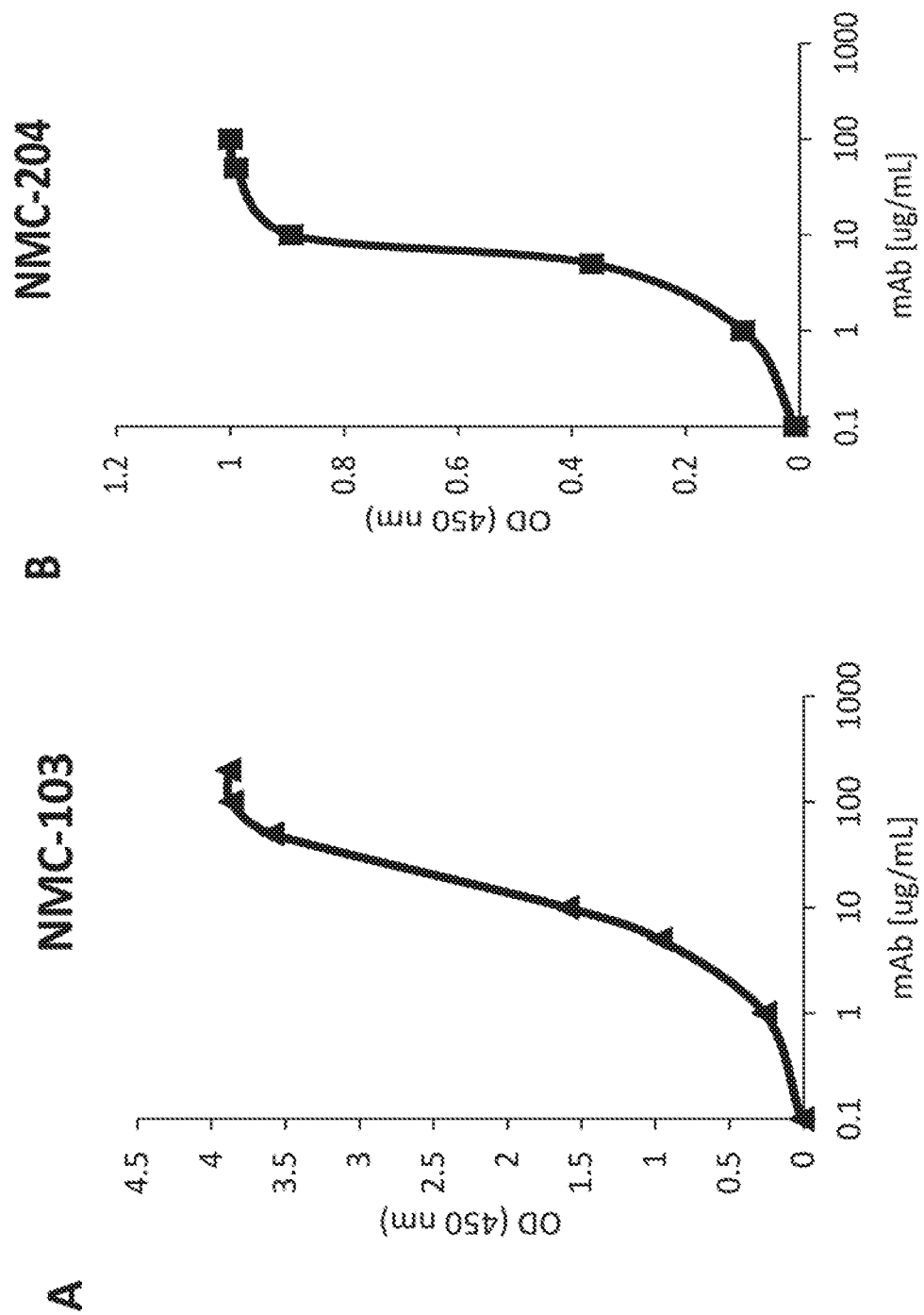

FIG. 7 depicts mAb NMC-103 and NMC-204 saturation curves. FIG. 7A shows that cell-ELISA binding of mAb NMC-103 to intact MIA PaCa-2 cells increased as the concentration of the antibody increased. However, this binding reached a plateau at concentrations of above 50 µg/mL of mAb NMC-103, demonstrating the saturation of antigen binding sites by the specific antibody NMC-103. Moreover, FIG. 7B depicts the binding saturation curve of mAb NMC-204 to intact MIA PaCa-2 cells. The binding of mAb NMC-204 to its antigen on the intact MIA PaCa-2 cells reached saturation at concentrations above 50 µg/mL of mAb NMC-204, demonstrating the binding saturation of antigen sites for mAb NMC-204.

Figures 8A, 8B, 8C:
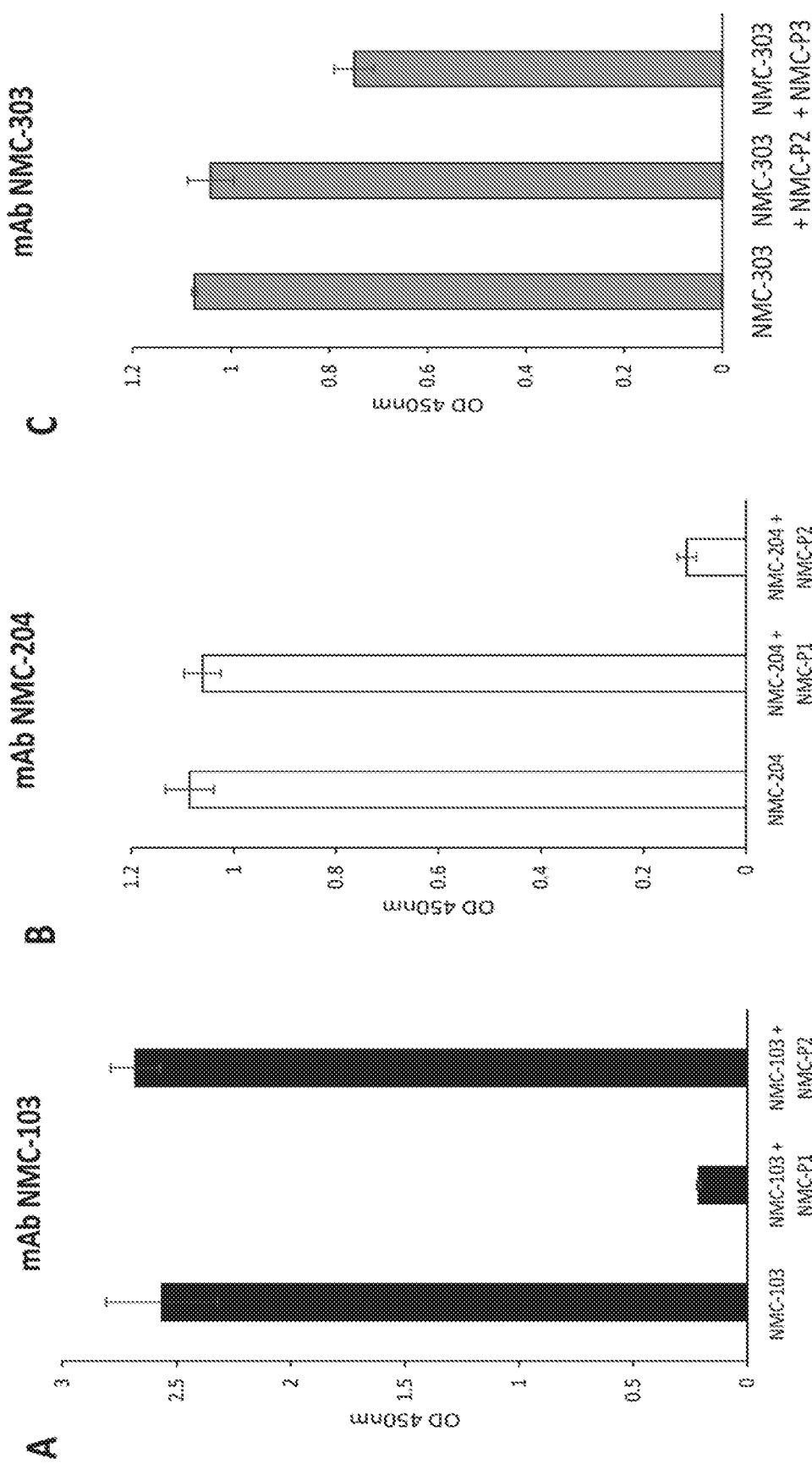

8.3 Example 3: mAb NMC-103. NMC-204 and NMC-303 were Specific for Extracellularly Accessible NMC-P1, NMC-P2 and NMC-P3 Sequences of HΩΩM2 on Intact Cancer Cells, Respectively The data shown in FIG. 8 demonstrated the specificity of mAbs NMC-103, NMC-204 and NMC-303 for NMC-P1, NMC-P2 and NMC-P3 sequences of HDM2 that are extracellularly accessible on the membrane of cancer cells. FIG. 8A shows the binding of mAb NMC-103 to intact human pancreatic cancer MIA PaCa-2 cells (left, solid bar). The binding of monoclonal antibody NMC-103 to its epitope of HDM2 that is accessible on the surface plasma membrane of MIA PaCa-2 cells was completely abolished when mAb NMC-103 was competed with soluble NMC-P1 (middle column, solid bar). In contrast, competition with NMC-P2 did not have any effect on the reactivity of NMC-103 with the epitope of HDM2 to which it binds and which is accessible on the cell surface of the MIA PaCa-2 cells (solid, filled bar).

On the other hand, as shown in FIG. 8B, mAb NMC-204's reactivity with intact MIA PaCa-2 cells was competed with NMC-P2 peptide and not with NMC-P1, demonstrating epitope specificity for another extracellularly accessible epitope/peptide of HDM2 expressed on the plasma membrane of MIA PaCa-2 cells.

The observation of the specificity of the newly generated mAbs for certain epitopes on HDM2 was further extended by the observation that mAb NMC-303's binding to intact MIA PaCa-2 was competed with NMC-P3 peptide and not with NMC-P2(FIG. 8C). Taken together, these data demonstrate the specificity of mAbs NMC-103, NMC-204 and NMC-303 for 3 different extracellularly accessible sequences of HDM2, namely NMC-P1, NMC-P2 and NMC-P3, respectively.

Figure 9:
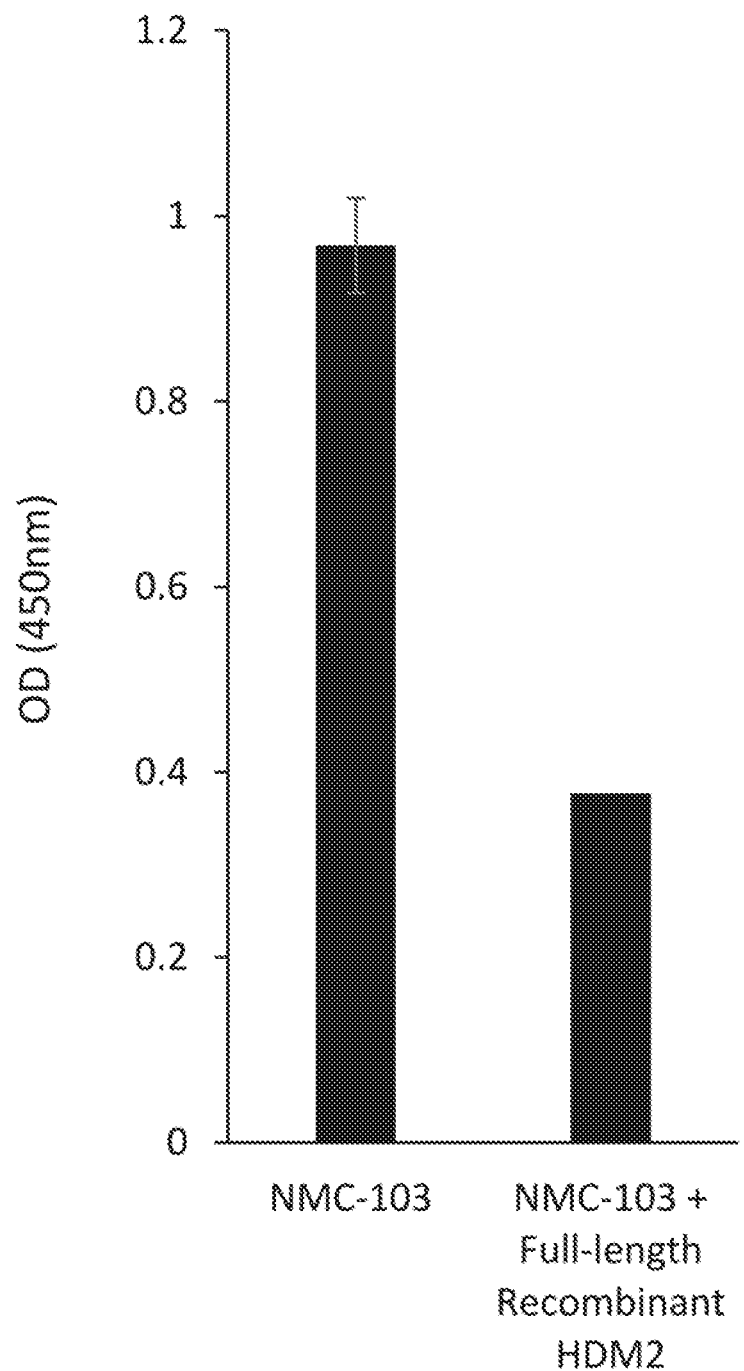
FIG. 9 shows that the binding of monoclonal antibody NMC-103 to its extracellularly accessible epitope of HDM2 on the plasma membrane of intact human pancreatic cancer MIA PaCa-2 cells was competed by the full-length recombinant HDM2 protein.

As demonstrated in FIG. 9, when mAb NMC-103 was pre-incubated with full-length recombinant HDM2, the binding of the antibody to intact MIA PaCa-2 cells was reduced. This result further confirms the specific binding of NMC antibodies to HDM2.

8.4 Example 4: A Plasma Membrane Marker Antibody, Antibody NMC-103 and Antibody NMC-204 Stain Plasma Membrane Surface of Intact Cells, while an Intracellular Marker Antibody does not The data presented herein (FIG. 10) showed that select HDM2-specific antibodies bound to the extracellularly accessible HDM2 on the plasma membrane of intact cancer cells (human pancreatic MiaPaCa-2 cells) that were treated with EDTA (10 mmols; pH7.2; 5 min, 37° C.). EDTA treatment therefore, appeared to have little or no effect on the expression of HDM2 on the cancer cells' surface membrane, strongly suggesting that the HDM2 protein antigen is an integral membrane protein. Additional data presented here show that antibodies to plasma membrane markers such as E-Cadherin (Transduction Lab, Cat. No. C37020) bound to intact cells, while antibodies specific for markers that are located intracellularly such as Cytochrome-C (Santa Cruz, Cat. No. sc-13156) were unable to bind to their targets due to the inaccessibility of the intracellular compartments in the intact cells.

8.5 Example 5: Extracellular Nrotease Digestion of Intact Cancer Cells Removed Extracellularly Accessible Sequences of M(H)DM2 on the Plasma Membrane of Intact Cancer Cells MAbs NMC-103, NMC-204 and NMC-303 were raised against amino acids 1-15 (NMC-P1), 15-25 (NMC-P2) and 475-491 (NMC-P3) of HDM2, respectively, and were highly specific for HDM2. As shown in the immunoblot of FIG. 2, all three mAbs NMC-103, NMC-204 and NMC-303 recognized and bound to purified FIDM2 protein, providing evidence that the unique antigenic epitopes recognized by the three mAbs in NMC-P1, NMC-P2 and NMC-P3, respectively, are de facto structures of intact FIDM2. The results of Cell-ELISAs in FIGS. 3-5 and 8 took the observations one step further by providing evidence that the M(H)DM2 epitopes are expressed extracellularly on the surface membrane of intact rodent and human cancer cells: (1) mAbs NMC-103, NMC-204 and NMC-303 bound to intact cancer cells (FIG. 3-5); (2) each mAb's binding was effectively competed with by its specific peptide but not by the other peptides (FIG. 8); (3) NMC-mAb's binding was also effectively competed by the intact FIDM2-protein (FIG. 9); (4) virtually no binding could be seen of mAbs NMC-103, NMC-204 or NMC-303 to intact normal human PBMCs (FIG. 6).

To further solidify the finding of the expression of M(H)DM2 on the surface membrane of cancer cells, binding by indirect immunofluorescence of mAbs NMC-103, NMC-204 and NMC-303, respectively, to cancer cells was examined before and after protease treatment of the cells. Extracellular protease digestion has been validated as a powerful means for evaluation of a cell surface localization of plasma membrane proteins (Besingi and Clark, 2015, Nat. Protoc. 10(12): 2074-2080; Schulein et al, 1996, J. Biol. Chem. 271(46):28844-28852): loss of binding of a cell surface antigen-specific antibody to cells after protease treatment indicates not only that the antigen is accessible to proteolysis but also, and most importantly, that the antigen is exposed on the extracellular surface of the cells. The accessibility, therefore, of extracellularly displayed M(H)DM2 protein antigen and particularly of the amino acid sequences of NMC-P1, NMC-P2 and NMC-P3, was evaluated by the antigen's susceptibility to digestion by trypsin. The effect of trypsin on the binding of mAbs NMC-103, NMC-204 and NMC-303, was then examined using cell ELISA and HRP reactivity at OD450 nm as described above.

Flow Cytometry Methodology: Cells that had been allowed to grow to about 80% confluency in 25 cm$^2$ tissue culture flasks were released with either EDTA (10 mmols; pH7.2; 5 min, 37° C.) or Trypsin (Gibco TrypLE Express), fixed with freshly made 4% buffered (pH 7.4) paraformaldehyde for 1 h at room temperature, washed several times with a large volume of ice-cold PBS, and blocked for 30 minutes at room temperature with 5% human serum albumin in PBS (intact, non-permeabilized cells). After establishing viability, the cell number was adjusted to 10$^6$ cells/ml and kept in ice-cold PBS until staining. Another set of the same cells was released with either EDTA or Trypsin and fixed with 4% buffered paraformaldehyde as above, then washed and blocked with 5% human serum albumin in PBS, and was treated separately with Triton X-100 (0.1% in PBS) (International Biotechnologies Inc. 07100) for 5 minutes at room temperature for membrane permeabilization. After washing off the Triton X-100 solution with PBS the cells were adjusted to 10$^6$ cells/ml and stored in ice-cold PBS. Cells (10$^6$/ml) from each preparation were then incubated either with 5 µg/ml of mAb to Na+/K+ ATPase α-1 (Abeam, Cat. No. ab2826), 5 µg/ml of mAb NMC-103, or 5 µg/ml of mAb NMC-204 for 90 min at room temperature. Following primary antibody incubation, cells were washed 3 times with ice-cold PBS followed by incubation with rabbit anti-mouse PE-Cy5 labeled secondary antibody (PE-Cy5-RaM IgG (H&L); Invitrogen, Cat. No. M35018) at room temperature. Sixty minutes later the cells were washed 3 times with PBS and subjected to flow cytometry analysis (BD Canto Flow Cytometry). Controls to establish background fluorescence included the analysis of samples of unstained cells as well as cells that had been processed with secondary antibody under the same conditions as used in the experimental samples.

To evaluate the extracellular versus intracellular accessibility of antibodies on an intact cell, the binding of an antibody to a plasma membrane marker, E-Cadherin (Transduction Lab C37020) and the binding of an antibody to an intracellular protein, Cytochrome-C(santa cruz sc-13156) were tested using intact human pancreatic cancer MiaPaCa-2 cells. The cell-ELISA results in FIG. 10 demonstrate the binding of E-Cadherin antibody to intact, EDTA-released MiaPaCa-2 cells (first bar from left). In contrast, mAb to Cytochrome-C showed only minimal binding to EDTA-released cells (second bar from left), which is indicative of the inaccessibility of intracellular targets in intact cells to large molecules such as antibodies. On the other hand, both mAbs NMC-103 and NMC-204 bound to intact, EDTA-released MIAPaCa-2 cells, establishing strong evidence for their interaction with their epitopes present in the extracellularly accessible sequences of HDM2.

To further validate that the epitopes of the plasma membrane M(H)DM2 are in fact extracellularly accessible sequences on cancer cells, binding of mAbs NMC-103, NMC-204 and NMC-303 was performed on mouse Lewis Lung LL/2 cancer cells under treatment conditions of EDTA versus trypsin. Both of these conditions were also tested on intact versus permeabilized cells. FIG. 11 panels A, B and C present flow cytometry data on % cells stained with mAbs NMC-103, NMC-204 and anti-Na+/K+ ATPase ITΩ-1, respectively. Each antibody was reacted with cells from four treatment conditions: EDTA-treated intact cells, EDTA-treated permeabilized cells, trypsin-treated intact cells, trypsin-treated permeabilized cells. EDTA-treated intact cells showed staining with mAb NMC-103 (70.4%), NMC-204 (51.2%) and anti-Na+/K+ ATPase a-1 antibody (29.9%). When EDTA-treated cells were permeabilized, staining with NMC-103, NMC-204 and anti-Na+/K+ ATPase a-1 increased to 75.8%, 52.85 and 63.8%, respectively. However, when compared with EDTA-treated cells, the binding of mAbs NMC-103, NMC-204 and anti-Na+/K+ ATPase a-1 to intact cells that were treated with trypsin reduced to 36.8%, 27% and 20.570, respectively, due to extracellular protease digestion of antibody recognition epitopes. However, when trypsin-treaded cells were permeabilized, the above reduction in binding was compensated by reactivity of the antibodies to intracellular MDM2 or Na+/K+ ATPase a-1. Taken together, results presented herein further demonstrate the accessibility of extracellular sequences of transmembrane M(H)DM2 on intact cancer cells which can be cleaved by extracellular protease treatment.

8.6 Example 6: Specific HDM2 Antibodies Inhibited the Growth of Intact Cancer Cells In Vitro Data presented herein demonstrate that antibodies that recognized extracellularly accessible sequences of HDM2 were able to inhibit the growth of cancer cells in vitro.

Methodology used: Human pancreatic cancer MIAPaCa-2 cells (8,000 cells/well) were pre-incubated with mAb NMC-103, NMC-204 and anti-Cytochrome-C antibody (Santa Cruz, Cat No. sc-13156) at 1, 5 and 10 µg/mL, respectively. Cells in the presence of one of the antibodies at various concentrations were then plated in triplicate in 96-well cell culture plates overnight. The next day, each plate well was analyzed morphologically and a picture was taken from each well using EVOS FL microscope. Cell count was also performed and the number of living cells was graphed as % of control.

Figures 12A, 12B, 12C:
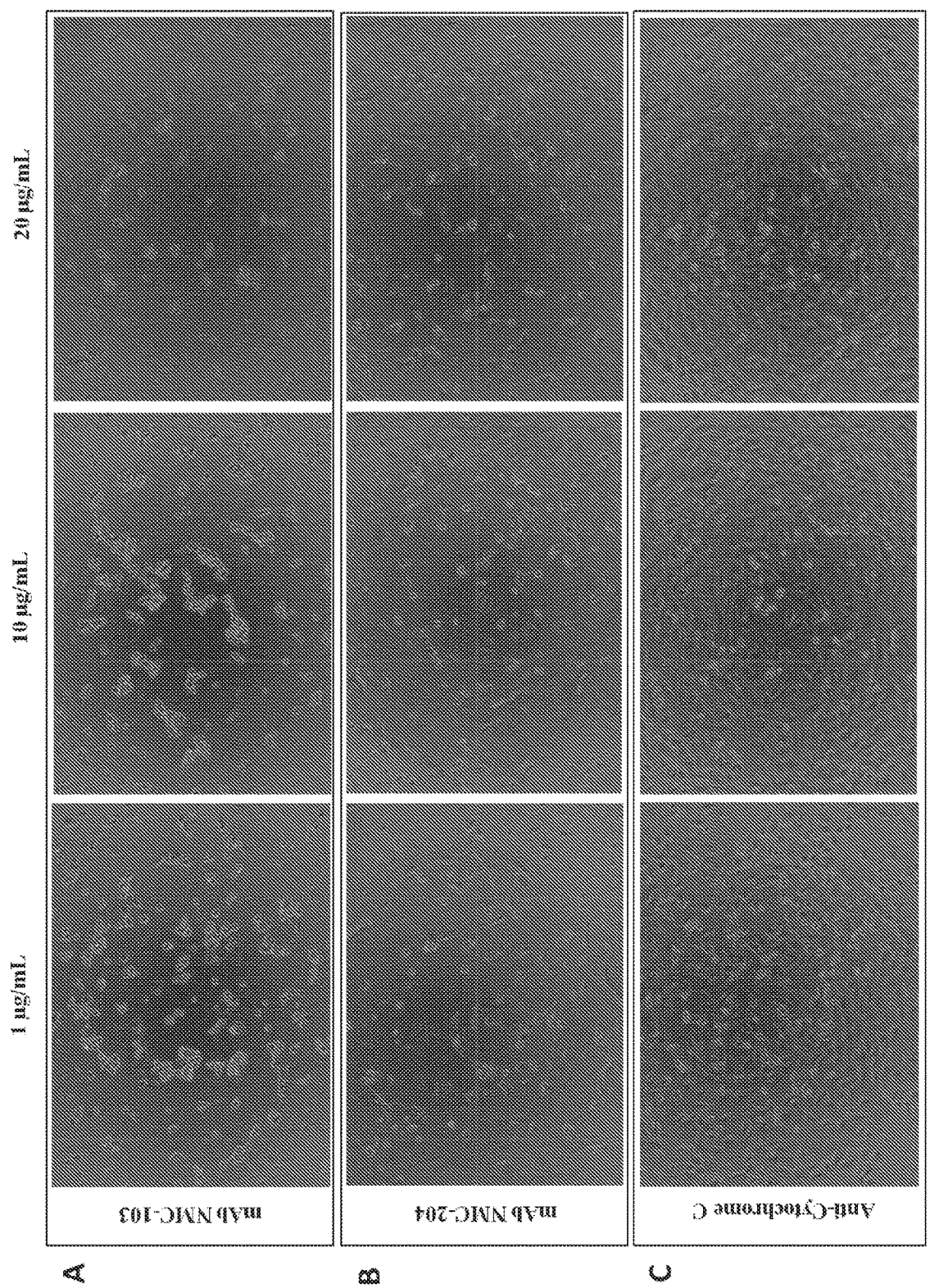
Figure 12D:
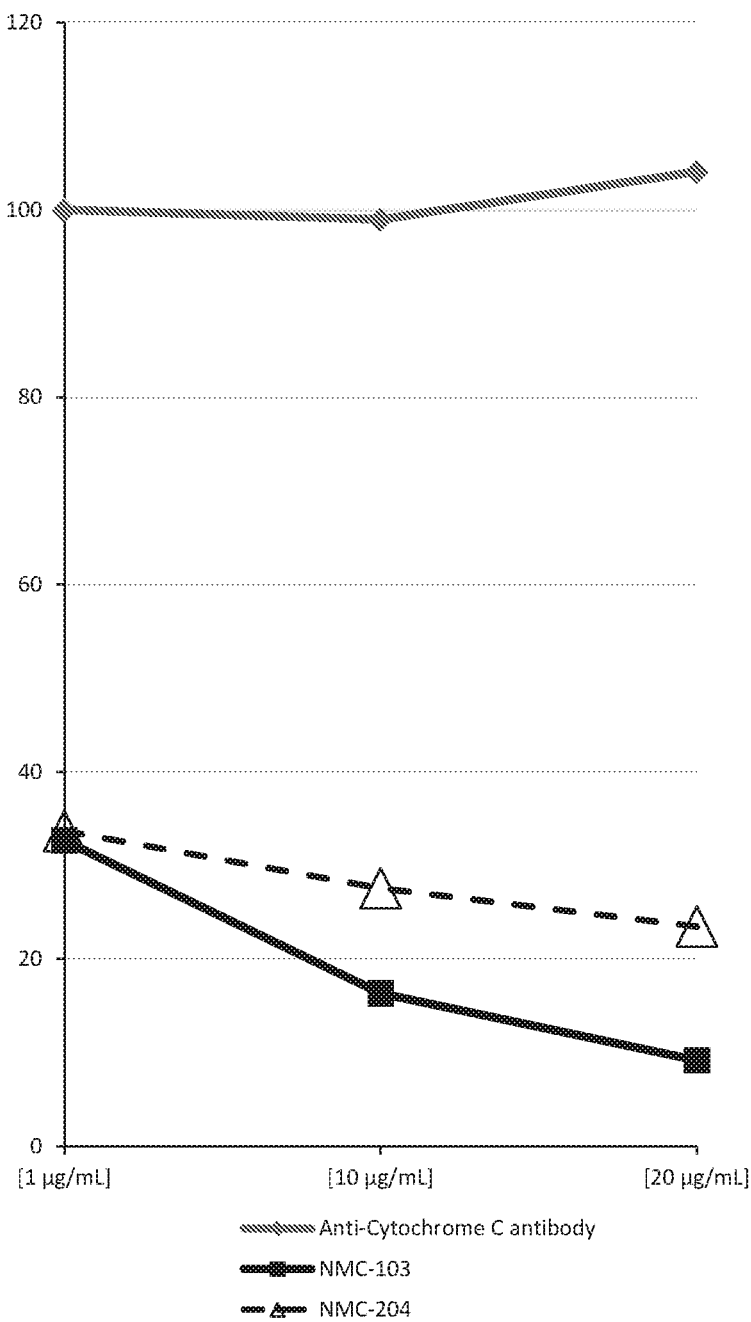

FIG. 12 (A-D) demonstrates that human pancreatic cancer MIAPaCa-2 cells that were treated with mAb NMC-103 or NMC-204 exhibited a concentration-dependent growth inhibition, while an antibody against an intracellular marker {i.e., Cytochrome C) had no effect on the growth of these cancer cells. As demonstrated in FIG. 12A, MIAPaCa-2 cells treated with 1 µg/mL (top panel, left image), 5 µg/mL (to panel, middle image) and 10 µg/mL (top panel, left image) mAb NMC-103 showed an increasing effect in inhibition of their growth. FIG. 12B presents images of the cells treated with 1, 10 and 20 µg/mL of mAb NMC-204, showing a concentration-dependent inhibition of cell growth. In contract, FIG. 12C demonstrates that treatment of MIAPaCa-2 cells with an antibody against Cytochrome-C, which was used as an intracellular marker control, had no effect on the growth of these cells at any of the 1, 10 and 20 µg/mL concentration. FIG. 12D quantifies the growth inhibitory effect of mAb NMC-103 at 1 µg/mL (65%), 5 µg/mL (84%) and 10 µg/mL (91%) (solid black line) and of NMC-204 at 1 µg/mL (65%), 5 µg/mL (73%>) and 10 µg/mL (77%) (dashed black line). In contrast, treatment with an antibody to Cytochrome C (an intracellular target; Santa Cruz, Cat. No. sc-13156) showed no sign of growth inhibition at 1 µg/mL (100%), 5 µg/mL (100%) and 10 µg/mL (104%) (solid gray line).

8.7 Example 7: HDM2-Specific Antibodies Initiated Cytotoxicity fCDC) Against Cancer Cells The data presented herein show the ability of HDM2-specific antibodies to not only bind to the extracellularly accessible sequences of HDM2 on the surface membrane of cancer cells but also to initiate a potent cytotoxic effect in the presence of fresh normal human serum (NHS). The cytotoxic effect was measured in pancreatic cancer cells as well as in normal human fibroblasts. Data presented herein demonstrated one such cytotoxic effect when human pancreatic cancer MIAPaCa-2 cells were treated with mAb NMC-103 in the presence of NHS.

Methodology used: Cells seeded in 24-well dishes were grown overnight at 37° C. in a humidified atmosphere supplied with 5% CO2-95% air mixture. The following day the cells were thoroughly washed with ice-cold PBS and incubated with HDM2-specific mAb NMC-103 diluted in culture medium containing 1% BSA to a final antibody concentration of 30 µg/ml. After 30 min, NHS was added to the cells at a final concentration of 1:10 in the culture medium with 1%) BSA together with 1% propidium iodide (PI) solution. Cells were then incubated with NHS for 2 hours and images were taken using EVOS FL fluorescent microscope (Life Technologies).

FIG. 13 demonstrates the cytotoxic effect of HDM2-specific mAb NMC-103 against human pancreatic cells. mAb NMC-103 in the presence of NHS triggered complement-mediated cytotoxicity in cancer cells, resulting in the death of the cancer cells as evident by the nuclear uptake of the cell-death marker Propidium Iodide (PI). FIG. 13C provides a quantitative representation of HDM2-specific antibody complement-dependent-cytotoxicity (CDC) against human pancreatic cancer cells. Cells treated with mAb NMC-103 (FIG. 13B) in the presence of NHS demonstrated cytotoxicity over 2 hours post-treatment as compared with cells treated with NHS in the absence of any antibody (FIG. 13A). Control experiment was performed with anti-Cytochrome C antibody or with cells left untreated in the presence of NHS.

8.8 Example 8: Evaluation of other Anti-HDM2 In Ah Antibodies in their Binding to NMC-P1. NMC-P2 and NMC-P3 and to Intact Cancer Cells There are a number of HDM2-specific monoclonal antibodies that are commercially available. To evaluate the binding of commercially available mAbs to HDM2, utilizing peptide- and cell-ELISA, we tested a number of such mAb for their binding to intact cancer cells. These mAbs included antibodies that were raised against various regions from the N-terminus or C-terminus, or segments in the middle of the HDM2 protein, and were tested for their binding to newly identified extracellularly accessible NMC-P1 and NMC-P2 sequences as well as to intact cancer cells.

Table 3 summarizes the commercially available mAbs that were tested, the companies that generated these mAbs, and amino acid residues of HDM2 against which they had been raised.

TABLE 3

Commercially available monoclonal antibodies that were tested.

| Antibody | Company | Cat. No. | Antigen Residues on HDM2 |
|---|---|---|---|
| MDM2 monoclonal antobpdy (MO1), clone 1A7 | ABNOVA | H00004193-M01 | 101-200 |
| MDM2 Antibody (D-7) | SANTA CRUZ | SC-13161 | 100-320 |
| p-MDM2 Antibody (2G2) | SANTA CRUZ | SC-53368 | 180-190 |
| MDM2 Antibody (SPM344) | SANTA CRUZ | SC-56430 | 154-167 |
| MDM2 Antibody (SMP14) | SANTA CRUZ | SC-965 | 154-167 |
| Anti-MDM2 clone 4B2C1.11 | MILLIPORE | MABE331 | Recombinant human MDM2 |
| Anti-MDM2 clone 3G9 | MILLIPORE | 04-1530 | |
| Anti-MDM2 clone 2A10 | MILLIPORE | MABE281 | His-tagged recombinant human MDM2 |
| Anit-MDM2 (Ab-1) Mouse mAb (IF2) | CALBIOCHEM | OP46 | 26-169 |
| Anti-MDM2 (Ab-3) Mouse mAb (4B11) | CALBIOCHEM | OP143 | 383-491 |
| Anti-MDM2 (Ab-4) Mouse mAb (2A9C1.18) | CALBIOCHEM | OP144 | 153-222 |
| Anti-MDM2 (Ab-5) Mouse mAb (4B2C1.11) | CALBIOCHEM | OP145 | 19-50 |

Utilizing Peptide-ELISA, FIGS. 14A and 14B demonstrated the lack of binding of any of these mAbs to either NMC-P1 or NMC-P2. In contrast, NMC-103 and NMC-204 showed strong binding to NMC-P1 and NMC-P2, respectively.

In these experiments, it was further evaluated whether HDM-2 binding components such as peptides, for example PNC-27, interfered with the binding of mAb antibodies to NMC-P1 and NMC-P2. Even though it is not known where exactly the HDM2-binding component of PNC-27 and PNC-28 peptides binds on HDM2, it has been reported to bind within amino acids 25-109 of HDM2 (Do et al., 2003, Oncogene 22(10): 1431-1444 ("Do 2003"); Chene, 2003, Nat. Rev. Cancer 3(2): 102-109). To rule out that PNC-27 and PNC-28 peptides bind to NMC-PI or NMC-P2, the peptides' binding to these HDM2 sequences was evaluated by peptide-ELISA. As shown in FIGS. 14A and 14B, PNC-27 (10 µg/mL) did not compete with the binding of NMC-103 and NMC-204 (1 µg/mL) to NMC-P1 and NMC-P2, respectively. It was found that PNC-27 does not bind to NMC-P1 or NMC-P2 regions of HDM2). Overall, these observations demonstrate that the HDM2-binding component of PNC-27 does not react with NMC-P1 or NMC-P2. Moreover, it has been demonstrated that the HDM-2 binding components of PNC-27 and PNC-28 have no anti-cancer activity by themselves and are only active when attached to a membrane resident peptide (MRP or Penetratin sequence) (see Kanovsky 2001, Do 2003, and Bowne 2008).

In the analysis of mAbs by cell-ELISA, despite the fact that none of the tested commercially available antibodies bound to either NMC-P1 or NMC-P2, an anti-HDM2 antibody raised against amino acid residues 19-50 of HDM2, termed "Anti-MDM2 (Ab-5) Mouse mAb (4B2C1.11)" (EMD Millipore, Cat. No. OP145), and an anti-HDM2 antibody termed "MDM2 monoclonal antibody (M01), clone 1A7" (Abnova, Cat. No. H00004193-M01) were identified as reactive with intact cancer cells (see FIG. 15A, showing data for MDM2 monoclonal antibody (MO1), clone 1A7). MDM2 monoclonal antibody (MO1), clone 1A7 was raised against amino acid 101 to 200 of full-length HDM2. Thus, the data demonstrate that epitopes of HDM2 other than NMC-P1, NMC-P2 and NMC-P3 may be extracellularly accessible on cancer cells for binding. In similar experiments, two HDM2-specific monoclonal antibodies that did not react with intact cancer cells were identified (FIG. 15B). One mAb was an anti-HDM2 antibody termed "Anti-MDM2 (Ab-4) Mouse mAb (2A9C1.18)" (EMD Millipore, Cat. No. OP144), which is raised against amino acid 153 to 222 of full length HDM2 (SEQ ID NO:4) that includes one Nuclear Localization Signal (NLS) and one Nuclear Export Signal (NES). Another HDM2-specific mAb that did not react with intact cancer cell membrane was an anti-HDM2 antibody termed "Anti-MDM2 (Ab-1) Mouse mAb (IF2)" (EMD Millipore, Cat. No. OP46), which is raised against amino acids 26-169 of HDM2 (FIG. 15B).

Figure 10:
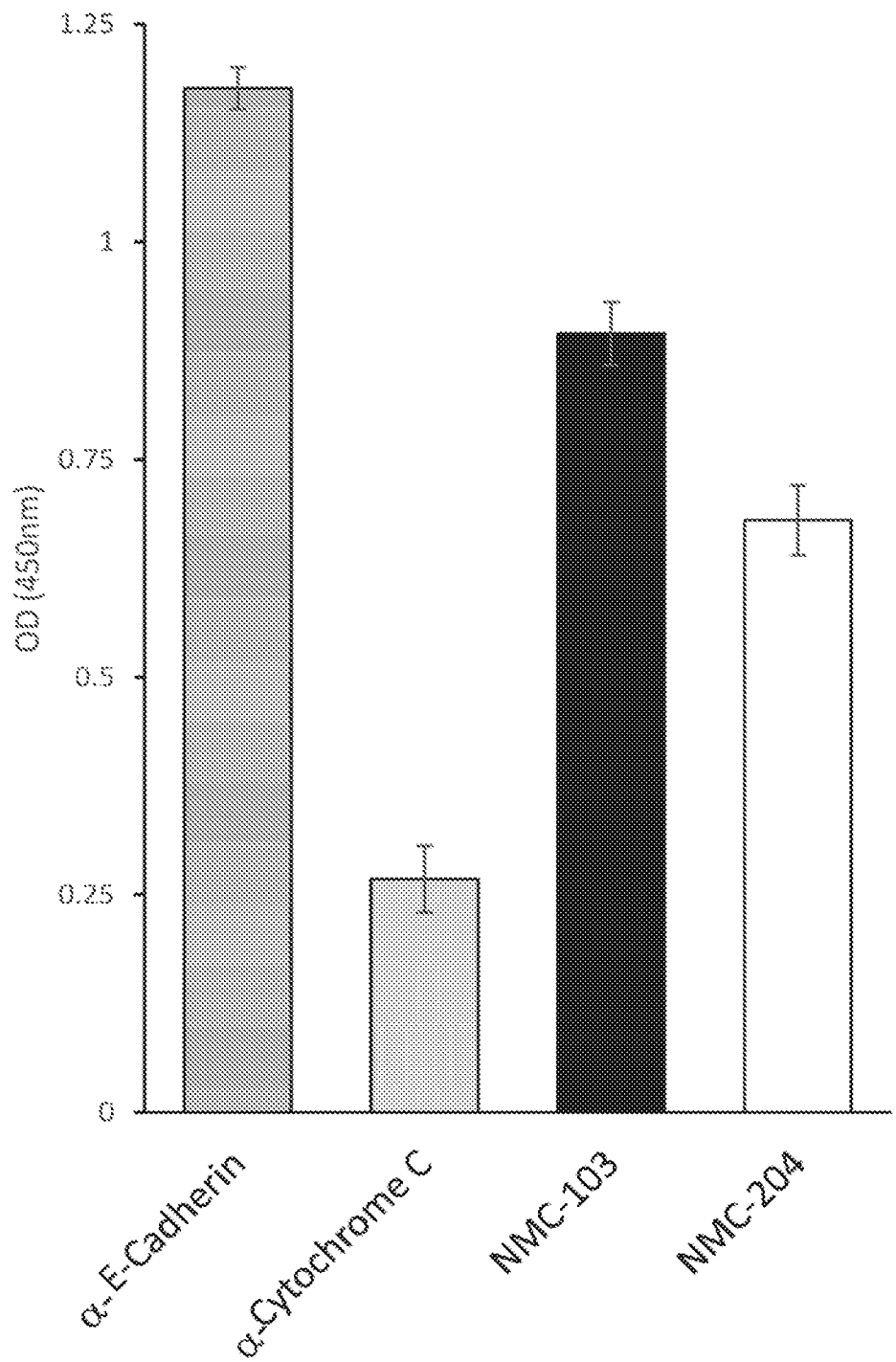
FIG. 10 shows the cell-ELISA binding results of monoclonal antibody NMC-103, monoclonal antibody NMC-204, an antibody against E-cadherin, and an antibody against Cytochrome-C to intact human pancreatic MiaPaCa-2 cells.

8.9 Example 9: In Vivo Anti-Tumor Effect of Antibodies that Target the Extracellularly Accessible Sequences of HΩM 2 in Cancer Cells As demonstrated above, there are select epitopes of HDM2 that are extracellularly accessible on cancer cells. Described herein are three (3) such extracellularly accessible segments of HDM2, namely NMC-P1 (SEQ ID NO: 1), NMC-P2 (SEQ ID NO: 2) and NMC-P3 (SEQ ID NO: 3). Data herein demonstrated that select antibodies raised against these 3 segments selectively and specifically bound to various types of cancers but not normal health cells (FIGS. 3-9). Moreover, results presented herein demonstrated the extracellular accessibility of these 3 segments of HDM2 on cancer cells (FIGS. 10 and 11). Furthermore, data herein show that HDM2-specific antibodies had both growth inhibitory and cytotoxic effect against cancer cells in vitro. Finally, the anti-tumor activity of HDM2-specific antibodies was evaluated in vivo. As an example, efficacy of mAb NMC-103 and NMC-204 on lung, colon and pancreatic cancer was tested.

Methodology used (Syngeneic Mouse Models of lung, colon and pancreatic cancer): To investigate the anti-tumor effects of HDM2-specific antibodies on lung, colon and pancreatic tumors in vivo, three well-known syngeneic mouse models of lung, colon and pancreatic cancer were used (Sharma et al, 1999, J. Immunol. 163 (9):5020-5028; McIntyre, 2015, Bioassays 37(8):909-920; Li, et al, 2015, Sci. Rep. 5:7856). Subcutaneous tumors were prepared by implanting either mouse Lewis Lung cancer LL/2 cells ($2.5 \times 10^5$ cells/mouse), mouse colon cancer MC-38 cells ($5 \times 10^5$ cells/mouse) or mouse pancreatic cancer Panc-2 cells ($2 \times 10^6$ cells/mouse) in the right flanks of 8-week-old female C57BL/6 mice (n=6-7). The mice were returned to their respective cages after tumor implantation. From day 7 after tumor implantation, the tumor volumes were measured 2 times/week with a digital caliper. In the case of MC-38 and Panc-2 study, treatment started when the tumors reached an average of 70-80 mm$^3$. In the case of LL/2 study, tumor cell inoculation and treatment were initiated simultaneously. Mice were micro-chipped and registered following tumor implantation. Tumor volume measurements and body weights were recorded and mice were randomized into groups that received: A) mAb NMC-103 at 0.4 mg/kg (3 times a week for 3 weeks), 2 mg/kg (2 times a week for 3 weeks), or 4 mg/kg (2 times a week for 3 weeks); B) NMC-204 at 0.4 mg/kg (3 times a week for 3 weeks); C) isotype control mouse IgG1 (Abcam, Cat. No. ab 18447) or IgG3 (Abcam, Cat. No. ab 18392) at 0.4 mg/kg (3 times a week for 3 weeks) or 4 mg/kg (2 times a week for 3 weeks); D) Gemcitabine (25 mg/kg) and nab-paclitaxel (5 mg/kg) 2 times a week for 3 weeks; or E) a combination of gemcitabine (25 mg/kg), nab-paclitaxel (5 mg/kg) and mAb NMC-103 (2 mg/kg; 2 times a week for 3 weeks) or (10 mg/kg; 2 times a week for 2 weeks). All tumors were injected subcutaneously and all treatments were performed by intraperitoneal injection. Any mouse displaying prolonged adverse clinical signs, or with body weight loss exceeding 15% relative to body weight at day 0, was euthanized. Tumor measurements from post-treatment with HDM2-specific antibodies versus isotype control mouse antibodies versus standard of care treatment (gemcitabine and nab-paclitaxel) were made, and results are presented in FIGS. 16-19.

FIG. 16 demonstrates the anti-tumor efficacy of mAb NMC-204 (0.4 mg/kg 3 times a week for 3 weeks; dashed line), in mice that were simultaneously inoculated with LL/2 Lewis Lung cancer cells. As presented in the tumor volume measurement graph, by day 21, treatment with NMC-204 reduced tumor volume (1446 mm$^3$) as compared with treatment with isotype control mouse IgG3 (2138 mm$^3$) These results demonstrate the efficacy of an anti-FIDM2-specific antibody (i.e., mAb NMC-204) that targets extracellularly accessible epitopes of FIDM2 on lung cancer cells. For future patient treatment, the dosing and method of administration can be further expanded, e.g., to oral or intravenous delivery of the drug for optimum effect.

FIGS. 17 and 18 demonstrate the efficacy of mAb NMC-103 and NMC-204 against MC-38 syngeneic mouse model of colon cancer, respectively. As presented in FIG. 17A, mice treated for 18 days with mAb NMC-103 (0.4 mg/kg; 3 times a week for 2.5 weeks; dashed line) grew to 1268 mm$^3$ while mice treated with isotype control mouse IgG1 reached a tumor volume of 2205 mm$^3$ (solid line). Moreover, immunohistochemical staining for Ki67 protein, a well-established cell proliferation marker (Li et al., 2015, Mol. Med. Rep. 11(3):1566-72), revealed that mice treated with mAb NMC-103 had only 5% of tumor cells that stained positive for Ki67, while 80% of tumors in mice treated with isotype control antibody stained positive for Ki67 (FIG. 17B). These results further confirm and are consistent with the growth inhibition result observed in vitro (FIG. 12). Furthermore, the anti-tumor efficacy of another FIDM2-specific antibody, mAb NMC-204, that recognizes a different extracellularly accessible segment of membrane HDM2, namely NMC-P2 (SEQ ID NO:2), was evaluated. As shown in FIG. 18A, tumor volume in mice treated with mAb NMC-204 (0.4 mg/kg; 3 times a week for 3 weeks) grew to 1670 mm$^3$ while tumor in the control antibody-treated group reached 2555 mm$^3$ in volume. Furthermore, FIG. 18B shows that mice treated with NMC-204 had 30% of their tumor cells stained positively for Ki67 while mice in the control group had approximately 80% of their tumor cells staining positively for Ki67, demonstrating the anti-proliferative effect of NMC-204 treatment on tumor growth.

The efficacy of FIDM2-specific antibody treatment and standard of care chemotherapy was further compared. Utilizing the Panc-2 syngeneic mouse model of pancreatic cancer, FIG. 19 demonstrates the synergistic effect of NMC-103 in combination with pancreatic cancer standard-of-care treatment drugs: Gemcitabine (G)+nab-Paclitaxel (nP). As shown in the tumor volume graph of FIG. 19, when tumors in mice reached approximately 70 mm$^3$, mice were divided into 4 groups (n=6) that received: A) isotype control mouse IgG1 (2 mg/kg); B) low dose Gemcitabine (25 mg/kg) and nab-Paclitaxel (5 mg/kg); C) NMC-103 (2 mg/kg); or D) a combination of low dose Gemcitabine (25 mg/kg), nab-Paclitaxel (5 mg/kg) and NMC-103 (2 mg/kg). All drugs were injected intraperitoneally 2 times a week for 3 weeks. After receiving the 6th dose on day 19, treatments were stopped for 2 weeks. By day 35, mice in groups that received either isotype control IgG (group A) or a combination of low dose Gemcitabine and nab-Paclitaxel (group B) reached an average of 2175 mm$^3$ (open triangle) and 2314 mm$^3$ (open circle), respectively. Both of these groups had reached morbidity criteria and were terminated. By day 35, tumors in mice of group C that received mAb NMC-103 (2 mg/kg) only reached on average 1523 mm$^3$ (filled triangle), whereas tumors in mice of group D that had received a combination of NMC-103 (2 mg/kg), Gemcitabine and nab-Paclitaxel were measured at an average of 797 mm$^3$ (filled circle). These two groups (groups C and D) of mice were then treated with a combination of NMC-103 (10 mg/kg), Gemcitabine and nab-Paclitaxel two times a week for 2 weeks. As demonstrated in FIG. 19, within 2 weeks tumors in both groups (C and D) reached the point where no measurable tumor was found.

The anti-tumor efficacy of NMC-103 and of its combination with pancreatic cancer standard of care treatment Gemcitabine (G) and nab-Paclitaxel (nP) was further evaluated in vivo utilizing the Panc-2 syngeneic mouse model of pancreatic cancer discussed above. In this Panc-2 study, treatment started after Panc-2 cell inoculation and when the tumors reached 80-100 mm$^3$, with mAb NMC-103 administered at 10 mg/kg, two times a week in a larger number of mice (n=8/group) than that used for the study of FIG. 19.

FIG. 27 shows the results of a study wherein when Panc-02 tumors reached 80-100 mm$^3$ in size, mice were randomly divided into 4 groups (n=8/group) that received: A) isotype control mouse IgG1 (10 mg/kg); B) low dose Gemcitabine (25 mg/kg) and nab-Paclitaxel (5 mg/kg); C) NMC-103 (10 mg/kg); or D) a combination of low dose Gemcitabine (25 mg/kg), nab-Paclitaxel (5 mg/kg) and NMC-103 (10 mg/kg). All drugs were injected intraperitoneally 2 times a week for 4 weeks. By day 30, mice in group A that had received isotype control antibody reached an average tumor size of 2028 mm³ and were terminated. By day 34, half of the mice in group B that had received low dose of the standard of care G & nP chemotherapy had died (n=4) and the tumor in the other half (n=4) had reached an average size of 1654 mm³. In contrast, all mice (n=8) in group C that had received NMC-103 were alive with average measurements of 230 mm³ that was due to scard and inflammation at the site of initial tumor inoculation. On the other hand, in group D that received NMC-103 in combination with G+nP, one mouse had died and the average measurements for the rest of the mice in that group (n=7) was 117 mm³ that was due to scars and inflammation at the siste of tumor inoculation. Both mice in groups C (n=8) and D (n=7) were then kept for another 4 weeks (62 days since the start of the study) with no further drug treatments during which time no sign of tumor growth beyond the initial scar size was observed, which demonstrated the lack of tumor in these mice.

As shown in FIG. 28, a Kaplan Meier survival analysis demonstrated significant survival benefit in mice that received NMC-103 alone or in combination with chemotherapy when compared to chemotherapy alone or control antibody under the experimental conditions described in FIG. 27. This study confirms the observations discussed above in connection with FIG. 19 and the ability of NMC-103 antibody to be used as single arm or in combination with chemotherapy.

To further evaluate the underlying immunological response of the long-term anti-tumor effect of NMC-103, at 62 days after the start of the study, mice that had previously received a combination of G+nP, mice in group C (mice that had previously been treated with NMC-103) and group D (mice that had been treated with a combination of NMC-103+G+nP), as described in FIG. 27, were re-challenged by a second round of Panc-2 inoculation (subcutaneous injection of 2×10⁶ cells/mouse), on the left dorsal flank. Tumor growth was monitored for 10 days at which point, a tumor of 90 mm³ . (FIG. 29) was measured in the mice from group B. In contrast, as shown in FIG. 29, no tumor was observed in mice from the two groups that had previously received NMC-103 antibody (Groups C and D). These studies demonstrate the ability of antibodies that target the extracellularly accessible epitopes of M(H)DM2/4 to robustly activate the host immune system and provide long-term anti-tumor immunity against cancer.

To further establish the effectiveness of NMC-103 antibody in the treatment of large size tumors (i.e. advanced cancers), in another Panc-2 study (with results shown in FIG. 30), mice were treated with pancreatic cancer standard of care (Gemcitabine (25 mg/kg)+nab-Paclitaxel (5 mg/kg)) for 19 days at which point the tumor reached a size of approximately 450 mm³. The mice were then randomly divided in 2 groups that received a single dose of: A) isotype control mouse IgG1 (10 mg/kg) or B) NMC-103 (10 mg/kg). As shown in FIG. 30, a single i.p. injection of NMC-103 reduced the tumor size by almost half 6 days post treatment (from 438 mm³ to 233 mm³).

To further evaluate the NMC-103 dose-dependent anti-tumor effect, in a separate study, the MC-38 syngeneic tumor in mice (n=5) was re-established and treatment carried out similarly to the study of FIG. 17 with the following modification: increase of antibody concentration from 0.4 mg/kg to 10 mg/kg. As shown in FIG. 31, mice treated with NMC-103 at 10 mg/kg, two times per week for three weeks resulted in a greater tumor reduction when compared to mice treated with NMC-103 at 0.4 mg/kg (FIG. 17). These data support the dose-dependent anti-tumor effect of antibodies that bind to extracellularly accessible epitopes of M(H) DM2/4.

Utilizing another syngeneic mouse model of colon cancer, CT-26 (Selby et al., 2016, PLoS One. 9; 11(9): e0161779), the anti-tumor efficacy of a chimeric version of monoclonal antibody NMC-303 was assessed. To create the chimeric version of monoclonal antibody NMC-303, isotype class-switching was performed on a mouse NMC-303 (having heavy variable regions of SEQ ID NO:40 and light chain variable regions of SEQ ID NO:41) to convert it from a mouse IgM to a chimeric IgG1. The mouse Heavy and Light chain variable regions (SEQ ID NO:40 and SEQ ID NO:41, respectively) were cloned into a human Ig gamma-1 chain and human Ig kappa chain as constant region. A total of eight (8) BALB/c mice were injected subcutaneously with CT-26 (800,000 cells/mouse). Mice were then divided into two groups (n=4) that received: A) control antibody (10 mg/kg) or B) the chimeric version of monoclonal antibody NMC-303 (10 mg/kg) two times a week for 3 weeks. FIG. 32A shows that by day 24 post tumor inoculation, mice treated with the chimeric version of monoclonal antibody NMC-303 (10 mg/kg) reached an average tumor size of 726 mm³, while mice treated with control antibody (10 mg/kg) had an average tumor size of 1746 mm³ . Furthermore, FIG. 32B shows the individual mouse tumor sizes on day 24 post tumor inoculation. Due to the human constant region of the chimeric version of the monoclonal antibody NMC-303, the anti-tumor efficacy of this antibody might be improved if tested in mouse models with human immune background. The above in vivo results further support the anti-tumor efficacy of antibodies raised against NMC-P3 immunogen that target the extracellularly accessible epitopes of the M(H)DM2/4 on cancer cells.

Taken together, these results demonstrate two important therapeutic aspects of M(H)DM2/4-specific antibodies: First, anti-M(H)DM2/4 antibodies that target extracellularly accessible sequences of M(H)DM2/4 are in themselves effective anti-cancer agents. Second, M(H)DM2/4 antibodies used in combination with low concentrations of chemotherapeutics have a potently synergistic anti-tumor effect. This is particularly important, considering the frequently observed side-effects and limitations of chemotherapy used at their clinically effective concentrations. In addition, these results demonstrate that M(H)DM2/4 antibodies lead to development of long-term anti-tumor immunity against cancer as demonstrated by prevention of recurrence of cancer and long-term survival of animals previously treated with M(H)DM2/4 antibodies.

The in vitro data showed an increase in plasma membrane M(H)DM2/4 when cells are treated with various types of chemotherapeutic agents such as Gemcitabine and Paclitaxel (data not shown). This treatment potentially makes those cells more susceptible to anti-EfDM2 antibody therapy, which further explains the synergistic effect of their combinatorial administration (FIG. 19).

8.10 Conclusions Based on Examples 1-9

Taken together, the data presented herein demonstrate that select M(H)DM2/4-specific antibodies that recognize extracellularly accessible segments of M(H)DM2/4 in cancers cell have growth inhibitory and cytotoxic effect against a variety of cancers while sparing normal untransformed cells. The selective anti-tumor effect of these antibodies is believed to be due at least in part to their recognition of extracellularly accessible epitopes of M(H)DM2/4 protein variants that are expressed on the surface of cancer cells while the expression levels of these M(H)DM2/4 variants on the cell surface of normal cells are low or absent.

Examples 10-12 below describe data obtained using other anti-HDM2 antibodies that bind to segments of HDM2 that are extracellularly accessible on cancer cells.

8.11 Example 10: Other HDM2-Specific Antibodies that also Bind to Intact Cells from Different Human Cancer Cell Lines and Freshly Isolated Primary Human Cancer Cells But not to Normal Cells To further extend the therapeutic and diagnostic potentials of other antibodies raised against M(H)DM2/4 we evaluated several other available antibodies for their binding and anti-tumor activity. As described above, some of these antibodies (i.e. Calbiochem/Millipore OP-46 and OP-144) did not react with extracellularly accessible epitopes of M(H)DM2/4, demonstrating lack of epitope availability on cancer cell membranes, indicating that not all anti-M(H)DM2/4 antibodies can be used for the treatment of cancer. However, several other anti-M(H)DM2/4 antibodies were shown to not only interact with extracellularly accessible epitopes on the cancer cell membrane, but also to have in vitro and/or in vivo anti-tumor activity.

The following anti-HDM2 antibodies were used in the experiments described in Examples 10-12: (i) polyclonal sc-813, N-20, rabbit IgG, from Santa Cruz (abbreviated throughout the specification as "N-20" or "sc-813 (N-20)"); (ii) monoclonal OP145, mouse IgG1, from Calbiochem (abbreviated throughout the specification as "OP145"); (iii) monoclonal OP46 (Ab-1), mouse IgG1, from Calbiochem (abbreviated throughout the specification as "OP46"); (iv) monoclonal OP 144 (Ab-4), mouse IgG1, from Calbiochem (abbreviated throughout the specification as "OP 144"); (v) polyclonal sc-812, C-18, rabbit IgG, from Santa Cruz (abbreviated throughout the specification as "C-18" or "sc-812 (C-18)"); and (vi) monoclonal 965 (SMP14), mouse IgG1, from Santa Cruz (abbreviated throughout the specification as "SMP14" or "965 (SMP14)"). Table 10, below, provides information regarding the HDM2 recognition sites of these antibodies (i.e., amino acids of HDM2 recognized by these antibodies), and whether or not these antibodies are cytotoxic to cancer cells. OP145, N-20, C-18 and SMP14 were cytotoxic to cancer cells tested, and OP46 and OP144 were not cytotoxic to cancer cells tested.

Utilizing Fluorescence-activated cell sorting (FACS), the data presented herein show that select FfDM2-specific antibodies bind to the surface membrane of live human cancer cells, human melanoma A2058 cells maintained in culture, and two primary patient-derived ovarian cancer cells OVCA-1 and OVCA-4 that had been freshly isolated from ovarian cancer tissues. In contrast, FACS analysis of live normal mouse spleenocytes demonstrated the absence of plasma membrane staining with the same HDM2-specific antibodies.

Methodology used: Intact cells released either with either EDTA or Trypsin were blocked with 5% human serum albumin. Cells were then incubated with the either polyclonal (N20) or monoclonal (OP145) HDM2-specific antibodies for 90 min on ice. Another set of cells prepared under the same conditions were incubated with the same antibodies that were pre-incubated with their corresponding blocking peptides before incubation with cells. Following primary antibody incubation, cells were washed 3 times with ice-cold PBS followed by FITC-secondary antibody incubation for 60 min Cells were then washed 3 times with PBS and were subjected to FACS analyzer.

FIG. 24 presents results of the FACS analysis of human melanoma, primary ovarian cancer, and normal mouse spleenocytes. FIG. 24A: area under curve #1 represents cells incubated with goat anti-rabbit secondary antibody only; area under curve #2 represents cells incubated with anti-HDM2 polyclonal antibody N-20 pre-incubated with its blocking peptide followed by goat anti-rabbit secondary antibody; area under curve #3 represents cells incubated with anti-HDM2 polyclonal antibody N-20 followed by goat anti-rabbit secondary antibody. FIG. 24B: area under curve #1 represents cells incubated with goat anti-mouse secondary antibody only; area under curve #2 represents cells incubated with anti-HDM2 monoclonal antibody OP 145 pre-incubated with its blocking peptide followed by goat anti-rabbit secondary antibody; area under curve #3 represents cells incubated with anti-HDM2 monoclonal antibody OP145 followed by goat anti-mouse secondary antibody. FIG. 24C: area under curve #1 represents cells incubated with goat anti-rabbit secondary antibody only; area under curve #2 represents trypsin-released cells incubated with anti-HDM2 polyclonal antibody N-20 followed by goat anti-rabbit secondary antibody; area under curve #3 represents EDTA-released cells incubated with anti-HDM2 polyclonal antibody N-20 pre-incubated with its blocking peptide followed by goat anti-rabbit secondary antibody; area under curve #4 represents EDTA-released cells incubated with anti-HDM2 polyclonal antibody N20 followed by goat anti-rabbit secondary antibody. FIGS. 24D & E: area under curve #1 represents cells incubated with goat anti-rabbit secondary antibody only; area under curve #2 represents cells incubated with anti-HDM2 polyclonal antibody N-20 pre-incubated with its blocking peptide followed by goat anti-rabbit secondary antibody; area under curve #3 represents cells incubated with anti-HDM2 polyclonal antibody N-20 followed by goat anti-rabbit secondary antibody. FIG. 24F: area under curve #1 represents cells incubated with goat anti-rabbit secondary antibody only; area under curve #2 represents trypsin-released cells incubated with anti-FIDM2 polyclonal antibody N-20 followed by goat anti-rabbit secondary antibody; area under curve #3 represents EDTA-released cells incubated with anti-FIDM2 polyclonal antibody N-20 pre-incubated with its blocking peptide followed by goat anti-rabbit secondary antibody; area under curve #4 represents EDTA-released cells incubated with anti-HDM2 polyclonal antibody N-20 followed by goat anti-rabbit secondary antibody.

EDTA-released intact human melanoma A2058 cells incubated with either an anti-FIDM2 polyclonal N-20 antibody (FIG. 24A; area under the curve #3) or monoclonal OP145 antibody (FIG. 24B; area under the curve #3) show cells that are stained positive for HDM2 on their cell surface. To control for epitope-specificity, no specific staining beyond background was observed when either one of these antibodies was pre-incubated with its corresponding blocking peptide prior to incubation with the cells (see FIGS. 24A and 24B; area under the curve #2). Interestingly, in the case of human melanoma cells released using trypsin, which cuts the external portion of cell surface proteins, no cell surface staining of HDM2 was observed (see FIG. 24C; area under the curve #3 when compared with cells released with EDTA, area under the curve #4), further indicating the presence of at least parts of the HDM2 protein on the external face of the plasma membrane. Moreover, freshly isolated tumors from two patients with ovarian cancer (OVCA-1 and OVCA-4) showed extensive surface staining when incubated with the polyclonal N-20 antibody (see FIGS. 24D and 24E; area under the curve #3). This staining was completely blocked when the antibody was pre-incubated with its blocking peptide prior to incubation with the cells (see FIGS. 24D and 24E; area under the curve #2). However, intact mouse normal spleenocytes did not stain over the background with the same antibodies (see FIG. 24F; compare staining when incubated with FIDM2-specific N-20 antibody in area under the curve #4, with staining in samples treated with the antibody pre-incubated with N-20 blocking peptide in area under the curve #3). Taken together, the results of FACS analysis strongly indicate the presence of extracellularly accessible epitopes of M(H)DM2 on the plasma membrane of the intact cancer cells and its absence in normal untransformed cells.

8.12 Example 11: Certain HDM2-Specific Antibodies Initiate Complement-Mediated Cytotoxicity Against Different Types of Cancers The data presented herein show the ability of select HDM2-specific antibodies to not only bind to the surface membrane of cancer cells but also to initiate a cytotoxic effect in the presence of fresh normal human serum (NHS). The cytotoxic effect was measured in various cancer cells such as human melanoma, pancreatic, breast and ovarian cancer cells as well as in normal human fibroblasts and blood cells.

Methodology used: Cells seeded in 24-well dishes were grown over night at 37° C. in a humidified atmosphere supplied with 5% CO2-95% air mixture. The following day the cells were thoroughly washed with ice-cold PBS and incubated with various HDM2-specific antibodies (i.e., OP145, N-20 and C-18 antibodies; see description of the antibodies in Table 10) or control antibodies (directed to the intra-cellular protein Cytochrome C) diluted in culture medium containing 1% BSA to a final antibody concentration of 5-10 ug/ml. After 30 min, NHS was added to the cells to make a final concentration of at 1:30 in the culture medium with 1% BSA together with 1% propidium iodide (PI) solution. A s controls for the role of complement in the fresh human serum, parallel cultures treated with HDM2-specific antibodies were exposed to fresh human serum that had been incubated for 30 min at 56° C. (HiNHS), a process that is known to disenable complement activity. Images were taken at 15, 30, 45 and 60 min post incubation using Olympus FluoView FV 1000 Confocal Laser Scanning Biological Microscope built on the Olympus 1X81 Inverted Microscope.

FIG. 25 demonstrates the cytotoxic effect of HDM2-specific antibodies against human pancreatic and ovarian cancer cells (FIG. 25A), and rodent pancreatic cells (FIG. 25B). OP145, N-20 and C-18 antibodies in the presence of NHS trigger complement-mediated cytotoxicity in cancer cells incubated with such antibodies, resulting in the death of the cancer cells as evident by the nuclear uptake of the cell-death marker Propidium Iodide (PI) (see FIG. 25A, panels b and e, for ovarian cancer cells incubated with OP145 and FIG. 25B, panels b and c, for pancreatic cancer cells incubated with N-20 and C-18, respectively). In the presence of control antibodies (i.e., anti-cytochrome C antibody, see FIG. 25A, panel c, and FIG. 25B, panel e) cancer cell death is similar to that of control NHS alone, without any antibodies (see FIG. 25A, panels a and d, and FIG. 25B, panel a) or normal cells (Fibroblasts, FIG. 25A, panel g) treated with HDM2-specific antibodies (i.e., there is no or minimal cell death as indicated by lack of PI staining, se FIGS. 25A, panels a, c, d, f and g, and FIG. 25B, panel 1). Further, no cytotoxicity was observed when cells were treated with anti-HDM2 monoclonal OP46 antibody (see FIG. 25B, panel d). FIG. 25C provides quantitative representations of HDM2-specific antibody-dependent complement cytotoxicity against human pancreatic cancer cells. Cells treated with anti-HDM2 (C-18) antibody in the presence of NHS demonstrated cytotoxicity over 15-30 min post-treatment, whereas anti-HDM2 OP46 shows no cytotoxic effect beyond that observed when cells were treated with control anti-Cytochrome C antibody or when cells were left untreated in the presence of NHS.

Moreover, HDM2-specific antibodies in the presence of heat-inactivated human serum (i.e., fresh human serum that had been incubated for 30 min at 56° C. (HiNHS)) did not have any cytotoxic effect on cancer cells (i.e., did not result in the death of the cancer cells as was evident by PI staining), demonstrating that the cytotoxic effect is due to complement activity.

Table 10 lists antibodies tested by the inventors and summarizes results obtained relating to the in vitro cytotoxic effects of various anti-HDM2 antibodies against cancer cells.

TABLE 10

Antibodies used and their ability to induce a cytotoxic effect in cancer cells in vitro.

| | HDM2 Recognition Site Amino Acid Nos. of SEQ ID NO: 4 | Cytotoxicity | Species Reactivity* | Host | Antibody Type | Company Purchased From |
|---|---|---|---|---|---|---|
| M(H)DM2 Abs | | | | | | |
| OP46 (Ab-1) | 26-169 | − | H | Mouse IgG1 | Monoclonal | Calbiochem |
| OP144 (Ab-4) | 153-222 | − | H & M | Mouse IgG1 | Monoclonal | Calbiochem |
| OP145 | 19-50 | + | H & M | Mouse IgG1 | Monoclonal | Calbiochem |
| sc-813 (N-20) | N-terminus | + | H & M | Rabbit IgG | Polyclonal | Santa Cruz |
| sc-812 (C-18) | C-terminus | + | H, M, R | Rabbit IgG | Polyclonal | Santa Cruz |
| 965 (SMP14) | 154-167 | + | H, M, R | Mouse IgG1 | Monoclonal | Santa Cruz |
| Control Antibodies | | | | | | |
| Cytochrome C | N/A | − | H | Mouse IgG1 | Monoclonal | Santa Cruz |
| Histone H4 | N/A | − | Broad Species | Mouse IgG$_{2a}$ | Monoclonal | Santa Cruz |
| Beta-Tubulin | N/A | − | H, M, R | Rabbit IgG | Polyclonal | Santa Cruz |

*H—binds to human protein; M—binds to murine protein; R—binds to rabbit protein

8.13 Example 12: Results Regarding In Vivo Anti-Tumor Effect of other Antibodies that Hind to Extracelliilarly Accessible Enitones of HΩM2

To further evaluate the anti-cancer activity of mAbs raised against extracellularly accessible epitopes of HDM2 (other than NMC-P1, NMC-P2 and NMC-P3) on cancer cells, studies of the anti-tumor efficacy of anti-HDM2 monoclonal antibody OP-145 (Calbiochem) and "MDM2 monoclonal antibody (M01), clone 1A7" (Abnova, Cat. No. H00004193-M01) were conducted. As demonstrated above, neither one of these antibodies showed reactivity to NMC-P1 and NMC-P2 (see FIGS. 14A-B), but both of these antibodies showed reactivity with intact cancer cells (see FIGS. 15A and 24B).

Evaluation of anti-tumor effects of antibody OP145 on pancreatic tumor growth in vivo: Subcutaneous tumors were prepared by implanting Panc02 cells (2×106 per mouse) in the right flanks of female 8-week-old C57BL/6 mice. The mice were returned to their respective cages after tumor implantation. From day 7 after tumor implantation, the tumor volumes were measured 2 times/week with a digital caliper. Treatment started when the tumors reached an average of 200 mm$^3$ (see FIG. 26, day 14). Mice were micro-chipped and registered following tumor implantation. Tumor volume measurements and body weights were recorded and mice were randomized into two groups that received either OP 145 antibody (by intra-tumoral injection of 0.1 mg/kg of mouse monoclonal antibody OP145, 3 times per week) or PBS. Three mice were treated with OP145, and five mice were treated with PBS. Any mouse displaying prolonged adverse clinical signs, or with body weight loss exceeding 15% from Day 0 body weight, was euthanized. Tumor measurements from the first 10 days post treatment with OP 145 antibody versus PBS were made, and results are represented in FIG. 26.

It was found that subcutaneous tumors in mice administered the OP145 antibody had a size of 260 mm$^3$ at 21 days post tumor cell injection, whereas subcutaneous tumors in mice administered PBS had a size of 375 mm$^3$ (see FIG. 26).

In vivo studies of the effect of "MDM2 monoclonal antibody (MO1), clone 1A7" against MC-38 syngeneic mouse model of colon cancer (using 0.4 mg/kg of the MOL clone 1A7 antibody; 3 times a week for 3 weeks, intraperitoneally; n=4) demonstrated that while the antibody-treated mice initially responded to the treatment (average tumor size after 6 doses was at 1588 mm$^3$ in antibody-treated group vs 1999 mm$^3$ in isotype control-treated group), tumors in both control and antibody-treated mice reached approximately 2500 mm$^3$ by third week (FIG. 23). During the same time period, mAb NMC-103 and NMC-204 given to mice at the same dose (0.4 mg/kg; 3 times a week for 3 weeks, intraperitoneally) demonstrated a significant ($p<0.005$) reduction in tumor volume with lasting anti-tumor activity (FIG. 19; open circle and open square, respectively; also see FIGS. 17A and 18A). This finding indicates that although mAb MO1 had strong binding to cells in vitro, the anti-tumor effect of NMC-103 and NMC-204 was superior to that of mAb MO1 (FIG. 23).

It must be noted that these results relating to in vivo anti-tumor efficacy of monoclonal antibodies OP-145 and MO1 must be interpreted with caution since the commercial antibody preparations used may not necessarily have the desired clonality, purity or pharmaceutically acceptable formulation for in vivo efficacy testing.

9. REFERENCES

Olson, D. C, Marechal, V., Momand, J., Chen, J., Romocki, C, and Levine, A. J., 1993, "Identification and characterization of multiple mdm-2 proteins and mdm-2-p53 protein complexes," Oncogene 8: 2353-2360.

Taubert H., Kappler M., Meye A., Bartel F., Schlott T., Lautenschlaeger C, Bache M., Schmidt H., Wuerl P., 2000, "A MboII polymorphism in exon 11 of the human MDM2 gene occurring in normal blood donors and in soft tissue sarcoma patients: an indication for an increased cancer susceptibility?" Mutat. Res. 456:39-44.

Liang H., Atkins H., Abdel-Fattah R., Jones S. N., Lunec J., 2004, "Genomic organization of the human MDM2 oncogene and relationship to its alternatively spliced mRNAs," Gene 338:217-223.

Sarafraz-Yazdi E, Bowne W B., Adler V, Sookraj K, V Wu, V Shteyler, H Patel, W Oxbury, P Brandt-Rauf, J Michl and M. Pincus, 2010, "Anti-cancer peptide, PNC-27, adopts an HDM2-binding conformation and kills cancer cells by binding to HDM2 in their membranes," PNAS 107:1918-1923

Sigalas, A. H. Calvert, J. J. Anderson, D. E. Neal and J. Lunec, 1996, "Alternatively spliced mdm2 transcripts with loss of p53 binding domain sequences: transforming ability and frequent detection in human cancer," Nat. Med. 2:912-917

Bartel F, Taubert H, Harris L. C., 2002, "Alternative and aberrant splicing of MDM2 mRNA in human cancer," Cancer Cell 2(1):9-15.

Bartel F., Harris L. C., Wiirl P. and Taubert T., 2004, "MDM2 and Its Splice Variant Messenger RNAs: Expression in Tumors and Down-Regulation Using Antisense Oligonucleotides," Mol Cancer Res 2:29.

Steinman H. A., Burstein E., Lengner C, Gosselin J., Pihan G., Duckett C. S., and Jones S. N., 2004, "An Alternative Splice Form of Mdm2 Induces p53-independent Cell Growth and Tumorigenesis," The Journal of Biological Chemistry 279:4877-4886.

Lukas J., Gao D., Keshmeshian M., Wen W., Tsao-Wei D., Rosenberg S., and Press M. F., 2001, "Alternative and Aberrant Messenger RNA Splicing of the mdm2 Oncogene in Invasive Breast Cancer," Cancer Res 61:3212

Evans S. C., Viswanathan M., Grier J. D., Narayana M., El-Naggar A. K. and Lozano G., 2001, "An alternatively spliced HDM2 product increases p53 activity by inhibiting HDM2," Oncogene 20:4041-4049

Matsumoto R, Tada M, Nozaki M, Zhang C L, Sawamura Y, Abe H., 1998, "Short alternative splice transcripts of the mdm2 oncogene correlate to malignancy in human astrocytic neoplasms," Cancer Res 58:609-13.

Tamborini E, Delia Tone G, Lavarino C, et al., 2001, "Analysis of the molecular species generated by MDM2 gene amplification in liposarcomas," Int J Cancer 92:790-6.

Schuster K., Fan L. and Harris L. C., 2007, "MDM2 Splice Variants Predominantly Localize to the Nucleoplasm Mediated by a COOH-Terminal Nuclear Localization Signal," Mol Cancer Research 5(4):403-412.

Fridman J S, Hernando E, Hemann M T, de Stanchina E, Cordon-Cardo C, Lowe S W., 2003, "Tumor promotion by Mdm2 splice variants unable to bind p53," Cancer Res. 63(18):5703-6.

Yang J Y, Zong C S, Xia W, Wei Y, Ali-Seyed M, Li Z, Broglio K, Berry D A, Hung M C, 2006, "MDM2 promotes cell motility and invasiveness by regulating E-cadherin degradation," Mol Cell Biol. 26(19):7269-82.

Li G, Gan Y, Fan Y, Wu Y, Lin H, Song Y, Cai X, Yu X, Pan W, Yao M, Gu J, Tu H., 2015, "Enriched environment inhibits mouse pancreatic cancer growth and down-regulates the expression of mitochondria-related genes in cancer cells," Sci Rep. 5:7856

Chames P, Baty D., 2009, "Bispecific antibodies for cancer therapy: the light at the end of the tunnel?" MAbs. 1(6):539-47

Page D B, Postow M A, Callahan M K, Allison J P, Wolchok J D., 2014, "Immune modulation in cancer with antibodies," Annu Rev Med. 65: 185-202.

Macor P, D Mezzanzanica, C Cossetti, P Alberti, et al., 2006, "Complment activated by chimeric anti-folate receptor antibodies is an efficient effector system to control ovarian carcinoma, Cancer Res. 66:3876-3883.

Li, B, S Shi, W Quian, L Zhao et al., 2008, "Development of novel tetravalent anti-CD20 antibodies with potent tumor activity," Cancer Res 68:2400-2408.

Konterman, R E, 2012, "Dual targeting strategies with bispecific antibodies," MAbs 4:182-197.

Gramer M J, E T van den Bremer, M D van Kampen, A Kundu et al., 2013, "Production of stable bispecific IgG1 by controlled Fab-arm exchange: scalability from bench to large-scale manufacturing by application of standard approaches," MAbs 5:962-973.

Shields R L. et al., 2001," High resolution mapping of the binding site on human IgG1 for Fc gamma R I, Fc gamma RII, Fc gamma RIII, and FcRn and design of IgG1 variants with improved binding to the Fc gamma R," J Biol Chem. 276(9):6591-604.

Steurer W. et al., 1995, "Ex vivo coating of islet cell allografts with murine CTLA4/Fc promotes graft tolerance," J Immunol. 155(3): 1165-74.

Idusogie E E. et al., 2001, "Engineered antibodies with increased activity to recruit complement," J Immunol. 166(4):2571-5.

Lazar G A. et al., 2006, "Engineered antibody Fc variants with enhanced effector function," PNAS 103(11): 4005-4010.

Ryan M C. et al., 2007, "Antibody targeting of B-cell maturation antigen on malignant plasma cells," Mol. Cancer Ther. 6: 3009-3018.

Richards J O et al., 2008, "Optimization of antibody binding to FcgammaRIIa enhances macrophage phagocytosis of tumor cells," Mol Cancer Ther. 7(8):2517-27.

Satoh M M, S Iida, K Shitara ara, 2006, "Non-fucosylated therapeutic antibodies as next-generation therapeutic antibodies, "Expert Opin Biol Ther 6:1161-1173.

Liu S D, C Chalouni, J C Young et al., 2015, "Afucosylated antibodies increase activation of FCgRIIIa-dependent signaling components to intensify processes promoting ADCC," Cancer Immunol Res. 3:173-183.

Banda N K, A K Wood, K Takahashi et al., 2008, "Initiation of the alternative pathway of murine complement by immune complexes is dependent on N-glycans in IgG antibodies," Arthritis Rheum 58:2081-3089.

Bechara C, Sagan S., 2013, "Cell-penetrating peptides: 20 years later, where do we stand?" FEBS Lett. 587(12): 1693-702.

Dupont E, Prochiantz A, Joliot A., 2015, "Penetratin Story: An Overview," Methods Mol Biol. 1324:29-37.

Rosal R1, Brandt-Rauf P, Pincus M R, Wang H, Mao Y, Li Y, Fine R L., 2005, "The role of alpha-helical structure in p53 peptides as a determinant for their mechanism of cell death: necrosis versus apoptosis," Adv Drug Deliv Rev. 57(4):653-60.

Bowne WB1, Sookraj K A, Vishnevetsky M, Adler V, Sarafraz-Yazdi E, Lou S, Koenke J, Shteyler V, Ikram K, Harding M, Bluth M H, Ng M, Brandt-Rauf P W, Hannan R, Bradu S, Zenilman M E, Michl J, Pincus M R., 2008, "The penetratin sequence in the anticancer PNC-28 peptide causes tumor cell necrosis rather than apoptosis of human pancreatic cancer cells," Ann Surg Oncol. 15(12): 3588-600.

Kanovsky M, Raffo A, Drew L, Rosal R, Do T, Friedman F K, Rubinstein P, Visser J, Robinson R, Brandt-Rauf P W, Michl J, Fine R L, Pincus M R., 2001, "Peptides from the amino terminal mdm-2-binding domain of p53, designed from conformational analysis, are selectively cytotoxic to transformed cells," Proc Natl Acad Sci USA. 98(22): 12438-43.

Torchilin V P, Levchenko T S, Rammohan R, Volodina N, Papahadjopoulos-Sternberg B, D'Souza G G., 2003, "Cell transfection in vitro and in vivo with nontoxic TAT peptide-liposome-DNA complexes," Proc Natl Acad Sci USA. 100(4): 1972-7.

Shin M C, Zhang J, Min K A, Lee K, Byun Y, David A E, He H, Yang V C, 2014, "Cell-penetrating peptides: achievements and challenges in application for cancer treatment," J Biomed Mater Res A. 102(2):575-87.

Kleemann E, Neu M, Jekel N, Fink L, Schmehl T, Gessler T, Seeger W, Kissel T., 2005, "Nano-carriers for DNA delivery to the lung based upon a TAT-derived peptide covalently coupled to PEG-PEL" J Control Release. 109 (1-3):299-316.

Olson E S, Aguilera T A, Jiang T, Ellies L G, Nguyen O T, Wong E, Gross L and Tsien R Y, 2009, "In vivo characterization of activatable cell penetrating peptides for targeting protease activity in cancer," Integr Biol (Camb). 1(5-6): 382-393.

Jain M, Chauhan S C, Singh A P, Venkatraman G, Colcher D, Batra S K, 2005, "Penetratin improves tumor retention of single-chain antibodies: a novel step toward optimization of radioimmunotherapy of solid tumors," Cancer Res. 65(17):7840-6.

Willam C, Masson N, Tian Y M, Mahmood S A, Wilson M I, Bicknell R, Eckardt K U, Maxwell P H, Ratcliffe P J, Pugh C W, 2002, "Peptide blockade of HIF alpha degradation modulates cellular metabolism and angiogenesis," Proc Natl Acad Sci USA. 99(16): 10423-8.

Bolhassani A., 201, "Potential efficacy of cell-penetrating peptides for nucleic acid and drug delivery in cancer," Biochim Biophys Acta. 1816(2):232-46.

Besingi R N, Clark P L, 2015, "Extracellular protease digestion to evaluate membrane protein cell surface localization" Nat Protoc. December; 10(12): 2074-2080.

Schiilein R, Rutz C and Rosenthal W., 1996, "Membrane Targeting and Determination of Transmembrane Topology of the Human Vasopressin V2 Receptor" JBC Vol. 271, No. 46, pp. 28844-28852.

Scholzen T, Gerdes J, 2000, "The Ki-67 protein: from the known and the unknown". Journal of Cellular Physiology. 182 (3): 311-22.

Schuster K, Fan L, Harris L C, 2007, "MDM2 splice variants predominantly localize to the nucleoplasm mediated by a COOH-terminal nuclear localization signal", Mol Cancer Res. 5(4):403-12.

Sherven Sharma, et al, 1999, "T Cell-Derived IL-10 Promotes Lung Cancer Growth by Suppressing Both T Cell and APC Function", J Immunol, 163 (9) 5020-5028.

McIntyre R. M, 2015, "Mouse models of colorectal cancer as preclinical models", Bioassays, 37(8): 909-920.

Li G, et al, 2015, "Enriched environment inhibits mouse pancreatic cancer growth and down-regulates the expression of mitochondria-related genes in cancer cells", Sci Rep. 5:7856.

Rosso M, Okoro D E, Bargonetti J. 2014, "Splice variants of MDM2 in oncogenesis", Subcell Biochem.; 85:247-61.

Volk, E. L., Fan L., Schuster K., el. al., 2009, "The MDM2-A splice variant of MDM2 alters transformation in vitro and the tumor spectrum in both Arf-null and p53-null models of tumorigenesis", Mol Cancer Res. 7(6): 863-869.

Do T N, Rosal R V, Drew L, Raffo A J, Michl J, Pincus M R, Friedman F K, Petrylak D P, Cassai N, Szmulewicz J, Sidhu G, Fine R L, Brandt-Rauf P W, 2003, "Preferential induction of necrosis in human breast cancer cells by a p53 peptide derived from the MDM2 binding site", Oncogene. 22(10): 1431-44.

Sookraj K A, Bowne W B, Adler V, Sarafraz-Yazdi E, Michl J, Pincus M R., 2010, "The anti-cancer peptide, PNC-27, induces tumor cell lysis as the intact peptide", Cancer Chemother Pharmacol, 66(2):325-31.

Rosal R, Brandt-Rauf P W, Pincus M R, Wang H, Mao Y, Fine R L, 2004, "The role of alpha-helical structure in p53 peptides as a determinant for their mechanism of cell death: necrosis versus apoptosis", Adv Drug Devi Rev 57:653-660

10. SEQUENCES

```
SEQ ID NO: 1 (NMC-P1)
MCNTNMSVPTDGAVT (SEQ ID NO: 2 (NMC-P2)
TTSQIPASEQE

SEQ ID NO: 3 (NMC-P3)
CPVCRQPIQMIVLTYFP
```

```
SEQ ID NO: 4 (Human HDM2 Protein):
MCNTNMSVPT DGAVTTSQIP ASEQETLVRP KPLLLKLLKS VGAQKDTYTM

KEVLFYLGQY IMTKRLYDEK QQHIVYCSND LLGDLFGVPS FSVKEHRKIY

TMIYRNLVVV NQQESSDSGT SVSENRCHLE GGSDQKDLVQ ELQEEKPSSS

HLVSRPSTSS RRRAISETEE NSDELSGERQ RKRHKSDSIS LSFDESLALC

VIREICCERS SSSESTGTPS NPDLDAGVSE HSGDWLDQDS VSDQFSVEFE

VESLDSEDYS LSEEGQELSD EDDEVYQVTV YQAGESDTDS FEEDPEISLA

DYWKCTSCNE MNPPLPSHCN RCWALRENWL PEDKGKDKGE ISEKAKLENS

TQAEEGFDVP DCKKTIVNDS RESCVEENDD KITQASQSQE SEDYSQPSTS

SSIIYSSQED VKEFEREETQ DKEESVESSL PLNAIEPCVI CQGRPKNGCI

VHGKTGHLMA CFTCAKKLKK RNKPCPVCRQ PIQMIVLTYF P
```

```
SEQ ID NO: 5 (Mouse MDM2 Protein):
MCNTNMSVST EGAASTSQIP ASEQETLVRP KPLLLKLLKS VGAQNDTYTM

KEIIFYIGQY IMTKRLYDEK QQHIVYCSND LLGDVFGVPS FSVKEHRKIY

AMIYRNLVAV SQQDSGTSLS ESRRQPEGGS DLKDPLQAPP EEKPSSSDLI

SRLSTSSRRR SISETEENTD ELPGERHRKR RRSLSFDPSL GLCELREMCS

GGSSSSSSS SESTETPSHQ DLDDGVSEHS GDCLDQDSVS DQFSVEFEVE

SLDSEDYSLS DEGHELSDED DEVYRVTVYQ TGESDTDSFE GDPEISLADY

WKCTSCNEMN PPLPSHCKRC WTLRENWLPD DKGKDKVEIS EKAKLENSAQ

AEEGLDVPDG KKLTENDAKE PCAEEDSEEK AEQTPLSQES DDYSQPSTSS

SIVYSSQESV KELKEETQDK DESVESSFSL NAIEPCVICQ GRPKNGCIVH

GKTGHLMSCF TCAKKLKKRN KPCPVCRQPI QMIVLTYFN
```

SEQ ID NO: 6 (Human HDM4 protein):
MTSFSTSAQCSTSDSACRISPGQINQVRPKLPLLKILHAAGAQGEMFTVK
EVMHYLGQYIMVKQLYDQQEQHMVYCGGDLLGELLGRQS FSVKDPS PL
YDMLRKNLVTLATATTDAAQTLALAQDHSMDIPSQDQLKQSAEESSTSRK
RTTEDDIPTLPTSEHKCIHSREDEDLIENLAQDETSRLDLGFEEWDVAGL
PWWFLGNLRSNYTPRSNGSTDLQTNQDVGTAIVSDTTDDLWELNESVSEQ
LGVGIKVEAADTEQTSEEVGKVSDKKVIEVGKNDDLEDSKSLSDDTDVEV
TSEDEWQCTECKKENSPSKRYCFRCWALRKDWYSDCSKLTHSLSTSDITA
IPEKENEGNDVPDCRRTISAPWRPKDAYIKKENSKLFDPCNSVEFLDLAH
SSESQETISSMGEQLDNLSEQRTDTENMEDCQNLLKPCSLCEKRPRDGNI
IHGRTGHLVTCFHCARRLKKAGAS CPICKKE IQLVIKVFIA SEQ ID NO: 7 (Mouse MDMX-S protein):
MTSHSTSAQCSASDSACRISSEQISQVRPKLQLLKILHAAGAQGEVETMK
EVMHYLGQYIMVKQLYDQQEQHMVYCGGDLLGDLLGCQ SFSVKDPS PL
YDMLRKNLVTSAS INTARC NRILQSQKKN M(H)DM2/4 Variants:

SEQ ID NO: 8 (HDM2 variant MDM2-A):
MCNTNMSVPTDGAVTTSQIPASEQETLD (2 8-222)
LDAGVSEHSGDWLDQDSVSDQFSVE FEVESLDSEDYSLSEEGQELSDED
DEVYQVTVYQAGESDTDSFEEDPE ISLADYWKCTSCNEMNPPLPSHCNR
CWALRENWLPEDKGKDKGE ISEKAKLENSTQAEEGFDVPDCKKTIVNDS
RESCVEENDDKITQASQSQESEDYSQPSTSSS IIYSSQEDVKEFEREET
QDKEESVESSLPLNAIEPCVICQGRPKNGCIVHGKTGHLMACFTCAKKLK
KRNKPCPVCRQPIQMIVLTYFP SEQ ID NO: 9 (HDM2 variant MDM2-A1):
MCNTNMSVPT DGAVTTSQIP ASEQETLD (28-222)
LDAGVSEH SGDWLDQDSV SDQFSVE FEV ESLDSEDYSL SEEGQEL
SDE DDEDY
(275-300) WKCTS CNEMNPPLPS HCNRCWALRE NWLPEDKGKD K
GEI SEKAKL ENSTQAEEGF DVPDCKKTIV NDSRESCVEE NDDKIT
QASQ SQESEDYSQP STSSSIIYSS QEDVKEFERE ETQDKEESVE S
SLPLNAIEP CVICQGRPKN GCIVHGKTGH LMACFTCAKK LKKRNKP
CPV CRQPIQMIVL TYFP SEQ ID NO: 10 (HDM2 variant MDM2-B):
MCNTNMSVPTDGAVTTSQIPASEQETLD (28-300)
YWKCTSCNEMNPPLPSHCNRCWALRENWLPEDKGKDKGEISEKAKLENST
QAEEGFDVPDCKKTIVNDSRESCVEENDDKITQASQSQESEDYSQPSTSS
SIIYSSQEDVKE FEREETQDKEESVESSLPLNAIEPCVICQGRPKNGCI
VHG KTGHLMACFTCAKKLKKRNKPCPVCRQPIQMIVLTYFP SEQ ID NO: 11 (HDM2 variant MDM2-C):
MCNTNMSVPTDGAVTTSQIPASEQETLVRPKPLLLKLLKSVGAQKDTYTM
KED (53-222)

LDAGVSEHSGDWLDQDSVSDQFSVE FEVESLDSEDYSLSEEGQELSDED
DEVYQVTVYQAGESDIDSFEEDPEISLADYWKCTSCNEMNPPLPSHCNRC
WALRENWLPEDKGKDKGE ISEKAKLENSTQAEEGEDVPDCKKTIVNDSR
ESCVEENDDKITQASQSQESEDYSQPSTSSSI IYSSQEDVKEFEREETQ
DKEESVESSLPLNAIEPCVICQGRPKNGCIVHGKTGHLMACFTCAKKLKK
RNKPCPVCRQPIQMIVLTYFP

SEQ ID NO: 12 (HDM2 variant MDM2-D):
MCNTNMSVPTDGAVTTSQIPASEQETLVRQ (30-388)
ESEDYSQPSTSSS IIYSSQEDVKE FEREETQDKEESVESS LPLNAIE
PCVICQGRPKNGCIVHGKTGHLMACFTCAKKLKKRNKPCPVCRQPIQMIV
LTYFP SEQ ID NO: 13 (HDM2 variant MDM2-E):
MCNTNMSVPTDGAVTTSQIPASEQETLVRPKPLLLKLLKSVGAQKDTYTM
KEVLFYLGQY IMTKRLYDEKQQHIVN (76-102) (103-491)
DCANLFPLVDLS IRELYISNYITLGI SEQ ID NO: 14 (HDM2 variant MDM2-F):
MCNTNMSVPTDGAVTTSQIPASEQETLVRPKPLLLKLLKSVGAQKDTYTM
KE (53-97)
KIYTMIYRNLWVNQQESSDSGTSVSENRCHLEGGSDQKDLVQELQEEKPS
SSHLVSRPSTSSRRRAISETEENSDELSGERQRKRHKSDS ISLSFDESL
ALCVIREICCERSSSSESTGTPSNPDLDAGVSEHSGDWLDQDSVSDQFSV
E FEVESLDSEDYSLSEEGQELSDEDDEVYQVTVYQAGESDTDSFEEDP
EISLADYWKCTSCNEMNPPLPSHCNRCWALRENWLPEDKGKDKGEISEKA
KLENSTQAEEGFDVPDCKKTIVNDSRESCVEENDDKITQASQSQESEDYS
QPSTSSSIIYSSQEDVKE FEREETQDKEESVESSLPLNAIEPCVICQGR
PKNGCIVHGKTGHLMACFTCA KKLKKRNKPCPVCRQPIQMIVLTYFP SEQ ID NO: 15 (HDM2 variant MDM2-G):
MCNTNMSVPTDGAVTTSQIPASEQETLVRPKPLLLKLLKSVGAQKDTYTM
KEVLFYLGQYIMTKRLYDEKQQHIVYCSNDLLGDLFGVPSFSVKEHRKI
YTMIYRNL\AA/NQQEE (115-169)
NSDELSGERQRKRHKSDS ISLSFDESLALCVIREICCERSSSSESTGTP
SNPDLDAGVSEHSGDWLDQDSVSDQFSVE FEVESLDSEDYSLSEEGQEL
SDEDDEVYQVTVYQAGESDTDSFEEDPEISLADYWKCTSCNEMNPPLPSH
CNRCWALRENWLPEDKGKDKGEISEKAKLENSTQAEEGFDVPDCKKTIVN -continued DSRESCVEENDDKITQASQSQESEDYSQPSTSSS IIYSSQEDVKE FER
EETQDKEESVESSLPLNATEPCVICQGRPKNGCIVHGKTGHLMACFTCAK
KLKKRNKPCPVCRQPIQMIVLTYFP SEQ ID NO: 16 (HDM2 variant MDM2-11):
MVRSRQMCNTNMSVPTDGAVTTSQIPASEQETLVRPKPLLLKLLKSVGAQ
KDTYTMKEVLFYLGQYIMTKRLYDEKQQHIVYCSNDLLGDLFGVPSFSVK
EHRKI YTMIYRNL\AA/NQQESSDSGTSVSENRCHLEGGSDQKDLVQEL
QEEKPSSSHLVSRPSTSSRRRAISE TEENSDELSGERQRKRHKSDS IS
LSFDESLALCVIREICCERSSSSESTGTPSNPDLDAGVSEHSGDWLDQDS
VSDQFSVEFEVESLDSEDYSLSEEGQELSDEDDEVYQVTVYQAGES DTD
S FEEDPEISLADYWKCTSCNEMNPPLPSHCNRCWALRENWLPEDKGKDK -continued GEISEKAKLENSTQAEEGFDVPDCKKTIVNDSRESCVEENDDKITQASQS
QESEDYSQPSTSSS IIYSSQEDVKEFEREETQDKEESVESSLPLNAIEP
CVICQGRPKNGCIVHGKTGHLMACFTCAKKLKKRNKPCPVCRQPIQMIVL
TYFP SEQ ID NO: 17 (HDM2 variant MDM2-KB2):
MCNTNMSVPTDGAVTTSQIPASEQETLVRPKPLLLKLLKSVGAQKDTYTM
KEDYWKCTSCNEMNPPLPSHCNRCWALRENWLPEDKGKDKGE ISEKAKL
ENS TQAEEGFDVPDCKKT IVNDSRESCVEENDDKITQASQSQESEDYS
QPSTSSSI I (157-248) YSSQEDVKEFEREETQDKEESVESSLPL
NAIEPCVICQGRPKNGCIVHGKTGHLMACFTCAKKLKKRNKPCPVCRQPI
QMIVLTYFP

TABLE 4 mAb NMC-103 Heavy Chain CDR and HFR Sequences using Chothia, AbM, Kabat, Contact and IMGT CDR definitions:

| Region | Definition | Sequence Fragment | Residues[1] | Length | SEQ ID NO: |
|---|---|---|---|---|---|
| HFR1 | Chothia | EVQLQESGGGLVQPGGSLRLSCTTS----- | 1-25 | 25 | 72 |
|  | AbM | EVQLQESGGGLVQPGGSLRLSCTTS----- | 1-25 | 25 | 72 |
|  | Kabat | EVQLQESGGGLVQPGGSLRLSCTTSGFTFT | 1-30 | 30 | 73 |
|  | Contact | EVQLQESGGGLVQPGGSLRLSCTTSGFTF- | 1-29 | 29 | 74 |
| CDR-H1 | Chothia | GFTFTHY--- | 26-32 | 7 | 18 |
|  | AbM | GFTFTHYYMS | 26-35 | 10 | 42 |
|  | Kabat | -----HYYMS | 31-35 | 5 | 43 |
|  | Contact | ----THYYMS | 30-35 | 6 | 44 |
|  | IMGT | -FTFTHYY-- | 27-33 | 7 | 144 |
| HFR2 | Chothia | YMSWVRQPPGKALEWLGFI | 33-51 | 19 | 75 |
|  | AbM | ---WVRQPPGKALEWLG-- | 36-49 | 14 | 76 |
|  | Kabat | ---WVRQPPGKALEWLG-- | 36-49 | 14 | 76 |
|  | Contact | ---WVRQPPGKALE----- | 36-46 | 11 | 77 |
| CDR-H2 | Chothia | -----RNKAKGYT--------- | 52-59 | 8 | 19 |
|  | AbM | ---FIRNKAKGYTAE------- | 50-61 | 12 | 45 |
|  | Kabat | ---FIRNKAKGYTAEYSASVKG | 50-68 | 19 | 46 |
|  | Contact | WLGFIRNKAKGYTAE------- | 47-61 | 15 | 47 |
|  | IMGT | ----IRNKAKGYTA-------- | 51-60 | 10 | 145 |
| HFR3 | Chothia | AEYSASVKGRFTISRDNSQSILYLQMNTLRPEDSATYYCAR | 60-100 | 41 | 78 |
|  | AbM | --YSASVKGRFTISRDNSQSILYLQMNTLRPEDSATYYCAR | 62-100 | 39 | 79 |
|  | Kabat | ---------RFTISRDNSQSILYLQMNTLRPEDSATYYCAR | 69-100 | 32 | 80 |
|  | Contact | --YSASVKGRFTISRDNSQSILYLQMNTLRPEDSATYYC-- | 62-98 | 37 | 81 |
| CDR-H3 | Chothia | --DIGDN | 101-105 | 5 | 20 |
|  | AbM | --DIGDN | 101-105 | 5 | 20 |
|  | Kabat | --DIGDN | 101-105 | 5 | 20 |
|  | Contact | ARDIGD- | 99-104 | 6 | 48 |
|  | IMGT | ARDIGDN | 99-105 | 7 | 146 |
| HFR4 | Chothia | -WGQGTLVTVSS | 106-116 | 11 | 82 |
|  | AbM | -WGQGTLVTVSS | 106-116 | 11 | 82 |
|  | Kabat | -WGQGTLVTVSS | 106-116 | 11 | 82 |
|  | Contact | NWGQGTLVTVSS | 105-116 | 12 | 83 |

[1]The listed residues are residue numbers of the heavy chain variable region (SEQ ID NO: 36) of NMC-103.

TABLE 5 mAb NMC-103 Light Chain CDR and HFR Sequences using
Chothia, AbM, Kabat, Contact and IMGT CDR definitions:

| Region | Definition | Sequence Fragment | Residues[2] | Length | SEQ ID ID: |
|---|---|---|---|---|---|
| LFR1 | Chothia | DIVMTQAAFSNPVTLGTSASISC------ | 1-23 | 23 | 84 |
|  | AbM | DIVMTQAAFSNPVTLGTSASISC------ | 1-23 | 23 | 84 |
|  | Kabat | DIVMTQAAFSNPVTLGTSASISC------ | 1-23 | 23 | 84 |
|  | Contact | DIVMTQAAFSNPVTLGTSASISCRSSKNL | 1-29 | 29 | 85 |
| CDR-L1 | Chothia | RSSKNLLHSNGITYLY-- | 24-39 | 16 | 21 |
|  | AbM | RSSKNLLHSNGITYLY-- | 24-39 | 16 | 21 |
|  | Kabat | RSSKNLLHSNGITYLY-- | 24-39 | 16 | 21 |
|  | Contact | ------LHSNGITYLYWY | 30-41 | 12 | 49 |
|  | IMGT | ---KNLLHSNGITY---- | 27-37 | 11 | 147 |
| LFR2 | Chothia | WYLQRPGQSPQLLIS | 40-54 | 15 | 86 |
|  | AbM | WYLQRPGQSPQLLIS | 40-54 | 15 | 86 |
|  | Kabat | WYLQRPGQSPQLLIS | 40-54 | 15 | 86 |
|  | Contact | --LQRPGQSPQ---- | 42-50 | 9 | 87 |
| CDR-L2 | Chothia | ----RVSNLAS | 55-61 | 7 | 22 |
|  | AbM | ----RVSNLAS | 55-61 | 7 | 22 |
|  | Kabat | ----RVSNLAS | 55-61 | 7 | 22 |
|  | Contact | LLISRVSNLA- | 51-60 | 10 | 50 |
|  | IMGT | ----RVS---- | 55-57 | 3 |  |
| LFR3 | Chothia | -GVPNRFSGSESGTDFTLRISRVEAEDVGVYFC | 62-93 | 32 | 88 |
|  | AbM | -GVPNRFSGSESGTDFTLRISRVEAEDVGVYFC | 62-93 | 32 | 88 |
|  | Kabat | -GVPNRFSGSESGTDFTLRISRVEAEDVGVYFC | 62-93 | 32 | 88 |
|  | Contact | SGVPNRFSGSESGTDFTLRISRVEAEDVGVYFC | 61-93 | 33 | 89 |
| CDR-L3 | Chothia | AQLLELPYT | 94-102 | 9 | 23 |
|  | AbM | AQLLELPYT | 94-102 | 9 | 23 |
|  | Kabat | AQLLELPYT | 94-102 | 9 | 23 |
|  | Contact | AQLLELPY- | 94-101 | 8 | 51 |
|  | IMGT | AQLLELPYT | 94-102 | 9 | 23 |
| LFR4 | Chothia | -FGGGTKLEIK | 103-112 | 10 | 90 |
|  | AbM | -FGGGTKLEIK | 103-112 | 10 | 90 |
|  | Kabat | -FGGGTKLEIK | 103-112 | 10 | 90 |
|  | Contact | TFGGGTKLEIK | 102-112 | 11 | 91 |

[2]The listed residues are residue numbers of the light chain variable region (SEQ ID NO: 37) of NMC-103.

TABLE 6 mAb NMC-204 Heavy Chain CDR and HFR Sequences using
Chothia, AbM, Kabat, Contact and IMGT CDR defintions:

| Region | Definition | Sequence Fragment | Residues[3] | Length | SEQ ID NO: |
|---|---|---|---|---|---|
| HFR1 | Chothia | EVQLQESGSVLVRPGASVKLSCKAS----- | 1-25 | 25 | 92 |
|  | AbM | EVQLQESGSVLVRPGASVKLSCKAS----- | 1-25 | 25 | 92 |
|  | Kabat | EVQLQESGSVLVRPGASVKLSCKASGDTLS | 1-30 | 30 | 93 |
|  | Contact | EVQLQESGSVLVRPGASVKLSCKASGDTL- | 1-29 | 29 | 94 |
| CDR-H1 | Chothia | GDTLSGS--- | 26-32 | 7 | 24 |
|  | AbM | GDTLSGSWMH | 26-35 | 10 | 52 |
|  | Kabat | -----GSWMH | 31-35 | 5 | 53 |
|  | Contact | ----SGSWMH | 30-35 | 6 | 54 |
|  | IMGT | GDTLSGSW-- | 26-33 | 8 | 148 |
| HFR2 | Chothia | WMHWAMQRPGQGLEWIGEI | 33-51 | 19 | 95 |
|  | AbM | ---WAMQRPGQGLEWIG-- | 36-49 | 14 | 96 |
|  | Kabat | ---WAMQRPGQGLEWIG-- | 36-49 | 14 | 96 |
|  | Contact | ---WAMQRPGQGLE----- | 36-46 | 11 | 97 |
| CDR-H2 | Chothia | -----HLNRGT--------- | 52-57 | 6 | 25 |
|  | AbM | ---EIHLNRGTTN------- | 50-59 | 10 | 55 |
|  | Kabat | ---EIHLNRGTTNYNEKFKG | 50-66 | 17 | 56 |
|  | Contact | WIGEIHLNRGTTN------- | 47-59 | 13 | 57 |
|  | IMGT | ----IHLNRGTT-------- | 51-58 | 8 | 143 |

TABLE 6-continued mAb NMC-204 Heavy Chain CDR and HFR Sequences using
Chothia, AbM, Kabat, Contact and IMGT CDR defintions:

| Region | Definition | Sequence Fragment | Residues[3] | Length | SEQ ID NO: |
|---|---|---|---|---|---|
| HFR3 | Chothia | TNYNEKFKGKATVTVDTSSSTAYVDLSSLTSEDSAVYYCAR | 58-98 | 41 | 98 |
|  | AbM | --YNEKFKGKATVTVDTSSSTAYVDLSSLTSEDSAVYYCAR | 60-98 | 39 | 99 |
|  | Kabat | ---------KATVTVDTSSSTAYVDLSSLTSEDSAVYYCAR | 67-98 | 32 | 100 |
|  | Contact | --YNEKFKGKATVTVDTSSSTAYVDLSSLTSEDSAVYYC-- | 60-96 | 37 | 101 |
| CDR-H3 | Chothia | --SPGFAY | 99-104 | 6 | 26 |
|  | AbM | --SPGFAY | 99-104 | 6 | 26 |
|  | Kabat | --SPGFAY | 99-104 | 6 | 26 |
|  | Contact | ARSPGFA- | 97-103 | 7 | 58 |
|  | IMGT | ARSPGFA- | 97-103 | 7 | 58 |
| HFR4 | Chothia | -WGQGTLVTVSA | 105-115 | 11 | 102 |
|  | AbM | -WGQGTLVTVSA | 105-115 | 11 | 102 |
|  | Kabat | -WGQGTLVTVSA | 105-115 | 11 | 102 |
|  | Contact | YWGQGTLVTVSA | 104-115 | 12 | 103 |

[3]The listed residues are residue numbers of the heavy chain variable region (SEQ ID NO: 38) of NMC-204.

TABLE 7 mAb NMC-204 Light Chain CDR and HFR Sequences using
Chothia, AbM, Kabat, Contact and IMGT CDR defintions

| Region | Definition | Sequence Fragment | Residues[4] | Length | SEQ ID NO: |
|---|---|---|---|---|---|
| LFR1 | Chothia | GIVMTQAAPSVPVTPGESVSISC------ | 1-23 | 23 | 104 |
|  | AbM | GIVMTQAAPSVPVTPGESVSISC------ | 1-23 | 23 | 104 |
|  | Kabat | GIVMTQAAPSVPVTPGESVSISC------ | 1-23 | 23 | 104 |
|  | Contact | GIVMTQAAPSVPVTPGESVSISCRSSKSL | 1-29 | 29 | 105 |
| CDR-L1 | Chothia | RSSKSLLHSNGNSYLY-- | 24-39 | 16 | 27 |
|  | AbM | RSSKSLLHSNGNSYLY-- | 24-39 | 16 | 27 |
|  | Kabat | RSSKSLLHSNGNSYLY-- | 24-39 | 16 | 27 |
|  | Contact | ------LHSNGNSYLYWF | 30-41 | 12 | 59 |
|  | IMGT | ---KSLLHSNGNSY | 27-37 | 11 | 141 |
| LFR2 | Chothia | WFLQRPGQSPQLLIY | 40-54 | 15 | 106 |
|  | AbM | WFLQRPGQSPQLLIY | 40-54 | 15 | 106 |
|  | Kabat | WFLQRPGQSPQLLIY | 40-54 | 15 | 106 |
|  | Contact | --LQRPGQSPQ---- | 42-50 | 9 | 107 |
| CDR-L2 | Chothia | ----RMSNLAS | 55-61 | 7 | 28 |
|  | AbM | ----RMSNLAS | 55-61 | 7 | 28 |
|  | Kabat | ----RMSNLAS | 55-61 | 7 | 28 |
|  | Contact | LLIYRMSNLA- | 51-60 | 10 | 60 |
|  | IMGT | ----RMS---- | 55-57 | 3 |  |
| LFR3 | Chothia | -GVPDRFSGSGSGTAFTLRITRVEAEDVGVYYC | 62-93 | 32 | 108 |
|  | AbM | -GVPDRFSGSGSGTAFTLRITRVEAEDVGVYYC | 62-93 | 32 | 108 |
|  | Kabat | -GVPDRFSGSGSGTAFTLRITRVEAEDVGVYYC | 62-93 | 32 | 108 |
|  | Contact | SGVPDRFSGSGSGTAFTLRITRVEAEDVGVYYC | 61-93 | 33 | 109 |
| CDR-L3 | Chothia | MQHLEYPFT | 94-102 | 9 | 29 |
|  | AbM | MQHLEYPFT | 94-102 | 9 | 29 |
|  | Kabat | MQHLEYPFT | 94-102 | 9 | 29 |
|  | Contact | MQHLEYPF- | 94-101 | 8 | 61 |
|  | IMGT | MQHLEYPFT | 94-102 | 9 | 29 |
| LFR4 | Chothia | -FGSGTKLEIK | 103-112 | 10 | 110 |
|  | AbM | -FGSGTKLEIK | 103-112 | 10 | 110 |
|  | Kabat | -FGSGTKLEIK | 103-112 | 10 | 110 |
|  | Contact | TFGSGTKLEIK | 102-112 | 11 | 111 |

[4]The listed residues are residue numbers of the light chain variable region (SEQ ID NO: 39) of NMC-204.

TABLE 8 mAb NMC-303 Heavy Chain CDR and HFR Sequences using
Chothia, AbM, Kabat and Contact CDR definitions:

| Region | Definition | Sequence Fragment | Residues[5] | Length | SEQ ID NO: |
|---|---|---|---|---|---|
| HFR1 | Chothia | QVQLQQPGAELVKPGASVKLSCKAS----- | 1-25 | 25 | 112 |
|  | AbM | QVQLQQPGAELVKPGASVKLSCKAS----- | 1-25 | 25 | 112 |
|  | Kabat | QVQLQQPGAELVKPGASVKLSCKASGYTFT | 1-30 | 30 | 113 |
|  | Contact | QVQLQQPGAELVKPGASVKLSCKASGYTF- | 1-29 | 29 | 114 |
| CDR-H1 | Chothia | GYTFTSY--- | 26-32 | 7 | 30 |
|  | AbM | GYTFTSYYMY | 26-35 | 10 | 62 |
|  | Kabat | -----SYYMY | 31-35 | 5 | 63 |
|  | Contact | ----TSYYMY | 30-35 | 6 | 64 |
| HFR2 | Chothia | YMYWVKQRPGQGLEWIGGI | 33-51 | 19 | 115 |
|  | AbM | ---WVKQRPGQGLEWIG-- | 36-49 | 14 | 116 |
|  | Kabat | ---WVKQRPGQGLEWIG-- | 36-49 | 14 | 116 |
|  | Contact | ---WVKQRPGQGLE | 36-46 | 11 | 117 |
| CDR-H2 | Chothia | -----NPRNGG--------- | 52-57 | 6 | 31 |
|  | AbM | ---GINPRNGGTN------- | 50-59 | 10 | 65 |
|  | Kabat | ---GINPRNGGTNFNEKFKN | 50-66 | 17 | 66 |
|  | Contact | WIGGINPRNGGTN------- | 47-59 | 13 | 67 |
| HFR3 | Chothia | TNFNEKFKNKATLTADKSSTTAYMQLSSLTSEDSAVYYCTR | 58-98 | 41 | 118 |
|  | AbM | --FNEKFKNKATLTADKSSTTAYMQLSSLTSEDSAVYYCTR | 60-98 | 39 | 119 |
|  | Kabat | ---------KATLTADKSSTTAYMQLSSLTSEDSAVYYCTR | 67-98 | 32 | 120 |
|  | Contact | --FNEKFKNKATLTADKSSTTAYMQLSSLTSEDSAVYYC-- | 60-96 | 37 | 121 |
| CDR-H3 | Chothia | --SGYYAMDY | 99-106 | 8 | 32 |
|  | AbM | --SGYYAMDY | 99-106 | 8 | 32 |
|  | Kabat | --SGYYAMDY | 99-106 | 8 | 32 |
|  | Contact | TRSGYYAMD- | 97-105 | 9 | 68 |
| HFR4 | Chothia | -WGQGTSVTVSS | 107-117 | 11 | 122 |
|  | AbM | -WGQGTSVTVSS | 107-117 | 11 | 122 |
|  | Kabat | -WGQGTSVTVSS | 107-117 | 11 | 122 |
|  | Contact | YWGQGTSVTVSS | 106-117 | 12 | 123 |

[5]The listed residues are residue numbers of the heavy chain variable region (SEQ ID NO:40) of NMC-303.

TABLE 9 mAb NMC-303 Light Chain CDR and HFR Sequences using
Chothia, AbM, Kabat and Contact CDR definitions:

| Region | Definition | Sequence Fragment | Residues[6] | Length | SEQ ID NO: |
|---|---|---|---|---|---|
| LFR1 | Chothia | DIQMTQTTSSLSASLGDRVTISC | 1-23 | 23 | 124 |
|  | AbM | DIQMTQTTSSLSASLGDRVTISC | 1-23 | 23 | 124 |
|  | Kabat | DIQMTQTTSSLSASLGDRVTISC | 1-23 | 23 | 124 |
|  | Contact | DIQMTQTTSSLSASLGDRVTISCRASQDI | 1-29 | 29 | 125 |
| CDR-L1 | Chothia | RASQDISNFLN- | 24-34 | 11 | 33 |
|  | AbM | RASQDISNFLN- | 24-34 | 11 | 33 |
|  | Kabat | RASQDISNFLN- | 24-34 | 11 | 33 |
|  | Contact | ------SNFLNWY | 30-36 | 7 | 69 |
| LFR2 | Chothia | WYQQKPDGTVKLLIY | 35-49 | 15 | 126 |
|  | AbM | WYQQKPDGTVKLLIY | 35-49 | 15 | 126 |
|  | Kabat | WYQQKPDGTVKLLIY | 35-49 | 15 | 126 |
|  | Contact | --QQKPDGTVK---- | 37-45 | 9 | 127 |
| CDR-L2 | Chothia | ----YTSRLHS | 50-56 | 7 | 34 |
|  | AbM | ----YTSRLHS | 50-56 | 7 | 34 |
|  | Kabat | ----YTSRLHS | 50-56 | 7 | 34 |
|  | Contact | LLIYYTSRLH- | 46-55 | 10 | 70 |
| LFR3 | Chothia | -GVPSRFSGSGSGTDYSLTISNLEQEDIATYFC | 57-88 | 32 | 128 |
|  | AbM | -GVPSRFSGSGSGTDYSLTISNLEQEDIATYFC | 57-88 | 32 | 128 |
|  | Kabat | -GVPSRFSGSGSGTDYSLTISNLEQEDIATYFC | 57-88 | 32 | 128 |
|  | Contact | SGVPSRFSGSGSGTDYSLTISNLEQEDIATYFC | 56-88 | 33 | 129 |
| CDR-L3 | Chothia | QQGNTLPRT | 89-97 | 9 | 35 |
|  | AbM | QQGNTLPRT | 89-97 | 9 | 35 |

TABLE 9-continued mAb NMC-303 Light Chain CDR and HFR Sequences using
Chothia, AbM, Kabat and Contact CDR definitions:

| Region | Definition | Sequence Fragment | Residues[6] | Length | SEQ ID NO: |
|---|---|---|---|---|---|
|  | Kabat | QQGNTLPRT | 89-97 | 9 | 35 |
|  | Contact | QQGNTLPR- | 89-96 | 8 | 71 |
| LFR4 | Chothia | -FGGGTKLEIK | 98-107 | 10 | 130 |
|  | AbM | -FGGGTKLEIK | 98-107 | 10 | 130 |
|  | Kabat | -FGGGTKLEIK | 98-107 | 10 | 130 |
|  | Contact | TFGGGTKLEIK | 97-107 | 11 | 131 |

[6]The listed residues are residue numbers of the light chain variable region (SEQ ID NO:41) of NMC-303.

mAb NMC-103 Heavy Chain Variable Region DNA
Sequence (SEQ ID NO: 132)
gaggtgcagctgcaggagtctggaggaggcttggtacagcctgggggttc tctgagactctcctgtacaacttctgggttcaccttcactcattactaca tgagctgggtccgccagcctccaggcaaggcacttgagtggttgggcttt attagaaataaagctaaggggttacacagcagagtacagtgcatctgtgaa gggtcggttcaccatctccagagataattcccaaagcatcctctatcttc aaatgaacaccctgagacctgaggacagtgccacttattactgtgcaaga gatattggggacaactggggtcaaggaaccttagtcaccgtctcctcag mAb NMC-103 Heavy Chain Variable Region Protein
Sequence (SEQ ID NO: 36) (Complementarity determining regions (CDRs) determined according to the IMGT numbering system are underlined):
EVQLQESGGGLVQPGGSLRLSCTTSG<u>FTFTHYYM</u>SWVRQPPGKALEWLG <u>FIRNKAKGYTA</u>EYSASVKGRFTISRDNSQSILYLQMNTLRPEDSATYYC <u>ARDIGDN</u>WGQGTLVTVSS mAb NMC-103 Light Chain Variable Region DNA
Sequence (SEQ ID NO: 134)
gatattgtgatgacgcaggctgccttctccaatccagtcactcttggaac atcagcttccatctcctgcaggtctagtaagaatctcctacatagtaatg gcatcacttatttgtattggtatctgcagaggccaggccagtctcctcag ctcctgatatctcgggtgtccaatctggcctcaggagtcccaaacaggtt cagtggcagtgagtcaggaactgatttcacactgagaatcagcagagtgg aggctgaggatgtgggtgtttatttctgtgctcaactgctagaactcccg tacacgttcggaggggggaccaagttggaaataaaac mAb NMC-103 Light Chain Variable Region Protein
Sequence (SEQ ID NO: 37) (Complementarity determining regions (CDRs) determined according to the IMGT numbering system are underlined):
DIλ/MTQAAFSNPVTLGTSASISCRSS<u>KNLLHSNGITY</u>LYWYLQRPGQS PQLLIS<u>RVS</u>NLASGVPNRFSGSESGTDFTLRISRVEAEDVGVYFC<u>AQLL</u>

<u>ELPYT</u>FGGGTKLEIK mAb NMC-204 Heavy Chain Variable Region DNA
Sequence (SEQ ID NO: 136)
gaggtgcagctgcaggagtctgggtctgtgctggtgaggcctggagctt cagtgaagctgtcctgcaaggcttctggcgacaccctcagcggctcctg gatgcactgggcgatgcagaggcctggacaaggccttgagtggattgga gagattcatcttaatagaggtactactaactacaatgagaagttcaagg gcaaggccacagtgactgtggacacatcctccagcacagcctacgtgga tctcagcagcctgacatctgaggactctgcggtctattactgtgcaaga agcccggggtttgcttactggggccaagggactctggtcactgtctctg cag mAb NMC-204 Heavy Chain Variable Region Protein
Sequence (SEQ ID NO: 38) (Complementarity determining regions (CDRs) determined according to the IMGT numbering system are underlined):
EVQLQESGSVLVRPGASVKLSCKAS<u>GDTLSGSWMH</u>WAMQRPGQGLEWI <u>GEIHLNRGTT</u>NYNEKEKGKATVTVDTSSSTAYVDLSSLTSEDSAVYYC <u>ARSPGFAY</u>WGQGTLVTVSA mAb NMC-204 Light Chain Variable Region DNA
Sequence (SEQ ID NO: 138)
ggcattgtgatgacccaggctgcaccctctgtacctgtcactcctggag agtcagtatccatctcctgcaggtctagtaagagtctcctgcatagtaa tggcaacagttacttgtattggttcctgcagaggccaggccagtctcct cagctcctgatatctcggatgtccaaccttgcctcaggagtcccagaca ggttcagtggcagtgggtcaggaactgctttcacactgagaatcactag agtggaggctgaggatgtgggtgtttattactgtatgcaacatctagaa tatcctttcacgttcggctcggggacaaagttggaaataaaac mAb NMC-204 Light Chain Variable Region Protein
Sequence (SEQ ID NO: 39) (Complementarity determining regions (CDRs) determined according to the IMGT numbering system are underlined):
GIVMTQAAPSVPVTPGESVSISCRSS<u>KSLLHSNGNSY</u>LYWFLQRPGQSP QLLIY<u>RMS</u>NLASGVPDRFSGSGSGTAFTLRITRVEAEDVGVYYC<u>MQHLE</u>

<u>YPFT</u>FGSGTKLEIK mAb NMC-303 Heavy Chain Variable Region DNA Sequence (SEQ ID NO: 140):
caggtccaactgcagcagcctggggctgaactggtgaagcctggggctt cagtgaagttgtcctgcaaggcttctggctacaccttcaccagctacta tatgtactgggtgaagcagaggcctggacaaggccttgagtggattggg gggattaatcctaggaatggtggtactaacttcaatgagaagttcaaga acaaggccacactgactgcagacaaatcctccaccacagcctacatgca actcagtagcctgacatctgaggactctgcggtctattactgtacaaga tctggttactatgctatggactattggggtcaaggaacctcagtcaccg tctcctca mAb NMC-303 Heavy Chain Variable Region Protein Sequence (SEQ ID NO: 40) (Complementarity determining regions (CDRs) determined according to the Kabat numbering system are underlined):
QVQLQQPGAELVKPGASVKLSCKASGYTFT<u>SYYMY</u>WVKQRPGQGLEWIG<u>GINPRNGGTNFNEKFKN</u>KATLTADKSSTTAYMQLSSLTSEDSAVYYCTR<u>SGYYAMDY</u>WGQGTSVTVSS mAb NMC-303 Light Chain Variable Region DNA Sequence (SEQ ID NO: 142):
gatatccagatgacacagactacatcctccctgtctgcctctctgggag acagagtcaccatcagttgcagggcaagtcaggacattagcaatttttt aaactggtatcagcagaaaccagatggaactgttaaactcctgatctac tacacatcaagattacactcaggagtcccatcaaggttcagtggcagtg ggtctggaacagattattctctcaccattagcaacctggagcaagaaga tattgccacttactttgccaacagggtaatacgcttcctcggacgttc ggtggaggcaccaagctggaaatcaaa mAb NMC-303 Light Chain Variable Region Protein Sequence (SEQ ID NO: 41) (Complementarity determining regions (CDRs) determined according to the Kabat numbering system are underlined):
DIQMTQTTSSLSASLGDRVTISC<u>RASQDISNFLN</u>WYQQKPDGTVKLLIY<u>YTSRLHSG</u>VPSRFSGSGSGTDYSLTISNLEQEDIATYFC<u>QQGNTLPRT</u>FGGGTKLEIK

INCORPORATION BY REFERENCE

Various references such as patents, patent applications, and publications are cited herein, the disclosures of which are hereby incorporated by reference herein in their entireties.

What is claimed is:

1. A method of treating a cancer expressing M(H)DM2/4 in a subject in need thereof, said method comprising administering to the subject: a composition comprising an antibody or an antigen-binding fragment thereof that binds to M(H)DM2/4,
wherein said antibody or antigen-binding fragment comprises: (i) a heavy chain variable region (VH) comprising VH complementarity determining region ("CDR") 1, VHCDR2, and VHCDR3; said VHCDR1, VHCDR2 and VHCDR3 being the CDRs of a VH that has the amino acid sequence of SEQ ID NO: 36, and (ii) a light chain variable region (VL) comprising VLCDR1, VLCDR2, and VLCDR3; said VLCDR1, VLCDR2, and VLCDR3 being the CDRs of a VL that has the amino acid sequence of SEQ ID NO: 37.

2. The method of claim 1, said method comprising administering to the subject the antibody or antigen-binding fragment, which is not bound to a cytotoxic component, and which inhibits tumor cell proliferation in vivo.

3. The method of claim 1, wherein the antibody or antigen-binding fragment-binds to an extracellularly accessible epitope of M(H)DM2/4 within a peptide having the amino acid sequence consisting of MCNTNMSVPTD-GAVT (SEQ ID NO:1).

4. The method of claim 1, wherein the antibody or antigen-binding fragment is a humanized antibody or antigen-binding fragment that binds to HDM2.

5. The method of claim 1, wherein the antibody or antigen-binding fragment comprises:
(A) VHCDR1, VHCDR 2, and VHCDR3 from a VH that has the amino acid sequence of SEQ ID NO: 36, wherein:
(i) the VHCDR1 has the amino acid sequence GFTFTHY (SEQ ID NO: 18), the VHCDR2 has the amino acid sequence RNKAKGYT (SEQ ID NO: 19), and the VHCDR3 has the amino acid sequence DIGDN (SEQ ID NO:20), as defined according to the Chothia system;
(ii) the VHCDR1 has the amino acid sequence GFTFTHYYMS (SEQ ID NO:42), the VHCDR2 has the amino acid sequence FIRNKAKGYTAE (SEQ ID NO:45), and the VHCDR3 has the amino acid sequence DIGDN (SEQ ID NO:20), as defined according to the AbM system;
(iii) the VHCDR1 has the amino acid sequence HYYMS (SEQ ID NO:43), the VHCDR2 has the amino acid sequence FIRNKAKGYTAEYSASVKG (SEQ ID NO:46), and the VHCDR3 has the amino acid sequence DIGDN (SEQ ID NO:20), as defined according to the Kabat system;
(iv) the VHCDR1 has the amino acid sequence THYYMS (SEQ ID NO:44), the VHCDR2 has the amino acid sequence WLGFIRNKAKGYTAE (SEQ ID NO:47), and the VHCDR3 has the amino acid sequence ARDIGD (SEQ ID NO:48), as defined according to the Contact system; or
(v) the VHCDR1 has the amino acid sequence FTFTHYY (SEQ ID NO: 144), the VHCDR2 has the amino acid sequence IRNKAKGYTA (SEQ ID NO: 145). and the VHCDR3 has the amino acid sequence ARDIGDN (SEQ ID NO: 146), as defined according to the IMGT system; and,
(B) VLCDR1, VLCDR2, and VLCDR 3 from a VL that has the amino acid sequence of SEQ ID NO: 37, wherein:
(i) the VLCDR1 has the amino acid sequence RSSKNLLHSNGITYLY (SEQ ID NO:21), the VLCDR2 has the amino acid sequence RVSNLAS (SEQ ID NO:22), and the VLCDR3 has the amino acid sequence AQLLELPYT (SEQ ID NO:23), as defined according to the Chothia, AbM or Kabat systems;
(ii) the VLCDR1 has the amino acid sequence LHSNGITYLWY (SEQ ID NO:49), the VLCDR2 has the amino acid sequence LLISRVSNLA (SEQ ID NO:50), and the VLCDR3 has the amino acid sequence AQLLELPY (SEQ ID NO:51), as defined according to the Contact system; or
(iii) the VLCDR1 has the amino acid sequence KNLLHSNGITY (SEQ ID NO: 147), the VLCDR2 has the amino acid sequence RVS, and the VLCDR3 has the amino acid sequence AQLLELPYT (SEQ ID NO:23), as defined according to the IMGT system.

6. The method of claim 5, wherein the antibody or antigen-binding fragment comprises a VH having at least 70% sequence identity to the amino acid sequence of SEQ ID NO:36; and a VL having at least 70% sequence identity to the amino acid sequence of SEQ ID NO:37.

7. The method of claim 1, wherein the antibody or antigen-binding fragment comprises a VH having the amino acid sequence of SEQ ID NO: 36, and a VL having the amino acid sequence of SEQ ID NO:37.

8. The method of claim 1, wherein the antibody or antigen-binding fragment binds to an extracellularly accessible epitope of HDM2; wherein the antibody or antigen-binding fragment is monoclonal; and wherein the cancer is a solid cancer or a liquid cancer; and wherein the antibody or antigen-binding fragment is administered intravenously, intraperitoneally, intramuscularly, subcutaneously, or intratumorally.

9. The method of claim 8, wherein the antibody or antigen-binding fragment is an immunoglobulin IgG.

10. The method of claim 9, wherein IgG is a human IgG1.

11. The method of claim 10, wherein the antibody or antigen-binding fragment mediates complement-dependent cytotoxicity (CDC) or antibody-dependent cell-mediated cytotoxicity (ADCC), and wherein the antibody or antigen-binding fragment is not conjugated to a cytotoxic drug.

12. The method of claim 8, wherein the antibody or antigen-binding fragment is conjugated to a cytotoxic drug.

13. The method of claim 8, wherein the antibody or antigen-binding fragment is an Fv fragment, a Fab fragment, a Fab' fragment, a F(ab') 2 fragment, or a single chain Fv (scFv).

14. The method of claim 8, wherein the cancer is a solid cancer.

15. The method of claim 14, wherein the solid cancer is a lung cancer, a cervical cancer, an endometrial cancer, an ovarian cancer, a pancreatic cancer, a melanoma, a breast cancer, a colon cancer, a bladder cancer, an astrocytic neoplasm, a glioblastoma, or a pediatric Rhabdomyosarcoma.

16. The method of claim 8, further comprising administering to the subject a cancer therapy different from said antibody or antigen-binding fragment.

17. The method of claim 16, wherein the cancer therapy is a chemotherapy.

18. The method of claim 16, wherein the cancer therapy is an immunotherapy, wherein the immunotherapy is an inhibitor of one or more inhibitory checkpoint molecules.

19. The method of claim 8, wherein the subject is a human.

20. The method of claim 8, wherein the antibody or antigen-binding fragment is purified.

\* \* \* \* \*

SEQUENCE LISTING

<160> NUMBER OF SEQ ID NOS: 148

<210> SEQ ID NO 1
<211> LENGTH: 15
<212> TYPE: PRT
<213> ORGANISM: Artificial Sequence
<220> FEATURE:
<223> OTHER INFORMATION: NMC-P1

<400> SEQUENCE: 1

Met Cys Asn Thr Asn Met Ser Val Pro Thr Asp Gly Ala Val Thr
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: NMC-P2

<400> SEQUENCE: 2

Thr Thr Ser Gln Ile Pro Ala Ser Glu Gln Glu
1               5                   10

<210> SEQ ID NO 3
<211> LENGTH: 17
<212> TYPE: PRT
<213> ORGANISM: Artificial Sequence
<220> FEATURE:
<223> OTHER INFORMATION: NMC-P3

<400> SEQUENCE: 3

Cys Pro Val Cys Arg Gln Pro Ile Gln Met Ile Val Leu Thr Tyr Phe
1               5                   10                  15

Pro

<210> SEQ ID NO 4
<211> LENGTH: 491
<212> TYPE: PRT
<213> ORGANISM: Homo sapiens

<400> SEQUENCE: 4

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
        355                 360                 365

```
Asp Ser Arg Glu Ser Cys Val Glu Glu Asn Asp Asp Lys Ile Thr Gln
    370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
            420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 5
<211> LENGTH: 489
<212> TYPE: PRT
<213> ORGANISM: Mouse

<400> SEQUENCE: 5

Met Cys Asn Thr Asn Met Ser Val Ser Thr Glu Gly Ala Ala Ser Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Asn Asp Thr Tyr
        35                  40                  45

Thr Met Lys Glu Ile Ile Phe Tyr Ile Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Val Phe Gly Val Pro Ser Phe Ser Val Lys Glu His
                85                  90                  95

Arg Lys Ile Tyr Ala Met Ile Tyr Arg Asn Leu Val Ala Val Ser Gln
            100                 105                 110

Gln Asp Ser Gly Thr Ser Leu Ser Glu Ser Arg Arg Gln Pro Glu Gly
        115                 120                 125

Gly Ser Asp Leu Lys Asp Pro Leu Gln Ala Pro Pro Glu Glu Lys Pro
    130                 135                 140

Ser Ser Ser Asp Leu Ile Ser Arg Leu Ser Thr Ser Ser Arg Arg Arg
145                 150                 155                 160

Ser Ile Ser Glu Thr Glu Glu Asn Thr Asp Glu Leu Pro Gly Glu Arg
                165                 170                 175

His Arg Lys Arg Arg Arg Ser Leu Ser Phe Asp Pro Ser Leu Gly Leu
            180                 185                 190

Cys Glu Leu Arg Glu Met Cys Ser Gly Gly Ser Ser Ser Ser Ser Ser
        195                 200                 205

Ser Ser Ser Glu Ser Thr Glu Thr Pro Ser His Gln Asp Leu Asp Asp
    210                 215                 220

Gly Val Ser Glu His Ser Gly Asp Cys Leu Asp Gln Asp Ser Val Ser
225                 230                 235                 240

Asp Gln Phe Ser Val Glu Phe Glu Val Glu Ser Leu Asp Ser Glu Asp
                245                 250                 255
```

```
Tyr Ser Leu Ser Asp Glu Gly His Glu Leu Ser Asp Glu Asp Asp Glu
            260                 265                 270

Val Tyr Arg Val Thr Val Tyr Gln Thr Gly Glu Ser Asp Thr Asp Ser
            275                 280                 285

Phe Glu Gly Asp Pro Glu Ile Ser Leu Ala Asp Tyr Trp Lys Cys Thr
            290                 295                 300

Ser Cys Asn Glu Met Asn Pro Pro Leu Pro Ser His Cys Lys Arg Cys
305                 310                 315                 320

Trp Thr Leu Arg Glu Asn Trp Leu Pro Asp Asp Lys Gly Lys Asp Lys
                325                 330                 335

Val Glu Ile Ser Glu Lys Ala Lys Leu Glu Asn Ser Ala Gln Ala Glu
            340                 345                 350

Glu Gly Leu Asp Val Pro Asp Gly Lys Lys Leu Thr Glu Asn Asp Ala
            355                 360                 365

Lys Glu Pro Cys Ala Glu Glu Asp Ser Glu Glu Lys Ala Glu Gln Thr
            370                 375                 380

Pro Leu Ser Gln Glu Ser Asp Asp Tyr Ser Gln Pro Ser Thr Ser Ser
385                 390                 395                 400

Ser Ile Val Tyr Ser Ser Gln Glu Ser Val Lys Glu Leu Lys Glu Glu
            405                 410                 415

Thr Gln Asp Lys Asp Glu Ser Val Glu Ser Ser Phe Ser Leu Asn Ala
            420                 425                 430

Ile Glu Pro Cys Val Ile Cys Gln Gly Arg Pro Lys Asn Gly Cys Ile
            435                 440                 445

Val His Gly Lys Thr Gly His Leu Met Ser Cys Phe Thr Cys Ala Lys
            450                 455                 460

Lys Leu Lys Lys Arg Asn Lys Pro Cys Pro Val Cys Arg Gln Pro Ile
465                 470                 475                 480

Gln Met Ile Val Leu Thr Tyr Phe Asn
                485

<210> SEQ ID NO 6
<211> LENGTH: 490
<212> TYPE: PRT
<213> ORGANISM: Homo sapiens

<400> SEQUENCE: 6

Met Thr Ser Phe Ser Thr Ser Ala Gln Cys Ser Thr Ser Asp Ser Ala
1               5                   10                  15

Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Met His Tyr Leu Gly Gln Tyr Ile Met Val Lys Gln
    50                  55                  60

Leu Tyr Asp Gln Gln Glu Gln His Met Val Tyr Cys Gly Gly Asp Leu
65                  70                  75                  80

Leu Gly Glu Leu Leu Gly Arg Gln Ser Phe Ser Val Lys Asp Pro Ser
            85                  90                  95

Pro Leu Tyr Asp Met Leu Arg Lys Asn Leu Val Thr Leu Ala Thr Ala
            100                 105                 110

Thr Thr Asp Ala Ala Gln Thr Leu Ala Leu Ala Gln Asp His Ser Met
        115                 120                 125

Asp Ile Pro Ser Gln Asp Gln Leu Lys Gln Ser Ala Glu Glu Ser Ser
```

-continued

```
            130                 135                 140
Thr Ser Arg Lys Arg Thr Thr Glu Asp Asp Ile Pro Thr Leu Pro Thr
145                 150                 155                 160

Ser Glu His Lys Cys Ile His Ser Arg Glu Asp Asp Leu Ile Glu
                165                 170                 175

Asn Leu Ala Gln Asp Glu Thr Ser Arg Leu Asp Leu Gly Phe Glu Glu
                180                 185                 190

Trp Asp Val Ala Gly Leu Pro Trp Trp Phe Leu Gly Asn Leu Arg Ser
            195                 200                 205

Asn Tyr Thr Pro Arg Ser Asn Gly Ser Thr Asp Leu Gln Thr Asn Gln
            210                 215                 220

Asp Val Gly Thr Ala Ile Val Ser Asp Thr Thr Asp Asp Leu Trp Phe
225                 230                 235                 240

Leu Asn Glu Ser Val Ser Glu Gln Leu Gly Val Gly Ile Lys Val Glu
                245                 250                 255

Ala Ala Asp Thr Glu Gln Thr Ser Glu Glu Val Gly Lys Val Ser Asp
                260                 265                 270

Lys Lys Val Ile Glu Val Gly Lys Asn Asp Asp Leu Glu Asp Ser Lys
            275                 280                 285

Ser Leu Ser Asp Asp Thr Asp Val Glu Val Thr Ser Glu Asp Glu Trp
            290                 295                 300

Gln Cys Thr Glu Cys Lys Lys Phe Asn Ser Pro Ser Lys Arg Tyr Cys
305                 310                 315                 320

Phe Arg Cys Trp Ala Leu Arg Lys Asp Trp Tyr Ser Asp Cys Ser Lys
                325                 330                 335

Leu Thr His Ser Leu Ser Thr Ser Asp Ile Thr Ala Ile Pro Glu Lys
                340                 345                 350

Glu Asn Glu Gly Asn Asp Val Pro Asp Cys Arg Arg Thr Ile Ser Ala
            355                 360                 365

Pro Val Val Arg Pro Lys Asp Ala Tyr Ile Lys Lys Glu Asn Ser Lys
            370                 375                 380

Leu Phe Asp Pro Cys Asn Ser Val Glu Phe Leu Asp Leu Ala His Ser
385                 390                 395                 400

Ser Glu Ser Gln Glu Thr Ile Ser Ser Met Gly Glu Gln Leu Asp Asn
                405                 410                 415

Leu Ser Glu Gln Arg Thr Asp Thr Glu Asn Met Glu Asp Cys Gln Asn
                420                 425                 430

Leu Leu Lys Pro Cys Ser Leu Cys Glu Lys Arg Pro Arg Asp Gly Asn
            435                 440                 445

Ile Ile His Gly Arg Thr Gly His Leu Val Thr Cys Phe His Cys Ala
            450                 455                 460

Arg Arg Leu Lys Lys Ala Gly Ala Ser Cys Pro Ile Cys Lys Lys Glu
465                 470                 475                 480

Ile Gln Leu Val Ile Lys Val Phe Ile Ala
                485                 490

<210> SEQ ID NO 7
<211> LENGTH: 127
<212> TYPE: PRT
<213> ORGANISM: Mouse

<400> SEQUENCE: 7

Met Thr Ser His Ser Thr Ser Ala Gln Cys Ser Ala Ser Asp Ser Ala
1               5                   10                  15
```

```
Cys Arg Ile Ser Ser Glu Gln Ile Ser Gln Val Arg Pro Lys Leu Gln
                20                  25                  30

Leu Leu Lys Ile Leu His Ala Ala Gly Ala Gln Gly Glu Val Phe Thr
            35                  40                  45

Met Lys Glu Val Met His Tyr Leu Gly Gln Tyr Ile Met Val Lys Gln
 50                  55                  60

Leu Tyr Asp Gln Gln Glu Gln His Met Val Tyr Cys Gly Gly Asp Leu
 65                  70                  75                  80

Leu Gly Asp Leu Leu Gly Cys Gln Ser Phe Ser Val Lys Asp Pro Ser
                85                  90                  95

Pro Leu Tyr Asp Met Leu Arg Lys Asn Leu Val Thr Ser Ala Ser Ile
            100                 105                 110

Asn Thr Ala Arg Cys Asn Arg Ile Leu Gln Ser Gln Lys Lys Asn
        115                 120                 125

<210> SEQ ID NO 8
<211> LENGTH: 296
<212> TYPE: PRT
<213> ORGANISM: Artificial Sequence
<220> FEATURE:
<223> OTHER INFORMATION: HDM2 variant MDM2-A

<400> SEQUENCE: 8

Met Cys Asn Thr Asn Met Ser Val Pro Thr Asp Gly Ala Val Thr Thr
 1               5                  10                  15

Ser Gln Ile Pro Ala Ser Glu Gln Glu Thr Leu Asp Leu Asp Ala Gly
                20                  25                  30

Val Ser Glu His Ser Gly Asp Trp Leu Asp Gln Asp Ser Val Ser Asp
            35                  40                  45

Gln Phe Ser Val Glu Phe Glu Val Glu Ser Leu Asp Ser Glu Asp Tyr
 50                  55                  60

Ser Leu Ser Glu Glu Gly Gln Glu Leu Ser Asp Glu Asp Asp Glu Val
 65                  70                  75                  80

Tyr Gln Val Thr Val Tyr Gln Ala Gly Glu Ser Asp Thr Asp Ser Phe
                85                  90                  95

Glu Glu Asp Pro Glu Ile Ser Leu Ala Asp Tyr Trp Lys Cys Thr Ser
            100                 105                 110

Cys Asn Glu Met Asn Pro Pro Leu Pro Ser His Cys Asn Arg Cys Trp
        115                 120                 125

Ala Leu Arg Glu Asn Trp Leu Pro Glu Asp Lys Gly Lys Asp Lys Gly
130                 135                 140

Glu Ile Ser Glu Lys Ala Lys Leu Glu Asn Ser Thr Gln Ala Glu Glu
145                 150                 155                 160

Gly Phe Asp Val Pro Asp Cys Lys Lys Thr Ile Val Asn Asp Ser Arg
                165                 170                 175

Glu Ser Cys Val Glu Glu Asn Asp Asp Lys Ile Thr Gln Ala Ser Gln
            180                 185                 190

Ser Gln Glu Ser Glu Asp Tyr Ser Gln Pro Ser Thr Ser Ser Ser Ile
        195                 200                 205

Ile Tyr Ser Ser Gln Glu Asp Val Lys Glu Phe Glu Arg Glu Glu Thr
    210                 215                 220

Gln Asp Lys Glu Glu Ser Val Glu Ser Ser Leu Pro Leu Asn Ala Ile
225                 230                 235                 240

Glu Pro Cys Val Ile Cys Gln Gly Arg Pro Lys Asn Gly Cys Ile Val
                245                 250                 255
```

```
His Gly Lys Thr Gly His Leu Met Ala Cys Phe Thr Cys Ala Lys Lys
            260                 265                 270

Leu Lys Lys Arg Asn Lys Pro Cys Pro Val Cys Arg Gln Pro Ile Gln
        275                 280                 285

Met Ile Val Leu Thr Tyr Phe Pro
    290                 295

<210> SEQ ID NO 9
<211> LENGTH: 270
<212> TYPE: PRT
<213> ORGANISM: Artificial Sequence
<220> FEATURE:
<223> OTHER INFORMATION: HDM2 variant MDM2-A1

<400> SEQUENCE: 9

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Asp Leu Asp Ala Gly
            20                  25                  30

Val Ser Glu His Ser Gly Asp Trp Leu Asp Gln Asp Ser Val Ser Asp
        35                  40                  45

Gln Phe Ser Val Glu Phe Glu Val Glu Ser Leu Asp Ser Glu Asp Tyr
    50                  55                  60

Ser Leu Ser Glu Glu Gly Gln Glu Leu Ser Asp Glu Asp Asp Glu Asp
65                  70                  75                  80

Tyr Trp Lys Cys Thr Ser Cys Asn Glu Met Asn Pro Pro Leu Pro Ser
                85                  90                  95

His Cys Asn Arg Cys Trp Ala Leu Arg Glu Asn Trp Leu Pro Glu Asp
            100                 105                 110

Lys Gly Lys Asp Lys Gly Glu Ile Ser Glu Lys Ala Lys Leu Glu Asn
        115                 120                 125

Ser Thr Gln Ala Glu Glu Gly Phe Asp Val Pro Asp Cys Lys Lys Thr
    130                 135                 140

Ile Val Asn Asp Ser Arg Glu Ser Cys Val Glu Glu Asn Asp Asp Lys
145                 150                 155                 160

Ile Thr Gln Ala Ser Gln Ser Gln Glu Ser Glu Asp Tyr Ser Gln Pro
                165                 170                 175

Ser Thr Ser Ser Ser Ile Ile Tyr Ser Ser Gln Glu Asp Val Lys Glu
            180                 185                 190

Phe Glu Arg Glu Glu Thr Gln Asp Lys Glu Glu Ser Val Glu Ser Ser
        195                 200                 205

Leu Pro Leu Asn Ala Ile Glu Pro Cys Val Ile Cys Gln Gly Arg Pro
    210                 215                 220

Lys Asn Gly Cys Ile Val His Gly Lys Thr Gly His Leu Met Ala Cys
225                 230                 235                 240

Phe Thr Cys Ala Lys Lys Leu Lys Lys Arg Asn Lys Pro Cys Pro Val
                245                 250                 255

Cys Arg Gln Pro Ile Gln Met Ile Val Leu Thr Tyr Phe Pro
            260                 265                 270

<210> SEQ ID NO 10
<211> LENGTH: 218
<212> TYPE: PRT
<213> ORGANISM: Artificial Sequence
<220> FEATURE:
<223> OTHER INFORMATION: HDM2 variant MDM2-B

<400> SEQUENCE: 10
```

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Asp Tyr Trp Lys Cys
            20                  25                  30

Thr Ser Cys Asn Glu Met Asn Pro Pro Leu Pro Ser His Cys Asn Arg
        35                  40                  45

Cys Trp Ala Leu Arg Glu Asn Trp Leu Pro Glu Asp Lys Gly Lys Asp
    50                  55                  60

Lys Gly Glu Ile Ser Glu Lys Ala Lys Leu Glu Asn Ser Thr Gln Ala
65                  70                  75                  80

Glu Glu Gly Phe Asp Val Pro Asp Cys Lys Lys Thr Ile Val Asn Asp
                85                  90                  95

Ser Arg Glu Ser Cys Val Glu Glu Asn Asp Asp Lys Ile Thr Gln Ala
            100                 105                 110

Ser Gln Ser Gln Glu Ser Glu Asp Tyr Ser Gln Pro Ser Thr Ser Ser
        115                 120                 125

Ser Ile Ile Tyr Ser Ser Gln Glu Asp Val Lys Glu Phe Glu Arg Glu
    130                 135                 140

Glu Thr Gln Asp Lys Glu Glu Ser Val Glu Ser Ser Leu Pro Leu Asn
145                 150                 155                 160

Ala Ile Glu Pro Cys Val Ile Cys Gln Gly Arg Pro Lys Asn Gly Cys
                165                 170                 175

Ile Val His Gly Lys Thr Gly His Leu Met Ala Cys Phe Thr Cys Ala
            180                 185                 190

Lys Lys Leu Lys Lys Arg Asn Lys Pro Cys Pro Val Cys Arg Gln Pro
        195                 200                 205

Ile Gln Met Ile Val Leu Thr Tyr Phe Pro
    210                 215

<210> SEQ ID NO 11
<211> LENGTH: 321
<212> TYPE: PRT
<213> ORGANISM: Artificial Sequence
<220> FEATURE:
<223> OTHER INFORMATION: HDM2 variant MDM2-C

<400> SEQUENCE: 11

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Asp Leu Asp Ala Gly Val Ser Glu His Ser Gly Asp
    50                  55                  60

Trp Leu Asp Gln Asp Ser Val Ser Asp Gln Phe Ser Val Glu Phe Glu
65                  70                  75                  80

Val Glu Ser Leu Asp Ser Glu Asp Tyr Ser Leu Ser Glu Glu Gly Gln
                85                  90                  95

Glu Leu Ser Asp Glu Asp Asp Glu Val Tyr Gln Val Thr Val Tyr Gln
            100                 105                 110

Ala Gly Glu Ser Asp Thr Asp Ser Phe Glu Glu Asp Pro Glu Ile Ser
        115                 120                 125

Leu Ala Asp Tyr Trp Lys Cys Thr Ser Cys Asn Glu Met Asn Pro Pro
    130                 135                 140
```

-continued

```
Leu Pro Ser His Cys Asn Arg Cys Trp Ala Leu Arg Glu Asn Trp Leu
145                 150                 155                 160

Pro Glu Asp Lys Gly Lys Asp Lys Gly Glu Ile Ser Glu Lys Ala Lys
                165                 170                 175

Leu Glu Asn Ser Thr Gln Ala Glu Glu Gly Phe Asp Val Pro Asp Cys
            180                 185                 190

Lys Lys Thr Ile Val Asn Asp Ser Arg Glu Ser Cys Val Glu Glu Asn
        195                 200                 205

Asp Asp Lys Ile Thr Gln Ala Ser Gln Ser Gln Glu Ser Glu Asp Tyr
    210                 215                 220

Ser Gln Pro Ser Thr Ser Ser Ser Ile Ile Tyr Ser Ser Gln Glu Asp
225                 230                 235                 240

Val Lys Glu Phe Glu Arg Glu Glu Thr Gln Asp Lys Glu Glu Ser Val
                245                 250                 255

Glu Ser Ser Leu Pro Leu Asn Ala Ile Glu Pro Cys Val Ile Cys Gln
                260                 265                 270

Gly Arg Pro Lys Asn Gly Cys Ile Val His Gly Lys Thr Gly His Leu
            275                 280                 285

Met Ala Cys Phe Thr Cys Ala Lys Lys Leu Lys Lys Arg Asn Lys Pro
        290                 295                 300

Cys Pro Val Cys Arg Gln Pro Ile Gln Met Ile Val Leu Thr Tyr Phe
305                 310                 315                 320

Pro

<210> SEQ ID NO 12
<211> LENGTH: 132
<212> TYPE: PRT
<213> ORGANISM: Artificial Sequence
<220> FEATURE:
<223> OTHER INFORMATION: HDM2 variant MDM2-D

<400> SEQUENCE: 12

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Gln Glu Ser
            20                  25                  30

Glu Asp Tyr Ser Gln Pro Ser Thr Ser Ser Ser Ile Ile Tyr Ser Ser
        35                  40                  45

Gln Glu Asp Val Lys Glu Phe Glu Arg Glu Glu Thr Gln Asp Lys Glu
    50                  55                  60

Glu Ser Val Glu Ser Ser Leu Pro Leu Asn Ala Ile Glu Pro Cys Val
65                  70                  75                  80

Ile Cys Gln Gly Arg Pro Lys Asn Gly Cys Ile Val His Gly Lys Thr
                85                  90                  95

Gly His Leu Met Ala Cys Phe Thr Cys Ala Lys Lys Leu Lys Lys Arg
            100                 105                 110

Asn Lys Pro Cys Pro Val Cys Arg Gln Pro Ile Gln Met Ile Val Leu
        115                 120                 125

Thr Tyr Phe Pro
    130

<210> SEQ ID NO 13
<211> LENGTH: 102
<212> TYPE: PRT
<213> ORGANISM: Artificial Sequence
<220> FEATURE:
```

<223> OTHER INFORMATION: HDM2 variant MDM2-E

<400> SEQUENCE: 13

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
            35                  40                  45

Thr Met Lys Glu Val Leu Phe Tyr Leu Gly Gln Tyr Ile Met Thr Lys
        50                  55                  60

Arg Leu Tyr Asp Glu Lys Gln Gln His Ile Val Asn Asp Cys Ala Asn
65                  70                  75                  80

Leu Phe Pro Leu Val Asp Leu Ser Ile Arg Glu Leu Tyr Ile Ser Asn
                85                  90                  95

Tyr Ile Thr Leu Gly Ile
            100
```

<210> SEQ ID NO 14
<211> LENGTH: 446
<212> TYPE: PRT
<213> ORGANISM: Artificial Sequence
<220> FEATURE:
<223> OTHER INFORMATION: HDM2 variant MDM2-F

<400> SEQUENCE: 14

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
            35                  40                  45

Thr Met Lys Glu Lys Ile Tyr Thr Met Ile Tyr Arg Asn Leu Val Val
        50                  55                  60

Val Asn Gln Gln Glu Ser Ser Asp Ser Gly Thr Ser Val Ser Glu Asn
65                  70                  75                  80

Arg Cys His Leu Glu Gly Gly Ser Asp Gln Lys Asp Leu Val Gln Glu
                85                  90                  95

Leu Gln Glu Glu Lys Pro Ser Ser His Leu Val Ser Arg Pro Ser
            100                 105                 110

Thr Ser Ser Arg Arg Arg Ala Ile Ser Glu Thr Glu Glu Asn Ser Asp
            115                 120                 125

Glu Leu Ser Gly Glu Arg Gln Arg Lys Arg His Lys Ser Asp Ser Ile
130                 135                 140

Ser Leu Ser Phe Asp Glu Ser Leu Ala Leu Cys Val Ile Arg Glu Ile
145                 150                 155                 160

Cys Cys Glu Arg Ser Ser Ser Glu Ser Thr Gly Thr Pro Ser Asn
                165                 170                 175

Pro Asp Leu Asp Ala Gly Val Ser Glu His Ser Gly Asp Trp Leu Asp
            180                 185                 190

Gln Asp Ser Val Ser Asp Gln Phe Ser Val Glu Phe Glu Val Glu Ser
            195                 200                 205

Leu Asp Ser Glu Asp Tyr Ser Leu Ser Glu Glu Gly Gln Glu Leu Ser
        210                 215                 220

Asp Glu Asp Asp Glu Val Tyr Gln Val Thr Val Tyr Gln Ala Gly Glu
225                 230                 235                 240
```

-continued

```
Ser Asp Thr Asp Ser Phe Glu Glu Asp Pro Glu Ile Ser Leu Ala Asp
                245                 250                 255

Tyr Trp Lys Cys Thr Ser Cys Asn Glu Met Asn Pro Leu Pro Ser
        260                 265                 270

His Cys Asn Arg Cys Trp Ala Leu Arg Glu Asn Trp Leu Pro Glu Asp
            275                 280                 285

Lys Gly Lys Asp Lys Gly Glu Ile Ser Glu Lys Ala Lys Leu Glu Asn
    290                 295                 300

Ser Thr Gln Ala Glu Glu Gly Phe Asp Val Pro Asp Cys Lys Lys Thr
305                 310                 315                 320

Ile Val Asn Asp Ser Arg Glu Ser Cys Val Glu Glu Asn Asp Asp Lys
                325                 330                 335

Ile Thr Gln Ala Ser Gln Ser Gln Glu Ser Glu Asp Tyr Ser Gln Pro
            340                 345                 350

Ser Thr Ser Ser Ser Ile Ile Tyr Ser Ser Gln Glu Asp Val Lys Glu
    355                 360                 365

Phe Glu Arg Glu Glu Thr Gln Asp Lys Glu Glu Ser Val Glu Ser Ser
            370                 375                 380

Leu Pro Leu Asn Ala Ile Glu Pro Cys Val Ile Cys Gln Gly Arg Pro
385                 390                 395                 400

Lys Asn Gly Cys Ile Val His Gly Lys Thr Gly His Leu Met Ala Cys
                405                 410                 415

Phe Thr Cys Ala Lys Lys Leu Lys Lys Arg Asn Lys Pro Cys Pro Val
            420                 425                 430

Cys Arg Gln Pro Ile Gln Met Ile Val Leu Thr Tyr Phe Pro
    435                 440                 445

<210> SEQ ID NO 15
<211> LENGTH: 436
<212> TYPE: PRT
<213> ORGANISM: Artificial Sequence
<220> FEATURE:
<223> OTHER INFORMATION: HDM2 variant MDM2-G

<400> SEQUENCE: 15

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Glu Asn Ser Asp Glu Leu Ser Gly Glu Arg Gln Arg Lys Arg
        115                 120                 125

His Lys Ser Asp Ser Ile Ser Leu Ser Phe Asp Glu Ser Leu Ala Leu
    130                 135                 140

Cys Val Ile Arg Glu Ile Cys Cys Glu Arg Ser Ser Ser Ser Glu Ser
145                 150                 155                 160
```

```
Thr Gly Thr Pro Ser Asn Pro Asp Leu Asp Ala Gly Val Ser Glu His
            165                 170                 175

Ser Gly Asp Trp Leu Asp Gln Asp Ser Val Ser Asp Gln Phe Ser Val
        180                 185                 190

Glu Phe Glu Val Glu Ser Leu Asp Ser Glu Asp Tyr Ser Leu Ser Glu
    195                 200                 205

Glu Gly Gln Glu Leu Ser Asp Glu Asp Asp Glu Val Tyr Gln Val Thr
210                 215                 220

Val Tyr Gln Ala Gly Glu Ser Asp Thr Asp Ser Phe Glu Glu Asp Pro
225                 230                 235                 240

Glu Ile Ser Leu Ala Asp Tyr Trp Lys Cys Thr Ser Cys Asn Glu Met
                245                 250                 255

Asn Pro Pro Leu Pro Ser His Cys Asn Arg Cys Trp Ala Leu Arg Glu
            260                 265                 270

Asn Trp Leu Pro Glu Asp Lys Gly Lys Asp Lys Gly Glu Ile Ser Glu
        275                 280                 285

Lys Ala Lys Leu Glu Asn Ser Thr Gln Ala Glu Glu Gly Phe Asp Val
    290                 295                 300

Pro Asp Cys Lys Lys Thr Ile Val Asn Asp Ser Arg Glu Ser Cys Val
305                 310                 315                 320

Glu Glu Asn Asp Asp Lys Ile Thr Gln Ala Ser Gln Ser Gln Glu Ser
                325                 330                 335

Glu Asp Tyr Ser Gln Pro Ser Thr Ser Ser Ser Ile Ile Tyr Ser Ser
            340                 345                 350

Gln Glu Asp Val Lys Glu Phe Glu Arg Glu Glu Thr Gln Asp Lys Glu
        355                 360                 365

Glu Ser Val Glu Ser Ser Leu Pro Leu Asn Ala Ile Glu Pro Cys Val
    370                 375                 380

Ile Cys Gln Gly Arg Pro Lys Asn Gly Cys Ile Val His Gly Lys Thr
385                 390                 395                 400

Gly His Leu Met Ala Cys Phe Thr Cys Ala Lys Lys Leu Lys Lys Arg
                405                 410                 415

Asn Lys Pro Cys Pro Val Cys Arg Gln Pro Ile Gln Met Ile Val Leu
            420                 425                 430

Thr Tyr Phe Pro
        435

<210> SEQ ID NO 16
<211> LENGTH: 497
<212> TYPE: PRT
<213> ORGANISM: Artificial Sequence
<220> FEATURE:
<223> OTHER INFORMATION: HDM2 variant MDM2-11

<400> SEQUENCE: 16

Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80
```

```
Val Tyr Cys Ser Asn Asp Leu Leu Gly Asp Leu Phe Gly Val Pro Ser
            85                  90                  95

Phe Ser Val Lys Glu His Arg Lys Ile Tyr Thr Met Ile Tyr Arg Asn
           100                 105                 110

Leu Val Val Val Asn Gln Gln Glu Ser Ser Asp Ser Gly Thr Ser Val
           115                 120                 125

Ser Glu Asn Arg Cys His Leu Glu Gly Gly Ser Asp Gln Lys Asp Leu
           130                 135                 140

Val Gln Glu Leu Gln Glu Glu Lys Pro Ser Ser Ser His Leu Val Ser
145                 150                 155                 160

Arg Pro Ser Thr Ser Arg Arg Ala Ile Ser Glu Thr Glu Glu
                165                 170                 175

Asn Ser Asp Glu Leu Ser Gly Glu Arg Gln Arg Lys Arg His Lys Ser
               180                 185                 190

Asp Ser Ile Ser Leu Ser Phe Asp Glu Ser Leu Ala Leu Cys Val Ile
               195                 200                 205

Arg Glu Ile Cys Cys Glu Arg Ser Ser Ser Glu Ser Thr Gly Thr
               210                 215                 220

Pro Ser Asn Pro Asp Leu Asp Ala Gly Val Ser Glu His Ser Gly Asp
225                 230                 235                 240

Trp Leu Asp Gln Asp Ser Val Ser Asp Gln Phe Ser Val Glu Phe Glu
                245                 250                 255

Val Glu Ser Leu Asp Ser Glu Asp Tyr Ser Leu Ser Glu Glu Gly Gln
                260                 265                 270

Glu Leu Ser Asp Glu Asp Asp Glu Val Tyr Gln Val Thr Val Tyr Gln
            275                 280                 285

Ala Gly Glu Ser Asp Thr Asp Ser Phe Glu Glu Asp Pro Glu Ile Ser
290                 295                 300

Leu Ala Asp Tyr Trp Lys Cys Thr Ser Cys Asn Glu Met Asn Pro Pro
305                 310                 315                 320

Leu Pro Ser His Cys Asn Arg Cys Trp Ala Leu Arg Glu Asn Trp Leu
                325                 330                 335

Pro Glu Asp Lys Gly Lys Asp Lys Gly Glu Ile Ser Glu Lys Ala Lys
                340                 345                 350

Leu Glu Asn Ser Thr Gln Ala Glu Glu Gly Phe Asp Val Pro Asp Cys
                355                 360                 365

Lys Lys Thr Ile Val Asn Asp Ser Arg Glu Ser Cys Val Glu Glu Asn
370                 375                 380

Asp Asp Lys Ile Thr Gln Ala Ser Gln Ser Gln Ser Glu Ser Glu Asp Tyr
385                 390                 395                 400

Ser Gln Pro Ser Thr Ser Ser Ile Ile Tyr Ser Ser Gln Glu Asp
                405                 410                 415

Val Lys Glu Phe Glu Arg Glu Thr Gln Asp Lys Glu Glu Ser Val
                420                 425                 430

Glu Ser Ser Leu Pro Leu Asn Ala Ile Glu Pro Cys Val Ile Cys Gln
                435                 440                 445

Gly Arg Pro Lys Asn Gly Cys Ile Val His Gly Lys Thr Gly His Leu
450                 455                 460

Met Ala Cys Phe Thr Cys Ala Lys Lys Leu Lys Lys Arg Asn Lys Pro
465                 470                 475                 480

Cys Pro Val Cys Arg Gln Pro Ile Gln Met Ile Val Leu Thr Tyr Phe
                485                 490                 495
```

Pro

<210> SEQ ID NO 17
<211> LENGTH: 243
<212> TYPE: PRT
<213> ORGANISM: Artificial Sequence
<220> FEATURE:
<223> OTHER INFORMATION: HDM2 variant MDM2-KB2

<400> SEQUENCE: 17

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Asp Tyr Trp Lys Cys Thr Ser Cys Asn Glu Met Asn
    50                  55                  60

Pro Pro Leu Pro Ser His Cys Asn Arg Cys Trp Ala Leu Arg Glu Asn
65                  70                  75                  80

Trp Leu Pro Glu Asp Lys Gly Lys Asp Lys Gly Glu Ile Ser Glu Lys
                85                  90                  95

Ala Lys Leu Glu Asn Ser Thr Gln Ala Glu Glu Gly Phe Asp Val Pro
            100                 105                 110

Asp Cys Lys Lys Thr Ile Val Asn Asp Ser Arg Glu Ser Cys Val Glu
        115                 120                 125

Glu Asn Asp Asp Lys Ile Thr Gln Ala Ser Gln Ser Gln Glu Ser Glu
    130                 135                 140

Asp Tyr Ser Gln Pro Ser Thr Ser Ser Ile Ile Tyr Ser Ser Gln
145                 150                 155                 160

Glu Asp Val Lys Glu Phe Glu Arg Glu Glu Thr Gln Asp Lys Glu Glu
                165                 170                 175

Ser Val Glu Ser Ser Leu Pro Leu Asn Ala Ile Glu Pro Cys Val Ile
            180                 185                 190

Cys Gln Gly Arg Pro Lys Asn Gly Cys Ile Val His Gly Lys Thr Gly
        195                 200                 205

His Leu Met Ala Cys Phe Thr Cys Ala Lys Lys Leu Lys Lys Arg Asn
    210                 215                 220

Lys Pro Cys Pro Val Cys Arg Gln Pro Ile Gln Met Ile Val Leu Thr
225                 230                 235                 240

Tyr Phe Pro
```

<210> SEQ ID NO 18
<211> LENGTH: 7
<212> TYPE: PRT
<213> ORGANISM: Artificial Sequence
<220> FEATURE:
<223> OTHER INFORMATION: mAb NMC-103 Heavy Chain in CDR-H1 region
      (Chothia)

<400> SEQUENCE: 18

```
Gly Phe Thr Phe Thr His Tyr
1               5
```

<210> SEQ ID NO 19
<211> LENGTH: 8
<212> TYPE: PRT
<213> ORGANISM: Artificial Sequence
<220> FEATURE:

```
<223> OTHER INFORMATION: mAb NMC-103 Heavy Chain in CDR-H2 region
      (Chothia)

<400> SEQUENCE: 19

Arg Asn Lys Ala Lys Gly Tyr Thr
1               5

<210> SEQ ID NO 20
<211> LENGTH: 5
<212> TYPE: PRT
<213> ORGANISM: Artificial Sequence
<220> FEATURE:
<223> OTHER INFORMATION: mAb NMC-103 Heavy Chain in CDR-H3 region
      (Chothia)

<400> SEQUENCE: 20

Asp Ile Gly Asp Asn
1               5

<210> SEQ ID NO 21
<211> LENGTH: 16
<212> TYPE: PRT
<213> ORGANISM: Artificial Sequence
<220> FEATURE:
<223> OTHER INFORMATION: mAb NMC-103 Light Chain in CDR-L1 region
      (Chothia)

<400> SEQUENCE: 21

Arg Ser Ser Lys Asn Leu Leu His Ser Asn Gly Ile Thr Tyr Leu Tyr
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: mAb NMC-103 Light Chain in CDR-L2 region
      (Chothia)

<400> SEQUENCE: 22

Arg Val Ser Asn Leu Ala Ser
1               5

<210> SEQ ID NO 23
<211> LENGTH: 9
<212> TYPE: PRT
<213> ORGANISM: Artificial Sequence
<220> FEATURE:
<223> OTHER INFORMATION: mAb NMC-103 Light Chain in CDR-L3 region
      (Chothia)

<400> SEQUENCE: 23

Ala Gln Leu Leu Glu Leu Pro Tyr Thr
1               5

<210> SEQ ID NO 24
<211> LENGTH: 7
<212> TYPE: PRT
<213> ORGANISM: Artificial Sequence
<220> FEATURE:
<223> OTHER INFORMATION: mAb NMC-204 Heavy Chain in CDR-H1 region
      (Chothia)

<400> SEQUENCE: 24

Gly Asp Thr Leu Ser Gly Ser
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: mAb NMC-204 Heavy Chain in CDR-H2 region
      (Chothia)

<400> SEQUENCE: 25

His Leu Asn Arg Gly Thr
1               5

<210> SEQ ID NO 26
<211> LENGTH: 6
<212> TYPE: PRT
<213> ORGANISM: Artificial Sequence
<220> FEATURE:
<223> OTHER INFORMATION: mAb NMC-204 Heavy Chain in CDR-H3 region
      (Chothia)

<400> SEQUENCE: 26

Ser Pro Gly Phe Ala Tyr
1               5

<210> SEQ ID NO 27
<211> LENGTH: 16
<212> TYPE: PRT
<213> ORGANISM: Artificial Sequence
<220> FEATURE:
<223> OTHER INFORMATION: mAb NMC-204 Light Chain in CDR-L1 region
      (Chothia)

<400> SEQUENCE: 27

Arg Ser Ser Lys Ser Leu Leu His Ser Asn Gly Asn Ser Tyr Leu Tyr
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: mAb NMC-204 Light Chain in CDR-L2 region
      (Chothia)

<400> SEQUENCE: 28

Arg Met Ser Asn Leu Ala Ser
1               5

<210> SEQ ID NO 29
<211> LENGTH: 9
<212> TYPE: PRT
<213> ORGANISM: Artificial Sequence
<220> FEATURE:
<223> OTHER INFORMATION: mAb NMC-204 Light Chain in CDR-L3 region
      (Chothia)

<400> SEQUENCE: 29

Met Gln His Leu Glu Tyr Pro Phe Thr
1               5

<210> SEQ ID NO 30
<211> LENGTH: 7
<212> TYPE: PRT
<213> ORGANISM: Artificial Sequence
<220> FEATURE:
<223> OTHER INFORMATION: mAb NMC-303 Heavy Chain in CDR-H1 region
      (Chothia)

<400> SEQUENCE: 30
```

```
Gly Tyr Thr Phe Thr Ser Tyr
1               5

<210> SEQ ID NO 31
<211> LENGTH: 6
<212> TYPE: PRT
<213> ORGANISM: Artificial Sequence
<220> FEATURE:
<223> OTHER INFORMATION: mAb NMC-303 Heavy Chain in CDR-H2 region
      (Chothia)

<400> SEQUENCE: 31

Asn Pro Arg Asn Gly Gly
1               5

<210> SEQ ID NO 32
<211> LENGTH: 8
<212> TYPE: PRT
<213> ORGANISM: Artificial Sequence
<220> FEATURE:
<223> OTHER INFORMATION: mAb NMC-303 Heavy Chain in CDR-H3 region
      (Chothia)

<400> SEQUENCE: 32

Ser Gly Tyr Tyr Ala Met Asp Tyr
1               5

<210> SEQ ID NO 33
<211> LENGTH: 11
<212> TYPE: PRT
<213> ORGANISM: Artificial Sequence
<220> FEATURE:
<223> OTHER INFORMATION: mAb NMC-303 Light Chain in CDR-L1 region
      (Chothia)

<400> SEQUENCE: 33

Arg Ala Ser Gln Asp Ile Ser Asn Phe Leu Asn
1               5                   10

<210> SEQ ID NO 34
<211> LENGTH: 7
<212> TYPE: PRT
<213> ORGANISM: Artificial Sequence
<220> FEATURE:
<223> OTHER INFORMATION: mAb NMC-303 Light Chain in CDR-L2 region
      (Chothia)

<400> SEQUENCE: 34

Tyr Thr Ser Arg Leu His Ser
1               5

<210> SEQ ID NO 35
<211> LENGTH: 9
<212> TYPE: PRT
<213> ORGANISM: Artificial Sequence
<220> FEATURE:
<223> OTHER INFORMATION: mAb NMC-303 Light Chain in CDR-L3 region
      (Chothia)

<400> SEQUENCE: 35

Gln Gln Gly Asn Thr Leu Pro Arg Thr
1               5

<210> SEQ ID NO 36
<211> LENGTH: 116
<212> TYPE: PRT
<213> ORGANISM: Artificial Sequence
```

```
<220> FEATURE:
<223> OTHER INFORMATION: mAb NMC-103 Heavy Chain Variable Region

<400> SEQUENCE: 36

Glu Val Gln Leu Gln Glu Ser Gly Gly Gly Leu Val Gln Pro Gly Gly
1               5                   10                  15

Ser Leu Arg Leu Ser Cys Thr Thr Ser Gly Phe Thr Phe Thr His Tyr
            20                  25                  30

Tyr Met Ser Trp Val Arg Gln Pro Gly Lys Ala Leu Glu Trp Leu
        35                  40                  45

Gly Phe Ile Arg Asn Lys Ala Lys Gly Tyr Thr Ala Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Pro Glu Asp Ser Ala Thr Tyr
                85                  90                  95

Tyr Cys Ala Arg Asp Ile Gly Asp Asn Trp Gly Gln Gly Thr Leu Val
            100                 105                 110

Thr Val Ser Ser
        115

<210> SEQ ID NO 37
<211> LENGTH: 112
<212> TYPE: PRT
<213> ORGANISM: Artificial Sequence
<220> FEATURE:
<223> OTHER INFORMATION: mAb NMC-103 Light Chain Variable Region

<400> SEQUENCE: 37

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Asn Leu Leu His Ser
            20                  25                  30

Asn Gly Ile Thr Tyr Leu Tyr Trp Tyr Leu Gln Arg Pro Gly Gln Ser
        35                  40                  45

Pro Gln Leu Leu Ile Ser Arg Val Ser Asn Leu Ala Ser Gly Val Pro
    50                  55                  60

Asn Arg Phe Ser Gly Ser Glu Ser Gly Thr Asp Phe Thr Leu Arg Ile
65                  70                  75                  80

Ser Arg Val Glu Ala Glu Asp Val Gly Val Tyr Phe Cys Ala Gln Leu
                85                  90                  95

Leu Glu Leu Pro Tyr Thr Phe Gly Gly Gly Thr Lys Leu Glu Ile Lys
            100                 105                 110

<210> SEQ ID NO 38
<211> LENGTH: 115
<212> TYPE: PRT
<213> ORGANISM: Artificial Sequence
<220> FEATURE:
<223> OTHER INFORMATION: mAb NMC-204 Heavy Chain Variable Region

<400> SEQUENCE: 38

Glu Val Gln Leu Gln Glu Ser Gly Ser Val Leu Val Arg Pro Gly Ala
1               5                   10                  15

Ser Val Lys Leu Ser Cys Lys Ala Ser Gly Asp Thr Leu Ser Gly Ser
            20                  25                  30

Trp Met His Trp Ala Met Gln Arg Pro Gly Gln Gly Leu Glu Trp Ile
        35                  40                  45
```

```
Gly Glu Ile His Leu Asn Arg Gly Thr Thr Asn Tyr Asn Glu Lys Phe
    50                  55                  60

Lys Gly Lys Ala Thr Val Thr Val Asp Thr Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Ser Pro Gly Phe Ala Tyr Trp Gly Gln Gly Thr Leu Val Thr
                100                 105                 110

Val Ser Ala
        115
```

<210> SEQ ID NO 39
<211> LENGTH: 112
<212> TYPE: PRT
<213> ORGANISM: Artificial Sequence
<220> FEATURE:
<223> OTHER INFORMATION: mAb NMC-204 Light Chain Variable Region

<400> SEQUENCE: 39

```
Gly Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Ser Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Thr Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
                100                 105                 110
```

<210> SEQ ID NO 40
<211> LENGTH: 117
<212> TYPE: PRT
<213> ORGANISM: Artificial Sequence
<220> FEATURE:
<223> OTHER INFORMATION: mAb NMC-303 Heavy Chain Variable Region

<400> SEQUENCE: 40

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Met Tyr Trp Val Lys Gln Arg Pro Gly Gln Gly Leu Glu Trp Ile
            35                  40                  45

Gly Gly Ile Asn Pro Arg Asn Gly Gly Thr Asn Phe Asn Glu Lys Phe
    50                  55                  60

Lys Asn Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Thr Arg Ser Gly Tyr Tyr Ala Met Asp Tyr Trp Gly Gln Gly Thr Ser
                100                 105                 110

Val Thr Val Ser Ser
            115
```

<210> SEQ ID NO 41
<211> LENGTH: 107
<212> TYPE: PRT
<213> ORGANISM: Artificial Sequence
<220> FEATURE:
<223> OTHER INFORMATION: mAb NMC-303 Light Chain Variable Region

<400> SEQUENCE: 41

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105

<210> SEQ ID NO 42
<211> LENGTH: 10
<212> TYPE: PRT
<213> ORGANISM: Artificial Sequence
<220> FEATURE:
<223> OTHER INFORMATION: mAb NMC-103 Heavy Chain in CDR-H1 region (AbM)

<400> SEQUENCE: 42

Gly Phe Thr Phe Thr His Tyr Tyr Met Ser
1               5                   10

<210> SEQ ID NO 43
<211> LENGTH: 5
<212> TYPE: PRT
<213> ORGANISM: Artificial Sequence
<220> FEATURE:
<223> OTHER INFORMATION: mAb NMC-103 Heavy Chain in CDR-H1 region
      (Kabat)

<400> SEQUENCE: 43

His Tyr Tyr Met Ser
1               5

<210> SEQ ID NO 44
<211> LENGTH: 6
<212> TYPE: PRT
<213> ORGANISM: Artificial Sequence
<220> FEATURE:
<223> OTHER INFORMATION: mAb NMC-103 Heavy Chain in CDR-H1 region
      (Contact)

<400> SEQUENCE: 44

Thr His Tyr Tyr Met Ser
1               5

<210> SEQ ID NO 45
<211> LENGTH: 12
<212> TYPE: PRT
<213> ORGANISM: Artificial Sequence
<220> FEATURE:

<223> OTHER INFORMATION: mAb NMC-103 Heavy Chain in CDR-H2 region (AbM)

<400> SEQUENCE: 45

Phe Ile Arg Asn Lys Ala Lys Gly Tyr Thr Ala Glu
1               5                   10

<210> SEQ ID NO 46
<211> LENGTH: 19
<212> TYPE: PRT
<213> ORGANISM: Artificial Sequence
<220> FEATURE:
<223> OTHER INFORMATION: mAb NMC-103 Heavy Chain in CDR-H2 region
      (Kabat)

<400> SEQUENCE: 46

Phe Ile Arg Asn Lys Ala Lys Gly Tyr Thr Ala Glu Tyr Ser Ala Ser
1               5                   10                  15

Val Lys Gly

<210> SEQ ID NO 47
<211> LENGTH: 15
<212> TYPE: PRT
<213> ORGANISM: Artificial Sequence
<220> FEATURE:
<223> OTHER INFORMATION: mAb NMC-103 Heavy Chain in CDR-H2 region
      (Contact)

<400> SEQUENCE: 47

Trp Leu Gly Phe Ile Arg Asn Lys Ala Lys Gly Tyr Thr Ala Glu
1               5                   10                  15

<210> SEQ ID NO 48
<211> LENGTH: 6
<212> TYPE: PRT
<213> ORGANISM: Artificial Sequence
<220> FEATURE:
<223> OTHER INFORMATION: mAb NMC-103 Heavy Chain in CDR-H3 region
      (Contact)

<400> SEQUENCE: 48

Ala Arg Asp Ile Gly Asp
1               5

<210> SEQ ID NO 49
<211> LENGTH: 12
<212> TYPE: PRT
<213> ORGANISM: Artificial Sequence
<220> FEATURE:
<223> OTHER INFORMATION: mAb NMC-103 Light Chain in CDR-L1 region
      (Contact)

<400> SEQUENCE: 49

Leu His Ser Asn Gly Ile Thr Tyr Leu Tyr Trp Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: mAb NMC-103 Light Chain in CDR-L2 region
      (Contact)

<400> SEQUENCE: 50

Leu Leu Ile Ser Arg Val Ser Asn Leu Ala
1               5                   10

<210> SEQ ID NO 51
<211> LENGTH: 8
<212> TYPE: PRT
<213> ORGANISM: Artificial Sequence
<220> FEATURE:
<223> OTHER INFORMATION: mAb NMC-103 Light Chain in CDR-L3 region
      (Contact)

<400> SEQUENCE: 51

Ala Gln Leu Leu Glu Leu Pro Tyr
1               5

<210> SEQ ID NO 52
<211> LENGTH: 10
<212> TYPE: PRT
<213> ORGANISM: Artificial Sequence
<220> FEATURE:
<223> OTHER INFORMATION: mAb NMC-204 Heavy Chain in CDR-H1 region (AbM)

<400> SEQUENCE: 52

Gly Asp Thr Leu Ser Gly Ser Trp Met His
1               5                   10

<210> SEQ ID NO 53
<211> LENGTH: 5
<212> TYPE: PRT
<213> ORGANISM: Artificial Sequence
<220> FEATURE:
<223> OTHER INFORMATION: mAb NMC-204 Heavy Chain in CDR-H1 region
      (Kabat)

<400> SEQUENCE: 53

Gly Ser Trp Met His
1               5

<210> SEQ ID NO 54
<211> LENGTH: 6
<212> TYPE: PRT
<213> ORGANISM: Artificial Sequence
<220> FEATURE:
<223> OTHER INFORMATION: mAb NMC-204 Heavy Chain in CDR-H1 region
      (Contact)

<400> SEQUENCE: 54

Ser Gly Ser Trp Met His
1               5

<210> SEQ ID NO 55
<211> LENGTH: 10
<212> TYPE: PRT
<213> ORGANISM: Artificial Sequence
<220> FEATURE:
<223> OTHER INFORMATION: mAb NMC-204 Heavy Chain in CDR-H2 region (AbM)

<400> SEQUENCE: 55

Glu Ile His Leu Asn Arg Gly Thr Thr Asn
1               5                   10

<210> SEQ ID NO 56
<211> LENGTH: 17
<212> TYPE: PRT
<213> ORGANISM: Artificial Sequence
<220> FEATURE:
<223> OTHER INFORMATION: mAb NMC-204 Heavy Chain in CDR-H2 region
      (Kabat)

<400> SEQUENCE: 56

Glu Ile His Leu Asn Arg Gly Thr Thr Asn Tyr Asn Glu Lys Phe Lys
1               5                   10                  15

Gly

<210> SEQ ID NO 57
<211> LENGTH: 13
<212> TYPE: PRT
<213> ORGANISM: Artificial Sequence
<220> FEATURE:
<223> OTHER INFORMATION: mAb NMC-204 Heavy Chain in CDR-H2 region
      (Contact)

<400> SEQUENCE: 57

Trp Ile Gly Glu Ile His Leu Asn Arg Gly Thr Thr Asn
1               5                   10

<210> SEQ ID NO 58
<211> LENGTH: 7
<212> TYPE: PRT
<213> ORGANISM: Artificial Sequence
<220> FEATURE:
<223> OTHER INFORMATION: mAb NMC-204 Heavy Chain in CDR-H3 region
      (Contact)

<400> SEQUENCE: 58

Ala Arg Ser Pro Gly Phe Ala
1               5

<210> SEQ ID NO 59
<211> LENGTH: 12
<212> TYPE: PRT
<213> ORGANISM: Artificial Sequence
<220> FEATURE:
<223> OTHER INFORMATION: mAb NMC-204 Light Chain in CDR-L1 region
      (Contact)

<400> SEQUENCE: 59

Leu His Ser Asn Gly Asn Ser Tyr Leu Tyr Trp Phe
1               5                   10

<210> SEQ ID NO 60
<211> LENGTH: 10
<212> TYPE: PRT
<213> ORGANISM: Artificial Sequence
<220> FEATURE:
<223> OTHER INFORMATION: mAb NMC-204 Light Chain in CDR-L2 region
      (Contact)

<400> SEQUENCE: 60

Leu Leu Ile Tyr Arg Met Ser Asn Leu Ala
1               5                   10

<210> SEQ ID NO 61
<211> LENGTH: 8
<212> TYPE: PRT
<213> ORGANISM: Artificial Sequence
<220> FEATURE:
<223> OTHER INFORMATION: mAb NMC-204 Light Chain in CDR-L3 region
      (Contact)

<400> SEQUENCE: 61

Met Gln His Leu Glu Tyr Pro Phe
1               5

<210> SEQ ID NO 62
<211> LENGTH: 10
<212> TYPE: PRT

```
<213> ORGANISM: Artificial Sequence
<220> FEATURE:
<223> OTHER INFORMATION: mAb NMC-303 Heavy Chain in CDR-H1 region (AbM)

<400> SEQUENCE: 62

Gly Tyr Thr Phe Thr Ser Tyr Tyr Met Tyr
1               5                   10

<210> SEQ ID NO 63
<211> LENGTH: 5
<212> TYPE: PRT
<213> ORGANISM: Artificial Sequence
<220> FEATURE:
<223> OTHER INFORMATION: mAb NMC-303 Heavy Chain in CDR-H1 region
      (Kabat)

<400> SEQUENCE: 63

Ser Tyr Tyr Met Tyr
1               5

<210> SEQ ID NO 64
<211> LENGTH: 6
<212> TYPE: PRT
<213> ORGANISM: Artificial Sequence
<220> FEATURE:
<223> OTHER INFORMATION: mAb NMC-303 Heavy Chain in CDR-H1 region
      (Contact)

<400> SEQUENCE: 64

Thr Ser Tyr Tyr Met Tyr
1               5

<210> SEQ ID NO 65
<211> LENGTH: 10
<212> TYPE: PRT
<213> ORGANISM: Artificial Sequence
<220> FEATURE:
<223> OTHER INFORMATION: mAb NMC-303 Heavy Chain in CDR-H2 region (AbM)

<400> SEQUENCE: 65

Gly Ile Asn Pro Arg Asn Gly Gly Thr Asn
1               5                   10

<210> SEQ ID NO 66
<211> LENGTH: 17
<212> TYPE: PRT
<213> ORGANISM: Artificial Sequence
<220> FEATURE:
<223> OTHER INFORMATION: mAb NMC-303 Heavy Chain in CDR-H2 region
      (Kabat)

<400> SEQUENCE: 66

Gly Ile Asn Pro Arg Asn Gly Gly Thr Asn Phe Asn Glu Lys Phe Lys
1               5                   10                  15

Asn

<210> SEQ ID NO 67
<211> LENGTH: 13
<212> TYPE: PRT
<213> ORGANISM: Artificial Sequence
<220> FEATURE:
<223> OTHER INFORMATION: mAb NMC-303 Heavy Chain in CDR-H2 region
      (Contact)

<400> SEQUENCE: 67

Trp Ile Gly Gly Ile Asn Pro Arg Asn Gly Gly Thr Asn
1               5                   10
```

<210> SEQ ID NO 68
<211> LENGTH: 9
<212> TYPE: PRT
<213> ORGANISM: Artificial Sequence
<220> FEATURE:
<223> OTHER INFORMATION: mAb NMC-303 Heavy Chain in CDR-H3 region
      (Contact)

<400> SEQUENCE: 68

Thr Arg Ser Gly Tyr Tyr Ala Met Asp
1               5

<210> SEQ ID NO 69
<211> LENGTH: 7
<212> TYPE: PRT
<213> ORGANISM: Artificial Sequence
<220> FEATURE:
<223> OTHER INFORMATION: mAb NMC-303 Light Chain in CDR-L1 region
      (Contact)

<400> SEQUENCE: 69

Ser Asn Phe Leu Asn Trp Tyr
1               5

<210> SEQ ID NO 70
<211> LENGTH: 10
<212> TYPE: PRT
<213> ORGANISM: Artificial Sequence
<220> FEATURE:
<223> OTHER INFORMATION: mAb NMC-303 Light Chain in CDR-L2 region
      (Contact)

<400> SEQUENCE: 70

Leu Leu Ile Tyr Tyr Thr Ser Arg Leu His
1               5                   10

<210> SEQ ID NO 71
<211> LENGTH: 8
<212> TYPE: PRT
<213> ORGANISM: Artificial Sequence
<220> FEATURE:
<223> OTHER INFORMATION: mAb NMC-303 Light Chain in CDR-L3 region
      (Contact)

<400> SEQUENCE: 71

Gln Gln Gly Asn Thr Leu Pro Arg
1               5

<210> SEQ ID NO 72
<211> LENGTH: 25
<212> TYPE: PRT
<213> ORGANISM: Artificial Sequence
<220> FEATURE:
<223> OTHER INFORMATION: mAb NMC-103 Heavy Chain in HFR1 region
      (Chothia)

<400> SEQUENCE: 72

Glu Val Gln Leu Gln Glu Ser Gly Gly Gly Leu Val Gln Pro Gly Gly
1               5                   10                  15

Ser Leu Arg Leu Ser Cys Thr Thr Ser
            20                  25

<210> SEQ ID NO 73
<211> LENGTH: 30
<212> TYPE: PRT
<213> ORGANISM: Artificial Sequence

```
<220> FEATURE:
<223> OTHER INFORMATION: mAb NMC-103 Heavy Chain in HFR1 region (Kabat)

<400> SEQUENCE: 73

Glu Val Gln Leu Gln Glu Ser Gly Gly Gly Leu Val Gln Pro Gly Gly
1               5                   10                  15
Ser Leu Arg Leu Ser Cys Thr Thr Ser Gly Phe Thr Phe Thr
            20                  25                  30

<210> SEQ ID NO 74
<211> LENGTH: 29
<212> TYPE: PRT
<213> ORGANISM: Artificial Sequence
<220> FEATURE:
<223> OTHER INFORMATION: mAb NMC-103 Heavy Chain in HFR1 region
      (Contact)

<400> SEQUENCE: 74

Glu Val Gln Leu Gln Glu Ser Gly Gly Gly Leu Val Gln Pro Gly Gly
1               5                   10                  15
Ser Leu Arg Leu Ser Cys Thr Thr Ser Gly Phe Thr Phe
            20                  25

<210> SEQ ID NO 75
<211> LENGTH: 19
<212> TYPE: PRT
<213> ORGANISM: Artificial Sequence
<220> FEATURE:
<223> OTHER INFORMATION: mAb NMC-103 Heavy Chain in HFR2 region
      (Chothia)

<400> SEQUENCE: 75

Tyr Met Ser Trp Val Arg Gln Pro Pro Gly Lys Ala Leu Glu Trp Leu
1               5                   10                  15
Gly Phe Ile

<210> SEQ ID NO 76
<211> LENGTH: 14
<212> TYPE: PRT
<213> ORGANISM: Artificial Sequence
<220> FEATURE:
<223> OTHER INFORMATION: mAb NMC-103 Heavy Chain in HFR2 region (Kabat)

<400> SEQUENCE: 76

Trp Val Arg Gln Pro Pro Gly Lys Ala Leu Glu Trp Leu Gly
1               5                   10

<210> SEQ ID NO 77
<211> LENGTH: 11
<212> TYPE: PRT
<213> ORGANISM: Artificial Sequence
<220> FEATURE:
<223> OTHER INFORMATION: mAb NMC-103 Heavy Chain in HFR2 region
      (Contact)

<400> SEQUENCE: 77

Trp Val Arg Gln Pro Pro Gly Lys Ala Leu Glu
1               5                   10

<210> SEQ ID NO 78
<211> LENGTH: 41
<212> TYPE: PRT
<213> ORGANISM: Artificial Sequence
<220> FEATURE:
<223> OTHER INFORMATION: mAb NMC-103 Heavy Chain in HFR3 region
      (Chothia)
```

<400> SEQUENCE: 78

Ala Glu Tyr Ser Ala Ser Val Lys Gly Arg Phe Thr Ile Ser Arg Asp
1               5                   10                  15

Asn Ser Gln Ser Ile Leu Tyr Leu Gln Met Asn Thr Leu Arg Pro Glu
            20                  25                  30

Asp Ser Ala Thr Tyr Tyr Cys Ala Arg
        35                  40

<210> SEQ ID NO 79
<211> LENGTH: 39
<212> TYPE: PRT
<213> ORGANISM: Artificial Sequence
<220> FEATURE:
<223> OTHER INFORMATION: mAb NMC-103 Heavy Chain in HFR3 region (AbM)

<400> SEQUENCE: 79

Tyr Ser Ala Ser Val Lys Gly Arg Phe Thr Ile Ser Arg Asp Asn Ser
1               5                   10                  15

Gln Ser Ile Leu Tyr Leu Gln Met Asn Thr Leu Arg Pro Glu Asp Ser
            20                  25                  30

Ala Thr Tyr Tyr Cys Ala Arg
        35

<210> SEQ ID NO 80
<211> LENGTH: 32
<212> TYPE: PRT
<213> ORGANISM: Artificial Sequence
<220> FEATURE:
<223> OTHER INFORMATION: mAb NMC-103 Heavy Chain in HFR3 region (Kabat)

<400> SEQUENCE: 80

Arg Phe Thr Ile Ser Arg Asp Asn Ser Gln Ser Ile Leu Tyr Leu Gln
1               5                   10                  15

Met Asn Thr Leu Arg Pro Glu Asp Ser Ala Thr Tyr Tyr Cys Ala Arg
            20                  25                  30

<210> SEQ ID NO 81
<211> LENGTH: 37
<212> TYPE: PRT
<213> ORGANISM: Artificial Sequence
<220> FEATURE:
<223> OTHER INFORMATION: mAb NMC-103 Heavy Chain in HFR3 region
      (Contact)

<400> SEQUENCE: 81

Tyr Ser Ala Ser Val Lys Gly Arg Phe Thr Ile Ser Arg Asp Asn Ser
1               5                   10                  15

Gln Ser Ile Leu Tyr Leu Gln Met Asn Thr Leu Arg Pro Glu Asp Ser
            20                  25                  30

Ala Thr Tyr Tyr Cys
        35

<210> SEQ ID NO 82
<211> LENGTH: 11
<212> TYPE: PRT
<213> ORGANISM: Artificial Sequence
<220> FEATURE:
<223> OTHER INFORMATION: mAb NMC-103 Heavy Chain in HFR4 region
      (Chothia)

<400> SEQUENCE: 82

Trp Gly Gln Gly Thr Leu Val Thr Val Ser Ser

```
1               5                   10
```

<210> SEQ ID NO 83
<211> LENGTH: 12
<212> TYPE: PRT
<213> ORGANISM: Artificial Sequence
<220> FEATURE:
<223> OTHER INFORMATION: mAb NMC-103 Heavy Chain in HFR4 region
      (Contact)

<400> SEQUENCE: 83

```
Asn Trp Gly Gln Gly Thr Leu Val Thr Val Ser Ser
1               5                   10
```

<210> SEQ ID NO 84
<211> LENGTH: 23
<212> TYPE: PRT
<213> ORGANISM: Artificial Sequence
<220> FEATURE:
<223> OTHER INFORMATION: mAb NMC-103 Light Chain in LFR1 region
      (Chothia)

<400> SEQUENCE: 84

```
Asp Ile Val Met Thr Gln Ala Ala Phe Ser Asn Pro Val Thr Leu Gly
1               5                   10                  15

Thr Ser Ala Ser Ile Ser Cys
            20
```

<210> SEQ ID NO 85
<211> LENGTH: 29
<212> TYPE: PRT
<213> ORGANISM: Artificial Sequence
<220> FEATURE:
<223> OTHER INFORMATION: mAb NMC-103 Light Chain in LFR1 region
      (Contact)

<400> SEQUENCE: 85

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Asn Leu
            20                  25
```

<210> SEQ ID NO 86
<211> LENGTH: 15
<212> TYPE: PRT
<213> ORGANISM: Artificial Sequence
<220> FEATURE:
<223> OTHER INFORMATION: mAb NMC-103 Light Chain in LFR2 region
      (Chothia)

<400> SEQUENCE: 86

```
Trp Tyr Leu Gln Arg Pro Gly Gln Ser Pro Gln Leu Leu Ile Ser
1               5                   10                  15
```

<210> SEQ ID NO 87
<211> LENGTH: 9
<212> TYPE: PRT
<213> ORGANISM: Artificial Sequence
<220> FEATURE:
<223> OTHER INFORMATION: mAb NMC-103 Light Chain in LFR2 region
      (Contact)

<400> SEQUENCE: 87

```
Leu Gln Arg Pro Gly Gln Ser Pro Gln
1               5
```

```
<210> SEQ ID NO 88
<211> LENGTH: 32
<212> TYPE: PRT
<213> ORGANISM: Artificial Sequence
<220> FEATURE:
<223> OTHER INFORMATION: mAb NMC-103 Light Chain in LFR3 region
      (Chothia)

<400> SEQUENCE: 88

Gly Val Pro Asn Arg Phe Ser Gly Ser Glu Ser Gly Thr Asp Phe Thr
1               5                   10                  15

Leu Arg Ile Ser Arg Val Glu Ala Glu Asp Val Gly Val Tyr Phe Cys
            20                  25                  30

<210> SEQ ID NO 89
<211> LENGTH: 33
<212> TYPE: PRT
<213> ORGANISM: Artificial Sequence
<220> FEATURE:
<223> OTHER INFORMATION: mAb NMC-103 Light Chain in LFR3 region
      (Contact)

<400> SEQUENCE: 89

Ser Gly Val Pro Asn Arg Phe Ser Gly Ser Glu Ser Gly Thr Asp Phe
1               5                   10                  15

Thr Leu Arg Ile Ser Arg Val Glu Ala Glu Asp Val Gly Val Tyr Phe
            20                  25                  30

Cys

<210> SEQ ID NO 90
<211> LENGTH: 10
<212> TYPE: PRT
<213> ORGANISM: Artificial Sequence
<220> FEATURE:
<223> OTHER INFORMATION: mAb NMC-103 Light Chain in LFR4 region
      (Chothia)

<400> SEQUENCE: 90

Phe Gly Gly Gly Thr Lys Leu Glu Ile Lys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: mAb NMC-103 Light Chain in LFR4 region
      (Contact)

<400> SEQUENCE: 91

Thr Phe Gly Gly Gly Thr Lys Leu Glu Ile Lys
1               5                   10

<210> SEQ ID NO 92
<211> LENGTH: 25
<212> TYPE: PRT
<213> ORGANISM: Artificial Sequence
<220> FEATURE:
<223> OTHER INFORMATION: mAb NMC-204 Heavy Chain in HFR1 region
      (Chothia)

<400> SEQUENCE: 92

Glu Val Gln Leu Gln Glu Ser Gly Ser Val Leu Val Arg Pro Gly Ala
1               5                   10                  15

Ser Val Lys Leu Ser Cys Lys Ala Ser
            20                  25
```

<210> SEQ ID NO 93
<211> LENGTH: 30
<212> TYPE: PRT
<213> ORGANISM: Artificial Sequence
<220> FEATURE:
<223> OTHER INFORMATION: mAb NMC-204 Heavy Chain in HFR1 region (Kabat)

<400> SEQUENCE: 93

Glu Val Gln Leu Gln Glu Ser Gly Ser Val Leu Val Arg Pro Gly Ala
1               5                   10                  15

Ser Val Lys Leu Ser Cys Lys Ala Ser Gly Asp Thr Leu Ser
            20                  25                  30

<210> SEQ ID NO 94
<211> LENGTH: 29
<212> TYPE: PRT
<213> ORGANISM: Artificial Sequence
<220> FEATURE:
<223> OTHER INFORMATION: mAb NMC-204 Heavy Chain in HFR1 region
      (Contact)

<400> SEQUENCE: 94

Glu Val Gln Leu Gln Glu Ser Gly Ser Val Leu Val Arg Pro Gly Ala
1               5                   10                  15

Ser Val Lys Leu Ser Cys Lys Ala Ser Gly Asp Thr Leu
            20                  25

<210> SEQ ID NO 95
<211> LENGTH: 19
<212> TYPE: PRT
<213> ORGANISM: Artificial Sequence
<220> FEATURE:
<223> OTHER INFORMATION: mAb NMC-204 Heavy Chain in HFR2 region
      (Chothia)

<400> SEQUENCE: 95

Trp Met His Trp Ala Met Gln Arg Pro Gly Gln Gly Leu Glu Trp Ile
1               5                   10                  15

Gly Glu Ile

<210> SEQ ID NO 96
<211> LENGTH: 14
<212> TYPE: PRT
<213> ORGANISM: Artificial Sequence
<220> FEATURE:
<223> OTHER INFORMATION: mAb NMC-204 Heavy Chain in HFR2 region (Kabat)

<400> SEQUENCE: 96

Trp Ala Met Gln Arg Pro Gly Gln Gly Leu Glu Trp Ile Gly
1               5                   10

<210> SEQ ID NO 97
<211> LENGTH: 11
<212> TYPE: PRT
<213> ORGANISM: Artificial Sequence
<220> FEATURE:
<223> OTHER INFORMATION: mAb NMC-204 Heavy Chain in HFR2 region
      (Contact)

<400> SEQUENCE: 97

Trp Ala Met Gln Arg Pro Gly Gln Gly Leu Glu
1               5                   10

<210> SEQ ID NO 98

```
<211> LENGTH: 41
<212> TYPE: PRT
<213> ORGANISM: Artificial Sequence
<220> FEATURE:
<223> OTHER INFORMATION: mAb NMC-204 Heavy Chain in HFR3 region
      (Chothia)

<400> SEQUENCE: 98

Thr Asn Tyr Asn Glu Lys Phe Lys Gly Lys Ala Thr Val Thr Val Asp
1               5                   10                  15

Thr Ser Ser Ser Thr Ala Tyr Val Asp Leu Ser Ser Leu Thr Ser Glu
            20                  25                  30

Asp Ser Ala Val Tyr Tyr Cys Ala Arg
        35                  40

<210> SEQ ID NO 99
<211> LENGTH: 39
<212> TYPE: PRT
<213> ORGANISM: Artificial Sequence
<220> FEATURE:
<223> OTHER INFORMATION: mAb NMC-204 Heavy Chain in HFR3 region (Kabat)

<400> SEQUENCE: 99

Tyr Asn Glu Lys Phe Lys Gly Lys Ala Thr Val Thr Val Asp Thr Ser
1               5                   10                  15

Ser Ser Thr Ala Tyr Val Asp Leu Ser Ser Leu Thr Ser Glu Asp Ser
            20                  25                  30

Ala Val Tyr Tyr Cys Ala Arg
        35

<210> SEQ ID NO 100
<211> LENGTH: 32
<212> TYPE: PRT
<213> ORGANISM: Artificial Sequence
<220> FEATURE:
<223> OTHER INFORMATION: mAb NMC-204 Heavy Chain in HFR3 region (Kabat)

<400> SEQUENCE: 100

Lys Ala Thr Val Thr Val Asp Thr Ser Ser Ser Thr Ala Tyr Val Asp
1               5                   10                  15

Leu Ser Ser Leu Thr Ser Glu Asp Ser Ala Val Tyr Tyr Cys Ala Arg
            20                  25                  30

<210> SEQ ID NO 101
<211> LENGTH: 37
<212> TYPE: PRT
<213> ORGANISM: Artificial Sequence
<220> FEATURE:
<223> OTHER INFORMATION: mAb NMC-204 Heavy Chain in HFR3 region
      (Contact)

<400> SEQUENCE: 101

Tyr Asn Glu Lys Phe Lys Gly Lys Ala Thr Val Thr Val Asp Thr Ser
1               5                   10                  15

Ser Ser Thr Ala Tyr Val Asp Leu Ser Ser Leu Thr Ser Glu Asp Ser
            20                  25                  30

Ala Val Tyr Tyr Cys
        35

<210> SEQ ID NO 102
<211> LENGTH: 11
<212> TYPE: PRT
<213> ORGANISM: Artificial Sequence
<220> FEATURE:
```

<223> OTHER INFORMATION: mAb NMC-204 Heavy Chain in HFR4 region
      (Chothia)

<400> SEQUENCE: 102

Trp Gly Gln Gly Thr Leu Val Thr Val Ser Ala
1               5                   10

<210> SEQ ID NO 103
<211> LENGTH: 12
<212> TYPE: PRT
<213> ORGANISM: Artificial Sequence
<220> FEATURE:
<223> OTHER INFORMATION: mAb NMC-204 Heavy Chain in HFR4 region
      (Contact)

<400> SEQUENCE: 103

Tyr Trp Gly Gln Gly Thr Leu Val Thr Val Ser Ala
1               5                   10

<210> SEQ ID NO 104
<211> LENGTH: 23
<212> TYPE: PRT
<213> ORGANISM: Artificial Sequence
<220> FEATURE:
<223> OTHER INFORMATION: mAb NMC-204 Light Chain in LFR1 region
      (Chothia)

<400> SEQUENCE: 104

Gly Ile Val Met Thr Gln Ala Ala Pro Ser Val Pro Val Thr Pro Gly
1               5                   10                  15

Glu Ser Val Ser Ile Ser Cys
            20

<210> SEQ ID NO 105
<211> LENGTH: 29
<212> TYPE: PRT
<213> ORGANISM: Artificial Sequence
<220> FEATURE:
<223> OTHER INFORMATION: mAb NMC-204 Light Chain in LFR1 region
      (Contact)

<400> SEQUENCE: 105

Gly Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu
            20                  25

<210> SEQ ID NO 106
<211> LENGTH: 15
<212> TYPE: PRT
<213> ORGANISM: Artificial Sequence
<220> FEATURE:
<223> OTHER INFORMATION: mAb NMC-204 Light Chain in LFR2 region
      (Chothia)

<400> SEQUENCE: 106

Trp Phe Leu Gln Arg Pro Gly Gln Ser Pro Gln Leu Leu Ile Tyr
1               5                   10                  15

<210> SEQ ID NO 107
<211> LENGTH: 9
<212> TYPE: PRT
<213> ORGANISM: Artificial Sequence
<220> FEATURE:
<223> OTHER INFORMATION: mAb NMC-204 Light Chain in LFR2 region
      (Contact)

-continued

```
<400> SEQUENCE: 107

Leu Gln Arg Pro Gly Gln Ser Pro Gln
1               5

<210> SEQ ID NO 108
<211> LENGTH: 32
<212> TYPE: PRT
<213> ORGANISM: Artificial Sequence
<220> FEATURE:
<223> OTHER INFORMATION: mAb NMC-204 Light Chain in LFR3 region
      (Chothia)

<400> SEQUENCE: 108

Gly Val Pro Asp Arg Phe Ser Gly Ser Gly Ser Gly Thr Ala Phe Thr
1               5                   10                  15

Leu Arg Ile Thr Arg Val Glu Ala Glu Asp Val Gly Val Tyr Tyr Cys
            20                  25                  30

<210> SEQ ID NO 109
<211> LENGTH: 33
<212> TYPE: PRT
<213> ORGANISM: Artificial Sequence
<220> FEATURE:
<223> OTHER INFORMATION: mAb NMC-204 Light Chain in LFR3 region
      (Contact)

<400> SEQUENCE: 109

Ser Gly Val Pro Asp Arg Phe Ser Gly Ser Gly Ser Gly Thr Ala Phe
1               5                   10                  15

Thr Leu Arg Ile Thr Arg Val Glu Ala Glu Asp Val Gly Val Tyr Tyr
            20                  25                  30

Cys

<210> SEQ ID NO 110
<211> LENGTH: 10
<212> TYPE: PRT
<213> ORGANISM: Artificial Sequence
<220> FEATURE:
<223> OTHER INFORMATION: mAb NMC-204 Light Chain in LFR4 region
      (Chothia)

<400> SEQUENCE: 110

Phe Gly Ser Gly Thr Lys Leu Glu Ile Lys
1               5                   10

<210> SEQ ID NO 111
<211> LENGTH: 11
<212> TYPE: PRT
<213> ORGANISM: Artificial Sequence
<220> FEATURE:
<223> OTHER INFORMATION: mAb NMC-204 Light Chain in LFR4 region
      (Contact)

<400> SEQUENCE: 111

Thr Phe Gly Ser Gly Thr Lys Leu Glu Ile Lys
1               5                   10

<210> SEQ ID NO 112
<211> LENGTH: 25
<212> TYPE: PRT
<213> ORGANISM: Artificial Sequence
<220> FEATURE:
<223> OTHER INFORMATION: mAb NMC-303 Heavy Chain in HFR1 region
      (Chothia)

<400> SEQUENCE: 112
```

Gln Val Gln Leu Gln Gln Pro Gly Ala Glu Leu Val Lys Pro Gly Ala
1               5                   10                  15

Ser Val Lys Leu Ser Cys Lys Ala Ser
            20                  25

<210> SEQ ID NO 113
<211> LENGTH: 30
<212> TYPE: PRT
<213> ORGANISM: Artificial Sequence
<220> FEATURE:
<223> OTHER INFORMATION: mAb NMC-303 Heavy Chain in HFR1 region (Kabat)

<400> SEQUENCE: 113

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr
            20                  25                  30

<210> SEQ ID NO 114
<211> LENGTH: 29
<212> TYPE: PRT
<213> ORGANISM: Artificial Sequence
<220> FEATURE:
<223> OTHER INFORMATION: mAb NMC-303 Heavy Chain in HFR1 region
      (Contact)

<400> SEQUENCE: 114

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe
            20                  25

<210> SEQ ID NO 115
<211> LENGTH: 19
<212> TYPE: PRT
<213> ORGANISM: Artificial Sequence
<220> FEATURE:
<223> OTHER INFORMATION: mAb NMC-303 Heavy Chain in HFR2 region
      (Chothia)

<400> SEQUENCE: 115

Tyr Met Tyr Trp Val Lys Gln Arg Pro Gly Gln Gly Leu Glu Trp Ile
1               5                   10                  15

Gly Gly Ile

<210> SEQ ID NO 116
<211> LENGTH: 14
<212> TYPE: PRT
<213> ORGANISM: Artificial Sequence
<220> FEATURE:
<223> OTHER INFORMATION: mAb NMC-303 Heavy Chain in HFR2 region (Kabat)

<400> SEQUENCE: 116

Trp Val Lys Gln Arg Pro Gly Gln Gly Leu Glu Trp Ile Gly
1               5                   10

<210> SEQ ID NO 117
<211> LENGTH: 11
<212> TYPE: PRT
<213> ORGANISM: Artificial Sequence
<220> FEATURE:
<223> OTHER INFORMATION: mAb NMC-303 Heavy Chain in HFR2 region
      (Contact)

<400> SEQUENCE: 117

Trp Val Lys Gln Arg Pro Gly Gln Gly Leu Glu
1               5                   10

<210> SEQ ID NO 118
<211> LENGTH: 41
<212> TYPE: PRT
<213> ORGANISM: Artificial Sequence
<220> FEATURE:
<223> OTHER INFORMATION: mAb NMC-303 Heavy Chain in HFR3 region
      (Chothia)

<400> SEQUENCE: 118

Thr Asn Phe Asn Glu Lys Phe Lys Asn Lys Ala Thr Leu Thr Ala Asp
1               5                   10                  15

Lys Ser Ser Thr Thr Ala Tyr Met Gln Leu Ser Ser Leu Thr Ser Glu
                20                  25                  30

Asp Ser Ala Val Tyr Tyr Cys Thr Arg
            35                  40

<210> SEQ ID NO 119
<211> LENGTH: 39
<212> TYPE: PRT
<213> ORGANISM: Artificial Sequence
<220> FEATURE:
<223> OTHER INFORMATION: mAb NMC-303 Heavy Chain in HFR3 region (AbM)

<400> SEQUENCE: 119

Phe Asn Glu Lys Phe Lys Asn Lys Ala Thr Leu Thr Ala Asp Lys Ser
1               5                   10                  15

Ser Thr Thr Ala Tyr Met Gln Leu Ser Ser Leu Thr Ser Glu Asp Ser
                20                  25                  30

Ala Val Tyr Tyr Cys Thr Arg
            35

<210> SEQ ID NO 120
<211> LENGTH: 32
<212> TYPE: PRT
<213> ORGANISM: Artificial Sequence
<220> FEATURE:
<223> OTHER INFORMATION: mAb NMC-303 Heavy Chain in HFR3 region (Kabat)

<400> SEQUENCE: 120

Lys Ala Thr Leu Thr Ala Asp Lys Ser Ser Thr Thr Ala Tyr Met Gln
1               5                   10                  15

Leu Ser Ser Leu Thr Ser Glu Asp Ser Ala Val Tyr Tyr Cys Thr Arg
                20                  25                  30

<210> SEQ ID NO 121
<211> LENGTH: 37
<212> TYPE: PRT
<213> ORGANISM: Artificial Sequence
<220> FEATURE:
<223> OTHER INFORMATION: mAb NMC-303 Heavy Chain in HFR3 region
      (Contact)

<400> SEQUENCE: 121

Phe Asn Glu Lys Phe Lys Asn Lys Ala Thr Leu Thr Ala Asp Lys Ser
1               5                   10                  15

Ser Thr Thr Ala Tyr Met Gln Leu Ser Ser Leu Thr Ser Glu Asp Ser
                20                  25                  30

Ala Val Tyr Tyr Cys
            35

<210> SEQ ID NO 122
<211> LENGTH: 11
<212> TYPE: PRT
<213> ORGANISM: Artificial Sequence
<220> FEATURE:
<223> OTHER INFORMATION: mAb NMC-303 Heavy Chain in HFR4 region
      (Chothia)

<400> SEQUENCE: 122

Trp Gly Gln Gly Thr Ser Val Thr Val Ser Ser
1               5                   10

<210> SEQ ID NO 123
<211> LENGTH: 12
<212> TYPE: PRT
<213> ORGANISM: Artificial Sequence
<220> FEATURE:
<223> OTHER INFORMATION: mAb NMC-303 Heavy Chain in HFR4 region
      (Contact)

<400> SEQUENCE: 123

Tyr Trp Gly Gln Gly Thr Ser Val Thr Val Ser Ser
1               5                   10

<210> SEQ ID NO 124
<211> LENGTH: 23
<212> TYPE: PRT
<213> ORGANISM: Artificial Sequence
<220> FEATURE:
<223> OTHER INFORMATION: mAb NMC-303 Light Chain in LFR1 region
      (Chothia)

<400> SEQUENCE: 124

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 125
<211> LENGTH: 29
<212> TYPE: PRT
<213> ORGANISM: Artificial Sequence
<220> FEATURE:
<223> OTHER INFORMATION: mAb NMC-303 Light Chain in LFR1 region
      (Contact)

<400> SEQUENCE: 125

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile
            20                  25

<210> SEQ ID NO 126
<211> LENGTH: 15
<212> TYPE: PRT
<213> ORGANISM: Artificial Sequence
<220> FEATURE:
<223> OTHER INFORMATION: mAb NMC-303 Light Chain in LFR2 region
      (Chothia)

<400> SEQUENCE: 126

Trp Tyr Gln Gln Lys Pro Asp Gly Thr Val Lys Leu Leu Ile Tyr
1               5                   10                  15

<210> SEQ ID NO 127
<211> LENGTH: 9

```
<212> TYPE: PRT
<213> ORGANISM: Artificial Sequence
<220> FEATURE:
<223> OTHER INFORMATION: mAb NMC-303 Light Chain in LFR2 region
      (Contact)

<400> SEQUENCE: 127

Gln Gln Lys Pro Asp Gly Thr Val Lys
1               5

<210> SEQ ID NO 128
<211> LENGTH: 32
<212> TYPE: PRT
<213> ORGANISM: Artificial Sequence
<220> FEATURE:
<223> OTHER INFORMATION: mAb NMC-303 Light Chain in LFR3 region
      (Chothia)

<400> SEQUENCE: 128

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 129
<211> LENGTH: 33
<212> TYPE: PRT
<213> ORGANISM: Artificial Sequence
<220> FEATURE:
<223> OTHER INFORMATION: mAb NMC-303 Light Chain in LFR3 region
      (Contact)

<400> SEQUENCE: 129

Ser Gly Val Pro Ser Arg Phe Ser Gly Ser Gly Ser Gly Thr Asp Tyr
1               5                   10                  15

Ser Leu Thr Ile Ser Asn Leu Glu Gln Glu Asp Ile Ala Thr Tyr Phe
            20                  25                  30

Cys

<210> SEQ ID NO 130
<211> LENGTH: 10
<212> TYPE: PRT
<213> ORGANISM: Artificial Sequence
<220> FEATURE:
<223> OTHER INFORMATION: mAb NMC-303 Light Chain in LFR4 region
      (Chothia)

<400> SEQUENCE: 130

Phe Gly Gly Gly Thr Lys Leu Glu Ile Lys
1               5                   10

<210> SEQ ID NO 131
<211> LENGTH: 11
<212> TYPE: PRT
<213> ORGANISM: Artificial Sequence
<220> FEATURE:
<223> OTHER INFORMATION: mAb NMC-303 Light Chain in LFR4 region
      (Contact)

<400> SEQUENCE: 131

Thr Phe Gly Gly Gly Thr Lys Leu Glu Ile Lys
1               5                   10

<210> SEQ ID NO 132
<211> LENGTH: 349
<212> TYPE: DNA
```

<213> ORGANISM: Artificial Sequence
<220> FEATURE:
<223> OTHER INFORMATION: mAb NMC-103 Heavy Chain Variable Region

<400> SEQUENCE: 132

```
gaggtgcagc tgcaggagtc tggaggaggc ttggtacagc ctgggggttc tctgagactc    60
tcctgtacaa cttctggtt caccttcact cattactaca tgagctgggt ccgccagcct   120
```
(Note: line 2 as read)

```
gaggtgcagc tgcaggagtc tggaggaggc ttggtacagc ctgggggttc tctgagactc    60
tcctgtacaa cttctgggtt caccttcact cattactaca tgagctgggt ccgccagcct   120
ccaggcaagg cacttgagtg gttgggcttt attagaaata agctaaggg ttacacagca   180
gagtacagtg catctgtgaa gggtcggttc accatctcca gagataattc caaagcatc   240
ctctatcttc aaatgaacac cctgagacct gaggacagtg ccacttatta ctgtgcaaga   300
gatattgggg acaactgggg tcaaggaacc ttagtcaccg tctcctcag               349
```

<210> SEQ ID NO 133
<211> LENGTH: 408
<212> TYPE: DNA
<213> ORGANISM: Artificial Sequence
<220> FEATURE:
<223> OTHER INFORMATION: mAb NMC-303 heavy chain

<400> SEQUENCE: 133

```
atgggatgga actatatcat cctcttttg gtagcaacag ctacaggtgt ccactcccag    60
gtccaactgc agcagcctgg ggctgaactg gtgaagcctg ggcttcagt gaagttgtcc   120
tgcaaggctt ctggctacac cttcaccagc tactatatgt actgggtgaa gcagaggcct   180
ggacaaggcc ttgagtggat tggggggatt aatcctagga atggtggtac taacttcaat   240
gagaagttca agaacaaggc cacactgact gcagacaaat cctccaccac agcctacatg   300
caactcagta gcctgacatc tgaggactct gcggtctatt actgtacaag atctggttac   360
tatgctatgg actattgggg tcaaggaacc tcagtcaccg tctcctca                408
```

<210> SEQ ID NO 134
<211> LENGTH: 337
<212> TYPE: DNA
<213> ORGANISM: Artificial Sequence
<220> FEATURE:
<223> OTHER INFORMATION: mAb NMC-103 Light Chain Variable Region

<400> SEQUENCE: 134

```
gatattgtga tgacgcaggc tgccttctcc aatccagtca ctcttggaac atcagcttcc    60
atctcctgca ggtctagtaa gaatctccta catagtaatg gcatcactta tttgtattgg   120
tatctgcaga ggccaggcca gtctcctcag ctcctgatat ctcgggtgtc caatctggcc   180
tcaggagtcc caaacaggtt cagtggcagt gagtcaggaa ctgatttcac actgagaatc   240
agcagagtgg aggctgagga tgtgggtgtt tatttctgtg ctcaactgct agaactcccg   300
tacacgttcg gagggggac caagttggaa ataaaac                             337
```

<210> SEQ ID NO 135
<211> LENGTH: 136
<212> TYPE: PRT
<213> ORGANISM: Artificial Sequence
<220> FEATURE:
<223> OTHER INFORMATION: mAb NMC-303 heavy chain variable region

<400> SEQUENCE: 135

Met Gly Trp Asn Tyr Ile Ile Leu Phe Leu Val Ala Thr Ala Thr Gly
1               5                  10                  15

Val His Ser Gln Val Gln Leu Gln Gln Pro Gly Ala Glu Leu Val Lys
            20                  25                  30

```
Pro Gly Ala Ser Val Lys Leu Ser Cys Lys Ala Ser Gly Tyr Thr Phe
        35                  40                  45

Thr Ser Tyr Tyr Met Tyr Trp Val Lys Gln Arg Pro Gly Gln Gly Leu
    50                  55                  60

Glu Trp Ile Gly Gly Ile Asn Pro Arg Asn Gly Gly Thr Asn Phe Asn
65                  70                  75                  80

Glu Lys Phe Lys Asn Lys Ala Thr Leu Thr Ala Asp Lys Ser Ser Thr
                85                  90                  95

Thr Ala Tyr Met Gln Leu Ser Ser Leu Thr Ser Glu Asp Ser Ala Val
            100                 105                 110

Tyr Tyr Cys Thr Arg Ser Gly Tyr Tyr Ala Met Asp Tyr Trp Gly Gln
            115                 120                 125

Gly Thr Ser Val Thr Val Ser Ser
    130                 135
```

<210> SEQ ID NO 136
<211> LENGTH: 346
<212> TYPE: DNA
<213> ORGANISM: Artificial Sequence
<220> FEATURE:
<223> OTHER INFORMATION: mAb NMC-204 Heavy Chain Variable Region

<400> SEQUENCE: 136

```
gaggtgcagc tgcaggagtc tgggtctgtg ctggtgaggc ctggagcttc agtgaagctg      60
tcctgcaagg cttctggcga caccctcagc ggctcctgga tgcactgggc gatgcagagg     120
cctggacaag gccttgagtg gattggagag attcatctta atagaggtac tactaactac     180
aatgagaagt tcaagggcaa ggccacagtg actgtggaca tcctccag cacagcctac       240 gtggatctca gcagcctgac atctgaggac tctgcggtct attactgtgc aagaagcccg     300
gggtttgctt actggggcca aggactctg gtcactgtct ctgcag                     346
```

<210> SEQ ID NO 137
<211> LENGTH: 381
<212> TYPE: DNA
<213> ORGANISM: Artificial Sequence
<220> FEATURE:
<223> OTHER INFORMATION: mAb NMC-303 light chain variable region

<400> SEQUENCE: 137

```
atgatgtcct ctgctcagtt ccttggtctc ctgttgctct gttttcaagg taccagatgt      60
gatatccaga tgacacagac tacatcctcc ctgtctgcct ctctgggaga cagagtcacc     120
atcagttgca gggcaagtca ggacattagc aattttttaa actggtatca gcagaaacca     180
gatggaactg ttaaactcct gatctactac acatcaagat acactcagg agtcccatca      240 aggttcagtg gcagtgggtc tggaacagat tattctctca ccattagcaa cctggagcaa     300
gaagatattg ccacttactt tgccaacag ggtaatacgc ttcctcggac gttcggtgga     360
ggcaccaagc tggaaatcaa a                                                381
```

<210> SEQ ID NO 138
<211> LENGTH: 337
<212> TYPE: DNA
<213> ORGANISM: Artificial Sequence
<220> FEATURE:
<223> OTHER INFORMATION: mAb NMC-204 Light Chain Variable Region

<400> SEQUENCE: 138

```
ggcattgtga tgacccaggc tgcaccctct gtacctgtca ctcctggaga gtcagtatcc      60
```

```
atctcctgca ggtctagtaa gagtctcctg catagtaatg caacagtta cttgtattgg    120 ttcctgcaga ggccaggcca gtctcctcag ctcctgatat atcggatgtc aaccttgcc    180 tcaggagtcc cagacaggtt cagtggcagt gggtcaggaa ctgctttcac actgagaatc    240
actagagtgg aggctgagga tgtgggtgtt tattactgta tgcaacatct agaatatcct    300
ttcacgttcg gctcggggac aaagttggaa ataaaac                            337
```

```
<210> SEQ ID NO 139
<211> LENGTH: 127
<212> TYPE: PRT
<213> ORGANISM: Artificial Sequence
<220> FEATURE:
<223> OTHER INFORMATION: mAb NMC-303 light chain variable region

<400> SEQUENCE: 139

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Phe Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Arg Thr Phe Gly Gly Gly Thr Lys Leu Glu Ile Lys
        115                 120                 125
```

```
<210> SEQ ID NO 140
<211> LENGTH: 351
<212> TYPE: DNA
<213> ORGANISM: Artificial Sequence
<220> FEATURE:
<223> OTHER INFORMATION: mAb NMC-303 Heavy Chain Variable Region

<400> SEQUENCE: 140
caggtccaac tgcagcagcc tggggctgaa ctggtgaagc ctggggcttc agtgaagttg    60
tcctgcaagg cttctggcta caccttcacc agctactata tgtactgggt gaagcagagg    120
cctggacaag gccttgagtg gattgggggg attaatccta ggaatggtgg tactaacttc    180
aatgagaagt tcaagaacaa ggccacactg actgcagaca atcctccac cacagcctac    240 atgcaactca gtagcctgac atctgaggac tctgcggtct attactgtac aagatctggt    300
tactatgcta tggactattg gggtcaagga acctcagtca ccgtctcctc a            351
```

```
<210> SEQ ID NO 141
<211> LENGTH: 11
<212> TYPE: PRT
<213> ORGANISM: Artificial Sequence
<220> FEATURE:
<223> OTHER INFORMATION: mAb NMC-204 Light Chain in CDR-L1 region (IMGT)

<400> SEQUENCE: 141

Lys Ser Leu Leu His Ser Asn Gly Asn Ser Tyr
1               5                   10
```

<210> SEQ ID NO 142
<211> LENGTH: 321
<212> TYPE: DNA
<213> ORGANISM: Artificial Sequence
<220> FEATURE:
<223> OTHER INFORMATION: mAb NMC-303 Light Chain Variable Region

<400> SEQUENCE: 142

```
gatatccaga tgacacagac tacatcctcc ctgtctgcct ctctgggaga cagagtcacc    60
atcagttgca gggcaagtca ggacattagc aattttttaa actggtatca gcagaaacca   120
gatggaactg ttaaactcct gatctactac acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttcctcggac gttcggtgga   300
ggcaccaagc tggaaatcaa a                                             321
```

<210> SEQ ID NO 143
<211> LENGTH: 8
<212> TYPE: PRT
<213> ORGANISM: Artificial Sequence
<220> FEATURE:
<223> OTHER INFORMATION: mAb NMC-204 Heavy Chain in CDR-H2 region (IMGT)

<400> SEQUENCE: 143

Ile His Leu Asn Arg Gly Thr Thr
1               5

<210> SEQ ID NO 144
<211> LENGTH: 7
<212> TYPE: PRT
<213> ORGANISM: Artificial Sequence
<220> FEATURE:
<223> OTHER INFORMATION: mAb NMC-103 Heavy Chain in CDR-H1 region (IMGT)

<400> SEQUENCE: 144

Phe Thr Phe Thr His Tyr Tyr
1               5

<210> SEQ ID NO 145
<211> LENGTH: 10
<212> TYPE: PRT
<213> ORGANISM: Artificial Sequence
<220> FEATURE:
<223> OTHER INFORMATION: mAb NMC-103 Heavy Chain in CDR-H2 region (IMGT)

<400> SEQUENCE: 145

Ile Arg Asn Lys Ala Lys Gly Tyr Thr Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: mAb NMC-103 Heavy Chain in CDR-H3 region (IMGT)

<400> SEQUENCE: 146

Ala Arg Asp Ile Gly Asp Asn
1               5

<210> SEQ ID NO 147
<211> LENGTH: 11
<212> TYPE: PRT

```
<213> ORGANISM: Artificial Sequence
<220> FEATURE:
<223> OTHER INFORMATION: mAb NMC-103 Light Chain in CDR-L1 region (IMGT)

<400> SEQUENCE: 147

Lys Asn Leu Leu His Ser Asn Gly Ile Thr Tyr
1               5                   10

<210> SEQ ID NO 148
<211> LENGTH: 8
<212> TYPE: PRT
<213> ORGANISM: Artificial Sequence
<220> FEATURE:
<223> OTHER INFORMATION: mAb NMC-204 Heavy Chain in CDR-H1 region (IMGT)

<400> SEQUENCE: 148

Gly Asp Thr Leu Ser Gly Ser Trp
1               5
```